US009193969B2

(12) United States Patent
Montefeltro et al.

(10) Patent No.: US 9,193,969 B2
(45) **Date of Patent: *Nov. 24, 2015**

(54) COMPOSITIONS AND METHODS FOR SELECTIVE DELIVERY OF OLIGONUCLEOTIDE MOLECULES TO SPECIFIC NEURON TYPES

(75) Inventors: Andrés Pablo Montefeltro, Barcelona (ES); Gabriel Alvarado Urbina, Nepean (CA); Analia Bortolozzi Biassoni, Barcelona (ES); Francesc Artigas Pérez, Barcelona (ES); Miquel Vila Bover, Barcelona (ES); Maria del Carmen Carmona Orozco, Terrassa (ES)

(73) Assignee: nLife Therapeutics, S.L., Granada (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/066,590

(22) Filed: Apr. 19, 2011

(65) Prior Publication Data

US 2012/0322991 A1 Dec. 20, 2012

Related U.S. Application Data

(60) Provisional application No. 61/325,515, filed on Apr. 19, 2010.

(30) Foreign Application Priority Data

Apr. 19, 2010 (EP) .................................... 10382087
Feb. 9, 2011 (EP) .................................... 11382031

(51) Int. Cl.

| | |
|---|---|
| ***C07H 21/04*** | (2006.01) |
| ***C12N 15/11*** | (2006.01) |
| ***A61K 47/48*** | (2006.01) |
| ***A61K 49/00*** | (2006.01) |
| ***C12N 15/113*** | (2010.01) |
| ***A61K 48/00*** | (2006.01) |

(52) U.S. Cl.

CPC ........ *C12N 15/111* (2013.01); *A61K 47/48046* (2013.01); *A61K 47/48092* (2013.01); *A61K 47/48215* (2013.01); *A61K 48/0033* (2013.01); *A61K 49/0002* (2013.01); *C12N 15/1138* (2013.01); *C12N 2310/11* (2013.01); *C12N 2310/14* (2013.01); *C12N 2310/321* (2013.01); *C12N 2310/341* (2013.01); *C12N 2310/351* (2013.01); *C12N 2310/3515* (2013.01); *C12N 2320/32* (2013.01)

(58) Field of Classification Search

None

See application file for complete search history.

(56) References Cited

FOREIGN PATENT DOCUMENTS

| | | | |
|---|---|---|---|
| WO | WO 2007/107789 | A2 | 9/2007 |
| WO | WO 2009/079790 | A1 | 7/2009 |
| WO | WO 2009/141625 | A1 | 11/2009 |
| WO | WO-2009141625 | A1 | 11/2009 |

OTHER PUBLICATIONS

"Serontonergic neuron targeting of siRNA," (2009) http://www.n-life.es/nLife/I_siRNA/Entradas/2009/9/25_Breaktrough_Delivery_siRNAs_in_Serotonergic_neurons._in-vivo.html, 1 pg.

Bortolozzi, A., et al., "Selective siRNA-mediated suppression of 5-$HT_{1A}$ autoreceptors evokes strong anti-depressant-like effects," *Molecular Psychiatry 17*:612-623, Macmillan Publishers Limited, England (2012).

Boudreau, R.L. and Davidson, B.L., "RNAi therapeutics for CNS disorders," *Brain Research 1338*:112-121, Elsevier B.V., Netherlands (2010).

Creese, I., et al., "Dopamine Receptor Binding Predicts Clinical and Pharmacological Potencies of Antischizophrenic Drugs," *Science 192*(4238):481-483, American Association for the Advancement of Science, United States (1976).

Lasne, M.-C., et al., "The Radiosynthesis of [*N—methyl*—$^{11}$C]—Sertraline," *Appl. Radiat. Isot. 40*(2):147-151, Pergamon Press plc, Great Britain (1989).

Pascoal, V., et al., "Transvascular Delivery of Sirnas into the Rat Brain in an Animal Model of Temporal Lobe Epilepsy," *Epilepsia 50*(Suppl. 10):4, Abstract 012,The International League Against Epilepsy, United States (2009).

Seeman, P. and Lee, T., "Antipsychotic Drugs: Direct Correlation between Clinical Potency and Presynaptic Action on Dopamine Neurons," *Science 188*(4194):1217-1219, American Association for the Advancement of Science, United States (1975).

Xia, C-F., et al., "Intravenous siRNA of Brain Cancer with Receptor Targeting and Avidin-Biotin Technology," *Pharmaceutical Research 24*(12):2309-2316, Springer Science + Business Media, LLC, United States (2007).

Yurt, F., et al., "Labeling of Sertraline with $^{131}$I and investigation of its radiopharmaceutical potential," *Journal of Radioanalytical and Nuclear Chemistry 251*(2):241-244, Kluwer Academic Publishers, Hungary (2002).

*Primary Examiner* — Kimberly Chong

(74) *Attorney, Agent, or Firm* — Sterne, Kessler, Goldstein & Fox PLLC

(57) ABSTRACT

The invention provides a conjugate comprising (i) a nucleic acid which is complementary to a target nucleic acid sequence and which expression prevents or reduces expression of the target nucleic acid and (ii) a selectivity agent which is capable of binding with high affinity to a neurotransmitter transporter. The conjugates of the present invention are useful for the delivery of the nucleic acid to a cell of interests and thus, for the treatment of diseases which require a down-regulation of the protein encoded by the target nucleic acid as well as for the delivery of imaging agents to the cells for diagnostic purposes.

43 Claims, 18 Drawing Sheets

C)

SEQUENCE LISTING

```
<160> NUMBER OF SEQ ID NOS: 70

<210> SEQ ID NO 1
<211> LENGTH: 70
<212> TYPE: RNA
<213> ORGANISM: Mus musculus

<400> SEQUENCE: 1

ggugguagug gugguaauag ugguggugau ggagaaggaa gaaguggagg aagaguguag      60

ggcuuacagg                                                              70
```

<210> SEQ ID NO 2
<211> LENGTH: 110
<212> TYPE: RNA
<213> ORGANISM: Mus musculus

<400> SEQUENCE: 2
caacaccaca acgucccugg agcccuucgg gacaggcggc aacgauacug gccucuccaa 60
cgugaccuuc agcuaccaag ugaucaccuc ucuuuugcug gggacgcuca 110

<210> SEQ ID NO 3
<211> LENGTH: 110
<212> TYPE: RNA
<213> ORGANISM: Mus musculus

<400> SEQUENCE: 3
gcccauggcu gcucuguacc aggugcucaa caaguggacu cugggucagg ucaccuguga 60
ccuguuuauc gcccuggaug ugcugugcug cacuucgucc auccugcacc 110

<210> SEQ ID NO 4
<211> LENGTH: 2321
<212> TYPE: RNA
<213> ORGANISM: Mus musculus

<400> SEQUENCE: 4
ugauaguugc aauaaccucc ucucuauucg aaaucccaau ucuucacgau ggaaguuuaa 60
accucggcga uucaaggaag aaaacccaaa cagaaaauau aaacuguaug gacaucuacc 120
augcccacua ggacugccac ccucugcccu auaucuggaa cuuugagguu caagacugcu 180
cugucucucc cucccucuug cucuagaaac aucuguuccc uuugggugue aauguacacu 240 gcugauucug gucuccaugc acucacggcu ggucugggaa aguuggaacu acuuuggguu 300
auggugcccu ggaauuguuu gccuugcuga auagcaaaag aucccuuucc ccaaugcaca 360
gcacccacuu ucuguauuuu guuuguuugu uuguuuuaac ucaaaaucaa gugacaaaga 420
ugucugcugg aguggacuua uaagcaagaa gccaggccca aaaggaagag ccaagaaggc 480
cugcggaugu uuuccugucc ugguguagc acucaccaaa gaaauugaca aucagacuau 540
uuggaaggaa gaguuuuauu ccuguaguuu guuggcuuuu cuguaaguuc uggaaaggcc 600
uuguggacug cagaaggcgc ccacugcugg ccagggaggg cucauugagg gugcugagau 660
gcccgggaug gcucaccuca cccucaguuu cuuuucuagg agugagcuau gccagagcag 720
cucaccuuga guuugcagcc uccggguucc uccacucacc ucucacagua uccaggagcu 780
aguagagaag uuugaguuug ugcaagaggu uggagacuua gaauuucuaa ggaagugugg 840
gugugaggca cguagaggag guaaggagca aaagggcucc uaagugcuuc caacuccugc 900
ggcgugccca gggggugggg gugaccuaaa ggggcaauuu uaagcauagg augcaaaguu 960
ucucaaucua ccccuucccc cuuucaagga acagcauugu guagcauuuc cuaaaaaugc 1020
ccggauuuau ucuccgggac auucugugcu cacacaaauu ucgcagaucu cugggcucuc 1080
auugugaagg guaucaacac cucaccauua ccuaccuagg aucuugaucu cagagaccua 1140
aaagagagag cgaucucugu ggagucccag ccaagucagc ccccaaauuc ugaggguaaa 1200
accaguuuug uguccucuca auuuuuaaag cauuuuucuc cgcuaggggu ucuuuuccug 1260
cuguuauuuu ugcuguccca cccccaccuc agagaagaaa auuauuuagg ugcuuccuuu 1320
gaauguacau uucuagcuaa gugagagggc aucaaauggu uuugcguuau aucugaacuu 1380
cgaauuuucu guugaauaau gguuuccuuu ucaagcaauu auacggagau uuuuuucacc 1440

-continued

```
ccccaucccc uucagcugua ucuuuccaau gucugcaccu gcuguuuuga aaacccgugc   1500

ugcauuuuuu uuuaaauugc caaaguugcu ggugagaucu cccccuugug uuuauaaaca   1560

gggagaaagg acugcccugc cacaugaagc cauuguuuuu auuuguuaaa cugagcaaag   1620

uuucuuuugc ucuacucuaa agugggaaug aguauuacag ucccuugcaa cagagccauu   1680

ucagaaugua agccuguagg guguccacac cugagagacu gacagggggu ucuguggaga   1740

agacgcacug ggcugggcuu cuccaguaca aacaguacuu guuuguaaau uuagcuugcu   1800

uuauuuguuu guuuguuuau uuauuuauca caaaaaugaa guagaacuau auggccaaau   1860

aauauuuuuc uguaugcuuu acuauuuuua gaccagauca uuuacuugaa auaaagauca   1920

uuuacuugaa auaaaucaau cccuaaauuu cagauguuaa auuggaaacc aagaccucua   1980

acuuccaguu cucuguauuu uuuuuuuucc aauuaggaau guuugaccgu gauggggggag   2040

gggcauugcu cuuguuacuu ugagaaagag acuuuaaaca agacuggaaa gggggcaccc   2100

agcuggaaua uaauugccaa guaauagagc aaucagagaa cuaagugcaa caugccgcac   2160

agcucuaaag aaccccugau gcuuguuuua uuuuaaaaua cuuguauuac aguaaaaugu   2220

uaaugcauca aaauuggccu ucacuuuucc uugugauaau aaaggacuuu aguaauggca   2280

augcuguaau aaacuaagac caguaaccua uauguaccuu u                        2321


<210> SEQ ID NO 5
<211> LENGTH: 19
<212> TYPE: RNA
<213> ORGANISM: Artificial sequence
<220> FEATURE:
<223> OTHER INFORMATION: Sense strand of mouse 5-HT1A-specific siRNA

<400> SEQUENCE: 5

ggaagagugu agggcuuac                                                  19


<210> SEQ ID NO 6
<211> LENGTH: 19
<212> TYPE: RNA
<213> ORGANISM: Artificial sequence
<220> FEATURE:
<223> OTHER INFORMATION: Antisense strand of mouse 5-HT1A-specific siRNA

<400> SEQUENCE: 6

guaagcccua cacucuucc                                                  19


<210> SEQ ID NO 7
<211> LENGTH: 19
<212> TYPE: RNA
<213> ORGANISM: Artificial sequence
<220> FEATURE:
<223> OTHER INFORMATION: Sense strand of a mouse 5-HT1A-specific siRNA

<400> SEQUENCE: 7

cgauacuggc cucuccaac                                                  19


<210> SEQ ID NO 8
<211> LENGTH: 19
<212> TYPE: RNA
<213> ORGANISM: Artificial sequence
<220> FEATURE:
<223> OTHER INFORMATION: Antisense strand of a mouse 5-HT1A-specific
      siRNA

<400> SEQUENCE: 8

guuggagagg ccaguaucg                                                  19
```

-continued

<210> SEQ ID NO 9
<211> LENGTH: 19
<212> TYPE: RNA
<213> ORGANISM: Artificial sequence
<220> FEATURE:
<223> OTHER INFORMATION: Sense strand of a mouse 5-HT1A-specific siRNA

<400> SEQUENCE: 9
ggugcucaac aaguggacu 19

<210> SEQ ID NO 10
<211> LENGTH: 19
<212> TYPE: RNA
<213> ORGANISM: Artificial sequence
<220> FEATURE:
<223> OTHER INFORMATION: Antisense strand of a mouse 5-HT1A-specific siRNA

<400> SEQUENCE: 10
aguccacuug uugagcacc 19

<210> SEQ ID NO 11
<211> LENGTH: 19
<212> TYPE: RNA
<213> ORGANISM: Artificial sequence
<220> FEATURE:
<223> OTHER INFORMATION: Sense strand of a mouse 5-HT1A-specific siRNA

<400> SEQUENCE: 11
cgauggaagu uuaaaccuc 19

<210> SEQ ID NO 12
<211> LENGTH: 19
<212> TYPE: RNA
<213> ORGANISM: Artificial sequence
<220> FEATURE:
<223> OTHER INFORMATION: Antisense strand of a mouse 5-HT1A-specific siRNA

<400> SEQUENCE: 12
gagguuuaaa cuuccaucg 19

<210> SEQ ID NO 13
<211> LENGTH: 21
<212> TYPE: DNA
<213> ORGANISM: Artificial sequence
<220> FEATURE:
<223> OTHER INFORMATION: Sense strand of a SERT-specific siRNA

<400> SEQUENCE: 13
cuccuggaac acuggcaact t 21

<210> SEQ ID NO 14
<211> LENGTH: 21
<212> TYPE: DNA
<213> ORGANISM: Artificial sequence
<220> FEATURE:
<223> OTHER INFORMATION: Sense strand synucleic-specific siRNA

<400> SEQUENCE: 14
gcuagcuaca acaaguucat t 21

<210> SEQ ID NO 15
<211> LENGTH: 21
<212> TYPE: DNA
<213> ORGANISM: Artificial sequence
<220> FEATURE:
<223> OTHER INFORMATION: Antisense strand SERT-specific siRNA

<400> SEQUENCE: 15
ugaacuuguu guagcuagct t 21

<210> SEQ ID NO 16
<211> LENGTH: 20
<212> TYPE: DNA
<213> ORGANISM: Artificial sequence
<220> FEATURE:
<223> OTHER INFORMATION: alpha-synuclein siRNA

<400> SEQUENCE: 16
ggaaagacaa aagaggugtt 20

<210> SEQ ID NO 17
<211> LENGTH: 20
<212> TYPE: DNA
<213> ORGANISM: Artificial sequence
<220> FEATURE:
<223> OTHER INFORMATION: alpha-synuclein siRNA

<400> SEQUENCE: 17
ggaaagacaa aagaggugtt 20

<210> SEQ ID NO 18
<211> LENGTH: 21
<212> TYPE: DNA
<213> ORGANISM: Artificial sequence
<220> FEATURE:
<223> OTHER INFORMATION: alpha-synuclein siRNA

<400> SEQUENCE: 18
ggaggaauuu uagaagaggt t 21

<210> SEQ ID NO 19
<211> LENGTH: 21
<212> TYPE: DNA
<213> ORGANISM: Artificial sequence
<220> FEATURE:
<223> OTHER INFORMATION: alpha-synucleic siRNA

<400> SEQUENCE: 19
uguuggagga gcaguggugt t 21

<210> SEQ ID NO 20
<211> LENGTH: 21
<212> TYPE: DNA
<213> ORGANISM: Artificial sequence
<220> FEATURE:
<223> OTHER INFORMATION: alpha-synucleic siRNA

<400> SEQUENCE: 20
ggaccaguug ggcaagaaut t 21

<210> SEQ ID NO 21
<211> LENGTH: 63
<212> TYPE: DNA
<213> ORGANISM: Artificial sequence
<220> FEATURE:
<223> OTHER INFORMATION: alpha-synuclein hairpins antisense

<400> SEQUENCE: 21
gatccccgga ccagttgggc aagaatttca agagaattct tgccaactgg tcctttttgg 60
aaa 63

<210> SEQ ID NO 22
<211> LENGTH: 64
<212> TYPE: DNA
<213> ORGANISM: Artificial sequence
<220> FEATURE:
<223> OTHER INFORMATION: alpha-synuclein hairpin antisense

<400> SEQUENCE: 22
ctagtttcca aaaaggacca gttgggcaag aattctcttg aaattcttgc ccaactggtc 60
cggg 64

<210> SEQ ID NO 23
<211> LENGTH: 21
<212> TYPE: DNA
<213> ORGANISM: Artificial sequence
<220> FEATURE:
<223> OTHER INFORMATION: synuclein siRNA

<400> SEQUENCE: 23
ggucuggcaa caguggcuga g 21

<210> SEQ ID NO 24
<211> LENGTH: 21
<212> TYPE: DNA
<213> ORGANISM: Artificial sequence
<220> FEATURE:
<223> OTHER INFORMATION: Synuclein siRNA

<400> SEQUENCE: 24
aacaguggcu gagaagacca a 21

<210> SEQ ID NO 25
<211> LENGTH: 21
<212> TYPE: DNA
<213> ORGANISM: Artificial sequence
<220> FEATURE:
<223> OTHER INFORMATION: Synuclein siRNA

<400> SEQUENCE: 25
auugcagcag ccacuggcuu u 21

<210> SEQ ID NO 26
<211> LENGTH: 21
<212> TYPE: DNA
<213> ORGANISM: Artificial sequence
<220> FEATURE:
<223> OTHER INFORMATION: Synuclein siRNA

<400> SEQUENCE: 26
aagugacaaa uguuggagga g 21

<210> SEQ ID NO 27
<211> LENGTH: 21
<212> TYPE: DNA
<213> ORGANISM: Artificial sequence
<220> FEATURE:
<223> OTHER INFORMATION: Synuclein siRNA

<400> SEQUENCE: 27
gaagaaggag ccccacagga a 21

-continued

```
<210> SEQ ID NO 28
<211> LENGTH: 21
<212> TYPE: DNA
<213> ORGANISM: Artificial sequence
<220> FEATURE:
<223> OTHER INFORMATION: Synuclein siRNA

<400> SEQUENCE: 28

cgggugugac agcaguagct t                                              21


<210> SEQ ID NO 29
<211> LENGTH: 21
<212> TYPE: DNA
<213> ORGANISM: Artificial sequence
<220> FEATURE:
<223> OTHER INFORMATION: Synuclein siRNA

<400> SEQUENCE: 29

uccugacaau gaggcuuaut t                                              21


<210> SEQ ID NO 30
<211> LENGTH: 21
<212> TYPE: DNA
<213> ORGANISM: Artificial sequence
<220> FEATURE:
<223> OTHER INFORMATION: Synuclein SiRNA

<400> SEQUENCE: 30

uccugacaau gaggcuuaut t                                              21


<210> SEQ ID NO 31
<211> LENGTH: 21
<212> TYPE: DNA
<213> ORGANISM: Artificial sequence
<220> FEATURE:
<223> OTHER INFORMATION: Synuclein siRNA

<400> SEQUENCE: 31

cuacgaaccu gaagccuaat t                                              21


<210> SEQ ID NO 32
<211> LENGTH: 21
<212> TYPE: DNA
<213> ORGANISM: Artificial sequence
<220> FEATURE:
<223> OTHER INFORMATION: Synuclein siRNA

<400> SEQUENCE: 32

cuacgaaccu gaagccuaat t                                              21


<210> SEQ ID NO 33
<211> LENGTH: 21
<212> TYPE: DNA
<213> ORGANISM: Artificial sequence
<220> FEATURE:
<223> OTHER INFORMATION: Synuclein siRNA

<400> SEQUENCE: 33

cuacgaaccu gaagccuaat t                                              21


<210> SEQ ID NO 34
<211> LENGTH: 21
<212> TYPE: DNA
<213> ORGANISM: Artificial sequence
<220> FEATURE:
<223> OTHER INFORMATION: Synuclein siRNA
```

<400> SEQUENCE: 34
cuauuguaga guggucuaut t 21

<210> SEQ ID NO 35
<211> LENGTH: 20
<212> TYPE: DNA
<213> ORGANISM: Artificial sequence
<220> FEATURE:
<223> OTHER INFORMATION: Synuclein siRNA

<400> SEQUENCE: 35
cuaugagccu gaagcuaatt 20

<210> SEQ ID NO 36
<211> LENGTH: 21
<212> TYPE: DNA
<213> ORGANISM: Artificial sequence
<220> FEATURE:
<223> OTHER INFORMATION: Synuclein siRNA

<400> SEQUENCE: 36
cuaugagccu gaagccuaat t 21

<210> SEQ ID NO 37
<211> LENGTH: 23
<212> TYPE: DNA
<213> ORGANISM: Artificial sequence
<220> FEATURE:
<223> OTHER INFORMATION: dopamine beta-hydroxylase siRNA

<400> SEQUENCE: 37
gaccacguac uggugcuaca uta 23

<210> SEQ ID NO 38
<211> LENGTH: 21
<212> TYPE: DNA
<213> ORGANISM: Artificial sequence
<220> FEATURE:
<223> OTHER INFORMATION: BAX siRNA

<400> SEQUENCE: 38
ucgauccugg augaaaccct g 21

<210> SEQ ID NO 39
<211> LENGTH: 21
<212> TYPE: DNA
<213> ORGANISM: Artificial sequence
<220> FEATURE:
<223> OTHER INFORMATION: tau siRNA

<400> SEQUENCE: 39
aatcacaccc aacgtgcaga a 21

<210> SEQ ID NO 40
<211> LENGTH: 21
<212> TYPE: DNA
<213> ORGANISM: Artificial sequence
<220> FEATURE:
<223> OTHER INFORMATION: tau siRNA

<400> SEQUENCE: 40
aactggcagt tctggagcaa a 21

-continued

```
<210> SEQ ID NO 41
<211> LENGTH: 22
<212> TYPE: DNA
<213> ORGANISM: Artificial sequence
<220> FEATURE:
<223> OTHER INFORMATION: tau siRNA (sense)

<400> SEQUENCE: 41

tcgaagtgat ggaagatcac gc                                              22


<210> SEQ ID NO 42
<211> LENGTH: 22
<212> TYPE: DNA
<213> ORGANISM: Artificial sequence
<220> FEATURE:
<223> OTHER INFORMATION: tau siRNA (antisense)

<400> SEQUENCE: 42

cttcactacc ttctagtgcg ac                                              22


<210> SEQ ID NO 43
<211> LENGTH: 22
<212> TYPE: DNA
<213> ORGANISM: Artificial sequence
<220> FEATURE:
<223> OTHER INFORMATION: tau siRNA (sense)

<400> SEQUENCE: 43

cagccgggag tcggcaaggt gc                                              22


<210> SEQ ID NO 44
<211> LENGTH: 22
<212> TYPE: DNA
<213> ORGANISM: Artificial sequence
<220> FEATURE:
<223> OTHER INFORMATION: tau siRNA (antisense)

<400> SEQUENCE: 44

cggccctcag cccttccacg tc                                              22


<210> SEQ ID NO 45
<211> LENGTH: 24
<212> TYPE: DNA
<213> ORGANISM: Artificial sequence
<220> FEATURE:
<223> OTHER INFORMATION: tau siRNA (sense)

<400> SEQUENCE: 45

acgtcctcgg cggcggcagt gtgc                                            24


<210> SEQ ID NO 46
<211> LENGTH: 24
<212> TYPE: DNA
<213> ORGANISM: Artificial sequence
<220> FEATURE:
<223> OTHER INFORMATION: tau SiRNA (antisense)

<400> SEQUENCE: 46

caggcgcctg cggcgtcaca cgtt                                            24


<210> SEQ ID NO 47
<211> LENGTH: 21
<212> TYPE: DNA
<213> ORGANISM: Artificial sequence
<220> FEATURE:
<223> OTHER INFORMATION: tau siRNA (sense)
```

<400> SEQUENCE: 47
acgtctccat ggcatctcag c 21

<210> SEQ ID NO 48
<211> LENGTH: 21
<212> TYPE: DNA
<213> ORGANISM: Artificial sequence
<220> FEATURE:
<223> OTHER INFORMATION: tau siRNA antisense

<400> SEQUENCE: 48
ttgctgagat gccatggaga c 21

<210> SEQ ID NO 49
<211> LENGTH: 22
<212> TYPE: DNA
<213> ORGANISM: Artificial sequence
<220> FEATURE:
<223> OTHER INFORMATION: tau siRNA (sense)

<400> SEQUENCE: 49
gtggccagat ggaagtaaaa tc 22

<210> SEQ ID NO 50
<211> LENGTH: 22
<212> TYPE: DNA
<213> ORGANISM: Artificial sequence
<220> FEATURE:
<223> OTHER INFORMATION: tau siRNA (antisense)

<400> SEQUENCE: 50
ccggtctacc ttcattttag ac 22

<210> SEQ ID NO 51
<211> LENGTH: 22
<212> TYPE: DNA
<213> ORGANISM: Artificial sequence
<220> FEATURE:
<223> OTHER INFORMATION: tau siRNA (sense)

<400> SEQUENCE: 51
gtggccagat gcaagtaaaa tc 22

<210> SEQ ID NO 52
<211> LENGTH: 22
<212> TYPE: DNA
<213> ORGANISM: Artificial sequence
<220> FEATURE:
<223> OTHER INFORMATION: tau siRNA (antisense)

<400> SEQUENCE: 52
ccggtctacg ttcattttag ac 22

<210> SEQ ID NO 53
<211> LENGTH: 25
<212> TYPE: DNA
<213> ORGANISM: Artificial sequence
<220> FEATURE:
<223> OTHER INFORMATION: tau siRNA

<400> SEQUENCE: 53
ggttcagcca tgctgcttca aagcc 25

-continued

<210> SEQ ID NO 54
<211> LENGTH: 25
<212> TYPE: DNA
<213> ORGANISM: Artificial sequence
<220> FEATURE:
<223> OTHER INFORMATION: tau siRNA

<400> SEQUENCE: 54
tgataatcga caggaggcga ggaca 25

<210> SEQ ID NO 55
<211> LENGTH: 21
<212> TYPE: DNA
<213> ORGANISM: Artificial sequence
<220> FEATURE:
<223> OTHER INFORMATION: Huntingtin siRNA

<400> SEQUENCE: 55
aagaggagga ggccgacgcc c 21

<210> SEQ ID NO 56
<211> LENGTH: 19
<212> TYPE: DNA
<213> ORGANISM: Artificial sequence
<220> FEATURE:
<223> OTHER INFORMATION: nonsense siRNA

<400> SEQUENCE: 56
aguacugcuu acgauacgg 19

<210> SEQ ID NO 57
<211> LENGTH: 19
<212> TYPE: DNA
<213> ORGANISM: Artificial sequence
<220> FEATURE:
<223> OTHER INFORMATION: nonsense siRNA

<400> SEQUENCE: 57
ccguaucgua agcaguacu 19

<210> SEQ ID NO 58
<211> LENGTH: 19
<212> TYPE: DNA
<213> ORGANISM: Artificial sequence
<220> FEATURE:
<223> OTHER INFORMATION: nNOS-specific siRNA

<400> SEQUENCE: 58
caaagagatc gacaccatc 19

<210> SEQ ID NO 59
<211> LENGTH: 21
<212> TYPE: DNA
<213> ORGANISM: Artificial sequence
<220> FEATURE:
<223> OTHER INFORMATION: nNOS specific siRNA

<400> SEQUENCE: 59
gatggtgtcg atctctttgt t 21

<210> SEQ ID NO 60
<211> LENGTH: 19
<212> TYPE: DNA
<213> ORGANISM: Artificial sequence
<220> FEATURE:
<223> OTHER INFORMATION: nNOS-specific siRNA

<400> SEQUENCE: 60
cacgcatgtc tggaaaggc 19

<210> SEQ ID NO 61
<211> LENGTH: 21
<212> TYPE: DNA
<213> ORGANISM: Artificial sequence
<220> FEATURE:
<223> OTHER INFORMATION: nNOS-specific siRNA

<400> SEQUENCE: 61
gcctttccag acatgcgtgt t 21

<210> SEQ ID NO 62
<211> LENGTH: 19
<212> TYPE: DNA
<213> ORGANISM: Artificial sequence
<220> FEATURE:
<223> OTHER INFORMATION: nNOS - specific siRNA

<400> SEQUENCE: 62
ggtctatcca atgtccaca 19

<210> SEQ ID NO 63
<211> LENGTH: 21
<212> TYPE: DNA
<213> ORGANISM: Artificial sequence
<220> FEATURE:
<223> OTHER INFORMATION: nNOS-specific siRNA

<400> SEQUENCE: 63
tgtggacatt ggatagacct t 21

<210> SEQ ID NO 64
<211> LENGTH: 19
<212> TYPE: DNA
<213> ORGANISM: Artificial sequence
<220> FEATURE:
<223> OTHER INFORMATION: iNOS-specific siRNA

<400> SEQUENCE: 64
ccaccagtat gcaatgaat 19

<210> SEQ ID NO 65
<211> LENGTH: 21
<212> TYPE: DNA
<213> ORGANISM: Artificial sequence
<220> FEATURE:
<223> OTHER INFORMATION: iNOS-specific siRNA

<400> SEQUENCE: 65
acaacaggaa ccuaccagct t 21

<210> SEQ ID NO 66
<211> LENGTH: 21
<212> TYPE: DNA
<213> ORGANISM: Artificial sequence
<220> FEATURE:
<223> OTHER INFORMATION: iNOS-specific siRNA

<400> SEQUENCE: 66
gcugguaggu uccuguugut t 21

-continued

<210> SEQ ID NO 67
<211> LENGTH: 21
<212> TYPE: DNA
<213> ORGANISM: Artificial sequence
<220> FEATURE:
<223> OTHER INFORMATION: iNOS-specific antisense

<400> SEQUENCE: 67
acagctcagt cccttcacca a 21

<210> SEQ ID NO 68
<211> LENGTH: 18
<212> TYPE: DNA
<213> ORGANISM: Artificial sequence
<220> FEATURE:
<223> OTHER INFORMATION: iNOS-specific antisense

<400> SEQUENCE: 68
tttgccttat actgttcc 18

<210> SEQ ID NO 69
<211> LENGTH: 19
<212> TYPE: RNA
<213> ORGANISM: Artificial sequence
<220> FEATURE:
<223> OTHER INFORMATION: nonsense siRNA

<400> SEQUENCE: 69
aguacugcuu acgauacgg 19

<210> SEQ ID NO 70
<211> LENGTH: 19
<212> TYPE: RNA
<213> ORGANISM: Artificial sequence
<220> FEATURE:
<223> OTHER INFORMATION: nonsense siRNA

<400> SEQUENCE: 70
ccguaucgua agcaguacu 19

COMPOSITIONS AND METHODS FOR SELECTIVE DELIVERY OF OLIGONUCLEOTIDE MOLECULES TO SPECIFIC NEURON TYPES

RELATED APPLICATIONS

This application claims priority benefit of U.S. Provisional Application 61/325,515 filed 19 Apr. 2010; European Patent Application EP10382087.4 filed 19 Apr. 2010; and European Patent Application EP11382031.0 filed 9 Feb. 2010; these applications are hereby incorporated by reference.

FIELD OF THE INVENTION

The present invention relates to conjugates comprising a nucleic acid specific for a target of interest and a group which allows the delivery of the nucleic acids to specific cells within the central nervous system by means of their affinity towards neurotransmitter transporter molecules on the surface of said cells.

BACKGROUND ART

The use of nucleic acids has proved effective for altering the state of a cell. The introduction of deoxyribonucleic acid (DNA) or ribonucleic acid (RNA) into a cell can be used to up- or down-regulate the expression of particular genes in the cell, thereby, impacting one or more biochemical pathways. Of the nucleic acid-based technologies used to alter cell physiology, RNA interference (RNAi) is the general term given for regulating the expression of genes at the post-transcriptional level in diversified organisms. RNAi gene silencing can be accomplished using homologous short (21-23 bp) dsRNA fragments known as short interfering or "siRNA." When a long dsRNA is introduced into a cell line, the cellular enzyme Dicer will cleave it into short interfering RNA (siRNA) molecules. This short interfering RNA molecule is now called the guided RNA. The guided RNA will guide the RNA-Induced-Silencing-Complex (RISC) to the homologous target mRNA. Once it forms a hybrid structure to the homologous mRNA sequence, the RISC will cleave the mRNA. As a result, protein that is encoded by the mRNA will no longer be produced, thereby causing the silencing of the gene. RNA interference refers to the process of sequence-specific post-transcriptional gene silencing in animals mediated by short interfering RNAs (siRNAs).

However, a major obstacle for the development of a RNAi-based therapeutic approaches for brain pathologies is the blood-brain barrier (BBB). The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show promising results in animal studies for treating CNS disorders.

Besides direct intrabrain administration, different strategies have been described for achieving gene silencing in the CNS by means of systemically-administered RNA interfering molecules. For instance, Kumar et al. (Nature, 2007, 448:39-44) have described conjugates of siRNA and a peptide derived from the rabies virus glycoprotein comprising a nonamer arginine and their ability to silence gene expression in the brain after intravenous injection. Xia et al. (Pharmaceutical Research, 2007, 24:2309-2316) have described conjugates comprising a biotinylated siRNA and a conjugate comprising avidin-anti-transferrin receptor antibody which are capable of silencing gene expression in the central nervous system after systemic delivery. WO200979790 describe conjugates comprising siRNA and a series of peptides collectively known as Angiopeps which are capable of crossing the blood-brain barrier by receptor-mediated transcytosis using the low-density lipoprotein receptor-related protein-1 (LRP-1) and which allows the delivery to the CNS of systemically administered conjugates comprising said peptides. WO2007107789 describes the use of compounds capable of causing RNA interference and which are specific for targets present in the CNS and the delivery to the CNS by the use of intranasal administration.

However, while all these systems allow the delivery of systemically administered siRNAs to the CNS, they do not allow delivery to specific cell types within the brain. In fact, no delivery system has been described to date which allows delivery of a therapeutic agent to a specific cell type within the CNS. The possibility of delivering siRNAs of known specificity to the central nervous system will be usesful for the treatment of diseases which are caused by an undesired activity/expression of a given gene, including depression, cognitive disorders, Parkinson's disease, Alzheimer's disease, etc.

Depression is recognized as a disease of the central nervous system. Depression is both biologically and genetically a heterogeneous disorder, with symptoms manifested at the psychological, behavioural and physiological level. Moreover, depression shows a high degree of co-morbidity with anxiety disorders and anxiety itself (typically anticipatory anxiety) is one of the most prevalent symptoms in depressive patients. Indeed, most anxiety disorders are also treated with antidepressant drugs.

The first drugs used in the treatment of major depression were the tricyclic antidepressants (TCAs) of the imipramine type and the monoamine oxidase inhibitors (MAOIs). These drugs were discovered in the late 1950s and proved efficacious, yet they presented a number of severe side effects that led to the development of new drugs, such as the Selective Serotonin Reuptake Inhibitors (SSRIs) or the selective Serotonin and Noradrenaline Reuptake Inhibitors (SNRIs).

The discovery that TCAs (and later, SSRIs and SNRIs) inhibited the reuptake of the monoamines serotonin (5-HT) and noradrenaline (NA) into the presynaptic cell, increasing levels of 5-HT within the synaptic cleft, thereby enhancing their activity at postsynaptic receptor, led to the first hypotheses of the ethiology of depression, i.e., that it was caused by a deficit of the activity of these monoaminergic neurotransmitter systems in the brain. Ever since, all marketed antidepressant drugs have targeted serotonergic and/or noradrenergic transporters or receptors.

5-HT receptors are located on the cell membrane of nerve cells and other cell types in animals. With the exception of the 5-$HT_3$ receptor, all other 5-HT receptors are G protein coupled seven transmembrane (or heptahelical) receptors that activate an intracellular second messenger cascade. Some of the identified 5-HT receptors include the 5-$HT_{1A}$ and the 5-$HT_{1B/1D}$ receptors expressed, presynaptically on serotonin neurons (autoreceptors) and on neurons postsynaptically located to 5-HT nerve terminals. The 5-HT receptor more directly linked with the antidepressant effects of SSRIs has been the 5-$HT_{1A}$ receptor.

New antidepressant drugs are now being registered with mechanisms of action based on relatively selective norepinephrine reuptake inhibition (NARI), e.g. reboxetine, or in the dual blockade (SNRIs), such as venlafaxine or duloxetine. Other drugs, such as nefazodone, trazodone or mirtazapine have a weaker action at monoamine transporters and block monoaminergic receptors instead.

However, notwithstanding the commercial success of SSRIs, these compounds have two major limitations: 1) only 60% of patients experience a therapeutic response (reduction to half of baseline severity), and 2) response occurs only after several weeks of continued treatment. This is due to a negative feedback mechanism that takes place in the pre-synaptic neuron. Briefly, high serotonin levels induced by the blockage of serotonin reuptake will not only activate the post-synaptic serotonin receptors, but also activate presynaptic autoreceptors, which serve as a feedback sensor for the cell. The activation of 5-$HT_{1A}$ autoreceptor by 5-HT (also called pre-synaptic 5-$HT_{1A}$ receptor or pre-synaptic 5-$HT_{1A}$R), or selective agonists, suppresses cell firing and impulse-dependent 5-HT release, whereas 5-$HT_{1B}$ receptors control 5-HT synthesis and release at terminal level. Both, 5-$HT_{1A}$ and 5-$HT_{1B}$ receptors, are also localized on neurons postsynaptic to 5-HT nerve terminals, mainly in cortico-limbic areas. The increase of extracellular 5-HT produced by reuptake blockade of sertraline (SERT, a SSRI) activates pre-synaptic 5-$HT_{1A}$ receptor in the midbrain raphe nuclei, suppressing cell firing and terminal release, an effect that attenuates the extracellular 5-HT increase produced by reuptake blockade. 5-$HT_{1B}$ autoreceptors exert a similar negative feedback at a local level. Following repeated administration of SSRIs, 5-$HT_{1A}$ autoreceptors desensitize, which enables serotoninergic neurons to recover cell firing and leads to an increase in extracellular 5-HT, to a level higher than that seen after single treatment. These (slowly proceeding) neurophysiological adaptations of the brain tissue are not only the reason why usually several weeks of continuous SSRI use are necessary for the antidepressant effect to become fully manifested, but also why increased anxiety is a common side effect in the first few days or weeks of use. It is known that the blockade of these negative feedback mechanisms with 5-$HT_{1A}$ and/or 5-$HT_{1B}$ receptor antagonists potentiates the 5-HT increase produced by SSRIs and, therefore, might serve to accelerate the clinical effects of SSRIs.

The pharmacological strategy to accelerate the antidepressant response by blocking the action of pre-synaptic 5-$HT_{1A}$ receptors during SSRI administration was tested using (±)pindolol. This compound is a $\beta_{1-2}$ adrenergic receptor antagonist with a putative antagonistic action on 5-$HT_{1A}$ receptors. (±)Pindolol antagonized several actions mediated by the activation of central 5-$HT_{1A}$ receptors, such as hypothermia or hormonal secretion. In general, the addition of pindolol to SSRIs accelerates the antidepressant response. However, although pindolol has been shown in some studies to partially occupy 5-$HT_{1A}$ receptors in the human brain at clinical doses, other studies have found a low occupancy. Additionally, it is not to be forgotten that 5-$HT_{1A}$ receptors are localized on the serotoninergic neurons as well as on neurons postsynaptic to the serotoninergic neurons. Indeed, an important concern is the lack of selectivity of these agents for pre-synaptic versus postsynaptic 5-$HT_{1A}$ receptors: the full blockade of postsynaptic receptors may cancel the increased transmission through forebrain 5-$HT_{1A}$ receptors produced by antidepressant drugs.

Thus, despite the advances made in the development of antidepressants, there is still the need of alternative compounds which specifically act on the pre-synaptic 5-$HT_{1A}$ receptors.

Parkinson's disease (PD) is a degenerative disorder of the central nervous system that often impairs the patient's motor skills, speech, and other functions (Olanow). The symptoms of Parkinson's disease result from the greatly reduced activity of dopaminergic cells in the pars compacta region of the substantia nigra (SNpc) (Olanow, Dawson). These neurons project to the striatum and their loss leads to alterations in the activity of the neural circuits within the basal ganglia that regulate movement, in essence an inhibition of the direct pathway and excitation of the indirect pathway. The direct pathway facilitates movement and the indirect pathway inhibits movement, thus the loss of these cells leads to a hypokinetic movement disorder. The lack of dopamine results in increased inhibition of the ventral anterior nucleus of the thalamus, which sends excitatory projections to the motor cortex, thus leading to hypokinesia.

PD is characterized by a progressive loss of dopaminergic neurons in the SNpc and the presence of intracellular inclusions designated as Lewy bodies (LB). Neurochemically, PD is marked by mitochondrial complex I dysfunction and increased indices of oxidative stress. Several pathogenic mechanisms have been proposed for PD including oxidative and nitrosative stress, mitochondrial dysfunction, protein misfolding and aggregation, and apoptosis. PD is mostly sporadic but some of the PD cases have been shown to be familial-linked. The first familial-linked PD gene identified was α-synuclein (α-syn) which in fact is the major component of LB in all PD patients. The normal function of α-synuclein is poorly understood. α-Synuclein can bind to lipids and, in neurons, is associated with presynaptic vesicles and the plasma membrane, possibly via lipid rafts. The deposited, pathological forms of α-synuclein are aggregated and show lower solubility than the normal protein. Three point mutations have been described to cause familial PD, but also duplications and triplications of the SNCA gene have been reported to be responsible of PD and Lewy body disease. Therefore, even without sequence variants, α-synuclein dosage can be causal for Lewy body disease.

α-Synuclein affects mitochondria and probably induces apoptosis. In fact, there is accumulating evidence for a close relationship between α-synuclein and oxidative damage: overexpression of mutant α-synuclein sensitizes neurons to oxidative stress and damage by dopamine and complex I inhibitors, resulting in increased protein carbonylation and lipid peroxidation in vitro and in vivo. Conversely, dysfunction of mitochondrial complex I has been associated to sporadic forms of PD. Complex I dependent oxidative damage and defective mitochondrial function is a main cause of neuronal degeneration and cell death in PD. Thus impaired mitochondrial function and ROS production increases the cytochrome c pool level in the mitochondrial intermembrane space, allowing its rapid release when the cell death agonist Bax is activated.

To sum up, the scenario in PD would be a situation of neuronal mitochondrial dysfunction with increase ROS production that on one hand would increase α-synuclein accumulation and on the other would activate Bax-mediated cell death. Further, α-synuclein accumulation, in turn, would increase cellular ROS production and induction of neuronal degeneration.

The most widely used treatment for PD is L-DOPA in various forms. However, only 1-5% of L-DOPA enters the dopaminergic neurons. The remaining L-DOPA is often metabolised to dopamine elsewhere, causing a wide variety of side effects. Dopa decarboxylase inhibitors like carbidopa and benserazide are also used for the treatment of PD since they help to prevent the metabolism of L-DOPA before it reaches the dopaminergic neurons and are generally given as combination preparations of carbidopa/levodopa and benserazide/levodopa. Moreover, dopamine agonists are moderately effective and act by stimulating some of the dopamine receptors. However, they cause the dopamine receptors to become progressively less sensitive, thereby eventually increasing the symptoms.

Antisense approaches might also be helpful, and have been reported to work in the rat and mouse brain. This approach is predicated on the idea that α-synuclein really is dispensable for CNS function in humans, as it appears to be in the mouse but perhaps even a modest decrease in protein levels would be enough to decrease PD progression.

However, despite the advances made in the development of PD therapeutics, there is still the need of alternative compounds which specifically are capable of preventing the reduced activity of dopaminergic cells in the pars compacta region of the substantia nigra.

Mesocortical and mesolimbic dopamine (DA) systems play a crucial role in many psychiatric disorders including schizophrenia. A general enhancement of brain dopaminergic neurotransmission in schizophrenia was suggested by pharmacologic evidence (Seeman and Lee, 1975; Creese et al, 1976). Current views, however, indicate a hyperactivity of subcortical DA transmission together with a hypoactive mesocortical. The overall efficacy of classical (DA D2 receptor antagonists) and atypical antipsychotics (APDs, preferential 5-$HT_{2A/2C}$ vs. DA D2 receptor antagonists) to treat positive (psychotic) symptoms is similar. In contrast, some agents of the latter group, and particularly clozapine, are superior to classical antipsychotics for the treatment of negative symptoms and cognitive impairment. This clinical feature has been related, at least in part, to the ability to increase DA release in the mesocortical pathway, an effect induced by atypical—but not classical-antipsychotics. Indeed, an optimal prefrontal DA function is crucial for working memory and executive functions.

DA release in mesocortical and mesolimbic DA pathways is regulated by several factors. Firstly, it depends on the firing mode (tonic/phasic) of VTA DA neurons. Secondly, it is tightly regulated by the activation of somatodendritic and terminal $D_{213}$ autoreceptors which control cell firing and DA release. Finally, the DA transporter (DAT)-mediated reuptake is one of the key mechanisms that define decay kinetics of extracellular DA concentrations. Previous studies indicate a different density of DAT in PFC and striatum.

Moreover, noradrenaline (NA) axons may contribute to the removal of DA from the extracellular brain space, since the NA transporter (NAT) shows a similar affinity for NA and DA. Thus, NAT inhibitors preferentially increase the extracellular DA concentration in the medial PFC (mPFC) compared to caudate and nucleus accumbens (NAc). Hence, NA axons from locus coeruleus (LC) neurons may contribute to regulate the extracellular DA concentration in PFC either by taking up or co-releasing DA. Some researchers have shown the effects of a new combination treatment based on NA-targeting drugs (NAT inhibitor plus $a_2$-adrenergic antagonist) to selectively enhance mesocortical DA transmission.

However, there is still a need for compounds capable of enhacing mesocortical DA transmission.

SUMMARY OF THE INVENTION

The inventors have developed nucleic acid constructs which contain a nucleic acid specific for given target gene and a selective inhibitor of a neurotransmitter transporter.

These constructs are shown to be particularly useful for the delivery of the nucleic acid of interest to the interior of a cell expressing the neurotransmitter transporter. Without wishing to be bound by any theory, it is believed that the inhibitor of a neurotransmitter transporter will bind to the corresponding neurotransmitter transporter in the surface of the cell wherein the transporter is expressed which will in turn translocate the complex nucleic acid-inhibitor to the interior of the cell. Thus, as illustrated in example 3 of the present invention, the administration of a construction comprising a siRNA specific for the serotonin 5-$HT_{1A}$ receptor and a specific serotonin-transporter inhibitor (sertraline) results in reduction of the 5-$HT_{1A}$ receptor in RNA and a lack of hypothermia response in response to 8-OH-DPAT (a measure of serotoninergic signalling) which is much higher than that obtained with the non-conjugated siRNA.

The skilled person will appreciate that the invention is not limited to conjugate for delivery to serotoninergic neurons. On the contrary, the results provided in the present invention illustrate that the mechanism used by the neurons to transport neurotransmitter are adequate means for promoting delivery to cells of small molecules attached to molecules showing affinity for said neurotransmitter transporter.

Thus, in a first aspect, the invention relates to a conjugate comprising:

i) at least one selectivity agent which binds specifically to one or more of a neurotransmitter transporter and
ii) at least one nucleic acid which is capable of specifically binding to a target molecule which is expressed in the same cell as the neurotransmitter transporter.

In a second aspect, the invention relates to a conjugate of the invention for use in medicine.

In a further aspect, the invention relates to a conjugate of the invention wherein (i) the selectivity agent is selected from the group of a selective serotonin reuptake inhibitor (SSRI), and
(ii) the oligonucleotide is capable of specifically binding to a target molecule selected from the group of the mRNA encoding the serotonin receptor type 1A (5-$HT_{1A}$) or the mRNA encoding the serotonine transporter (5-HHT transporter or SERT) or mRNA encoding the serotonin receptor type 1B (5-$HT_{1B}$) or the mRNA encoding the TREK-1 potassium channel or the Gir-K potassium channel.

for use in the treatment or prevention of a depression-related disorder.

In a further aspect, the invention relates to a conjugate of the invention wherein (i) the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker) and
(ii) the oligonucleotide is capable of specifically binding to a target molecule which is the mRNA encoding alpha-synuclein for use in the treatment or prevention of a disease associated with impairments in neuroatransminter vesicles function and the deposition of Lewy bodies.

In a further aspect, the invention relates to a conjugate of the invention wherein (i) the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker) and (ii) the oligonucleotide is capable of specifically binding to a target molecule which is the mRNA encoding BAX for use in the treatment or prevention of a disease associated neuronal apoptosis and cell death (i.e. Parkinson and Alzheimer).

In a further aspect, the invention relates to a conjugate of the invention wherein (i) the selectivity agent is selected from the group of a Norepinephrine Reuptake Inhibitor (NRI) and (ii) the oligonucleotide is capable of specifically binding to a target molecule which is the mRNA encoding dopamine beta hydroxilase or the mRNA encoding the Norepinephrine transporter (NET) the dopamine beta hidroxilase polypeptide for use in the treatment or prevention of a disease associated dopamine deficit in noradrenergic projections like memory and cognitive process associated with dementia, depression and neurodegenerative diseases.

In a further aspect, the invention relates to a conjugate of the invention wherein (i) the selectivity agent is selected from the group of a Norepinephrine Reuptake Inhibitor (NRI) and (ii) the oligonucleotide is capable of specifically binding to a target molecule which is the mRNA encoding the Norepinephrine transporter (NET) or the Norepinephrine transporter (NET) polypeptide for use in the treatment or prevention of a disease associated dopamine deficit in noradrenergic projections like memory and cognitive process associated with dementia, depression and neurodegenerative diseases.

In a further aspect, the invention relates to a conjugate of the invention wherein (i) the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker) and (ii) the oligonucleotide is capable of specifically binding to a target molecule which is the mRNA encoding Tau for use in the treatment or prevention of a disease associated with neurodegeneration by mutations in tau protein like Alzheimer.

In a further aspect, the invention relates to a conjugate of the invention wherein (i) the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker) and (ii) the oligonucleotide is capable of specifically binding to a target molecule which is the mRNA encoding Huntingtin for use in the treatment or prevention of a neurodegenerative disease produced by the accumulation of a altered (intra-gene duplication) expression of Huntingtin.

In a further aspect, the invention relates to a conjugate of the invention wherein (i) the selectivity agent is selected from the group of a Norepinephrine Reuptake Inhibitor (NRI) and (ii) the oligonucleotide is capable of specifically binding to a target molecule which is the mRNA encoding dopamine beta hydroxilase or the mRNA encoding the Norepinephrine transporter (NET)

for use in the treatment or prevention of a disease associated dopamine deficit in noradrenergic projections like memory and cognitive process associated with dementia, depression and neurodegenerative diseases.

In another aspect, the invention relates to a conjugate comprising a (i) at least one selectivity agent which binds specifically to one or more of a neurotransmitter transporter and (ii) a contrast agent or a labelling agent.

In yet another aspect, the invention relates to a conjugate comprising a contrast agent of a labelling agent for use as a diagnostic agent.

These and other objects of the present invention will be further described in the detailed description section that follows, and they are not intended to be limiting of the present invention. Unless otherwise defined, all technical and scientific terms used herein have the same meaning as commonly understood by one ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps.

DETAILED DESCRIPTION OF THE INVENTION

Figure 1:
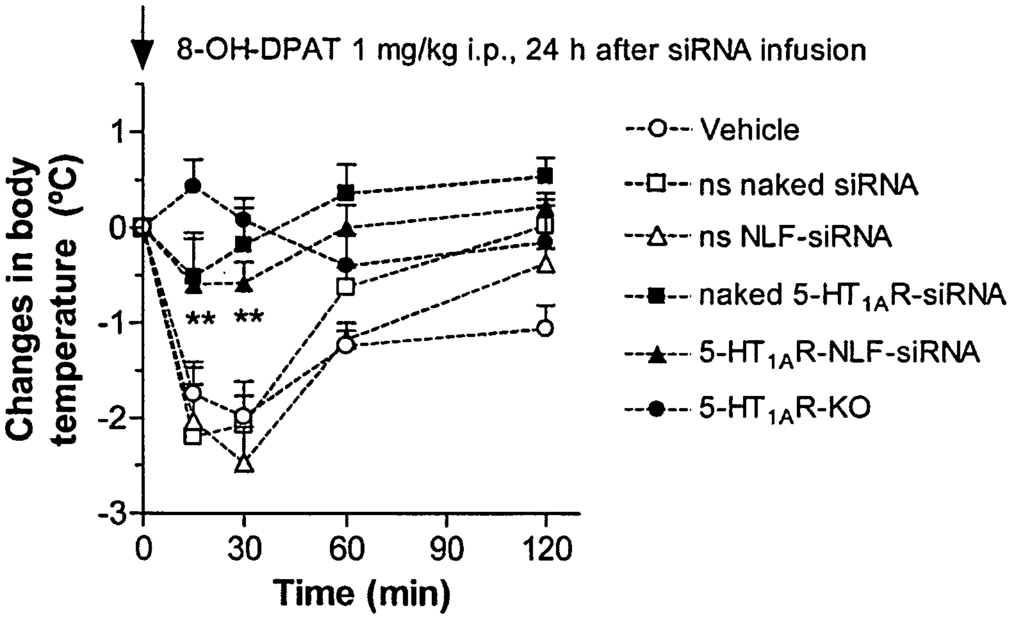
FIG. 1. Absence of hypothermia response induced by (R)-(+)-8-hydroxy-2-(di-n-propylamino)tetralin hydrobromide (8-OH-DPAT, selective 5-$HT_{1A}$R agonist) in mice having received locally 5-$HT_{1A}$R-targeting-siRNA (naked or conjugated) into dorsal raphe nucleus (DRN) as an example of functional measure of presynaptic 5-$HT_{1A}$R activity. Mice received: i) vehicle, ii) nonsense naked siRNA (ns naked siRNA), iii) nonsense NLF-siRNA (ns NLF-siRNA), iv) naked 5-$HT_{1A}$R-siRNA or v) 5-$HT_{1A}$R-NLF-siRNA (0.3 μg/1 μl/2 days into DRN). Additional group of 5-$HT_{1A}$R knockout (5-$HT_{1A}$R-KO) mice was also evaluated. Temperature body was assessed 5 min before and 15, 30, 60 and 120 min after 8-OH-DPAT administration (1 mg/kg i.p.). Values are shown as mean of changes in body temperature±SEM from 5-7 mice per group. ** $p<0.01$ significantly different from vehicle, ns naked siRNA and ns NLF-siRNA respectively, using repeated-measure ANOVA with treatment as the between factor and time as within-subject variable, followed by multiple comparison Newman-Keuls test.

The authors of the present invention have observed that, unexpectedly, it is possible to specifically target a nucleic acid to a cell of interest which expresses a neurotransmitter transporter by covalently coupling said nucleic acid to a molecule which is capable of specifically binding to said neurotransmitter transporter and, more in particular, to an inhibitor of said transporter.

A. Conjugates of the Invention

In a first aspect, the invention relates to a conjugate comprising:

i) at least one selectivity agent which binds specifically to one or more of a neurotransmitter transporter, ii) at least one oligonucleotide which is capable of specifically binding to a target molecule which is expressed in the same cell as the neurotransmitter transporter.

The term "conjugate", as used herein, refers to any compound resulting from the covalent attachment of two or more individual compounds. In the present invention, conjugate refers to a molecule comprising a nucleic acid a selectivity agent which are covalently coupled, being said coupling direct or via a linking compound.

The terms "covalent coupling" or "covalent attachment" mean that the nucleic acid and the selectivity agent are either directly covalently joined to one another, or else are indirectly covalently joined to one another through an intervening moiety or moieties, such as a linker, or a bridge, or a spacer, moiety or moieties.

A.1. The Selectivity Agent

The expression "selectivity agent which binds specifically to one or more of a neurotransmitter transporter", as used herein, refers to any substance which binds to a neurotransmitter transporter. This binding specificity allows the delivery of a molecule which is attached to said selectivity agent to the cell, tissue or organ which contains said neurotransmitter transporter. In this way, a conjugate carrying said selectivity agent will be directed specifically to said cells when administered to an animal or contacted in vitro with a population of cells of different types.

As used herein, specific binding of a first molecule to a second molecule refers to the ability of the first molecule to bind said second molecule in a way that is measurably different from a non-specific interaction. A selectivity agent according to the present invention may show a Kd for the target (the neurotransmitter transporter) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-16}$ M, alternatively at least about $10^{-11}$ M, alternatively at least about $10^{-12}$ M or greater.

The term "neurotransmitter transporter", as used herein, refers to a protein belonging to a class of membrane transport proteins that span the cellular membranes of neurons and which primary function is to carry neurotransmitters across these membranes and to direct their further transport to specific intracellular locations. Neurotransmitter transporters which may be targeted by the selectivity agents of the invention include, without limitation, uptake carriers present in the plasma membrane of neurons and glial cells, which pump neurotransmitters from the extracellular space into the cell. This process relies on the Na+ gradient across the plasma membrane, particularly the co-transport of Na+. Two families of proteins have been identified. One family includes the transporters for GABA, monoamines such as noradrenaline, dopamine, serotonin, and amino acids such as glycine and proline. Common structural components include twelve putative transmembrane α-helical domains, cytoplasmic N- and C-termini, and a large glycosylated extracellular loop separating transmembrane domains three and four. This family of homologous proteins derives their energy from the co-transport of $Na^+$ and $Cl^-$ ions with the neurotransmitter into the cell ($Na^+/Cl^-$ neurotransmitter transporters). The second family includes transporters for excitatory amino acids such as glutamate. Common structural components include putative 6-10 transmembrane domains, cytoplasmic N- and C-termini, and glycosylations in the extracellular loops. The excitatory amino acid transporters are not dependent on Cl—, and may require intracellular K+ ions (Na+/K+-neurotransmitter transporters) (Liu, Y. et al. (1999) Trends Cell Biol. 9: 356-363).

Neurotransmitter transporters which may be targeted by the selectivity agents of the invention also include neurotransmitter transporters present in intracellular vesicle membranes, typically synaptic vesicles, which primary function is concentrating neurotransmitters from the cytoplasm into the vesicle, before exocytosis of the vesicular contents during synaptic transmission. Vesicular transport uses the electrochemical gradient across the vesicular membrane generated by a H+-ATPase. Two families of proteins are involved in the transport of neurotransmitters into vesicles. One family uses primarily proton exchange to drive transport into secretory vesicles and includes the transporters for monoamines and acetylcholine. For example, the monoamine transporters exchange two luminal protons for each molecule of cytoplasmic transmitter. The second family includes the GABA transporters, which relies on the positive charge inside synaptic vesicles. The two classes of vesicular transporters show no sequence similarity to each other and have structures distinct from those of the plasma membrane carriers (Schloss, P. et al. (1994) Curr. Opin. Cell Biol. 6: 595-599; Liu, Y. et al. (1999) Trends Cell Biol. 9: 356-363).

Specific types of neurotransmitter transporters that can be targeted with the selectivity agents of the invention include glutamate/aspartate transporters, including, excitatory amino acid transporter 1 (EAAT1), excitatory amino acid transporter 2 (EAAT2), excitatory amino acid transporter 3 (EAAT3), excitatory amino acid transporter 4 (EAAT4), excitatory amino acid transporter 5 (EAAT5), vesicular glutamate transporter 1 (VGLUT1), vesicular glutamate transporter 2 (VGLUT2) and vesicular glutamate transporter 3 (VGLUT3); GABA transporters, including, GABA transporter type 1 (GAT1), GABA transporter type 2 (GAT2), GABA transporter type 3 (GAT3), Betaine transporter (BGT1) and vesicular GABA transporter (VGAT); glycine transporters, including, glycine transporter type 1 (GlyT1), glycine transporter type 2 (GlyT2); monoamine transporters, including, dopamine transporter (DAT), norepinephrine transporter (NET), serotonin transporter (SERT), vesicular monoamine transporter 1 (VMAT1), vesicular monoamine transporter 2 (VMAT2); adenosine transporters, including, equilibrative nucleoside transporter 1 (ENT1), equilibrative nucleoside transporter 2 (ENT2), equilibrative nucleoside transporter 3 (ENT3) and equilibrative nucleoside transporter 4 (ENT4) and vesicular acetylcholine transporter (VAChT).

In a preferred embodiment, the selectively agent is not a peptide.

In a preferred embodiment, the selectivity agent is selected from the group of serotonine reuptake inhibitors (SRI), a selective serotonin reuptake inhibitor (SSRI), a serotonin-norepinephrine reuptake inhibitor (SNRI), a noradrenergic and specific serotoninergic antidepressant (NASSA), a noradrenaline reuptake inhibitor (NRI), a dopamine reuptake inhibitor (DRI), an endocannabinoid reuptake inhibitor (eCBRI), an adenosine reuptake inhibitor (AdoRI), an excitatory Amino Acid Reuptake Inhibitor (EAARI), a glutamate reuptake inhibitor (GluRI), a GABA Reuptake Inhibitor (GRI), a glycine Reuptake Inhibitor (GlyRI) and a Norepinephrine-Dopamine Reuptake Inhibitor (NDRI).

The term "serotonine reuptake inhibitor" or "SRI, refers to a molecule which is capable of blocking serotonine uptake and includes both selective serotonin reuptake inhibitors (SSRI) (which block specifically serotonin uptake without substantially affecting other neurotransmitter) as well as non-selective serotonine reuptake inhibitors such as serotonin-norepinephrine reuptake inhibitors (SNRI) and serotonin-norepinephrine-dopamine reuptake inhibitors (SNDRI).

The term "serotonin selective reuptake inhibitors" or "SSRI" refers to selective inhibitors of serotinine reuptake without substantially affecting other neurotransmitter reuptake or transporter systems. These compounds act primarily at the presynaptic serotoninergic cell leading to an increase in the extracellular level of the neurotransmitter serotonin, thereby increasing the level of serotonin available to bind to the postsynaptic receptor and reversing the deficit of the activity of this monoaminergic neurotransmitter system in the brain. Illustrative non-limitative examples of SSRI include sertraline (CAS 79617-96-2), a sertraline-structural analog, fluoxetine (CAS 54910-89-3), fluvoxamine (CAS 54739-18-3), paroxetine (CAS 61869-08-7), indapline (CAS 63758-79-2), zimeldine (CAS 56775-88-3), citalopram (CAS 59729-33-8) and escitalopram (CAS 219861-08-2). Assays for determining whether a given compound is acting as a SSRI are, for instance, the ability to reduce ex vivo uptake of serotonin and of antagonizing the serotonin-depleting action of p-chloroamphetamine without affecting rat heart uptake of intravenous [$^3$H]norepinephrine as described essentially in Koe et al. (J. Pharmacol. Exp. Ther., 1983, 226:686-700).

In a preferred embodiment, the SSRI is sertraline or a structural analog thereof having the structure (I)

I

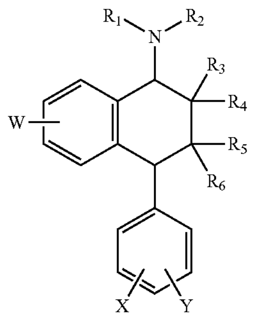

wherein, independently, $R_1$, $R_2$, $R_3$, $R_4$, $R_5$ and $R_6$ are hydrogen or an optionally substituted $C_1$-$C_6$ alkyl; X and Y are each selected from the group consisting of hydrogen, fluoro, chloro, bromo, trifluoromethyl, $C_1$-$C_3$ alkoxy, and cyano; and W is selected from the group consisting of hydrogen, fluoro, chloro, bromo, trifluoromethyl, nitro and $C_1$-$C_3$ alkoxy. In some embodiment, the sertraline analogs are in the cis isomeric configuration. The term "cis-isomeric" refers to the cyclohexene ring (i.e. they are both oriented on the same side of the ring). Because both the 1- and the 4-carbons are asymmetrically substituted, each cis-compound has two optically active enantiomeric forms denoted (with reference to the I-carbon) as the cis-(1R) and cis-(1S) enantiomers.

Certain useful sertraline analogs are the following compounds, in either the (1S)-enantiomeric or the (1S)(1R) racemic forms, and their pharmaceutically acceptable salts:

cis-N-methyl-4-(3,4-dichlorophenyl)-1,2,3,4-tetrahydro-Inaphthalenamine;

cis-N-methyl-4-(4-bromophenyl)-1,2,3,4-tetrahydro-Inaphthalenamine;

cis-N-methyl-4-(4-chlorophenyl)-1,2,3,4-tetrahydro-Inaphthalenamine;

cis-N-methyl-4-(3-trifluoromethyl-phenyl)-1,2,3,4-tetrahydro-1-naphthalenamine;

cis-N-methyl-4-(3-trifluoromethyl-4-chlorophenyl)-1,2,3,4-tetrahydro-1-naphthalenamine;

cis-N,N-dimethyl-4-(4-chlorophenyl)-1,2,3,4-tetrahydro-1-naphthalenamine;

cis-N,N-dimethyl-4-(3-trifluoromethyl-phenyl)-1,2,3,4-tetrahydro-1-naphthalenamine and cis-Nmethyl-4-(4-chlorophenyl)-7-chloro-1,2,3,4-tetrahydro-1-naphthalenamine.

Of interest also is the (1R)-enantiomer of cis-N-methyl-4-(3,4-dichlorophenyl)-1,2,3,4-tetrahydro-1-naphthalenamine.

Sertraline analogs are also described in U.S. Pat. No. 4,536,518. Other related compounds include (S,S)—N-desmethylsertraline, rac-cis-N-desmethylsertraline, (1 S,4S)-desmethyl sertraline, 1-des(methylamine)-1-oxo-2-(R,S)-hydroxy sertraline, (1R,4R)-desmethyl sertraline, sertraline, sulfonamide, sertraline (reverse) methane sulfonamide, 1R,4R sertraline, enantiomer, N,N-dimethyl sertraline, nitro sertraline, sertraline aniline, sertraline iodide, sertraline sulfonamide NH2, sertraline sulfonamide ethanol, sertraline nitrile, sertraline-CME, dimethyl sertraline reverse sulfonamide, sertraline reverse sulfonamide (CH2linker), sertraline B-ring ortho methoxy, sertraline A-ring methyl ester, sertraline A-ring ethanol, sertraline N,Ndimethylsulfonamide, sertraline A ring carboxylic acid, sertraline B-ring paraphenoxy, sertraline B-ring para-trifluoromethane, N,N-dimethyl sertraline B-Ring and para-trifluoromethane, and UK-416244. Structures of these analogs are shown below.

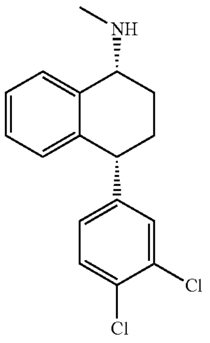

1R,4R sertraline enantiomer

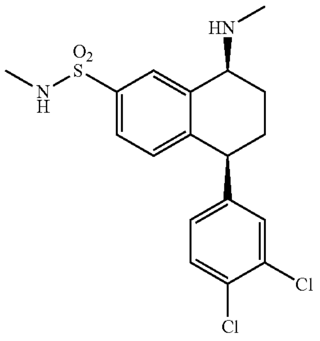

Sertraline sulfonamide

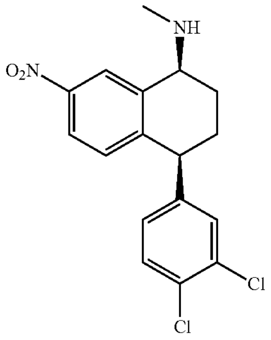

Nitro Sertraline

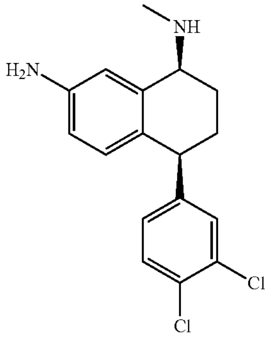

Sertraline aniline

-continued

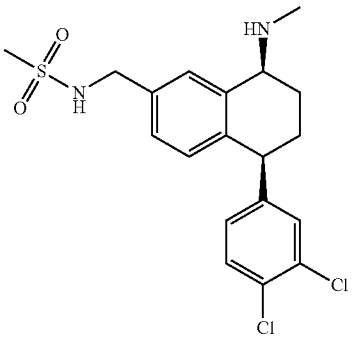

Setraline Reverse Sulfinamide (CH2 linker)

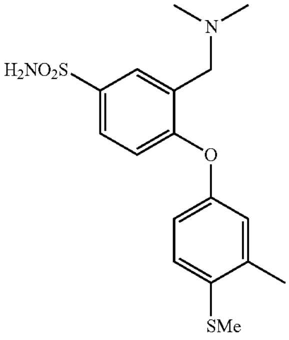

UK-416244

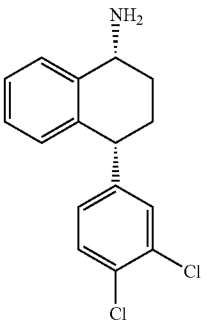

(1R,4R)-desmethylsertraline

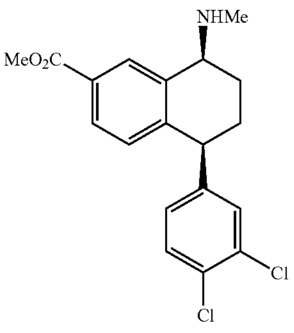

Sertraline A-RingMethyl ester

-continued
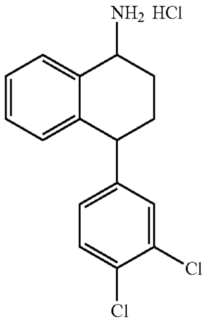
rac-cis-N-demethyl sertraline hydrochloride
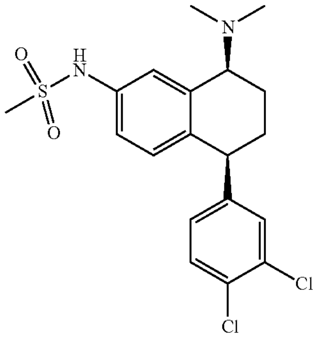
Dimethyl sertraline reverse sulfonamide
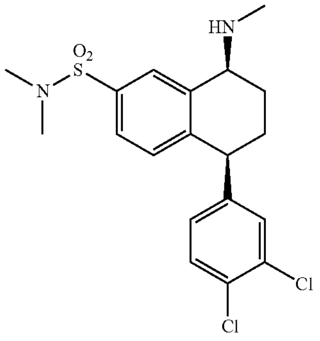
Sertraline N,N-Dimethylsulfonamide
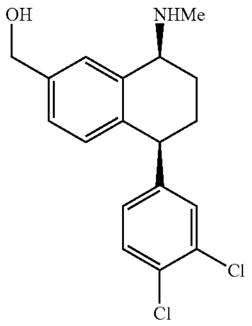
Setraline A-Ring ethanol
-continued
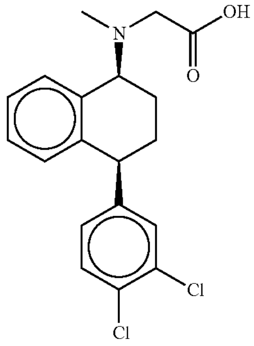
Sertraline-CME
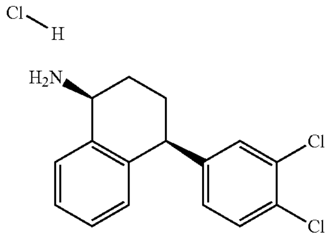
(1S,4S)-Desmethyl sertraline hydrochloride
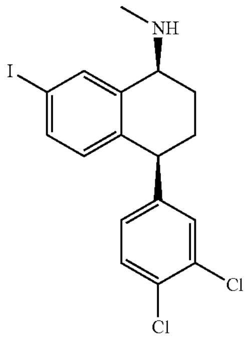
Sertraline iodine
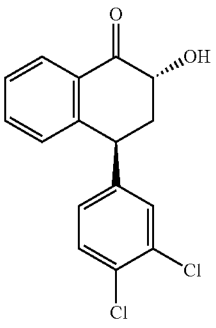
1-Des(methylamine)-1-oxo-2-(R,S)hydroxyl sertraline -continued

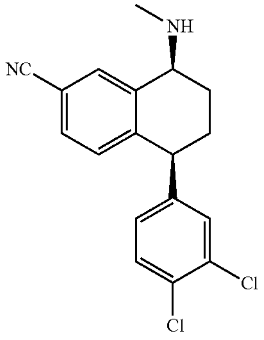

Sertraline nitrile

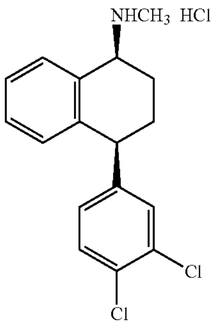

Sertraline hydrochloride

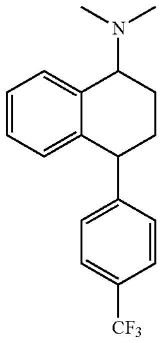

N,N-dimethyl sertraline B•ring paratrifluoromethane

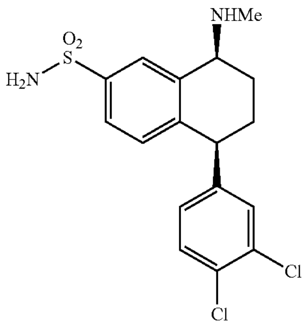

Setraline sulfonamide NH2

-continued

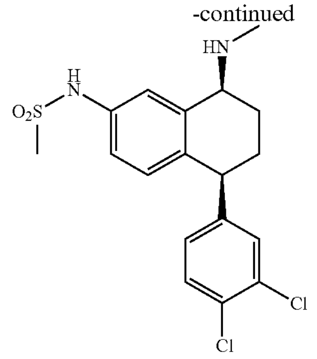

Sertraline (Reverse) Methanesulfonamide

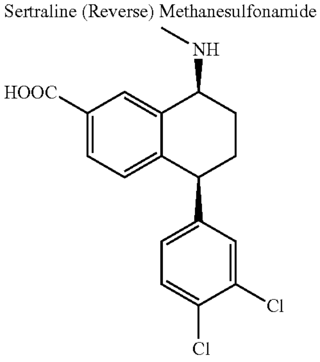

Sertraline A-Ring Carboxylic acid

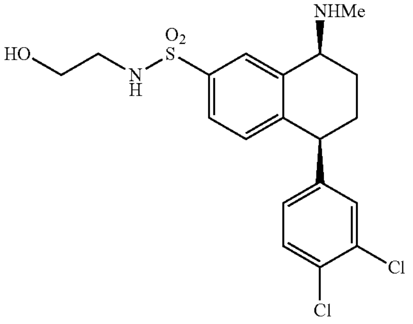

Sertraline sulfonamide ethanol

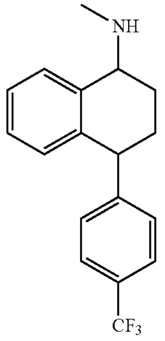

Sertraline B-Ring paratrifluoromethane

The term "serotonin-norepinephrine reuptake inhibitor" or "SNRI" refers to a family of compounds which are capable of inhibiting the reuptake of serotonin by blocking the serotonine transporter and the reuptake of norepinephrine by blocking the norepinephrine transporter. This family includes compounds such as venlafaxine (CAS 93413-69-5), desvenlafaxine (CAS 93413-62-8), duloxetine (CAS116539-59-4), milnacipran (CAS 92623-85-3), Sibutramine (106650-

56-0), Tramadol (CAS 27203-92-5) and Bicifadine (CAS 71195-57-8). Assays for determining whether a given compound is acting as a SNRI are, for instance, the ability to reduce the uptake of serotonin and norepinephrine by brain synaptosomes as described essentially in Bolden-Watson C, Richelson E. (Life Sci. 1993; 52(12):1023-9). A particular type of SNRIs are tricyclic antidepressants which are SNRIs having a general molecular structure comprising three rings Prominent among the tricyclic anti-depressants are the linear tricyclics, e.g., imipramine, desipramine, amitriptyline, nortriptyline, protriptyline, doxepin, ketipramine, mianserin, dothiepin, amoxapine, dibenzepin, melitracen, maprotiline, flupentixol, azaphen, tianeptine and related compounds showing similar activity. Angular tricyclics include indriline, clodazone, nomifensin, and related compounds. A variety of other structurally diverse anti-depressants, e.g., iprindole, wellbatrin, nialamide, milnacipran, phenelzine and tranylcypromine have been shown to produce similar activities. They are functionally equivalent to the tricyclic anti-depressants and are therefore included within the scope of the invention. Thus, the term tricyclic anti-depressant is intended by the present inventor to embrace the broad class of anti-depressants described above together with related compounds sharing the common property that they all possess anti-depressant activity and which include, without limitation, compounds such as amitriptyline, amitriptylinoxide, carbamazepine, butriptyline, clomipramine, demexiptiline, desipramine, dibenzepin, dimetacrine, dosulepin/dothiepin, Doxepin, Imipramine, Imipraminoxide, Iprindole, Lofepramine, Melitracen, Metapramine, Nitroxazepine, Nortriptyline, Noxiptiline, pregabalin, Propizepine, Protriptyline, Quinupramine and Trimipramine.

The term "noradrenaline reuptake inhibitor", "NRI", "NERI", adrenergic reuptake inhibitor" or "ARI" refers to a family of compounds which are capable of blocking reuptake of noradrenaline and adrenaline by blocking the action of the norepinephrine transporter (NET). This family of compounds includes the selective NRIs which block exclusively the NET without affecting other monoamine transporters as well as non-selective NRIs such as the SNRIs, which block the norepinephrine transporter and the serotinine transporter (see above), the norepinephrine-dopamine reuptake inhibitors (NDRI), which block the norepinephrine and the dopamine transporters (see below), triciclyc antidepressants and tetracyclic antidepressants (see above). Suitable selective NRIs adequate for the present invention include, without limitation, Atomoxetine/Tomoxetine (Strattera or CAS 83015-26-3), Mazindol (Mazanor, Sanorex or CAS 22232-71-9), Reboxetine (Edronax, Vestra or CAS 98819-76-2) and Viloxazine (Vivalan or CAS 46817-91-8).

The term "dopamine reuptake inhibitor" or "DRI" acts as a reuptake inhibitor for the neurotransmitter dopamine by blocking the action of the dopamine transporter (DAT). This in turn leads to increased extracellular concentrations of dopamine and therefore an increase in dopaminergic neurotransmission. Suitable DRIs include, without limitation, pharmaceutical drugs such as amineptine, Benzatropine/Benztropine, Bupropion, dexmethylphenidate, Esketamine, Etybenzatropine/Ethybe, Ponalide, Fencamfamine, Fencamine, Ketamine, Lefetamine, Medifoxamine, Mesocarb, Methylphenidate, Nefopam, Nomifensine, Pipradrol, Prolintane, Pyrovalerone, Tiletamine and Tripelennamine; research chemicals such as altropane, amfonelic acid, benocyclidine, brasofensine, bromantane, DBL-583, dichloropane, diclofensine, Dieticyclidine, difluoropine, gacyclidine, GBR-12,935, indatraline, ioflupane, Iometopane, manifaxine, radafaxine, tametraline, tesofensine, troparil and vanoxerine. Suitable DRIs can be identified using assays known to the skilled artisan such as the determination of the capacity of the putative DRI in inhibiting high-affinity uptake of the dopamine by synaptosomal preparations prepared from rat corpus striatum carried out as described using methods published by Kula et al., (Life Sciences 34: 2567-2575, 1984)

The term "endocannabinoid reuptake inhibitor" or "eCBRI", as used herein, refers to any compound which is acts as a reuptake inhibitor for endocannabinoids by blocking the action of the endocannabinoids transporter. Compounds having this activity can be identified using the method described in Beltramo, M. et al. (Science, 1997, 277:1094-1097) based on the ability of the putative endocannabinoid reuptake inhibitor to block uptake of anandamide by rat neurons and astrocytes and include, without limitation, AM404, arvanil and olvanil.

The term "adenosine reuptake inhibitor" or "AdoRI" refers to a compound which acts as a reuptake inhibitor for the purine nucleoside and neurotransmitter adenosine by blocking the action of one or more of the equilibrative nucleoside transporters (ENTs). This in turn leads to increased extracellular concentrations of adenosine and therefore an increase in adenosinergic neurotransmission. Compounds having AdoRI activity can be identified using an in vitro assay based on the ability of the putative AdoRI in inhibiting adenosine uptake by erythrocytes as well as in vivo assays based on the ability of the putative AdoRI of inhibiting the vasodilator effect of adenosine as well as of preventing adenosine-mediated promotion of the growth of collateral vessels, all of which can be carried out essentially as described in U.S. Pat. No. 6,984,642. Suitable AdoRI include, without limitation, acadesine, acetate, Barbiturates, Benzodiazepines, Calcium Channel Blockers, Carbamazepine, Carisoprodol, Cilostazol, Cyclobenzaprine, Dilazep, Dipyridamole, Estradiol, Ethanol (Alcohol), Flumazenil, Hexobendine, Hydroxyzine, Indomethacin, Inosine, KF24345, Meprobamate, Nitrobenzylthioguanosine, Nitrobenzylthioinosine, Papaverine, Pentoxifylline, Phenothiazines, Phenyloin, Progesterone, Propentofylline, Propofol, Puromycin, R75231, RE 102 BS, Soluflazine, Toyocamyc in, Tracazo late, Tricyclic Antidepressants.

The term "Excitatory Amino Acid Reuptake Inhibitor" or "EAARI", refer to compounds which inhibit the reuptake of excitatory Amino Acid by blocking of the Excitatory Amino Acid transporter or EEATs. Many compounds are known to bind to EAATs and inhibit transporter function. Inhibitors of EAATs fall into two major classes that differ in their mode of action: non-transportable blockers and competitive substrates. Suitable EAARIs include, without limitation, DL-threo-beta-Benzyloxyaspartate, kainite, dihydrokainate, 2S4R4MG, threo-β-hydroxyaspartate, L-trans-pyrrolidine-2,4-dicarboxylic acid (t-2,4-PDC) Suitable EEARIs can be identified for instance using the assay described by Shimamotot et al. (Molecular Pharmacology, 1998, 53:195-201) based on the ability of the putative EEARI to inhibit uptake of radiolabelled glutamate by Cos-1 cells expressing the human excitatory amino acid transporter-1 (EAAT1) or the human excitatory amino acid transporter-2 (EEAT2).

The term "glutamate reuptake inhibitor" or "GluRI", refers to a compound which acts as a reuptake inhibitor for the glutamate by blocking the action of one or more of the glutamate transporters. Suitable inhibitors of glutamate reuptake encompass any one of those inhibitors that are already known in the art, including, illustratively, threo-3hydroxy-DL-aspartic acid (THA), (2S)-trans-pyrrolidine-2,4-dicarboxylic acid (PDC), aminocaproic acid, and (2S,3S)-3-{3-[4-(Trifluoromethyl)benzoylamino]benzyloxy}aspartate.

Compounds having GluRI activity can be identified for instance using the assay described by Shimamotot et al. (Molecular Pharmacology, 1998, 53:195-201) based on the ability of the putative GluRI to inhibit uptake of radiolabelled glutamate into Cos-1 cells expressing the human excitatory amino acid transporter-1 (EAAT1) or the human excitatory amino acid transporter-2 (EEAT2).

The term "GABA Reuptake Inhibitor" or "GRI", refers to a compound which acts as a reuptake inhibitor for the neurotransmitter gamma-aminobutyric acid (GABA) by blocking the action of the gamma-aminobutyric acid transporters (GATs). This in turn leads to increased extracellular concentrations of GABA and therefore an increase in GABAergic neurotransmission. Suitable inhibitors of GABA reuptake include, without limitation, adhyperforin (found in *Hypericum perforatum* (St. John's Wort)), CI-966, deramciclane (EGIS-3886), Guvacine (C10149), hyperforin (found in *Hypericum perforatum* (St. John's Wort)), Nipecotic acid, NNC 05-2090, NNC-711, SKF-89976A, SNAP-5114, stiripentol and Tiagabine (Gabitril) which are described in Borden L A et al. (Eur J. Pharmacol. 1994, 269: 219-224). Methods for detecting whether a given compound is a GABA reuptake inhibitor are known in the art and are described, e.g., in U.S. Pat. No. 6,906,177; U.S. Pat. No. 6,225,115; U.S. Pat. No. 4,383,999 and Ali, F. E., et al. (J. Med. Chem. 1985, 28, 653-660). These methods usually comprise contacting a cell with radiolabelled GABA and detecting the uptake of the GABA in the presence and absence of a candidate compound.

The term "glycine Reuptake Inhibitor" or "GlyRI" refers to a compound which acts as a reuptake inhibitor for the neurotransmitter glycine by blocking the action of the glycine transporters (GlyTs) including compounds which block the glicyne transporter (type 1) GlyT1 which is involved in removing of glycine from the synaptic cleft as well as GlyT2, which is required for the reuptake and reloading of glycine into the synaptic vesicle (Gomeza et al., 2003; Curr Opin Drug Discov Devel 6(5): 675-82). Suitable glycine reuptake inhibitors for use in the present invention include GlyT1-specific inhibitors such as N-methyl-N-[[(1R,2S)-1,2,3,4-tetrahydro-6-methoxy-1-phenyl-2-naphthalenyl]methy 1 glycine (the free base of MTHMPNMglycine), 4-[3-fluoro-4-propoxyphenyl]-spiro[2H-1-benzopyran-2,4'-piperidine]-1'-acetic acid (the free base of FPPSBPAA) which are described in WO0007978 and WO0136423, ALX 5407, sarcosine, 5,5-diary)-2-amino-4-pentenoates or the compounds described in WO0208216 as well as GlyT2-specific inhibitors such as those described in WO05044810A, which contents are incorporated by reference in their entirety. Methods for detecting GlyT1-specific or GlyT2-specific reuptake inhibitors are known in the art and include, for instance, the method described in WO05018676A or WO05044810 wherein cells expressing the relevant receptor (GlyT1 or GlyT2) are contacted with radiolabelled glycine in the presence of the compound which reuptake inhibitory activity is to be tested and the amount of glycine which is found inside the cell after a given time is determined.

The term "Norepinephrine-Dopamine Reuptake Inhibitor" or "NDRI", as used herein, refers to a compound which acts as a reuptake inhibitor for the neurotransmitters norepinephrine and dopamine by blocking the action of the norepinephrine transporter (NET) and the dopamine transporter (DAT), respectively. This in turn leads to increased extracellular concentrations of both norepinephrine and dopamine and therefore an increase in adrenergic and dopaminergic neurotransmission. Suitable NDRIs for use in the conjugates of the present invention include, without limitation, Amineptine (Survector, Maneon, Directin), Bupropion (Wellbutrin, Zyban), Dexmethylphenidate (Focalin), Fencamfamine (Glucoenergan, Reactivan), Fencamine (Altimina, Sicoclor), Lefetamine (Santenol), Methylphenidate (Ritalin, Concerta), Nomifensine (Merital), Pipradrol (Meretran), Prolintane (Promotil, Katovit), Pyrovalerone (Centroton, Thymergix), Nefopam (Acupan), adhyperforin (found in *Hypericum perforatum* (St. John's Wort)), hyperforin (found in *Hypericum* perforatum (St. John's Wort)), Cocaine, Desoxypipradrol (2-DPMP), D1phenylprolinol (D2PM), Methylenedioxypyrovalerone (MDPV), Cilobamine, Manifaxine (GW-320, 659), Radafaxine (GW-353,162), Tametraline (CP-24,441)

In a preferred embodiment, the conjugate of the invention contains a selectivity agent which is a selective serotonin reuptake inhibitor (SSRI). In a still more preferred embodiment, the SSRI is sertraline or a structural analog thereof as defined above.

A.2. The Nucleic Acid of the Conjugates of the Invention

The second component of the conjugates according to the present invention is a nucleic acid which is capable of specifically binding to a target molecule which is expressed in the same cell as the neurotransmitter transporter. Typically, the nucleic acid of the invention is capable of inhibiting the function of the target molecule. Thus, if the target molecule is an mRNA, then the nucleic acid (typically a siRNA, a shRNA or an antisense nucleic acid) acts by inhibiting the translation of the mRNA leading to a decrease in the levels of the protein encoded by the mRNA. If the target molecule is a protein, then the nucleic acid (typically an aptamer) acts by inhibiting the activity of the protein.

The term "nucleic acid", as used herein, refers to a polymer having two or more deoxyribonucleotide, ribonucleotide or nucleotide analog molecules as well as molecules that are structurally similar to a native nucleic acid, but differ from the native nucleic acid (e.g., through chemical modification) at one or more of the nucleic acid backbone (e.g., phosphate in native nucleic acids), nucleic acid sugar (e.g., deoxyribose for native DNA and ribose in native RNA), and nucleic acid base (e.g., adenosine, cytosine, guanine or thymidine in native nucleic acids)

The oligonucleotide can be a double stranded or single stranded oligonucleotide including, without limitation, small interference RNAs (siRNA), small hairpin RNAs (shRNA), microRNAs (miRNA), antisense oligonucleotides or ribozymes. If double stranded nucleic acids are used, these comprise a first sense strand which is complementary to the target nucleic acid and a second antisense strand which is complementary to the sense, which allows the formation of the double stranded DNA by base pairing between the first and second strand.

The term "antisense strand" refers to the strand of a double stranded nucleic acid which includes a region that is substantially complementary to a target sequence Where the region of complementarity is not fully complementary to the target sequence, the mismatches are most tolerated outside nucleotides 2-7 of the 5' terminus of the antisense strand The term "sense strand," as used herein, refers to the strand of a dsRNA that includes a region that is substantially complementary to a region of the antisense strand The term small interfering RNA ("siRNA") refers to small inhibitory RNA duplexes that induce the RNA interference pathway. These molecules may vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand The term "siRNA" includes duplexes of two separate strands. As used herein, siRNA molecules are not limited to RNA molecules but further encompass nucleic acids with one or more chemically modified nucleotides, such as morpholinos.

The term "shRNA" or "short hairpin RNA" as used herein refers to a dsRNA where the two strands are connected by an uninterrupted chain of nucleotides between the 3'-end of one strand and the 5' end of the respective other strand to form a duplex structure.

The term "micro RNA" or "miRNA" refers to short single-stranded RNA molecules, typically of about 21-23 nucleotides in length capable of regulating gene expression. miRNAs may be synthetic (i.e., recombinant) or natural. Natural miRNAs are encoded by genes that are transcribed from DNA and processed from primary transcripts ("pri-miRNA") to short stem-loop structures ("pre-miRNA"), and finally to mature miRNA. Mature miRNA molecules are partially complementary to one or more mRNA molecules, and down-regulate gene expression via a process similar to RNA interference, or by inhibiting translation of mRNA.

An "antisense sequence," as used herein includes antisense or sense oligonucleotides comprising a single-stranded nucleic acid sequence (either RNA or DNA) capable of binding to target mRNA (sense) or DNA (antisense) sequences. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

As used herein, the term "ribozyme" or "RNA enzyme" or "catalytic RNA" refers to an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome, the ligase activity of a DNA ligase, and a number of other chemical reactions performed by conventional protein enzymes.

An "aptamer" as used herein refers to a nucleic acid ligand that binds to more than one site on a target molecule where binding is not "complementary," i.e., is not due to base-pair formation between a nucleic acid ligand and a target nucleic acid sequence. An aptamer can be designed which binds to any envisionable target, including polypeptides. Aptamers offer the utility for biotechnological and therapeutic applications as they offer molecular recognition properties that rival that of the commonly used biomolecule, antibodies. In addition to their selective recognition, aptamers offer advantages over antibodies as they can be engineered completely in a test tube, are readily produced by chemical synthesis, possess desirable storage properties, and elicit little or no immunogenicity in therapeutic applications. Aptamers can be synthesized through repeated rounds of in vitro partition, selection and amplification, a methodology known in the state of the art as "SELEX", (Systematic Evolution of Ligands by Exponential Enrichment) (Shamah et al, Acc. Chem. Res. 2008, 41 pp. 130-8). Alternatively, they can be synthesized, for example, by step-wise solid phase.

The nucleic acid of the invention may contain one or more modifications in the nucleobases, in the sugars and/or in the internucleotide linkages.

Modifications to one or more backbone residues of the nucleic acids may comprise one or more of the following: 2' sugar modifications such as 2'-O-methyl (2'-OMe), 2'-β-methoxyethyl (2'-MOE), 2'-O-methoxyethoxy, 2'-Fluoro (2'-F), 2'Allyl, 2'-O-[2-(methylamino)-2-oxoethyl], 2'-O-(N-methylcarbamate); 4' sugar modifications including 4'-thio, 4'-$CH_2$—O-2'-bridge, 4-$(CH_2)_2$—O-2'-bridge; Locked Nucleic Acid (LNA); Peptide Nucleic Acid (PNA); Intercalating nucleic acid (INA); Twisted intercalating nucleic acid (TINA); Hexitol nucleic acids (FINA); arabinonucleic acid (ANA); cyclohexane nucleic acids (CNA); cyclohexenyl-nucleic acid (CeNA); threosyl nucleic acid (TNA); Morpholino oligonucleotides; Gap-mers; Mix-mers; Incorporation Arginine-rich peptides; addition of 5'-phosphate to synthetic RNAs; RNA Aptamers (Que-Gewirth NS, Gene Ther. 2007 February; 14(4):283-91.); RNA Aptamers regulated with antidotes on the subject of the specific RNA aptamer (ref. Oney S, Oligonucleotides. 2007 Fall;17(3):265-74.) or any combinations thereof.

Modifications to one or more internucleoside linkages of the nucleic acids may comprise one or more of the following: Phosphorothioate, phosphoramidate, phosphorodiamidate, phosphorodithioate, phosphoroselenoate, phosphorodiselenoate, phosphoroanilothioate and phosphoranilidate, or any combinations thereof.

A Locked Nucleic Acid (LNA), often referred to as inaccessible RNA, is a modified RNA nucleotide. The ribose moiety of an LNA nucleotide is modified with an extra bridge connecting the 2' and 4' carbons ($O_2$',C4'-methylene bridge). The bridge "locks" the ribose in the 3'-endo structural conformation, which is often found in the A-form of DNA or RNA. LNA nucleotides can be mixed with DNA or RNA bases in the nucleic acid whenever desired. Such oligomers are commercially available. The locked ribose conformation enhances base stacking and backbone pre-organization. This significantly increases the thermal stability (melting temperature) and hybridization affinity of LNA-modified nucleic acids, besides having improved mismatch discrimination abilities. These properties make them very useful for antisense-based techniques. Further, LNA anti-miR oligonucleotides have been tested in primates with encouraging results and low toxicity.

Peptide Nucleic Acid (PNA) is an artificially synthesized polymer similar to DNA or RNA and is used in biological research and medical treatments. PNA is not known to occur naturally. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right. Since the backbone of PNA contains no charged phosphate groups, the binding between PNA/DNA strands is stronger than between DNA/DNA strands due to the lack of electrostatic repulsion. Mixed base PNA molecules are true mimics of DNA molecules in terms of base-pair recognition. PNA/PNA binding is stronger than PNA/DNA binding.

Intercalating nucleic acid (INA) is a modified nucleic acid analogue comprised of normal deoxyribonucleotides covalently linked to hydrophobic insertions. INA has high affinity for complementary DNA with stabilization of up to 11 degrees for each modification. INA has a higher specificity for a fully matched target over mismatched targets than normal DNA. Utilizing that INAs have higher affinity for DNA makes it possible to use shorter probes and thereby enhance specificity even further. Further, INA is a DNA selective oligonucleotide analogue, with a unique ability to discriminate between DNA and RNA. Even though INAs have high affinities for complementary DNA, it has a lower affinity for a complementary sequence of complementary INAs. Twisted intercalating nucleic acids are denoted TINA.

Hexitol nucleic acids (HNA) are oligonucleotides built up from natural nucleobases and a phosphorylated 1,5-anhydrohexitol backbone. Molecular associations between HNA and RNA are more stable than between HNA and DNA and between natural nucleic acids (dsDNA, dsRNA, DNA/RNA). Other synthetically modified oligonucleotides comprise ANA (arabinonucleic acid), CNA (cyclohexane nucleic acids), CeNA (cyclohexenylnucleic acid) and TNA (threosyl nucleic acid).

Morpholinos are synthetic molecules which are the product of a redesign of the natural nucleic acid structure. Structurally, the difference between morpholinos and DNA or RNA is that while Morpholinos have standard nucleobases, those bases are bound to 6-membered morpholine rings instead of deoxyribose/ribose rings and non-ionic phosphorodiamidate intersubunit linkages replace anionic phosphodiester linkages. Morpholinos are sometimes referred to as PMO (phosphorodiamidate morpholino oligonucleotide). The 6-membered morpholine ring has the chemical formula $O—(CH_2—CH_2)_2—NH$.

Gapmers or "gapped oligomeric compounds" are RNA-DNA-RNA chimeric oligonucleotide probes, where windows or 'gaps' of DNA are inserted into an otherwise normal or modified RNA oligonucleotide known as "wings". This modification increases oligonucleotide stability in vivo and the avidity of the interaction of the probe with the target, so that shorter probes can be used effectively. Preferrably, the wings are 2'-O-methyl (OMe) or 2'-O-methoxyethyl (MOE) modified ribonucleotides that protect the internal block from nuclease degradation. Moreover, the nucleotides forming the gap or the wings may be connected by phosphodiester bonds or by phosphorothioate bonds, thus making it resistant to RNase degradation. Additionally, the nucleotides forming the wings may also be modified by incorporating bases connected by 3' methylphosphonate linkages.

The nucleic acid of the conjugates of the invention are capable of specifically binding to a target molecule which is expressed in the same cell as the neurotransmitter transporter. The binding of the nucleic acid to the target molecule can occur via Watspn-Crick interactions wherein the target molecule is a nucleic acid which contains a sequence which is complementary to the sequence of the nucleic acid. Alternatively, when the target molecule is a polypeptide, the nucleic acid of the conjugates of the invention can also interact with said molecule, in which case the nucleic acid is acting as an aptamer.

Wherein the nucleic acid which forms part of the conjugates of the invention is complementary to the nucleic acid sequence of the target mRNA, different criteria are available to the skilled person for selecting the most adequate nucleic acid. By way of example, when the nucleic acid forming part of the conjugate is a siRNA, this can be selected by scanning the mRNA sequence of the target for AA dinucleotides and recording the 19 nucleotides immediately downstream of the AA. Other methods can also been used to select the nucleic acid targets. In one example, the selection of the siRNA target sequence is purely empirically determined (see, e.g., Sui G et al., Proc. Natl. Acad. Sci. USA 99:5515-20 (2002)), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (see, e.g., Lee N S et al., Nature Biotechnol. 20:500-05 (2002)).

Alternatively, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In still yet another embodiment, the target sequence for RNAi is a 21-mer sequence fragment. The 5 end of the target sequence has dinucleotide "NA", where "N" can be any base and "A" represents adenine. The remaining 19-mer sequence has a GC content of between 35% and 55%. In addition, the remaining 19-mer sequence does not include any four consecutive A or T (i.e., AAAA or TTTT), three consecutive G or C (i.e., GGG or CCC), or seven "GC" in a row.

Additional criteria can also be used for selecting RNAi target sequences. For instance, the GC content of the remaining 19-mer sequence can be limited to between 45% and 55%. Moreover, any 19-mer sequence having three consecutive identical bases (i.e., GGG, CCC, TTT, or AAA) or a palindrome sequence with 5 or more bases is excluded. Furthermore, the remaining 19-mer sequence can be selected to have low sequence homology to other genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. 19-mer sequences producing no hit to other human genes under the BLASTN search can be selected. During the search, the e-value may be set at a stringent value (such as "1").

The effectiveness of the siRNA sequences, as well as any other RNAi sequence derived according to the present invention in silencing expression of the target gene, can be evaluated using various methods known in the art.

The terms "silence" and "inhibit the expression of," "down-regulate the expression of," "suppress the expression of," and the like, in as far as they refer to a target gene, herein refer to the at least partial suppression of the expression of a target gene, as manifested by a reduction of the amount of target mRNA, which may be isolated from a first cell or group of cells in which a target gene is transcribed and which has or have been treated such that the expression of a target gene is inhibited, as compared to a second cell or group of cells substantially identical to the first cell or group of cells but which has or have not been so treated (control cells). The degree of inhibition is usually expressed in terms of:

(mRNA in control cells)−(mRNA in treated cells)*
100 percent (mRNA in control cells)

Alternatively, the degree of inhibition may be given in terms of a reduction of a parameter that is functionally linked to target gene expression, e.g., the amount of protein encoded by a target gene or the number of cells displaying a certain phenotype. In principle, target genome silencing may be determined in any cell expressing the target, either constitutively or by genomic engineering, and by any appropriate assay. However, when a reference is needed in order to determine whether a given nucleic inhibits the expression of a target gene by a certain degree and therefore is encompassed by the instant invention, the assay provided in the Examples below and those known in the art shall serve as such reference. For example, in certain instances, expression of a target gene is suppressed by at least about 5 percent, 10 percent, 15 percent, 20 percent, 25 percent, 30 percent, 35 percent, 40 percent, 45 percent, or 50 percent by administration of the double-stranded oligonucleotide. In some embodiments, a target gene is suppressed by at least about 60 percent, 70 percent, or 80 percent by administration of the double-stranded oligonucleotide. In some embodiments, the target gene is suppressed by at least about 85 percent, 90 percent, or 95 percent by administration of the double-stranded oligonucleotide.

For instance, the nucleic acid sequence according to the present invention can be introduced into a cell that expresses the target gene. The mRNA level of the target gene in the cell can be detected by using RT-PCR, Northern blot or any other standard methods). Alternatively, the level of the polypeptide encoded by the target mRNA can be measured using Western blot, ELISA or any other immunological or non-immunlogical method. A substantial change in the expression level of mRNA or of the protein encoded by the target gene after the introduction of the siRNA sequence is indicative of the effectiveness of the siRNA sequence in suppressing the expression of the target gene. In one specific example, the expression levels of other genes are also monitored before and after the introduction of the siRNA sequence. An siRNA sequence which has inhibitory effect on target gene expression but does not significantly affect the expression of other genes can be selected. In another specific example, multiple siRNA or other RNAi sequences can be introduced into the same target cell. These siRNA or RNAi sequences specifically inhibit target gene expression but not the expression of other genes. In yet another specific example, siRNA or other RNAi sequences that inhibit the expression of the target gene and other gene or genes can be used.

The skilled person will appreciate that the specific choice of nucleic acid molecule which is incorporated into the conjugates of the invention will depend on the type of selectivity agent present in the conjugate. Thus, the nucleic acid will be specific for a target molecule which is expressed in the cells which express the neurotransmitter transporter which is specifically bound by the selectivity agent.

In a preferred embodiment, the nucleic acid is specific for the serotonin receptor type 1A (5-$HT_{1A}$). In those cases wherein the nucleic acid is an antisense, a siRNA, a shRNA or a ribozyme, the nucleic acid acts by base-pairing with the target molecule, in which case the target molecule is the mRNA encoding the serotonin receptor type 1A (5-$HT_{1A}$). If the nucleic acid is an aptamer, the target molecule is the serotonin receptor type 1A (5-$HT_{1A}$) polypeptide.

The term "type 1A serotonin receptor" or "5-$HT_{1A}$R", as used herein, refers to a type of serotonin receptor which is found predominantly in the presynaptic serotoninergic neuron. These receptors are activated by extracellular serotonin resulting in the reduction of the cell firing activity and, in turn, in a decrease in serotonin release in major forebrain areas. This negative feedback limits the increment of synaptic serotonin that can be induced by antidepressants acutely. Over time, the somatodendritic autoreceptors become desensitized, allowing the full effect of the SSRIs to be expressed in the forebrain. This time period has been found to correspond to the latency for the onset of antidepressant activity [Perez, V., et al., The Lancet, 1997, 349: 1594-1597]. Thus, in cells wherein the serotonin type 1A receptor is inactivated, the increase in extracellular serotonin as a consequence of the blocking in the serotonin transporter will not lead to a reduction in the cell firing activity, thus preventing the negative feed-back associated with the treatment by inhibitors of the serotonine reuptake.

The type 1A serotonin receptor which can be targeted by the nucleic acid of the conjugates of the invention can be any type 1A serotonin receptor including, without limitation, the human 5-$HT_{1A}$R, which sequence is given in the SwissProt database under accession number P08908, the mouse 5-$HT_{1A}$R, which sequence is given in the SwissProt database under accession number Q64264, the rat 5-$HT_{1A}$R, which sequence is given in the SwissProt database under accession number P19327, the dog 5-$HT_{1A}$R, which sequence is given in the SwissProt database under accession number Q6XXX9.

The skilled person will appreciate that the nucleic acid of the invention specific towards the mRNA encoding the 5-$HT_{1A}$R can be selected using any of the methods mentioned above and tested for its ability to induce a substantial decrease in the levels of the corresponding mRNA. The authors of the present invention have identified regions within the sequence of the 5-$HT_{1A}$R mRNA which can be preferentially targeted by the nucleic acids of the invention. These regions correspond to regions which are highly conserved among different species or regions corresponding to non-coding regions of the primary transcript in order to avoid potential interference with translation complexes inside the coding region.

Thus, in a preferred embodiment, the nucleic acid sequences are complementary to a region corresponding to nucleotides 621 to 1640 or to nucleotides 1880 to 2400 within the mouse 5-$HT_{1A}$R mRNA (Sequence with accession number NM__008308 in the NCBI database) or to the corresponding regions in the 5-$HT_{1A}$R cDNAs of other species. Said corresponding regions can be determined by pairwise alignment of said cDNAs with the mouse 5-$HT_{1A}$R cDNA or by multiple alignment of different 5-$HT_{1A}$R cDNAs and identification of the regions in said other cDNAs which overlap with the selected regions in the mouse 5-$HT_{1A}$R cDNA.

Methods for pairwise alignment of two given nucleic acid sequences are widely known to the skilled person and can be carried out by standard algorithms of the type BLASTN [BLAST Manual, Altschul, S., et al., NCBI NLM NIH Bethesda, Md. 20894, Altschul, S., et al., J. Mol. Biol. 215: 403-410 (1990)] using the default parameters. Methods for the alignment of multiple nucleic acid sequences can be carried out using standard algorithms of the type CLUSTALW (Thompson J D et al, Nucleic Acids Res, 1994, 22:4673-4680) using the default parameters. Once the regions in the 5-$HT_{1A}$R cDNA in different species have been identified, it is possible to identify suitable nucleic acid sequences that can be incorporated into the nucleic acids of the conjugates of the invention. In a preferred embodiment, the conjugate of the invention comprises a nucleic acid sequence which comprises a sequence which is targeted towards a region in 5-$HT_{1A}$R mRNA selected from the group of SEQ ID NO:1 (nucleotides 1841 to 1910 of the mouse 5-$HT_{1A}$R mRNA), SEQ ID NO:2 (nucleotides 591 to 700 of the mouse 5-$HT_{1A}$R mRNA), SEQ ID NO:3 (nucleotides 831 to 940 of the mouse 5-$HT_{1A}$R mRNA) and SEQ ID NO:4 (nucleotides 2120 to 4441 of the mouse 5-$HT_{1A}$R mRNA).

In a still more preferred embodiment, the nucleic acid of the conjugates of the invention comprises a sequence selected from the group of SEQ ID NO 5, SEQ ID NO 7, SEQ ID NO: 9, and SEQ ID NO: 11 (see Table 2).

If the nucleic acids are provided as double-stranded nucleic acids (e.g. as siRNAs), the oligonucleotides are matched to the corresponding antisense strand which are provided in SEQ ID NO 6, SEQ ID NO 8, SEQ ID NO: 10, and SEQ ID NO: 12 (see Table 2).

In another embodiment, the nucleic acid of the invention is directed to the mRNA encoding the serotonine transporter (wherein the nucleic acid acts by base pairing with the target) or to the serotonine transporter as such (wherein the nucleic acid acts as an aptamer by directly binding and inhibiting the activity of the polypeptide)

The term "serotonine transporter" or "SERT", as used herein, refers to a polypeptide which is an integral membrane protein that transports the neurotransmitter serotonin from synaptic spaces into presynaptic neurons. The sequences of the human, rat, mouse and bovine SERT are provided in the SwissProt database under accession numbers P31645, P31652, Q60857 and Q9XT49 respectively. Similarly as with the nucleic acids targeting $5\text{-HT}_{1A}$R cDNA, any region in the SERT cDNA can be targeted as long as it results in a substantial inhibition in the levels of the corresponding mRNA or the protein encoded by said mRNA. Thus, suitable SERT-specific nucleic acids can be identified as described above by measuring the levels of the SERT mRNA or SERT protein in cells expressing SERT after said cells have been contacted with the nucleic acid to be tested.

By way of example, a SERT-specific siRNAs as described in Mol. Psychiatry. 2005 August; 10(8):782-9, 714 and J. Recept. Signal Transduct. Res. 2006; 26:527-47 can be used. In a still more preferred embodiment, the SERT-specific siRNA contains the sequence (SEQ ID NO: 13)
5' CUCCUGGAACACUGGCAACdTdT 3'

In yet another embodiment, the SERT-specific siRNAs comprises as sequence as described in Table X.

| RNA oligonucleotide identification | Sequence (5'-3' direction) | SEQ ID NO: |
|---|---|---|
| siRNA-A-s (sense) | GCUAGCUACAACAAGUUCATT | 14 |
| siRNA-A-a (antisense) | UGAACUUGUUGUAGCUAGCTT | 15 |

Besides the pre-synaptic $5\text{-HT1}_A$, it is also possible to modulate $5\text{-HT1}_A$ action by modulating some ion channels that are downstream the $5\text{-HT1}_A$ action, such as TREK-1 or GIRK. These channels modulate neuron activity by hiperpolarizing the membrane by producing a big influx of potassium. This change in membrane potential, inhibit the neuron firing. It has been proposed that a TREK-1 or GirK agontism will increase the neuron activity. This will at the end, disrupting the pre-synaptic $5\text{-HT}_{1A}$ inhibition effect in presence of high levels of serotonin.

In another embodiment, the nucleic acid of the invention is directed to the mRNA encoding an ion channel acting downstream of $5\text{-HT}_{1A}$ action (wherein the nucleic acid acts by base pairing with the target) or to the ion channel acting downstream of $5\text{-HT}_{1A}$ as such (wherein the nucleic acid acts as an aptamer by directly binding and inhibiting the activity of the polypeptide). Those channels modulate the neuron activity by hiperpolarizing the membrane by producing a big influx of potassium. This change in membrane potential inhibits neuron firing. This will at the end disrupt the presynaptic $5\text{-HT}_{1A}$ inhibition effect in presence of high levels of serotonin. In a preferred embodiment the ion channel acting downstream of $5\text{-HT}_{1A}$ is TREK-1. or GIRK.

The term "TREK-1", as used herein, refers to a polypeptide also known as KCNK2, TREK, TPKCl, $K_2p2.1$, TREK1, hTREK-1c, hTREK-1e, MGC126742, MGC126744 and KCNK2 which is a two-pore-domain background potassium channel formed by two homodimers that create a channel that leaks potassium out of the cell to control resting membrane potential. The channel can be opened, however, by certain anesthetics, membrane stretching, intracellular acidosis, and heat. In humans, there are three isoforms resulting from alternative splicing of the TREK gene and which are provided in the NCBI database under accession numbers NP_001017424.1, NP_001017425.2 and NP_055032.1. The dog (*Canis familiaris*), chimpanzee (*Pan troglodytes*), cow (*Bos taurus*), rat (*Rattus norvegicus*) and mouse (*Mus musculus*) ortholgues of TREK-1 are provided in the NCBI Protein database under accession numbers XP_849278, XP_001171677, NP_777111, NP_742038 and NP_034737, respectively. Similarly as with the nucleic acids targeting $5\text{-HT}_{1A}$R cDNA, any region in the TREK-1 cDNA can be targeted as long as it results in a substantial inhibition in the levels of the corresponding mRNA or the protein encoded by said mRNA. Thus, suitable TREK-1-specific nucleic acids can be identified as described above by measuring the levels of the TREK-1 mRNA or TREK-1 protein in cells expressing TREK-1 after said cells have been contacted with the nucleic acid to be tested.

TREK-1 specific siRNA that can be used in the conjugates of the present invention include, without limitation, the sc-37180 siRNA provided by Santa Cruz Biotechnology, and the antisense molecules described in US2009317811.

The terms G protein-coupled inwardly-rectifying potassium channels, GIRKs or Kir3 x, as used herein, refer to any member of the family of inward-rectifier potassium ion channels which are activated (opened) via a signal transduction cascade starting with ligand stimulated G protein-coupled receptors (GPCRs). GPCRs in turn release activated G-protein βγ subunits (Gβγ) from inactive heterotrimeric G protein complexes (Gαβγ). Finally the Gβγ dimeric protein interacts with GIRK channels to open them so that they become permeable to potassium ions resulting in hyperpolarization of the cell. G protein-coupled inwardly-rectifying potassium channels are a type of G protein-gated ion channels because of this direct activation of GIRK channels by G protein subunits.

Suitable GIRKs include, without limitation, all members of the J subfamily including member 3 (also known as GIRK1 or Kir3.1) such as for instance the human GIRK1 corresponding to the nucleic acid identified in the NCBI gene database under accession number U39196 or the brain variant thereof known as GIRKd, member 6 (also known as GIRK2 or K1r3.2) such as for instance the human GIRK2 corresponding to the nucleic acid identified in the NCBI gene database under accession number U24660, member 9 (also known as GIRK3 or Kir3.3) such as for instance the human GIRK3 corresponding to the nucleic acid identified in the NCBI gene database under accession number U52152, member 5 (also known as GIRK4 or Kir 3.4) such as for instance the human GIRK4 corresponding to the nucleic acid identified in the NCBI gene database under accession number U39195, member 2 (also known as IRK1 or Kir2.1) such as for instance the human IRK1 corresponding to the nucleic acid identified in the NCBI gene database under accession number U24055 and member 4 (also known as IRK3 or Kir2.3) such as for instance the human IRK3 corresponding to the nucleic acid identified in the NCBI gene database under accession number U07364).

Suitable nucleic acids capable of targeting a GIRK include, for instance, the ribozymes, antisense molecules described in WO2005054848.

Those nucleic acids targeted to the $5\text{-HT}_{1A}$R mRNA or the $5\text{-HT}_{JA}$R protein, to the SERT mRNA or protein, to the TREK-1 mRNA or protein or to the GIRK mRNA or protein are preferably coupled to a selectivity agent which is capable of binding to a neurotransmitter transporter present in cells wherein the 5-$HT_{1A}$R, SERT, TREK-1 or GIRK is expressed, namely, a dopaminergic neuron. Accordingly, the conjugates of the invention comprise a 5-$HT_{1A}$R-specific nucleic acid, a SERT-specific nucleic acid, a TREK-1-specific nucleic acid or a GIRK-specific nucleic acid which is coupled to a selectivity agent capable of binding to a serotonin transporter, which can be a non-selective serotonin transporter (such as a SRI or a SNRI) or, more preferably, a selective serotonin reuptake inhibitor (SSRI).

In another embodiment, the nucleic acid which forms part of the conjugates of the invention is directed to synuclein.

The term "synuclein", as used herein, refers to a polypeptide of the synuclein member family which contains a highly conserved alpha-helical lipid-binding motif with similarity to the class-A2 lipid-binding domains of the exchangeable apolipoproteins and which are capable of forming intracellular aggregates known as Lewy bodies which appear in certain neural diseases such as Parkinson's disease, Alzheimer's disease and Lewy body disease. The term "synuclein" refers to α-synuclein, β-synuclein or γ-synuclein. In a preferred embodiment, the nucleic acids forming part of the conjugates of the invention are specific for α-synuclein The sequences of the human, rat, mouse and bovine α-synuclein are provided in the SwissProt database under accession numbers P37840, P37377, O55042 and Q3T0G8 respectively. Similarly as with the nucleic acids targeting 5-$HT_{1A}$R cDNA, the α-synuclein-specific nucleic acids can be identified or selected using any method as described above and tested for their capacity to induce a substantial inhibition in the levels of the corresponding mRNA or the protein encoded by said mRNA. Thus, suitable α-synuclein-specific nucleic acids can be identified as described above by measuring the levels of the α-synuclein mRNA or α-synuclein protein in cells expressing α-synuclein after said cells have been contacted with the nucleic acid to be tested.

In a preferred embodiment, the α-synuclein-specific nucleic acids are directed against a region of the human α-synuclein-cDNA. In another embodiment, the nucleic acid of the invention is directed to the mRNA encoding an ion channel acting downstream of 5-$HT_{1A}$ action (wherein the nucleic acid acts by base pairing with the target) or to the ion channel acting downstream of 5-$HT_{1A}$ as such (wherein the nucleic acid acts as an aptamer by directly binding and inhibiting the activity of the polypeptide). Those channels modulate the neuron activity by hiperpolarizing the membrane by producing a big influx of potassium. This change in membrane potential inhibits neuron firing. This will at the end disrupt the pre-synaptic 5-$HT_{1A}$ inhibition effect in presence of high levels of serotonin. In a preferred embodiment the ion channel acting downstream of 5-$HT_{1A}$ is TREK-1.

Suitable target regions within the α-synuclein-mRNA include, without limitation, those described in WO07135426 (for instance nucleic acids, and in particular siRNAs, comprising a sequence selected from the group of siRNAs as described in WO2006039253 such as SEQ ID NO: 16
5'-GGAAAGACAAAAGAGGUGdTdT-3'

SEQ ID NO: 17
5'-GGAAAGACAAAAGAGGUGdTdT-3'

SEQ ID NO: 18
5'-GGAGGAAUUUUAGAAGAGGdTdT-3'

SEQ ID NO: 19
5'-UGUUGGAGGAGCAGUGGUGdTdT-3'

SEQ ID NO: 20
5'-GGACCAGUUGGGCAAGAAUdTdT-3' or hairpin oligonucleotides having the sequence

5'-GATCCCCGGACCAGTTGGGCAAGAATTTCAAGAGAATTCTTGCCAACTGGTCCTTTTTGGAAA-3'
and

5'-CTAGTTTCCAAAAAGGACCAGTTGGGCAAGAATTCTCTTGAAATTCTTGCCCAACTGGTCCGGG-3' corresponding respectively to SEQ ID NO:21 and 22

Other synuclein-specific siRNA sequences are those described in US2008139799 (sequences depicted in Example XVII, which contents are hereby incorporated by reference) and siRNA sequences as described in WO2009079399 selected from the group of:

SEQ ID NO: 23
5'-GGUGUGGCAACAGUGGCUGAG-3'

SEQ ID NO: 24
5'-AACAGUGGCUGAGAAGACCAA-3'

SEQ ID NO: 25
5'-AUUGCAGCAGCCACUGGCUUU-3'

SEQ ID NO: 26
5'-AAGUGACAAAUGUUGGAGGAG-3'

SEQ ID NO: 27
5'-GAAGAAGGAGCCCCACAGGAA-3'

SEQ ID NO: 28
5'-CGGGUGUGACAGCAGUAGCdTdT-3'

SEQ ID NO: 29
5'-UCCUGACAAUGAGGCUUAUdTdT-3'

SEQ ID NO: 30
5'-U*CCUGACAAUGAGGCUUAUdT*dT-3'

SEQ ID NO: 31
5'-CUACGAACCUGAAGCCUAAdTdT-3'

SEQ ID NO: 32
5'-C*UACGAACCUGAAGCCUAAdT*dT-3'

SEQ ID NO: 33
5'-C*UACGAACCUGAAGCCUAAdT*dT-3'

SEQ ID NO: 34
5'-CUAUUGUAGAGUGGUCUAUdTdT-3'

SEQ ID NO: 35
5'-C*UAUGAGCCUGAAGC*UAAT*T-3'

SEQ ID NO: 36
5'-C*UAUGAGCCUGAAGCCUAAT*T-3' wherein * indicates phosphorothiate linkage, underlined nucleotides indicate a 2'-O-Me modification.

Those are preferably coupled to a selectivity agent which is capable of binding to a neurotransmitter transporter present in cells wherein synuclein is expressed. Accordingly, the conjugates of the invention comprise a synuclein-specific nucleic acid which is coupled to a selectivity agent capable of mediating internalization into monoaminergic neurons. Accordingly, the nucleic acids targeted to the synuclein mRNA or protein are coupled to an agent capable of promoting internalization of said nucleic acid into serotoninergic, noradrenergic and/or dopaminergic neurons. Thus, in a preferred embodiment, the synuclein-specific nucleic acid is coupled to a selectivity agent for serotonergic, noradrenergic and dopaminergic neurons that is selected from the group of a dopamine reuptake inhibitor (DRI), a Norepinephrine-Dopamine Reuptake Inhibitor (NDRI) (SNDRI or Triple-Blocker).

In another embodiment, the nucleic acid which forms part of the conjugates of the invention is directed to nitric oxid synthase (NOS).

As used herein, "nitric oxide synthase" or "NOS" mean a naturally occurring enzyme which catalyzes in vivo synthesis of nitric oxide. Nitric oxide (NO) is synthesized from the guanidino group of L-arginine by a family of enzymes termed nitric oxide synthase (NOS). The term applies to all isoforms of nitric oxide synthase (NOS) found in living systems and includes, without limitation, the constitutive form of NOS, the endothelial nitric oxide synthase (eNOS), neuronal nitric oxide synthase (nNOS) and inducible nitric oxide synthase (NOS).

The sequences of the human, rat, mouse, dog and bovine iNOS are provided in the SwissProt database under accession numbers P35228, Q06518, P29477, 062699 and Q27995 respectively. The sequences of the human, rat, mouse and bovine eNOS are provided in the SwissProt database under accession numbers P29474, Q62600, P70313 and P29473 respectively. The sequences of the human, rat, mouse and bovine nNOS are provided in the SwissProt database under accession numbers P29475, P29476, Q9Z0J4 and P29473, respectively.

Any region in the NOS cDNA can be targeted as long as it results in a substantial inhibition in the levels of the corresponding mRNA or the protein encoded by said mRNA. Thus, suitable NOS-specific nucleic acids can be identified as described above by measuring the levels of the NOS mRNA or protein in cells expressing NOS after said cells have been contacted with the nucleic acid to be tested or by determining the activity of NOS in treated cells. Nos activity can be measured by any method known in the art for determining the iNOS, eNOS and nNOS activities as the case may be. For instance, the NOS activity can be determined by measuring the conversion of [$^3$H]-arginine to [$^3$H] L-citruline by radiometric method or in the formation of nitric oxide using the Griess assay.

Suitable NOS-specific silencing agents include, without limitation, the nNOS-specific siRNAs described in WO08100591 obtained by the following polynucleotide pairs:

- CAAAGAGATCGACACCATC (SEQ ID NO: 58) (sense), GATGGTGTCGATCTCTTTGTT (SEQ ID NO:59) (antisense);
- CACGCATGTCTGGAAAGGC (SEQ ID NO:60) (sense) and GCCTTTCCAGACATGCGTGTT (SEQ ID NO:61) (antisense);
- GGTCTATCCAATGTCCACA (SEQ ID NO:62) (sense) and TGTGGACATTGGATAGACCTT (SEQ ID NO:63) (antisense)
- The iNOS-specific siRNA having the sequence 5CCACCAGTATGCAATGAAT-3 (SEQ ID NO:64)
- The eNOS-specific siRNA available from Invitrogen (Carlsbad, Calif.) having oligo identification numbers HSS107326, HSS107327 and HSS107328
- The NOS-specific siRNAs described in Table 2 of Fang et al. (RNA, 2010, 16:1429-1435)
- The iNOS-specific siRNAs having the sequences 5'-ACAACAGGAACCUACCAGCTT-3' (SEQ ID NO:65) (sense) and 5'-GCUGGUAGGUUCCUGUUGUTT-3' (SEQ ID NO:66) (antisense).

Illustrative and non limitative NOS specific antisense include suitable for use in the present invention include:

- the iNOS-specific antisense oligonucleotide having the sequence 5'-ACAGCTCAGTCCCTTCACCAA-3' (SEQ ID NO:67) as described in Grasso et al. (Exp. Biol. Med., 2003, 228:491-8).
- the iNOS-specific antisense oligonucleotide having the sequence 5'-TTTGCCTTATACTGTTCC-3' (SEQ ID NO:68) as described by Hemmrich et al. (Am. J. Physiol. Cell Physiol., 2003, 285: C489-C498).
- The iNOS-specific antisense oligonucleotides described in Tables 1 and 2 in WO0152902.
- The NOS-specific antisense molecules described in Table 1 of Fang et al. (RNA, 2010, 16:1429-1435)

The NOS-specific silencing agents are preferably coupled to a selectivity agent which is capable of binding to a neurotransmitter transporter present in cells wherein NOS is expressed. Accordingly, the conjugates of the invention comprise a NOS-specific nucleic acid which is coupled to a selectivity agent capable of mediating internalization into monoaminergic neurons. Accordingly, the nucleic acids targeted to the synuclein mRNA or protein are coupled to an agent capable of promoting internalization of said nucleic acid into serotoninergic, noradrenergic and/or dopaminergic neurons. Thus, in a preferred embodiment, the synuclein-specific nucleic acid is coupled to a selectivity agent for serotonergic, noradrenergic and dopaminergic neurons that is selected from the group of a dopamine reuptake inhibitor (DRI), a Norepinephrine-Dopamine Reuptake Inhibitor (NDRI) (SNDRI or Triple-Blocker).

In another embodiment, the nucleic acid which forms part of the conjugates of the invention is directed to the noradrenaline transporter.

The term "noradrenaline transporter", "NAT", "norepinephrine transporter" or "NET" are used herein indistinctly to refer to a monoamine transporter that transports the neurotransmitters norepinephrine (noradrenaline) and dopamine from the synapse back to its vesicles for storage until later use. NET is 617 amino acids in length, contains 12 transmembrane domains which is encoded by the SLC6A2 gene.

The sequences of the human, dog (*Canis familiaris*), chimpanzee (*Pan troglodytes*, cow (*Bos taurus*), rat (*Rattus norvegicus*) and mouse (*Mus musculus*) norepinephrine transporters are provided in the NCBI database under accession numbers P23975, XM_544398.2, XM_001167680.1, NM_174608.2, NM_031343.1 and NM_009209.2, respectively. Any region in the NET cDNA can be targeted as long as it results in a substantial inhibition in the levels of the corresponding mRNA or the protein encoded by said mRNA. Thus, suitable NET-specific nucleic acids can be identified as described above by measuring the levels of the NET mRNA or protein in cells expressing NET after said cells have been contacted with the nucleic acid to be tested.

Suitable NET-specific nucleic acids include, without limitation, any SLC6A2-specific RNAi such as the RNAis available from Invitrogen under accession numbers HSS109852, HSS109853 and HSS185858.

In another embodiment, the nucleic acid which forms part of the conjugates of the invention is directed to dopamine-β-hydroxylase.

The term "dopamine-β-hydroxylase", as used herein, refers to a polypeptide which is capable of converting dopamine to norepinephrine.

The sequences of the human, rat, mouse and bovine dopamine-β-hydroxylase are provided in the NCBI protein database under accession numbers NP_000778, NP_037290, NP_620392 and NP_851338 respectively. Similarly as with the nucleic acids targeting other nucleic acids according to the invention, any region in the dopamine-β-hydroxylase cDNA can be targeted as long as it results in a substantial inhibition in the levels of the corresponding mRNA or the protein encoded by said mRNA. Thus, suitable dopamine-β-hydroxylase-specific nucleic acids can be identified as described above by measuring the levels of the dopamine-β-hydroxylase mRNA or protein in cells expressing dopamine-β-hydroxylase after said cells have been contacted with the nucleic acid to be tested.

Suitable dopamine-β-hydroxylase-specific nucleic acids include, without limitation, the nucleic acid described in WO2008019159 having the sequence

```
                              (SEQ ID NO: 37)
5'-GACCACGUACUGGUGCUACAUTA-3'
```

As well as commercially available dopamine-β-hydroxylase-specific nucleic acids such as the dopamine-β-hydroxylase-specific siRNA available from Santa Cruz Biotechnology (Catalog #sc-35180), from Invitrogen (Catalog #HSS175953, HSS175954 and HSS175955), from Abnova (Catalog #H00001621-R01), Applied Biosystems (siRNA ids s3946, s3947 and s3945).

Those nucleic acids targeted to the dopamine-β-hydroxylase mRNA or protein are preferably coupled to a selectivity agent which is capable of binding to a neurotransmitter transporter present in cells wherein dopamine-β-hydroxylase is expressed and wherein a decrease in the dopamine-β-hydroxylase is required to compensate for a neurotransmitter deficiency which is causing a given pathological condition. Accordingly, the conjugates of the invention comprise an dopamine-β-hydroxylase specific nucleic acid which is coupled to a selectivity agent capable of binding to a Norepinephrine Reuptake Inhibitor (NRI).

In another embodiment, the nucleic acid forming part of the conjugates of the invention is specific for BAX. The term "BAX" or "BCL2-associated X protein" as used herein, refers to a pro-apoptotic BCL-2 family member which activation involves subcellular translocation and dimerization. In viable cells, a substantial portion of BCL2-associated X protein is monomeric and found either in the cytosol or loosely associated with membranes. Following a death stimulus, cytosolic monomeric BCL2-associated X protein translocates to the mitochondria where it becomes a cross-linkable, integral membrane protein. The ability of BCL2-associated X protein to form distinct ion-conductive membrane pores may be, in part, responsible for mitochondrial dysfunction that leads to cell death (Korsmeyer et al., Cold Spring Harb. Symp. Quant. Biol., 1999, 64, 343-350; Korsmeyer et al., Cell Death Differ., 2000, 7, 1166-1173). The term "BAX" refers to any of the splice variants thereof, including BAX-alpha (GenBank accession number L22473), BAX-beta (GenBank accession number NM004324)), BAX-gamma (Oltvai et al., Cell, 1993, 74, 609-619), BAX-delta (GenBank accession number AI382305) (Apte et al., Genomics, 1995, 26, 592-594), BAX-omega (GenBank accession number AF008196) (Zhou et al., J. Biol. Chem., 1998, 273, 11930-11936) and BAX-epsilon (GenBank accession number AF007826) (Shi et al., Biochem. Biophys. Res. Commun., 1999, 254, 779-785). Nucleotide sequences encoding BAX-alpha BAX-beta and BAX-gamma are disclosed and claimed in U.S. Pat. Nos. 5,691,179 and 5,955,595. Nucleotide sequences encoding BAX-omega are disclosed and claimed in U.S. Pat. No. 6,140,484 and corresponding PCT publication WO 97/01635. Also disclosed in U.S. Pat. No. 6,140,484 is a 22-mer antisense oligonucleotide directed against the exon5/intron5 junction of human BAX-omega.

Suitable BAX-specific nucleic acids for use in the conjugates according to the present invention include:

- the sequence 5'-UCGAUCCUGGAUGAAACCCtg-3' (SEQ ID NO: 38) (as described in CN101255422),
- Antisense oligonucleotides targeting bases 83-102 and 103-122 of human BAX as described in (Manfredini et al., Antisense Nucleic Acid Drug Dev., 1998, 8, 341-350) and neutrophils (Dibbert et al., Proc. Natl. Acad. Sci. U.S.A., 1999, 96, 13330-13335).
- Any of the sequences disclosed in US20040077583 (Tables 1 and 3), which contents are herein incorporated by reference.

Those nucleic acids targeted to the bax mRNA or protein are preferably coupled to a selectivity agent which is capable of binding to a neurotransmitter transporter present in cells wherein BAX is expressed. Accordingly, the conjugates of the invention comprise a BAX-specific nucleic acid which is coupled to a selectivity agent capable f mediating internalization into serotonergic, noradrenergic and dopaminergic neurons. Thus, in a preferred embodiment, the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker).

In another embodiment, the nucleic acids of the conjugates of the invention are targeted to the microtubule-associated protein tau mRNA or protein. The term "tau" refers to any protein of the tau protein family including, but not limited to, native tau protein monomer, precursor tau proteins, tau peptides, tau intermediates, metabolites and tau derivatives of any origin including human (P10636), dog (XM_844939), chimpanzee (NM_001009068.1), mouse (Z12133), zebrafish (BI981282.1) and *C. Elegans* (NM_001027407.2) and which are capable of suffering hyper-phosphorylation resulting in the self-assembly of tangles of paired helical filaments and straight filaments, which are involved in the pathogenesis of Alzheimer's disease and other tau pathologies.

Suitable tau-specific nucleic acids include, without limitation:

- the siRNAs described in WO2005118858 having the sequences

```
                              (SEQ ID NO: 39)
5'-AATCACACCCAACGTGCAGAA-3'

                              (SEQ ID NO: 40)
5'-AACTGGCAGTTCTGGAGCAAA-3'
```

and the siRNAs described in US2004241854 having the sequences

| Sense strand | SEQ ID NO: | Antisense strand | SEQ ID NO: |
|---|---|---|---|
| TCGAAGTGATGGAAGATCACGC | 41 | CTTCACTACCTTCTAGTGCGAC | 42 |
| CAGCCGGGAGTCGGCAAGGTGC | 43 | CGGCCCTCAGCCCTTCCACGTC | 44 |
| ACGTCCTCGGCGGCGGCAGTGTGC | 45 | CAGGCGCCTGCGGCGTCACACGTT | 46 |
| ACGTCTCCATGGCATCTCAGC | 47 | TTGCTGAGATGCCATGGAGAC | 48 |
| GTGGCCAGATGGAAGTAAAATC | 49 | CCGGTCTACCTTCATTTTAGAC | 50 |
| GTGGCCAGATGCAAGTAAAATC | 51 | CCGGTCTACGTTCATTTTAGAC | 52 |

the tau-specific antisense nucleic acids described by Caceres et al. (J. Neuroscience, 1991, 11:1515-1523 having the sequences:

SEQ ID NO: 53
GGTTCAGCCATGCTGCTTCAAAGCC
and

SEQ ID NO: 54
TGATAATCGACAGGAGGCGAGGACA

Those nucleic acids targeted to the tau mRNA or protein are preferably coupled to a selectivity agent which is capable of binding to a neurotransmitter transporter present in cells wherein Tau is expressed. Accordingly, the conjugates of the invention comprise a Tau-specific nucleic acid which is coupled to a selectivity agent capable of mediating internalization into monoaminergic neurons, in particular, serotonergic, noradrenergic and dopaminergic neurons. Thus, in a preferred embodiment, the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker).

In another embodiment, the nucleic acids of the conjugates of the invention are targeted to the Huntingtin mRNA or protein. The term "Huntingtin" refers to a 350 kDa protein of unknown function with the UniPortKB data bank accession number P42858 as well as proteins encoded by the nucleic acid sequence deposited under accession number L12392 and orthologs thereof found in dog (NCBI Accession number XP_536221.2), chimpanzee (NCBI Accession number XP_517080.2), cow (NCBI Accession number XP_871851.2), rat (NCBI Accession number XP_573634.1) or mouse (NCBI Accession number NP_034544.11) as well as variants thereof resulting from the expansion of CAG repeats (CAGE-37 in the wild-type protein to CAG35-121 repeats in the mutant protein). The CAG expansion results in the production of a mutant protein containing an expansion in the poly-glutamine tract in the huntingtin protein.

Suitable huntingtin-specific nucleic acids include, without limitation, the antisense oligonucleotides described in Tables 4 and 5 in US2008039418A as well as in Tables 1, 2, 7, 8, 9 and 10 in U.S. Pat. No. 7,320,965, the siRNA described in US2005042646A and having the sequence (SEQ ID NO: 55)
5'-AAGAGGAGGAGGCCGACGCCC-3'

Those nucleic acids targeted to the Huntingtin mRNA or protein are preferably coupled to a selectivity agent which is capable of binding to a neurotransmitter transporter present in cells wherein Huntingtin is expressed. Accordingly, the conjugates of the invention comprise a Huntingtin-specific nucleic acid which is coupled to a selectivity agent capable of mediating internalization into monoaminergic neurons, in particular, serotonergic, noradrenergic and dopaminergic neurons. Thus, in a preferred embodiment, the selectivity agent is selected from the group of a dopamine reuptake inhibitor (DRI) or Norepinephrine-Dopamine Reuptake Inhibitor (NDRI) or a Serotonin-Norepinephrine-Dopamine Reuptake Inhibitor (SNDRI or Triple-Blocker).

Suitable combinations of selectivity agents and nucleic acids according to the present invention are summarized in Table I.

| Neurotransmitter transporter | Selectivity agent | Target nucleic acid of the oligonucleotide |
|---|---|---|
| SERT | SSRI (sertraline) | 5-$HT_{1A}$ |
| SERT | SSRI (sertraline) | SERT |
| SERT | SSRI (sertraline) | 5-$HT_{1B}$ |
| SERT | SSRI (sertraline) | TREK-1 |
| DAT, SERT or NET | SDNRI (TripleBlocker) or DNRI (Nomifensine) | Alpha-synuclein |
| DAT, SERT or NET | DAT, SERT or NET SDNRI (TripleBlocker) or DNRI (Nomifensine | NOS (iNOS, eNOS or nNOS) |
| DAT, SERT or NET | SDNRI (TripleBlocker) or DNRI (Nomifensine) | BAX |
| NET | NRI (Reboxetine) | Dopamine-beta-hydroxylase |
| NET | NRI (Reboxetine), SDNRI, DNRI | NET |
| DAT, SERT or NET | SDNRI (TripleBlocker) or DNRI (Nomifensine) | Tau |
| DAT, SERT or NET | SDNRI (TripleBlocker) or DNRI (Nomifensine) | Huntingtin |

A.3. Linker Regions of the Conjugates of the Invention

The nucleic acid and the selectivity agent may be directly coupled. However, it is preferred that both moieties are linked by a connecting group.

The terms "connecting group" and "linker" and grammatical equivalents thereof are used herein to refer to an organic moiety that connects two parts of a compound. The selectivity agent can be attached to any sense or antisense nucleotide within the nucleic acid, but it can be preferably coupled through the 3' terminal nucleotide and/or 5' terminal nucleotide. An internal conjugate may be attached directly or indirectly through a linker to a nucleotide at a 2' position of the ribose group, or to another suitable position.

In the case wherein the nucleic acid is a double-stranded nucleic acid, the conjugate can be attached to the sense 3' terminal nucleotide, the sense 5' terminal nucleotide, the antisense 3' terminal nucleotide, and/or the antisense 5' terminal nucleotide.

Though not wishing to be limited by definitions or conventions, in this application the length of the linker is described by counting the number atoms that represent the shortest distance between the atom that joins the conjugate moiety to the linker and the oxygen atom of the terminal phosphate moiety associated with the oligonucleotide through which the linker is attached to the oligonucleotide. In cases where the linker comprises one or more ring structures, counting the atoms around the ring that represent the shortest path is preferred.

Suitable linker groups for use in the present invention include, without limitation, modified or unmodified nucleotides, nucleosides, polymers, sugars, carbohydrates, polyalkylenes such as polyethylene glycols and polypropylene glycols, polyalcohols, polypropylenes, mixtures of ethylene and propylene glycols, polyalkylamines, polyamines such as polylysin and spermidine, polyesters such as poly(ethyl acrylate), polyphosphodiesters, aliphatics, and alkylenes. Moreover, linkers/linker chemistries that are based on omega-amino-1,3-diols, omega-amino-1,2-diols, hydroxyprolinols, omega-amino-alkanols, diethanolamines, omega-hydroxy-1,3-diols, omega-hydroxy-1,2-diols, omega-thio-1,3-diols, omega-thio-1,2-diols, omega-carboxy-1,3-diols, omega-carboxy-1,2-diols, co-hydroxy-alkanols, omega-thio-alkanols, omega-carboxy-alkanols, functionalized oligoethylene glycols, allyl amine, acrylic acid, allyl alcohol, propargyl amine, propargyl alcohol, and more, can be applied in this context to generate linkers of the appropriate length.

The linker may also confer other desirable properties on the oligonucleotide conjugate improved aqueous solubility, optimal distance of separation between the conjugate moiety and the oligonucleotide, flexibility (or lack thereof), specific orientation, branching, and others.

Preferably, said connecting group has the following structure

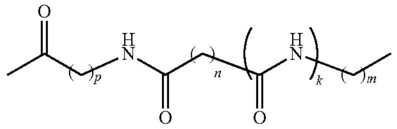

wherein m, n and p are selected from 0, 1, 2, 3, 4, 5, 6, 7, 8, 9, 10, 11, 12 and 13, wherein the sum of m+n+p is an integer number selected from 7, 8, 9, 10, 11, 12, 13, 14, 15, 16, 17 and 18 and wherein k is 0 or 1.

In a preferred embodiment, p is 5, n is 2, k is 1 and m is 6 giving a linker having the structure:

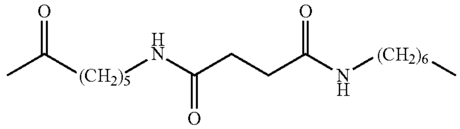

In another preferred embodiment, p is 5, n and k are 0 and m is 6 giving a linker having the structure:

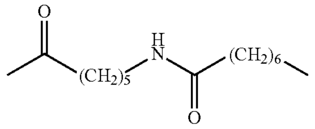

In a particular embodiment, the linker comprises more than one coupling for the selectivity agent. In a preferred embodiment, the linker is a bivalent or trivalent linker, i.e. 2 or 3 molecules of selectivity agent can be coupled, respectively.

In the case wherein more than one molecule of selectivity agent are coupled to the nucleic acid through a linker, said molecules can represent the same or different selectivity agents.

In a particular embodiment, the bivalent or trivalent linker has the following formula:

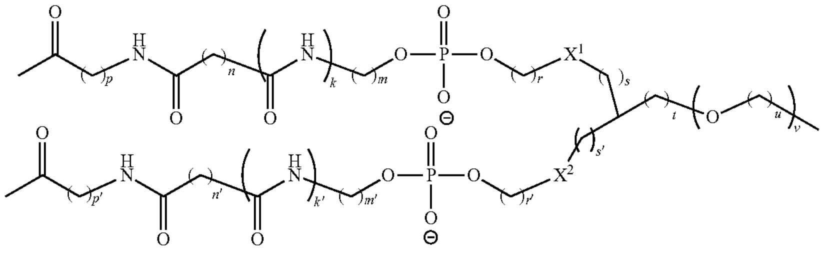

or

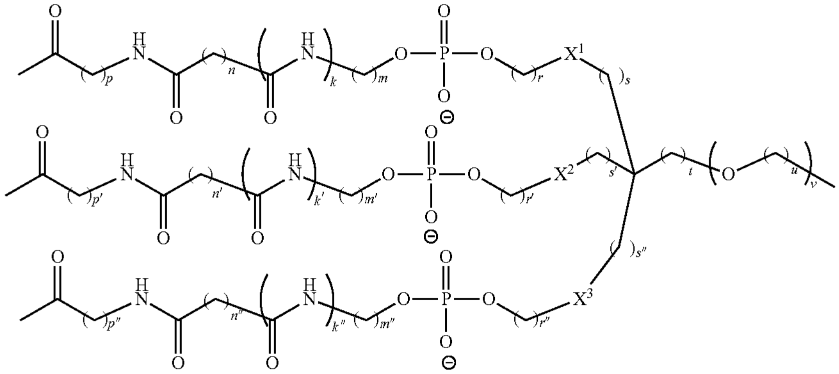

wherein m, m', m", n, n', n", p, p', p", r, r', r", s, s', s", t and u are independently selected from 0, 1, 2, 3, 4, 5, 6, 7, 8, 9, 10, 11, 12 and 13;

k, k', k" and v are independently selected from 0 and 1; and $X^1$, $X^2$ and $X^3$ independently selected from $CH_2$, O, S, NH, CO, C(O)O and C(O)NH.

Depending on the values of the above mentioned groups, branched linkers can be symmetrical or asymmetrical.

In a particular embodiment, the linker is a bivalente linker as shown above wherein p and p' are 5, n and n' are 2, k and k' are 1 and m and m' are 6. In a particular embodiment, the linker is a bivalente linker wherein p and p' are 5, n, n', k and k' are 0 and m and m' are 6.

In a particular embodiment, the linker is a bivalent linker as shown above wherein r and r' are 4, s and s' are 1, t and v are 0 and $X^1$ and $X^2$ represent C(O)NH. In another embodiment, the linker is a bivalent linker wherein r is 2, r' is 0, s is 1, s' is 0, t and v are 0 and $X^1$ and $X^2$ represent $CH_2$.

In a particular embodiment, the linker is a bivalente linker wherein p and p' are 5, n and n' are 2, k and k' are l, m and m' are 6, r and r' are 4, s and s' are 1, t and v are 0 and $X^1$ and $X^2$ represent C(O)NH.

In another embodiment, the linker is a bivalente linker wherein p and p' are 5, n and n' are 2, k and k' are l, m and m' are 6, r is 2, r' is 0, s is 1, s' is 0, t and v are 0 and $X^1$ and $X^2$ represent $CH_2$.

In another embodiment, the linker is a bivalente linker wherein p and p' are 5, n, n', k and k' are 0 and m and m' are 6, r and r' are 4, s and s' are 1, t and v are 0 and X' and $X^2$ represent C(O)NH.

In another embodiment, the linker is a bivalente linker wherein p and p' are 5, n, n', k and k' are 0 and m and m' are 6, r is 2, r' is 0, s is 1, s' is 0, t and v are 0 and $X^1$ and $X^2$ represent $CH_2$.

In a particular embodiment, the linker is a trivalent linker as shown above wherein p, p' and p" are 5, n, n' and n" are 2, k, k' and k" are 1 and m, m' and m" are 6. In a particular embodiment, the linker is a trivalent linker wherein p, p' and p" are 5, n, n', n", k, k' and k" are 0 and m, m' and m" are 6.

In a particular embodiment, the linker is a trivalent linker as shown above wherein r, r' and r" are 3, s, s' and s" are 1, t is 1, v is 0 and X', $X^2$ and $X^3$ represent O. In another embodiment, the linker is a trivalent linker wherein r, r' and r" are 3, s, s' and s" are 1, t is 1, u is 3, v is 1 and X', $X^2$ and $X^3$ represent O.

In a particular embodiment, the linker is a trivalent linker wherein p, p' and p" are 5, n, n' and n" are 2, k, k' and k" are l, m, m' and m" are 6, r, r' and r" are 3, s, s' and s" are 1, t is 1, v is 0 and $X^1$, $X^2$ and $X^3$ represent O.

In another embodiment, the linker is a trivalent linker wherein p, p' and p" are 5, n, n' and n" are 2, k, k' and k" are l, m, m' and m" are 6, r, r' and r" are 3, s, s' and s" are 1, t is 1, u is 3, v is 1 and X', $X^2$ and $X^3$ represent O.

In another embodiment, the linker is a trivalent linker wherein p, p' and p" are 5, n, n', n", k, k' and k" are 0, m, m' and m" are 6, r, r' and r" are 3, s, s' and s" are 1, t is 1, v is 0 and X', $X^2$ and $X^3$ represent O.

In another embodiment, the linker is a trivalent linker wherein p, p' and p" are 5, n, n', n", k, k' and k" are 0, m, m' and m" are 6, r, r' and r" are 3, s, s' and s" are 1, t is 1, u is 3, v is 1 and X', $X^2$ and $X^3$ represent O.

A.4. Targeting Moieties of the Conjugates of the Invention

Another modification of the conjugates of the invention involve chemically linking to the nucleic acid or to the protecting group one or more moieties or conjugates which enhance the activity, cellular distribution or cellular uptake of the nucleic acid. Such moieties include but are not limited to lipid moieties such as a cholesterol moiety (Letsinger et al, Proc. Natl. Acid. Sci. USA, 199, 86, 6553-6556), cholic acid (Manoharan et al, Biorg. Med. Chem. Let., 1994 4 1053-1060), a thioether, e.g., beryl-S-tritylthiol (Manoharan et al, Ann. N.Y. Acad. Sci., 1992, 660, 306-309; Manoharan et al, Biorg. Med. Chem. Let., 1993, 3, 2765-2770), a thiocholesterol (Oberhauser et al, Nucl. Acids Res., 1992, 20, 533-538), an aliphatic chain, e.g., dodecandiol or undecyl residues (Saison-Behmoaras et al, EMBO J, 1991, 10, 1111-1118; Kabanov et al, FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al, Tetrahedron Lett., 1995, 36, 3651-3654; Shea et al, Nucl. Acids Res., 1990, 18, 3777-3783), a polyamine or a polyethylene glycol chain (Manoharan et al., Nucleosides and Nucleotides, 1995, 14, 969-973), or adamantane acetic acid (Manoharan et al., Tetrahedron Lett., 1995, 36, 3651-3654), a palmityl moiety (Mishra et al, Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Alternatively, the moiety capable of enhancing cellular distribution may be a low molecular weight compound or polypeptide which is capable of being specifically translocated across biological barriers by the use of receptor-mediated endocytosis using specific transporters present in said biological barriers. A wide array of uptake receptors and carriers, with a even wider number of receptor-specific ligands, are known in the art. Preferred ligands for receptors that mediates endocytosis and/or transcytosis for use in accordance with present invention include e.g. ligands for, or that specifically bind to the thiamine transporter, folate receptor, vitamin B 12 receptors, asialoglycoprotein receptors, alpha (2,3)-sialoglycoprotein receptor (with e.g., the FC5 and FC44 nanobodies consisting of llama single-domain antibodies (sdAbs) as receptor-specific ligands), transferrin-1 and -2 receptors, scavenger receptors (class A or B, types I, II or III, or CD36 or CD163), low-density lipoprotein (LDL) receptor, LDL-related protein 1 receptor (LRP1, type B), the LRP2 receptor (also known as megalin or glycoprotein 330), diphtheria toxin receptor (DTR, which is the membrane-bound precursor of heparin-binding epidermal growth factor-like growth factor (HB-EGF)), insulin receptor, insulin-like growth factors (IGF) receptors, leptin receptors, substance P receptor, glutathione receptor, glutamate receptors and mannose 6-phosphate receptor.

Preferred ligands that bind to these receptors, for use in accordance with the present invention include e.g. ligands selected from the group consisting of lipoprotein lipase (LPL), alpha2-macroglobulin (alpha2M), receptor associated protein (RAP), lactoferrin, desmoteplase, tissue- and urokinase-type plasminogen activator (tPA/uPA), plasminogen activator inhibitor (PAI-I), tPA/uPA:PAI-I complexes, melanotransferrin (or P97), thrombospondin 1 and 2, hepatic lipase, factor VIIa/tissue-factor pathway inhibitor (TFPI), factor VIIIa, factor IXa, Abetal-40, amyloid-beta precursor protein (APP), CI inhibitor, complement C3, apolipoproteinE (apoE), pseudomonas exotoxin A, CRM66, HIV-I Tat protein, rhinovirus, matrix metalloproteinase 9 (MMP-9), MMP-13 (collagenase-3), spingolipid activator protein (SAP), pregnancy zone protein, antithrombin III, heparin cofactor II, alpha1-antitrypsin, heat shock protein 96 (HSP-96), platelet-derived growth factor (PDGF), apolipoprotein) (apoJ, or clusterin), ABETA bound to apoJ and apoE, aprotinin, angiopepl, very-low-density lipoprotein (VLDL), transferrin, insulin, leptin, an insulin-like growth factor, epidermal growth factors, lectins, peptidomimetic and/or humanized monoclonal antibodies or peptides specific for said receptors (e.g., sequences HAIYPRH and THRPPMWSPVWP that bind to the human transferrin receptor, or anti-human transferrin receptor (TfR) monoclonal antibody A24), hemoglobin, non-toxic portion of a diphtheria toxin polypeptide chain, all or a portion of the diphtheria toxin B chain (including DTB-His (as described by Spilsberg et al., 2005, Toxicon., 46(8):900-6)), all or a portion of a non-toxic mutant of diphtheria toxin CRM197, apolipoprotein B, apolipoprotein E (e.g., after binding to polysorb-80 coating on nanoparticles), vitamin D-binding protein, vitamin A/retinol-binding protein, vitamin B12/cobalamin plasma carrier protein, glutathione and transcobalamin-B 12.

A.5. Protecting Groups

The nucleic acids forming part of the conjugates of the invention have to be preserved from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Preferably, the nucleic acids are chemically modified by the presence of a group which prevents nuclease-mediated degradation.

For purposes of the present invention, “cap structure” or “protecting group” shall be understood to mean chemical modifications, which have been incorporated at either terminus of the oligonucleotide. Non-limiting examples of the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Details are described in WO97/26270, incorporated by reference herein. The 3'-cap includes, for example, 4',5'-methylene nucleotide; 1-(beta-D-erythrofuranosyl) nucleotide: 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties. See also Beaucage and Iyer, 1993, Tetrahedron 49, 1925; the contents of which are incorporated by reference herein.

In a preferred embodiment, the cap structure which is attached to the nucleic acid sequence of the conjugates of the invention has the following general structure:

$$M\text{-}L1_d\text{-}[(A\text{-}L2)_a\text{-}(B\text{-}L3)_b]_c\text{-}$$

wherein:

M is H, a lipid moiety or a targeting group as defined above;

A and B represent monomer units independently selected from the group consisting of a monosaccharide and a ($C_2$-$C_{20}$) alkylene glycol;

L1, L2 and L3 are linking compounds independently selected from the group consisting of phosphodiester, phosphorothioate, carbamate, methylphosphonate, guanidinium, sulfamate, sulfamide, formacetal, thioformacetal, sulfone, amide and mixtures thereof;

a and b are integers ranging from 0 to 50;

c is an integer ranging from 0 and 30;

d is an integer which is at least 1.

A lipid moiety, as used herein, refers to a group of organic compounds that has lipophilic or amphipathic properties, including, but not limited to, fats, fatty oils, essential oils, waxes, steroids, sterols, phospholipids, glycolipids, sulpholipids, aminolipids, chromolipids (lipochromes), and fatty acids, The term “lipid” encompasses both naturally occurring and synthetically produced lipids. Lipid moieties usually increase lipophilic properties of the oligonucleotide and facilitate the intracellular uptake in vivo of the oligonucleotide construction. Suitable lipids that can be used include fatty acids; fats; oils; waxes; cholesterol; sterols; fat-soluble vitamins, such as vitamins A, D, E and K; monoglycerides; diglycerides, and phospholipids. Preferred fatty acids are those selected from the group consisting of lauroic acid (C12), myristic acid (C14), palmitic acid (C16), stearic acid (C18), docosanoic acid (C22), and hybrid of lithocholic acid and oleylamine (lithocholic-oleyamine, C43). The lipid may be selected by the skilled person according to the circumstances by taking into consideration the target tissue, the target cell, the administration route, the pathway that the oligonucleotide is expected to follow, etc.

The term “monosaccharide”, as used herein and is well known in the art, refers to a simple form of a sugar that consists of a single saccharide unit which cannot be further decomposed to smaller saccharide building blocks or moieties. Preferred sugar moieties for this conjugation group are selected from the group consisting of furanose, fructose, glucose, galactose, mannose, a modified monosaccharide, sialic acid and eritrose and mixtures thereof. The monosaccharides may be in its lineal or cyclic forms (hemiacetalic cyclic isomers). The furanose is any simple sugar containing a five-membered furan-based ring, such as a D-ribose or a fructose residue (D-(−)-fructofuranose). With the combination of the monosaccharides, multiple sugar structures can be attained. The fructooligosaccharides (FOS) and the galactooligosaccharides (GOS) are combinations of special interest, as well as the disaccharides sacarose or lactose; or the polysaccharides inulin, dextrin, starch or glycogen.

The terms “alkylene glycol”, “poly(alkylene glycol)” an “alkylene oxide”, as used herein, encompasses a family of polyether polymers which share the general formula $—O—[(CH_2)_m—O—]_n$-, wherein m represents the number of methylene groups present in each alkylene glycol unit, and n represents the number of repeating units, and therefore represents the size or length of the polymer. The term includes. without limitation, ethylene glycol, propylene glycol, dialkylene glycol (for example, diethylene glycol), trialkylene glycol (for example, triethylene glycol), and glycols such as corresponding mono- and di-alkyl ethers of the aforementioned glycols, wherein the alkyl ethers are lower alkyl ethers having 1 to 6 carbon atoms (for example, methyl, ethyl, propyl ether and the like)

In another embodiment, the group of formula (I) has a ($C_2$-$C_{20}$)alkylene glycol monomer unit, which may be any linear or branched molecules from 2 to 20 carbon atoms, or, depending on the values of a and b, a polyalkylene glycol polymer with several ($C_2$-$C_{20}$) alkylene glycol monomer units. Preferably, the alkylene glycol group is selected from $C_{16}$-$C_{20}$ alkylene glycol. Still more preferably, the alkylene glycol group is a $C_{1-8}$ alkylene glycol.

Protecting groups adequate for the conjugates of the present invention include, without limitation:

$$M\text{-}L1_d\text{-}[(A\text{-}L2)_a\text{-}(B\text{-}L3)_b]_c\text{-}$$

- PEG+Sugar, corresponding to the above formula wherein M is H, d is 0, A is PEG, B is a sugar, a and b are each 1 and L1 and L2 are phosphodiester bonds;
- PEG+$(Sugar)_2$, corresponding to the above formula wherein A is PEG, B is a sugar, a is 1, b is 2, M is H and d is 0 and L1 and L2 are phosphodiester bonds;
- (PEG)2+Sugar, corresponding to the above formula wherein A is PEG, B is a sugar, a is 2, b is 1, M is H and d is 0 and L1 and L2 are phosphodiester bonds;
- (PEG)3+Sugar, corresponding to the above formula wherein A is PEG, B is a sugar, a is 3, b is 1, M is H and d is 0 and L1 and L2 are phosphodiester bonds;
- (PEG)5+Sugar corresponding to the above formula wherein A is PEG, B is a sugar, a is 5, b is 1, M is H and d is 0 and L1 and L2 are phosphodiester bonds
- The terms "PEG" and "sugar" are used essentially as described above and include furanose as sugar and a PEG selected from the group of C3, C9 and C18 spacers.

B. Structure of the Conjugates of the Invention

The different elements of the conjugates according to the present invention may be arranged in different manners. Thus, the selectivity agent may be coupled to the 5' end and/or to the 3' end of the nucleic acid. Moreover, the nucleic acid and the selectivity agent may be directly linked or may be connected by a linker. Similarly, the linker may be coupled to the 5' end and/or to the 3' end of the nucleic acid. Thus, wherein the nucleic acid of the invention contains a single nucleic acid chain, the possible arrangements are:

- a nucleic acid comprising a selectivity agent attached to the 5' end,
- a nucleic acid comprising a selectivity agent attached to the 3' end,
- a nucleic acid comprising a selectivity agent attached to the 5' and a protecting group attached to the 3' end and
- a nucleic acid comprising a protecting group attached to the 5' end and a selectivity agent attached to the 3' end.
- A nucleic acid modified comprising a first and a second selectivity agent, being said first and second selectivity agents the same or different, both selectivity agents connected to the two ends of a bifunctional linker which is connected to the 5' end of the nucleic acid,
- A nucleic acid modified comprising a first and a second selectivity agent, being said first and second selectivity agents the same or different, both selectivity agents connected to the two ends of a bifunctional linker which is connected to the 3' end of the nucleic acid,
- A nucleic acid modified comprising four selectivity agents, being said selectivity agents the same or different, wherein two of the selectivity agents are connected to both ends of a first to bifunctional linker which is connected to the 5' of the nucleic acid end and wherein two of the selectivity agents are connected to both ends of a second bifunctional linker which is connected to the 3' of the nucleic acid.

In addition, the conjugate of the invention may contain more than one nucleic acid chain that modulates the expression of the target molecule. For example, a construction of this invention can contain up to five different nucleic acids joined in tandem through phosphodiesters targeted at different regions of a given target molecule.

Moreover, in those cases wherein the nucleic acid is a double stranded nucleic acid, the selectivity agent may be coupled to the sense and/or to the antisense strand and may be directly coupled or connected by a linker group.

The nucleic acids forming part of the conjugates of the invention have to be protected from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Cellular exonucleases use free 5' ends as targets. Thus, in the case of single stranded nucleic acids, the selectivity agent may act as a stabilizing moiety when coupled to the 5' of the nucleic acid. However, in the case of conjugates comprising a double stranded nucleic acids or a single stranded nucleic acid in which the selectivity agent is linked to the 3' end, the conjugate may further comprise an stabilising moiety or cap structure which is usually a group which prevents degradation of the nucleic acid by the activity of exonucleases. In the case of double stranded nucleic acids, the following possible arrangements exist:

[1] the selectivity agent is attached to the 5' end of one of the strands, in which case it is useful to attach a cap structure to the 5' end of the opposite strand. Additionally, a cap structure may also be present in one or two of the 3' ends.

[2] the selectivity agent is attached to the 3' end of one of strands, in which case it is is useful to attach a cap structure to the 5' ends of the sense and of the antisense strand. Additionally, a cap structure may be present at the free 3' end.

[3] The conjugate comprising more than one selectivity agent which may be the same or different in which case, the selectivity agents are coupled to the 5' ends of the sense and of the antisense strand. Optionally, a cap structure may be coupled to one or two of the free 3' ends.

In a preferred embodiment, the nucleic acid is a double stranded RNA wherein the selectivity agent is linked to the 5' end of the antisense strand and the protecting group is linked to the 5' end of the sense strand. In a still more preferred embodiment, the protecting group has the structure $$M\text{-}L1_d\text{-}[(A\text{-}L2)_a\text{-}(B\text{-}L3)_b]_c\text{-}$$

wherein M is H, d is 0, A is a C18 spacer of polyethylene glycol, B is a furanose, a is 2, b and c are 1 and L2 and L3 are phosphodiester bonds In a preferred embodiment, the conjugate of the invention comprises (i) at least one selectivity agent which binds specifically to one or more of a neurotransmitter transporter wherein the selectivity agent is selected from the group consisting of a serotonin reuptake inhibitor (SRI), a selective serotonin reuptake inhibitor (SSRI), a serotonin-norepinephrine reuptake inhibitor (SNRI) and (ii) a nucleic acid acid which is capable of specifically binding to a target molecule wherein the target molecule is selected from the group consisting of the serotonin receptor type 1A ($5\text{-}HT_{1A}$), the mRNA encoding the serotonin receptor type 1A ($5\text{-}HT_{1A}$), the serotonin transporter protein and the mRNA encoding the serotonin transporter.

In a more preferred embodiment, the nucleic acid which is capable of specifically binding to the mRNA encoding the serotonin receptor type 1A (5-$HT_{1A}$) comprises a sequence selected from the group of SEQ ID NO:1, SEQ ID NO:2, SEQ ID NO:3 and SEQ ID NO:4.

In a still more preferred embodiment, the conjugate of the invention has the structure (I)

(I)

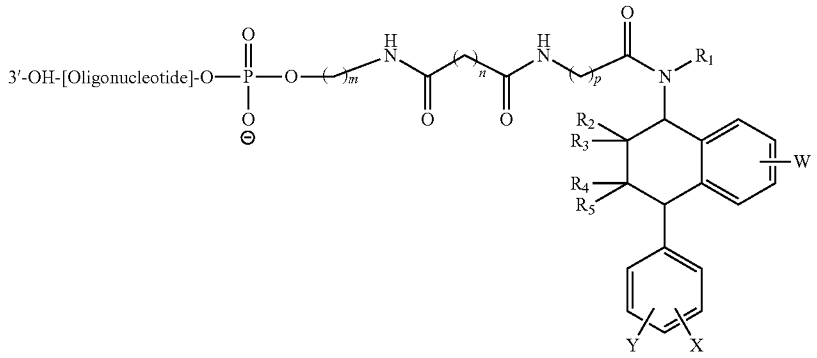

wherein $R^1$, $R^2$, $R^3$, $R^4$ and $R^5$ are independently selected from hydrogen and $C_1$-$C_6$ alkyl;

X and Y are independently selected from hydrogen, halogen, $C_1$-$C_3$ alkyl, $C_1$-$C_3$ haloalkyl, $OR^a$ and $SR^b$, wherein $R^a$ and $R^b$ are independently selected from $C_1$-$C_3$ alkyl and $C_6$-$C_{10}$ aryl;

W is selected from hydrogen, halogen, CN, $NO_2$, $C_1$-$C_3$ alkyl, $C_1$-$C_3$ haloalkyl, $NR^cR^d$, $SO_2NR^eR^f$, $NR^gSO_2R^h$, $CO_2R^i$, wherein $R^c$, $R^d$, $R^e$, $R^f$, $R^g$, $R^h$ and $R^i$ are independently selected from hydrogen and $C_1$-$C_3$ alkyl;

m, n and p are selected from 1, 2, 3, 4, 5, 6, 7, 8, 9, 10, 11, 12 and 13, wherein the sum of m+n+p is an integer number selected from 7, 8, 9, 10, 11, 12, 13, 14, 15, 16, 17 and 18 and wherein the oligonucleotide comprises a sequence selected from the group of SEQ ID NO:1, SEQ ID NO:2, SEQ ID NO:3 and SEQ ID NO:4.

In another embodiment, the conjugate of the invention has the structure:

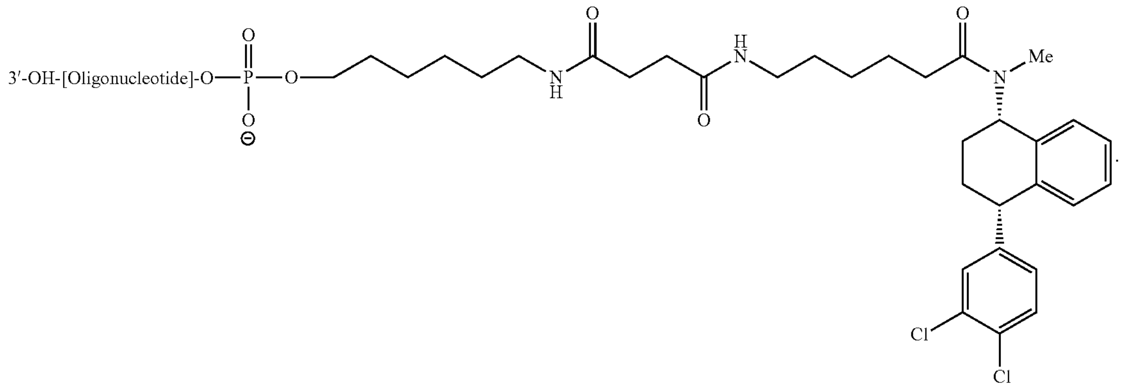

wherein the oligonucleotide comprises a sequence selected from the group of SEQ ID NO:1, SEQ ID NO:2, SEQ ID NO:3 and SEQ ID NO:4.

In a still more preferred embodiment, the conjugate of the invention has the structure (XIV)

(XIV)

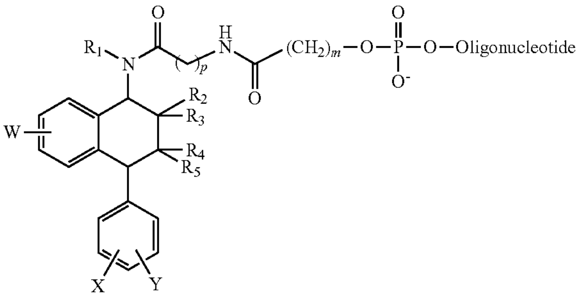

wherein $R^1$, $R^2$, $R^3$, $R^4$ and $R^5$ are independently selected from hydrogen and $C_1$-$C_6$ alkyl;

X and Y are independently selected from hydrogen, halogen, $C_1$-$C_3$ alkyl, $C_1$-$C_3$ haloalkyl, $OR^a$ and $SR^b$, wherein $R^a$ and $R^b$ are independently selected from $C_1$-$C_3$ alkyl and $C_6$-$C_{10}$ aryl;

W is selected from hydrogen, halogen, CN, $NO_2$, $C_1$-$C_3$ alkyl, $C_1$-$C_3$ haloalkyl, $NR^cR^d$, $SO_2NR^eR^f$, $NR^gSO_2R^h$, $CO_2R^i$, wherein $R^c$, $R^d$, $R^e$, $R^f$, $R^g$, $R^h$ and $R^i$ are independently selected from hydrogen and $C_1$-$C_3$ alkyl;

m and p are selected from 1, 2, 3, 4, 5, 6, 7, 8, 9, 10, 11, 12 and 13, wherein the sum of m+p is an integer number selected from 7, 8, 9, 10, 11, 12, 13, 14, 15, 16, 17 and 18 and wherein the oligonucleotide comprises a sequence selected from the group of SEQ ID NO:1, SEQ ID NO:2, SEQ ID NO:3 and SEQ ID NO:4.

In a particular embodiment, the conjugate has the structure (7)

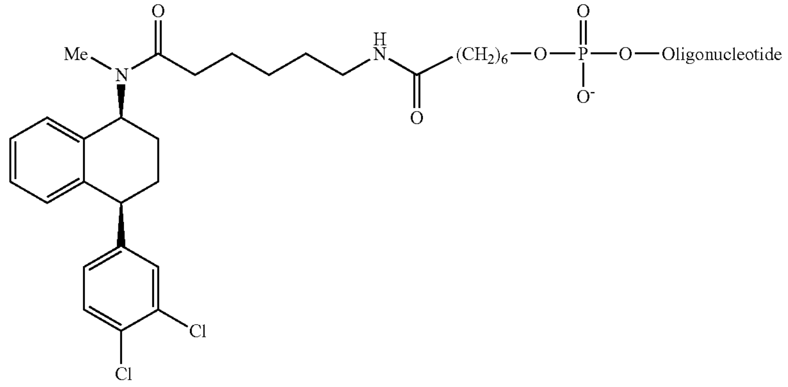

wherein the oligonucleotide comprises a sequence selected from the group of SEQ ID NO:1, SEQ ID NO:2, SEQ ID NO:3 and SEQ ID NO:4.

In yet another preferred embodiment, the conjugate of the invention comprises a double stranded nucleic acid wherein the 5' end of the sense strand is coupled to the protecting group and the 5' end of the antisense strand is coupled to the selectivity agent. Wherein the protecting group has the structure:

$$M\text{-}L1_d\text{-}[(A\text{-}L2)_a\text{-}(B\text{-}L3)_b]_c\text{-}$$

wherein M is H, d is 0, A is a C18 spacer of polyethylene glycol, B is a furanose, a is 2, b and c are 1 and L2 and L3 are phosphodiester bonds and wherein the protecting group is sertraline, the compound of the invention has the structure: C18-phosphodiester-C18-phosphodiester-furanose-phosphodiester-aRNA strand sRNA strand-peptide link-sertraline In a still more preferred embodiment, the compound of the invention has the structure:

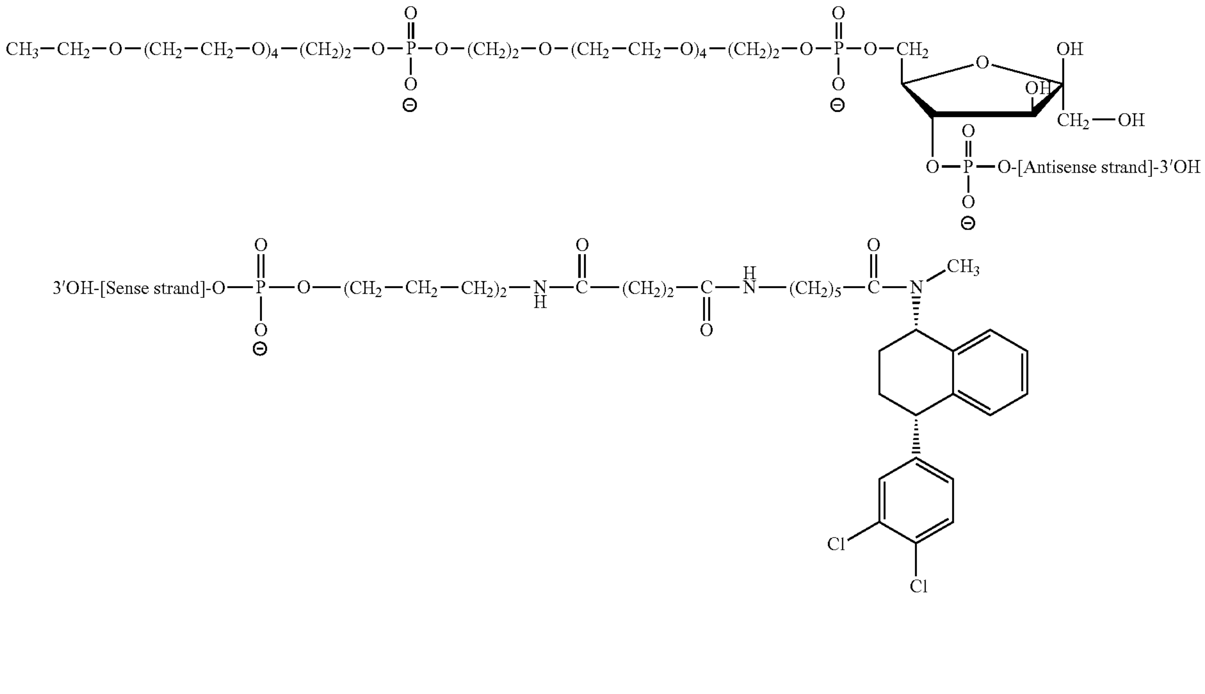

In a still more preferred embodiment, the compound of the invention has the structure:

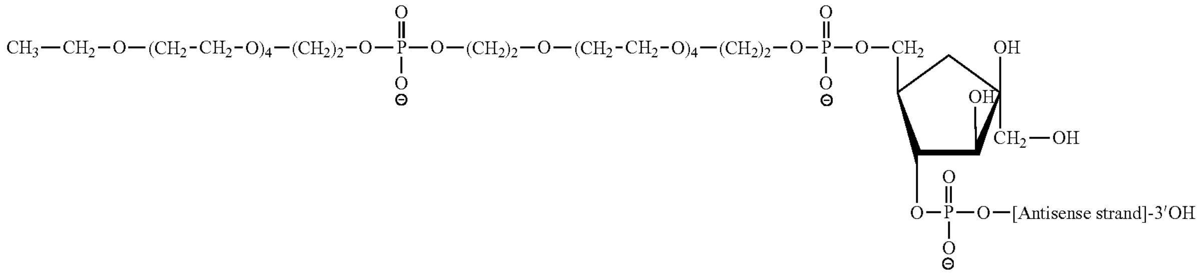

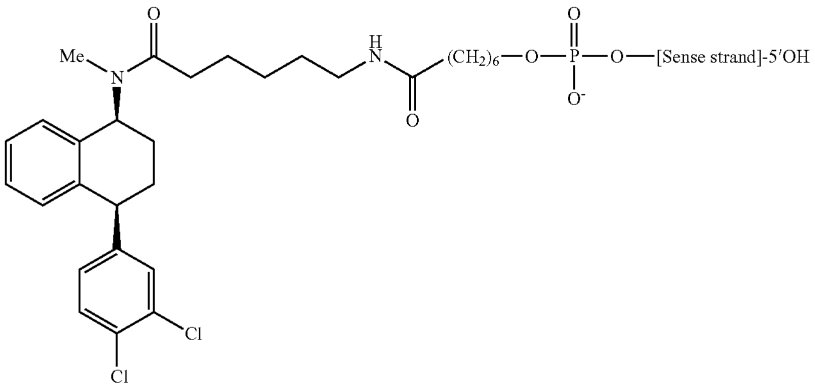

In another embodiment, the conjugate has the following structure:

(XIV)

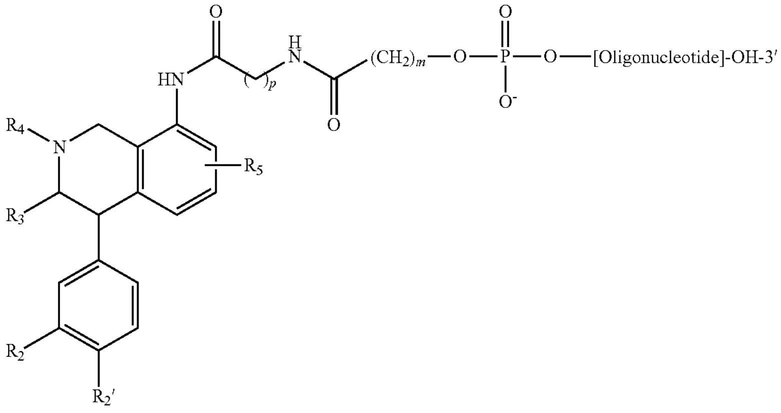

wherein $R_1$ denotes hydrogen, a lower alkyl group or a benzyl group $R_2$ denotes hydrogen, methyl, chlorine of fluorine groups $R_2$' denotes hydrogen, methyl, methoxy, hydroxyl or halogen atoms $R_3$ and $R_4$ denote hydrogen, a lower alkyl group $R_5$ denotes hydrogen, chloreine or methoxy group in the 5- or 6-position and p is 2-6.

In a still more preferred embodiment, the conjugate has the following structure

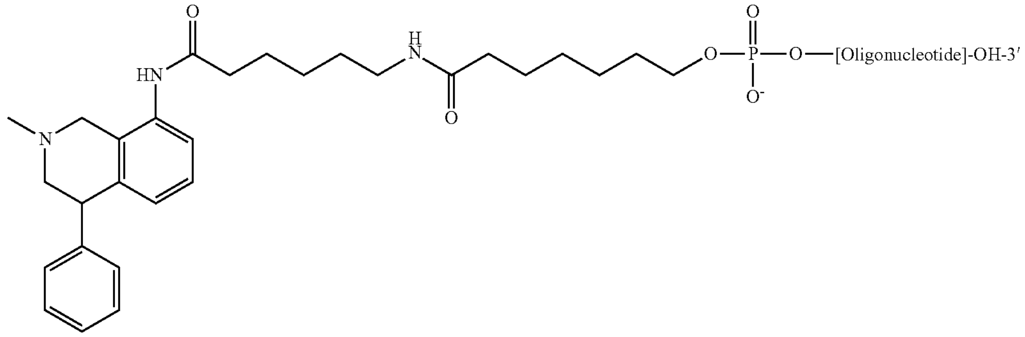

(9)

In a still more preferred embodiment, the oligonucleotide forming part of the conjugates defined above are capable of bindng specifically to a target molecule selected from the group consisting of:

dopamine-β-hydroxylase,
the mRNA encoding dopamine-β-hydroxylase,
BAX,
the mRNA encoding BAX,
tau,
the mRNA encoding Tau,
Huntingtin and
the mRNA encoding Huntingtin In the sense of the invention, the protecting group of formula may be linked to the 5'-OH or 3'-OH groups of the oligonucleotide by means of the linking compound (referred in the group of formula (I) as "L""), thus obtaining a conjugate-oligonucleotide. The chemical properties of the oligonucleotide and the group of formula (I) allow several embodiments.

For instance, it is possible to link into a single oligonucleotide molecule a variable number of groups of formula (I), typically from 2 to 4, depending if the oligonucleotide is double-stranded or single-stranded with the proviso that the linking is made through the 5'-OH and/or 3'-OH. It is also possible that a chain of several groups of formula (I) are linked to the oligonucleotide, said groups of formula (I) being linked to each other by means of linking compounds, such as phosphoramidite derivated ones that produce a phosphodiester bond between the molecules and/or the oligonucleotide. Also, the oligonucleotide construction may contain a chain of several groups of formula (I) linked to one end of the oligonucleotide and another group of formula (I) linked to another end of the oligonucleotide.

Also, the nucleotide constructions of the invention can contain more than one targeting agent, distributed with all the possible combinations among the 5'-OH and 3'-OH termini of the two strands of the oligonucleotide or joined to the group of formula (I). Moreover, if there is more than one targeting agent, these can be linked in tandem to the group of formula (I) and/or the oligonucleotide.

If the oligonucleotide construction contains more than one targeting agent, different combinations are possible. For instance, the protecting group can be linked to the 5'-OH or 3'-OH terminal groups of one of the strands of the oligonucleotide. Another possible combination includes a drug compound linked to the 5'-OH group of one oligonucleotide strand and a serial of aptamers joined to the terminal unit of the group formula (I) that is bound to the other oligonucleotide strand.

C. Pharmaceutical Compositions of the Invention

The inventors have found that the conjugates of the invention have the ability of modulating the expression of the nucleic acid which is targeted by the nucleic acid sequences of the conjugates. For instance, in the case of conjugates comprising a nucleic acid specific for the pre-synaptic 5-$HT_{1A}$R, when the construction is administered to a subject, it can effectively induce a specific knock-down of 5-$HT_{1A}$R in the subjects midbrain raphe nuclei (i.e. an area in the brain where the bodies of serotonergic neurons are located).

Thus, the skilled person will appreciate that the conjugates of the invention are adequate for the treatment of diseases which may benefit from the reduction in the expression levels of the genes which are targeted by the nucleic acids present in the conjugates of the invention. Thus, in another aspect, the invention relates to a conjugate according to the invention for use in medicine. Additionally, the invention also relates to a pharmaceutical composition comprising a conjugate according to the invention and a pharmaceutically-acceptable excipient.

Appropriate amounts of oligonucleotide constructions of the invention can be formulated with pharmaceutically acceptable excipients and/or carriers to obtain a pharmaceutical composition. A composition that includes a conjugate according to the invention can be delivered to a subject by a variety of routes. Exemplary routes include intrastriatal, intracerebroventricular, intrathecal, intraparenchymal (e.g., in the striatum), intranasal, and ocular delivery. The composition can also be delivered systemically, e.g., by intravenous, subcutaneous or intramuscular injection, which is particularly useful for delivery of the conjugates to peripheral neurons. Additionally, it is also possible to administer the conjugates of the invention intranasally which allows systemic administration by a non-aggressive mode of administration. Also, intraventricular administration may also be adequate. A preferred route of delivery is directly to the brain, e.g., into the ventricles or the hypothalamus of the brain, or into the lateral or dorsal areas of the brain.

The pharmaceutical compositions of the invention may comprise a plurality of different conjugates, wherein the different conjugates comprise nucleic acids which target different regions of the same target molecule. Thus, the pharmaceutical compositions may comprises at least 2, at least 3, at least 4, at least 5, at least 6 and more different conjugataes comprising each a different nucleic acid.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

In a preferred embodiment of the present invention, the conjugates are formulated in accordance with standard procedure as a pharmaceutical composition adapted for delivered administration to human beings and other mammals. Typically, compositions for intravenous or intraventricular administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing the conjugates of the invention can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

For embodiments in which the composition is delivered across the blood-brain barrier, the composition includes, for example, a liposome as described, for example, in U.S. Pat. No. 6,372,250 (Pardridge), and a pharmaceutically acceptable carrier. Liposomes as described herein can deliver biologically active agents across the blood-brain barrier, followed by expression in the brain. Liposomes and nanoparticles are exemplary forms of nanocontainers that are commonly used for encapsulation of drugs. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol, along with a small amount (1 percent) of cationic lipid, such as didodecyldimethylammonium bromide (DDAB) to stabilize the DNA within the liposome.

The liposome can be replaced with a nanoparticle or any other molecular nanocontainer with a diameter less than 200 nm that can encapsulate the DNA and protect the nucleic acid from nucleases while the formulation is still in the blood or in transit from the blood to the intracellular compartment of the target cell. Also, instead of using conjugation agents such as PEG strands, one or more other polymeric substances, such as sphingomylein, can be attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of DNA to any group of cells or organs which have specific target receptors. The liposomes may be used to deliver DNA to organs, such as liver, lung and spleen.

Other suitable containers for the delivery of the conjugates of the invention include dendrimers. The term "dendrimer" refers to a macromolecule having a core and having multiple shells of branching structures emanating from the core. The shape and size of a dendritic carrier can vary. In some instances, the dendritic carrier can be approximately spherical or globular in shape. Furthermore, the dendritic carrier can have a diameter in the range of about 15 angstroms (A) to about 250 A, with a corresponding range of molecular weights, e.g., from about 500 Daltons to about 2 million Daltons. Dendrimers can be obtained commercially from various sources (e.g., Dendritech, Midland, Mich.) or synthesized by methods known to those skilled in the art. Dendritic molecules can roughly be divided into the low-molecular weight and the high-molecular weight species. The first category includes dendrimers and dendrons whereas the second encompasses dendronized polymers, hyperbranched polymers, and brush-polymers (also called bottle-brushes). Dendrimers and dendrons are repeatedly branched, monodisperse, and usually highly symmetric compounds. There is no apparent difference in defining dendrimer and dendron. A dendron usually contains a single chemically addressable group that is called the focal point. Because of the lack of the molar mass distribution high-molar-mass dendrimers and dendrons are macromolecules but not polymers. The properties of dendrimers are dominated by the functional groups on the molecular surface. Dendritic encapsulation of functional molecules allows for the isolation of the active site, a structure that mimics the structure of active sites in biomaterials because dendritic scaffolds separate internal and external functions. For example, a dendrimer can be water-soluble when its end-group is a hydrophilic group, like a carboxyl group.

Dendrimers may be generally characterised by the following features: (i) an initiator core (I) which may have one or more reactive sites and be point-like or of significant size so as to effect the final topology of the dendrimer; (ii) one or more layers of branched repeating units attached to the initiator core; (iii) functional terminal groups, such as anionic or cationic groups, attached, optionally through linking groups, to the surface of the dendrimer.

Dendrimers contemplated herein may comprise lysine, or lysine analogue building units. The term "lysine analogue" refers to a molecule which has a single apex carboxyl group for attachment to the previous layer of building units, and two or three primary amine groups to which can be attached further building units, blocking groups, linkers or aryl acid groups. Examples of "lysine analogues" contemplated herein are described in PCT/AU2007/000352, for example glycyl-lys. In some particular examples, the dendrimer comprises only lysine or one type of lysine analogue as the building unit.

Other dendrimers contemplated herein include those comprising polyamidoamine (PAMAM), poly(etherhydroxylamine) (PEHAM) or polypropyleneimine building units. In particular examples thereof, the dendrimer has only polyamidoamine (PAMAM), poly(etherhydroxylamine) (PEHAM) or polypropyleneimine as the building unit.

The core moiety may contain only 1 point of attachment for a building unit or may contain 2, 3 or more points, which may or may not be further utilized for the attachment of building units. Typically, the point of attachment is a free amino group. Core moieties may consist of, comprise or be derived from a building unit or may be a molecule different to the building units. Exemplary core moieties are illustrated herein and described in PCT/AU2007/000352.

The liposomes and dendrimers may be combined with any suitable pharmaceutical carrier for intravenous administration. Intravenous administration of the composition is the preferred route since it is the least invasive. Other routes of administration are possible, if desired. Suitable pharmaceutically acceptable carriers include saline, Tris buffer, phosphate buffer, or any other aqueous solution. An appropriate dosage can be established by procedures well known to those of ordinary skill in the art.

D. Therapeutic Uses of the Conjugates of the Invention

It will be appreciated that the clinical condition that can be treated with the conjugates of the invention will depend on the specificity of the nucleic acid which forms part of the conjugates. Thus, the conjugates of the invention can be used for the treatment of any disease which can be improved by knocking down a gene of interest in a cell that expresses a neurotransmitter transporter. The skilled person will understand that the conjugates are useful for the treatment of diseases characterized by abnormal expression of a protein in a cell (e.g. accumulation of α-synuclein in Lewy bodies) or for diseases wherein the target protein is expressed at normal levels but which can be improved by decreasing the expression of said target protein.

D.1. Conjugates Comprising Nucleic Acids Targeted to $5\text{-HT}_{1a}$ Receptors, Serotonine Transporter or Ion Channels Located in Serotonergic Neurons As mentioned above, when a SSRI is administered to a subject in need thereof, there is a negative feedback mechanism that takes place as a result of the activation of $5\text{-HT}_{1A}$ receptors located in serotonergic neurons (the pre-synaptic $5\text{-HT}_{1A}$R). The action of SSRI leads to high serotonin levels induced by the blockage of serotonin reuptake mediated by the serotonin reuptake transporters (SERT), which are located in the serotonergic neurons. This fact will not only activate the postsynaptic serotonin receptors, but also pre-synaptic $5\text{-HT}_{1A}$R, which serve as a feedback sensor for the cell. The activation of these $5\text{-HT}_{1A}$R causes a decrease in serotonin levels because of the suppression of cell firing and impulse-dependent serotonin release, therefore limiting the effect of the administered SSRI.

This effect is shown for instance in examples 2 and 3 of the present invention, wherein it is shown that the infusion of a conjugate comprising sertraline and a $5\text{-HT}_{1A}$R-specific siRNA are capable of preventing the hypothermic response induced by the selective $5\text{-HT}_{1A}$R agonist). This effect allows the use of the conjugates of the invention in all those clinical conditions wherein it is desired to knock-down the expression of a gene which is complementary to the nucleic acid forming part of the conjugates.

This is a significant discovery in the field of antidepressant therapy, since the oligonucleotides of the invention can be useful in order to neutralise the adverse effects of commercial SSRIs mentioned above, namely, slow onset of action and limited efficacy. Additionally, by employing the highly selective oligonucleotide constructions of the present invention, only low doses of the therapeutic oligonucleotide need to be administered to achieve the desired effect. As a result, the constructions of the invention are useful in the treatment of diseases which are related to an abnormal concentration of serotonin that is present in the synaptic area, especially those that are related to the deficient transmission of serotonin (i.e. decreased levels of serotonin concentration in the synapse), such as depression-related disorders.

Accordingly, if the nucleic acid is targeted against a component of the presynaptic serotoninergic neurons, the conjugates will be adequate for the treatment of diseases wherein a decreased activity of the presynaptic serotoninergic neurons is required. Thus, in another aspect, the invention relates to a conjugate of the invention wherein (i) the selectivity agent is selected from the group of a selective serotonin reuptake inhibitor (SSRI), a serotonin-norepinephrine reuptake inhibitor (SNRI) or a noradrenergic and a specific serotoninergic antidepressant (NASSA) and (ii) the oligonucleotide is capable of specifically binding to a target molecule selected from the group of the serotonin receptor type 1A ($5\text{-HT}_{1A}$) mRNA, the serotonine transporter mRNA, the TREK-1 mRNA, the serotonin receptor type 1A ($5\text{-HT}_{1A}$) polypeptide, the serotinine transporter polypeptide and the TREK-1 polypeptide for use in the treatment or prevention of a depression-related disorder.

Alternatively, the invention relates to a method for treatment or prevention of a depression-related disorder which comprises the administration to a subject in need thereof of the conjugate of the invention wherein (i) the selectivity agent is selected from the group of a selective serotonin reuptake inhibitor (SSRI), a serotonin-norepinephrine reuptake inhibitor (SNRI) or a noradrenergic and a specific serotoninergic antidepressant (NASSA) and (ii) the oligonucleotide is capable of specifically binding to a target molecule selected from the group of the encoding the serotonin receptor type 1A ($5\text{-HT}_{1A}$) mRNA, the serotonine transporter mRNA, the TREK-1 mRNA, the serotonin receptor type 1A ($5\text{-HT}_{1A}$) polypeptide, the serotinine transporter polypeptide and the TREK-1 polypeptide.

The expression “depression-related disorder”, as used herein, refers to those conditions which are charactreised by an abnormally low level of serotonin in the synapse and which are defined in the Diagnostic and Statistical Manual of Mental Disorders—Fourth Edition (DSM-IV), published by the American Psychiatric Association, Washington D.C. and includes, without limitation, major depression, long-term depression, treatment resistant depression, dysthymia, mental states of depressed mood characterised by feelings of sadness, despair, discouragement, “blues”, melancholy, feelings of low self esteem, guilt and self reproach, withdrawal from interpersonal contact, and somatic symptoms such as eating and sleep disturbances. Preferably, the depression-related disorder is selected from the group consisting in: major depression, obsessive-compulsive disorder (OCD), pervasive developmental disorders (PDDs), post-traumatic stress disorder (PTSD), anxiety disorders, bipolar disorders, eating disorders and chronic pain.

Figure 8:
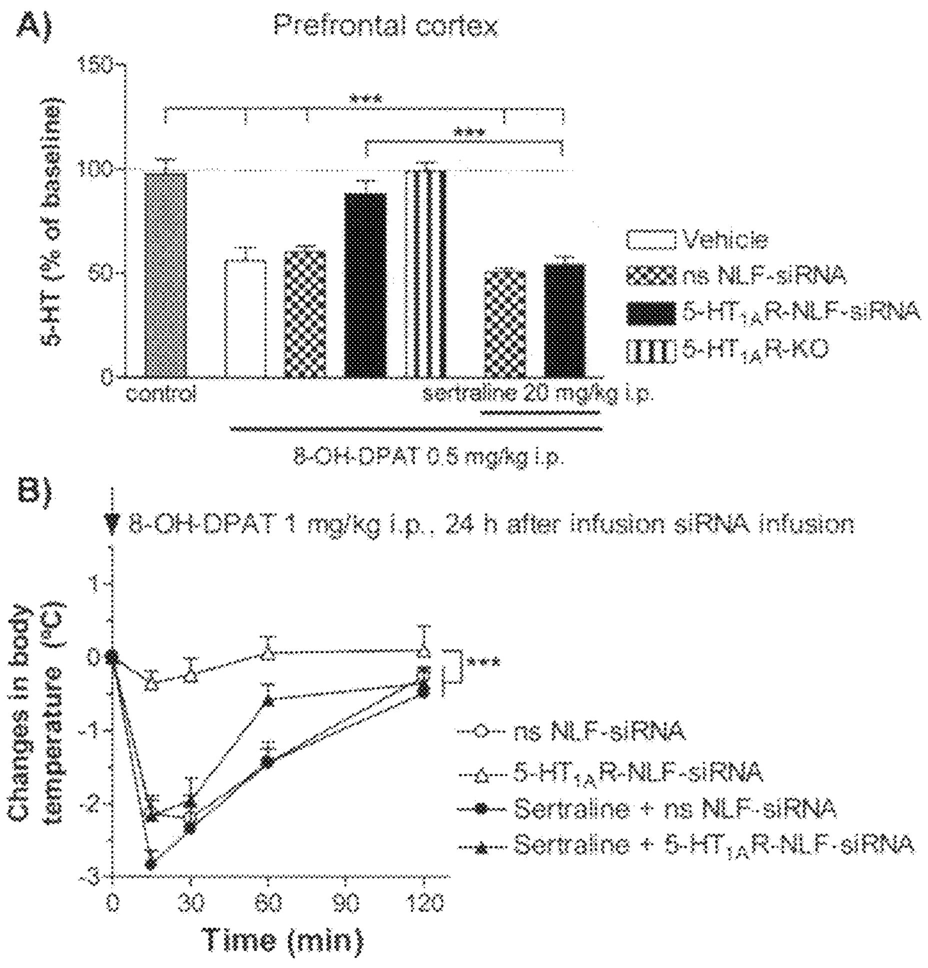
FIG. 8. Effect of sertraline (selective inhibitor of serotonin transporter-5-HTT) on delivery of conjugated 5-$HT_{1A}$R-NLF-siRNA to 5-HT neuron. A) Acute sertraline injection (20 mg/kg i.p.) avoided the silencing of 5-$HT_{1A}$ autoreceptor by conjugated 5-$HT_{1A}$R-NLF-siRNA and the acute 8-OHD-PAT administration (selective 5-$HT_{1A}$R agonist, 0.5 mg/kg i.p.) reduced the 5-HT levels in medial prefrontal cortex. The groups of mice were: i) vehicle, ii) nonsense NLF-siRNA (ns NLF-siRNA), iii) 5-$HT_{1A}$R-targeting NLF-siRNA (5-$HT_{1A}$R-NLF-siRNA) and iv) 5-$HT_{1A}$R knockout (5-$HT_{1A}$R-KO). Mice received an acute injection of the selective 5-HTT inhibitor, sertraline (20 mg/kg i.p.) 3 h before siRNA infusion into D3V (30 μg/2.5 μl/1 day, i.c.v.). In addition, a group of mice received vehicle i.p. and vehicle into D3V. The microdialysis experiments were conducted 24 h after i.c.v. vehicle or siRNA administrations. Data are expressed as percentage of baseline and are shown as mean±SEM (n=5-8 mice/group). * $p<0.001$ significantly different from control and 5-$HT_{1A}$R-NLF-siRNA groups, using one-way ANOVA followed by multiple comparison Newman-Keuls test. B) Effect of 8-OH-DPAT administration (1 mg/kg i.p.) on body temperature in NLF-siRNA mice previously treated with selective 5-HTT inhibitor, sertraline (20 mg/kg i.p.). The groups of mice were similar than in panel A. Unlike 5-$HT_{1A}$R-NLF-siRNA group, 8-OH-DPAT administrations produced a hypothermia response in sertraline-pretreated 5-HT1AR-NLF-siRNA mice. Values are shown as mean of changes in body temperature±SEM from 6-10 mice per group. * $p<0.001$ using two-way ANOVA followed by multiple comparison Newman-Keuls test.

Additionally, the conjugates of the invention comprising a selectivity reagent specific for serotonergic neurons and an oligonucleotide that down-regulates the $5\text{-HT}_{1A}$ receptor, the serotonin release at the prefrontal cortex is increased approximately 150-200% of the baseline value as compared with the 50% increase produced by the antidepressant alone (see FIG. 8). As mentioned before, traditional antidepressants are designed to improve the transmission of serotonin but have limited effects due to the activation of the pre-synaptic 5-$HT_{1A}$ receptors. Thus, with the oligonucleotide constructions of the invention the major limitations of said anti-depressants (slow onset of action and limited efficacy) are overcome. As a result, a positive response to the antidepressant treatment can be achieved within a short period of time and the number of patients responding to the treatment can be improved in relation to the treatment with only the commercial anti-depressants (i.e. SSRI). Thus, in another aspect, the invention relates to a method for the treatment of a depression-related disorder which comprises the administration of a conjugate according to the invention and an anti-depressant.

The oligonucleotide construction of the invention can simultaneously be administered with the current anti-depressants (SSRIs, NARIs, MAOI, TCA, etc.). The administration of an oligonucleotide sequence blocking the expression of the 5-$HT_{1A}$ autoreceptors allows to improve the effect of these antidepressants by inhibiting the attenuation of the extracellular 5-HT increase produced by reuptake blockade.

D.2. Conjugates Comprising Nucleic Acids Targeted to Synuclein

In another aspect, the invention relates to a conjugate of the invention wherein (i) the selectivity agent is selected from the group of a dopamine reuptake inhibitor (DRI) and a Norepinephrine-Dopamine Reuptake Inhibitor (NDRI) and (ii) the oligonucleotide is capable of specifically binding to a target molecule which is the mRNA encoding alpha-synuclein or the alpha-synuclein polypeptide for the treatment or prevention of a disease associated with the deposition of Lewy bodies.

The term "disease associated with the deposition of Lewy bodies" refers to a condition which is characterised by disorders of alpha-synuclein metabolism, which gives rise to the formation of abnormal neuronal alpha-synuclein inclusions. More particular Lewy body disorders include Parkinson's disease (PD), dementia with Lewy bodies (DLB), PD with dementia (PDD) and multiple system atrophy.

Preferably, the conjugate of the present invention may be administered together with a commercial antidepressant, such as a SSRI, for the treatment of depression and/or depression-related disorders.

D.3. Conjugates Comprising Nucleic Acids Targeted to the Norepinephrine Transporter As explained in the background section, an increase in mesocortical DA transmission may be useful for the treatment of schizophrenia. Since the NA transporter (NAT) shows a similar affinity for NA and DA, NAT inhibitors preferentially increase the extracellular DA concentration in the medial PFC (mPFC) compared to caudate and nucleus accumbens (NAc). Hence, NA axons from locus coeruleus (LC) neurons may contribute to regulate the extracellular DA concentration in PFC either by taking up or co-releasing DA.

In another aspect, the invention relates to a conjugate of the invention wherein (i) the selectivity agent is selected from the group of a dopamine reuptake inhibitor, a noradrenaline reuptake inhibitor, a serotonine-noradrenaline reuptake inhibitor and a norepinephrine-Dopamine Reuptake Inhibitor (NDRI) and (ii) the oligonucleotide is capable of specifically binding to a target molecule which is the mRNA encoding the norepinephrine transporter or the norepinephrine polypeptide for the treatment or prevention of a disease mediated by or responsive to the inhibition of norepinephrine reuptake.

Such medical conditions include, by way of example, pain disorders such as neuropathic pain and chronic pain, depressive disorders such as major depression, affective disorders such as an anxiety disorder, attention deficit hyperactivity disorder, cognitive disorders such as dementia, and stress urinary incontinence.

D.4. Conjugates Comprising Nucleic Acids Targeted to Dopamine-Beta-Hydroxylase

As explained in the background section, an increase in mesocortical DA transmission may be useful for the treatment of schizophrenia. This increase may be achieved by the use of inhibitors of the noradrenaline transporter or, alternatively, by inhibiting dopamine-beta-hydroxilase. This enzyme is responsible for the conversion from dopamine to noradrenaline and thus, when knocked down, would result in an increase in the level of dopamine in NA neurons. This will result in turn in noradrenergic vesicles containing NA and a higher level of DA. This increase the DA level in NA protection zones improving the cognitive and memory related function in the brain.

Thus, in another aspect, the invention relates to a conjugate of the invention wherein (i) the selectivity agent is selected from the group of a norepinephrine transporter inhibitor (SDNRI) and a Norepinephrine-Dopamine Reuptake Inhibitor (NDRI) and (ii) the oligonucleotide is capable of specifically binding to a target molecule which is the mRNA encoding dopamine-beta-hydroxylase or the dopamine-beta-hydroxylase polypeptide for the treatment or prevention of a disease associated with a dopamine deficit in noradrenergic projections.

The expression "disease associated with dopamine deficit in noradrenergic projections", as used herein, refers to memory and cognitive process associated with dementia, depression and neurodegenerative diseases.

D.5. Conjugates Comprising Nucleic Acids Targeted to BAX

In another aspect, the invention relates to a conjugate of the invention wherein (i) the selectivity agent is selected from the group of a serotonin-dopamine-norpeinephrine reuptake inhibitor (SDNRI) and a Norepinephrine-Dopamine Reuptake Inhibitor (NDRI) and (ii) the oligonucleotide is capable of specifically binding to a target molecule which is the mRNA encoding BAX or the BAX polypeptide for the treatment or prevention of a disease associated with neuronal apoptosis and cell death.

The term "disease associated with neuronal apoptosis and cell death", as used herein, refers to the 'end-point' of many human neurological disorders, including but not limited to Alzheimer's, Parkinson's and Huntington's diseases, stroke/trauma, multiple and amyotrophic lateral sclerosis. Apoptotic death of hippocampal and cortical neurons is responsible for the symptoms of Alzheimer's disease; death of midbrain neurons that use the neurotransmitter dopamine underlies Parkinson's disease; Huntington's disease involves the death of neurons in the striatum, which control body movements; and death of lower motor neurons manifests as amyotrophic lateral sclerosis. Additionally, brain ischemia and trauma induce necrosis of a small brain area, which then propagates neuronal cell loss by apoptosis to a larger brain area, due to the neurotoxic material released by the necrotic cells. Apoptotic neuronal cell loss is also observed in the ageing brain, as a physiological process.

D.6. Conjugates Comprising Nucleic Acids Targeted to Tau

In another aspect, the invention relates to a conjugate of the invention wherein (i) the selectivity agent is selected from the group of a serotonin-dopamine-norpeinephrine reuptake inhibitor (SDNRI) and a Norepinephrine-Dopamine Reuptake Inhibitor (NDRI) and (ii) the oligonucleotide is capable of specifically binding to a target molecule which is the mRNA encoding tau or the Tau polypeptide for use in the treatment or prevention of a tau associated disease.

The term "tau associated disease", as used herein, refers to diseases associated with abnormalities in Tau as well as diseases that are "tauopathies." Tau-associated diseases include, but are not limited to, frontotemporal dementia, including the subtype of frontotemporal dementia and Parkinsonism linked to chromosome 17 (FTDP-17), progressive supranuclear palsy, corticobasal degeneration, Pick's disease, agyrophilic grain disease, as well as Parkinson's disease, Down syndrome, post-encephalic Parkinsonism, myotonic dystrophy, Niemann-Pick C disease, dementia pugilistica, Blint disease, prion diseases, amyotrophic lateral sclerosis, Parkinsonism-dementia complex of Guam, multiple sclerosis, glaucoma, diabetic retinopathy, and traumatic brain injury; as well as Huntington's disease, Lewy body dementia, Charcot-Marie-Tooth disease, hereditary spastic paraplegia, and multiple system atrophy. "Tauopathy" as defined herein means a neurodegenerative disease associated with fibrillar forms of Tau protein (tangles) in brain. These diseases include AD; however, other tauopathies include, but are not limited to, frontotemporal dementia, including the subtype of frontotemporal dementia and Parkinsonism linked to chromosome 17 (FTDP-17), progressive supranuclear palsy, corticobasal degeneration, Pick's disease, and agyrophic grain disease.

D.7. Conjugates Comprising Nucleic Acids Targeted to Huntingtin

In another aspect, the invention relates to a conjugate of the invention wherein (i) the selectivity agent is selected from the group of a serotonin-dopamine-norpeinephrine reuptake inhibitor (SDNRI) and a Norepinephrine-Dopamine Reuptake Inhibitor (NDRI) and (ii) the oligonucleotide is capable of specifically binding to a target molecule which is the mRNA encoding Huntingtin or the Huntingtin polypeptide for the treatment or prevention of a huntingtin-associated disease.

The term "huntingtin-associated disease", as used herein, refers to diseases caused by aberrant conformation or aggregation or expression of mutant huntingtin protein and includes, without limitation, Huntington disease and variants thereof.

The amount of the therapeutic of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs. Suitable dose ranges for intracranial administration are generally about 10 3 to 10 15 infectious units of viral vector per microliter delivered in 1 to 3000 microliters of single injection volume. Addition amounts of infections units of vector per micro liter would generally contain about 10 4, 10 5, 10 6, 10 7, 10 8, 10 9, 10 10, 10 11, 10 12, 10 13, 10 14 infectious units of viral vector delivered in about 10, 50, 100, 200, 500, 1000, or 2000 microliters. Effective doses may be extrapolated from dose-responsive curves derived from in vitro or in vivo test systems.

For the intraventricular administration of the conjugates of the invention, multiple catheters having access ports can be implanted in a given patient for a complete therapy.

In a preferred embodiment, there is one port and catheter system per cerebral or cerebellar hemisphere, and perhaps several. Once the implantations are performed by a neurosurgeon, the patient's neurologist can perform a course of therapy consisting of repeated bolus injections of the conjugates over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned, or explanted as well. The device material should not interfere with magnetic resonance imaging, and, of course, the small interfering RNA preparations must be compatible with the access port and catheter materials and any surface coatings.

E. Synthesis of the Conjugates of the Invention

The conjugates of the invention are typically synthesized using standard procedures in organic synthesis. The skilled person will appreciate that the exact steps of the synthesis will depend on the exact structure of the conjugate which has to be synthesized. For instance, if the conjugate comprises a single nucleic acid strand conjugated to the selectivity agent through its 5' end, then the synthesis is usually carried out as explained below by contacting an amino-activated oligonucleotide and a reactive activated selectivity reagent.

Wherein the conjugate comprises a double stranded nucleic acid, then the sense and antisense strands are synthesized separately and annealed in vitro using standard molecular biology procedures. In a typical conjugate, the first the nucleic acid strands carries the selectivity agent and the second nucleic acid strands carries a protecting group. In a still more preferred embodiment, the selectivity agent is coupled to the 5' end of the first nucleic acid strand and/or the protecting group is attached to the 5' end of the second nucleic acid strand, although the attachment of the selectivity agent or of the protecting group can also be carried out at the 3' ends of the nucleic acid strands.

Synthesis of the conjugates can be carried out as follows:

[1] Conjugates Having the Structure

Selectivity agent-[Oligonucleotide]-3' are typically synthesized using the following steps:

(i) Activating the selectivity agent. Preferably, the activation group in the selectivity agent is a succinimide group or an amino group;

(ii) Activating the oligonucleotide on its 5' end. Preferably, the activation group in the oligonucleotide is amino group (wherein the selectivity agent has been activated by a succinimide group) or a carboxyl group (wherein the selectivity agent has been activated by an amine group) and (iii) contacting the activated selectivity agent with the activated oligonucleotide under conditions adequate for the reaction between the two activation groups.

[2] Conjugates Having the Structure

Protecting group-[Sense strand]-3'3'-[Antisense strand]-Selectivity agent are typically synthesized using the following steps:

(i) Activating the selectivity agent. Preferably, the activation group in the selectivity agent is a succinimide or an amino group, (ii) Activating the sense strand on its 5' end. Preferably, the activation group in the oligonucleotide is amino group (wherein the selectivity agent has been activated by a succinimide group) or a carboxyl group (wherein the selectivity agent has been activated by an amine group), (iii) contacting the activated selectivity agent with the activated sense strand under conditions adequate for the reaction between the two activation groups, (iv) Adding the protecting group to the immobilised antisense strand. This step is preferably carried out using an oligonucleotide which reactive groups are blocked by acetylation or benzylation (the furanose groups), 2-cyanoethylation (the phosphodiester linkages) and FMOC (the exocyclic amino groups).

(v) Annealing the sense and antisense strands

E.1. Synthesis of Conjugates Comprising a Nucleic Acid and SSRI Attached to the 5' End The conjugates of the invention can be prepared using techniques known by those skilled in the art. The synthesis of conjugates may involve the selective protection and deprotection of functional groups. Suitable protecting groups are well known for the skilled person in the art. For example, a general review of protecting groups in organic chemistry is provided by Wuts, P. G. M. and Greene T. W. in *Protecting Groups in Organic Synthesis* ($4^{th}$ Ed. Wiley-Interscience), and by Kocienski P. J. in *Protecting Groups* ($3^{rd}$ Ed. Georg Thieme Verlag).

In the context of the present invention, the following terms have the meaning detailed below:

The term "$C_1$-$C_6$ alkyl" relates to a linear or branched hydrocarbon radical consisting of carbon and hydrogen atoms, which does not contain unsaturation, having one to six, preferably one to three ($C_1$-$C_3$ alkyl), carbon atoms and which is joined to the rest of the molecule by a single bond. Examples of alkyl groups include but are not limited to alkyl groups such as methyl, ethyl, propyl, isopropyl, butyl, isobutyl, t-butyl, pentyl and hexyl. Preferably alkyl refers to methyl.

The term "halogen" refers to to bromo, chloro, iodo or fluoro.

The term "haloalkyl" refers to an alkyl group as defined above wherein at least one hydrogen atom has been replaced by halogen. Examples of haloalkyl groups include but are not limited to $CF_3$, $CCl_3$, $CHF_2$, $CF_2CF_3$. Preferably haloalkyl refers to $CF_3$.

The term "$C_6$-$C_{10}$ aryl" refers to an aromatic group having between 6 and 10 carbon atoms, comprising 1 or 2 aromatic nuclei, bound by means of a carbon-carbon bond or fused, including for example phenyl, naphthyl and diphenyl. Preferably "aryl" refers to phenyl.

The term "heterocyclyl" refers to a stable 3- to 10-membered ring radical, preferably a 5- or 6-membered ring, which consists of carbon atoms and from one to five heteroatoms selected from the group consisting of nitrogen, oxygen, and sulphur and which can be partially or fully saturated or aromatic ("heteroaryl"). For the purposes of this invention, the heterocycle can be a monocyclyl, bicyclyl or tricyclyl ring system, which can include systems of fused rings. In a particular embodiment, the heterocyclyl group is succinimide.

The compounds of the present invention represented by the above described formula (I) may include stereisomers depending on the presence of chiral centres. The single isomers, enantiomers or diastereoisomers and mixtures thereof fall within the scope of the present invention.

Unless otherwise indicated, the compounds used in the invention are intended to include compounds that only differ in the presence of one or more isotopically enriched atoms. For example, compounds having the present structures except for the substitution of a hydrogen with deuterium or tritium, or the substitution of a carbon with a $^{13}C$— or $^{14}C$-enriched carbon or a $^{15}N$-enriched nitrogen are within the scope of this invention.

i. Synthesis Using an Amino-Derivatized Nucleic Acid and an Activated Sertraline-Derivative In a first embodiment, the conjugates according to the invention may be obtained by coupling a amino-derivatized nucleic acid to an activated derivative form of sertraline or analog thereof, wherein the activated derivative of a selectivity agent is a compound of formula (II):

(II)

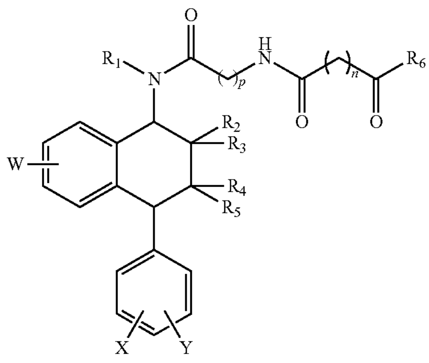

wherein $R^1$, $R^2$, $R^3$, $R^4$ and $R^5$ are independently selected from hydrogen and $C_1$-$C_6$ alkyl;

X and Y are independently selected from hydrogen, halogen, $C_1$-$C_3$ alkyl, $C_1$-$C_3$ haloalkyl, $OR^a$ and $SR^b$, wherein $R^a$ and $R^b$ are independently selected from $C_1$-$C_3$ alkyl and $C_6$-$C_{10}$ aryl;

$R^6$ is a carbonyl activating radical;

W is selected from hydrogen, halogen, CN, $NO_2$, $C_1$-$C_3$ alkyl, $C_1$-$C_3$ haloalkyl, $NR^cR^d$, $SO_2NR^eR^f$, $NR^gSO_2R^h$, $CO_2R^i$, wherein $R^c$, $R^d$, $R^e$, $R^f$, $R^g$, $R^h$ and $R^i$ are independently selected from hydrogen and $C_1$-$C_3$ alkyl;

n and p are selected from 1, 2, 3, 4, 5, 6, 7, 8, 9, 10, 11, 12 and 13.

The term "carbonyl activating radical" refers to a substituent of a carbonyl that renders that carbonyl prone to nucleophilic addition. In a particular embodiment, it forms, together with the carbonyl group, an anhydride, an acid halide or an ester group. In a preferred embodiment, the carbonyl activating radical is selected from halogen, —OC(O)R, —OR', —SR"; wherein R, R' and R" are independently selected from $C_1$-$C_6$ alkyl, haloalkyl, heterocyclyl, aryl and heteroaryl.

In a particular embodiment, $R^6$ is a succinimidoxy group. Therefore, in another embodiment, the conjugates according to the invention may be obtained by coupling a amino-derivatized nucleic acid to an activated derivative form of sertraline or analog thereof, wherein the activated derivative of a selectivity agent is a compound of formula (III):

(III)

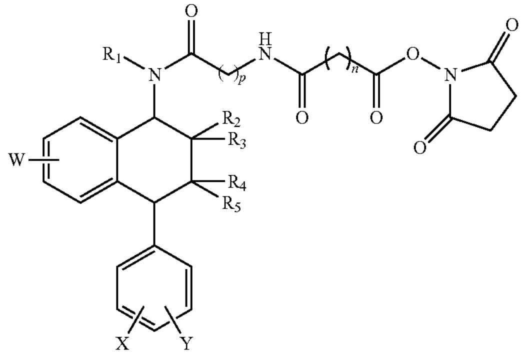

wherein $R^1$, $R^2$, $R^3$, $R^4$ and $R^5$ are independently selected from hydrogen and $C_1$-$C_6$ alkyl;

X and Y are independently selected from hydrogen, halogen, $C_1$-$C_3$ alkyl, $C_1$-$C_3$ haloalkyl, $OR^a$ and $SR^b$, wherein $R^a$ and $R^b$ are independently selected from $C_1$-$C_3$ alkyl and $C_6$-$C_{10}$ aryl;

W is selected from hydrogen, halogen, CN, $NO_2$, $C_1$-$C_3$ alkyl, $C_1$-$C_3$ haloalkyl, $NR^cR^d$, $SO_2NR^cR^f$, $NR^gSO_2R^h$, $CO_2R^i$, wherein $R^c$, $R^d$, $R^e$, $R^f$, $R^g$, $R^h$ and $R^i$ are independently selected from hydrogen and $C_1$-$C_3$ alkyl;

n and p are selected from 1, 2, 3, 4, 5, 6, 7, 8, 9, 10, 11, 12 and 13.

According to a particular embodiment, the activated compound of formula (III) is compound (1):

(1)

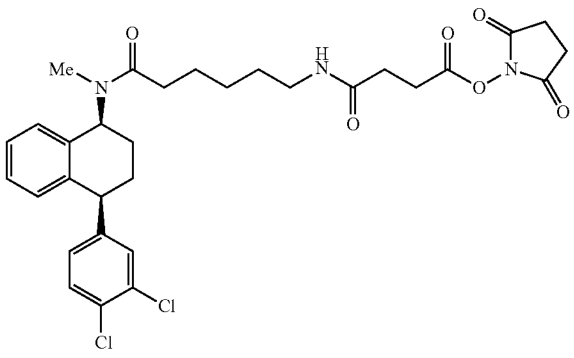

According to one embodiment, the compounds of formula (I) may be prepared by a sequence comprising:

a) reacting a compound of formula (IV)

(IV)

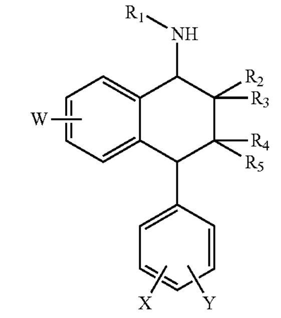

and an acylating agent of formula (V):

(V)

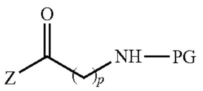

wherein p is as defined above, Z is halogen or OH and PG is an amine protecting group to yield a compound of formula (VI)

(VI)

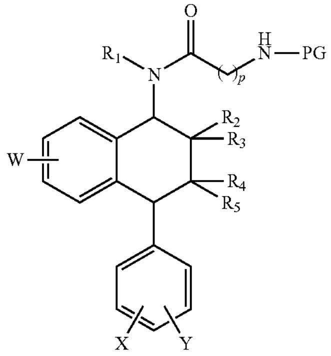

Commonly used protecting groups for amines include carbamates, such as tert-butyl, benzyl, 2,2,2-trichloroethyl, 2-trimethylsilylethyl, 9H-fluorenylmethyl (Fmoc), allyl or nitrophenyl carbamates; amides, such as formamides, acetamides, trifluoroacetamides, sulfonamides, trifluoromethanesulfonyl amides or tert-butylsulfonyl amides; and aryl or arylakylamines, such as p-methoxyphenyl, benzyl, p-methoxybenzyl, 3,4-dimethoxybenzyl, dimethoxytrityl or monomethoxytrityl amines. In a particular embodiment, the acylating agent of formula (V) is 9H-fluorenylmethoxycarbonyl-6-aminohexanoic acid.

Compounds of formula (IV) can in turn be prepared for example as described in U.S. Pat. No. 6,455,736. In particular, when the compound of formula (IV) is sertraline, it can be obtained from the corresponding chlorohydrate (commercially available) by treatment with a suitable base, including organic or inorganic bases such a alkali or alkaline earth carbonates or hydroxides, ammonia or amines, such as trimethylamine, triethylamine, diisopropylethylamine, pyridine, piperidine, morpholine and the like.

b) deprotecting the amino protecting group in the compound of formula (IV) to yield a compound of formula (VII):

(VII)

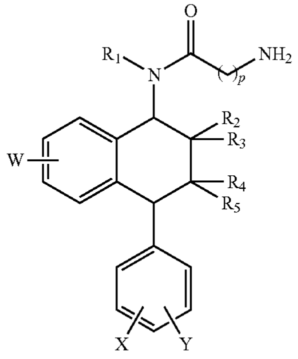

Suitable deprotecting conditions are known for the skilled person, for example in *Protecting Groups in Organic Synthesis* (Wuts, P. G. M. and Greene T. W., 4th Ed. Wiley-Interscience) and in *Protecting Groups* (Kocienski P. J., 3rd Ed. Georg Thieme Verlag). In a particular embodiment, the protecting group is removed in the presence of an amine, such as piperidine, morpholine, dicyclohexylamine, diisopropylethylamine or dimethylaminopyridine, preferably in the presence of piperidine.

c) reacting the compound of formula (VII) with an acylating agent of formula (VIII) or (IX):

(VII)

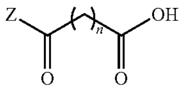

(IXI)

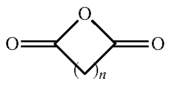

wherein n is as defined above and Z is halogen or OH, leading to a compound of formula (X):

(X)

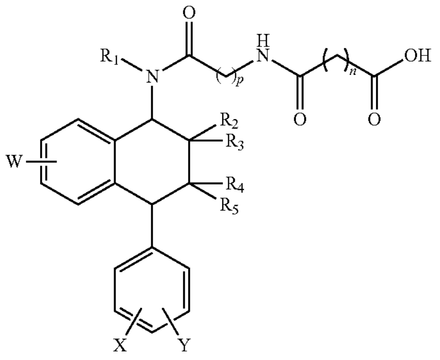

In a particular embodiment, the acylating agent of formula (VII) is succinic anhydride, d) treating a compound of formula (X) with a carbonyl activating group.

The term “carbonyl activating group” refers to a compound that converts the carbonyl of a carboxylic acid group to one that is more prone to nucleophilic addition, such as e.g. anhydrides, carboxylic acid halides, carbodiimides, halogenating agents, disulfides, etc. In a particular embodiment, the carbonyl activating group is selected from halogentaing agent, R(O)COC(O)R, RC(O)halogen, R'OH, R"SH, R"SSR"; wherein R, R' and R" are independently selected from $C_1$-$C_6$ alkyl, haloalkyl, heterocyclyl, aryl and heteroaryl.

In a particular embodiment, the carbonyl activating group is N-hydroxy-succinimide. In this case, the reaction is preferably performed in the presence of a further carbonyl activating group.

Therefore, in a particular embodiment, step d) comprises treating a compound of formula (X) with N-hydroxysuccinimide in the presence of a further carbonyl activating group.

Carbonyl activating group suitable for this process include carbodiimides, such as dicyclohexylcarbodiimide (DCC) and diisopropylcarbodiimide (DIC) and triazolols, such as 1-hydroxy-benzotriazole (HOBt) and 1-hydroxy-7-aza-benzotriazole (HOAt). In a preferred embodiment, the compound of formula (VI) is reacted with N-hydroxysuccinimide in the presence of diisopropylcarbodiimide to afford the activated derivative of formula (II).

According to another aspect, the invention is directed to an intermediate of formula (VI), (VI)

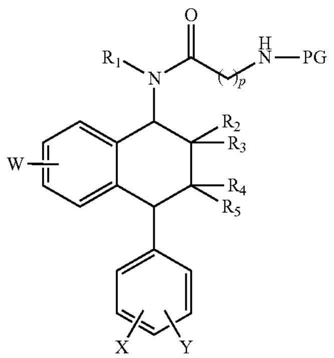

wherein $R^1$-$R^5$, X, Y, W, p and PG are as defined above. In a preferred embodiment, $R^1$ is methyl, $R^2$-$R^5$ are hydrogen, X and Y are chloride, W is hydrogen, p is 5 and PG is 9H-fluorenylmethoxycarbonyl. More preferably, the compound of formula (VI) is compound (2)

(2)

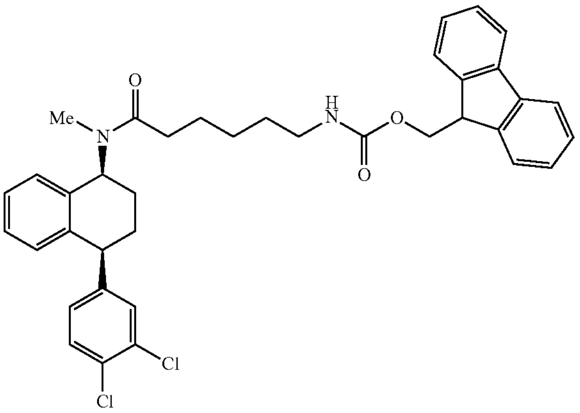

According to another aspect, the invention is directed to an intermediate of formula (VII), (VII)

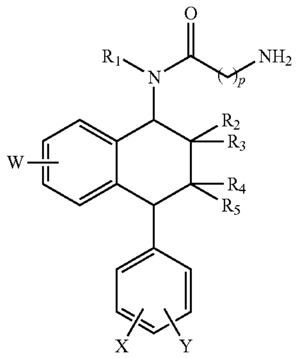

wherein $R^1$-$R^5$, X, Y, W and p are as defined above. In a preferred embodiment, $R^1$ is methyl, $R^2$-$R^5$ are hydrogen, X and Y are chloride, W is hydrogen and p is 5. More preferably, the compound of formula (V) is compound (3)

(3)

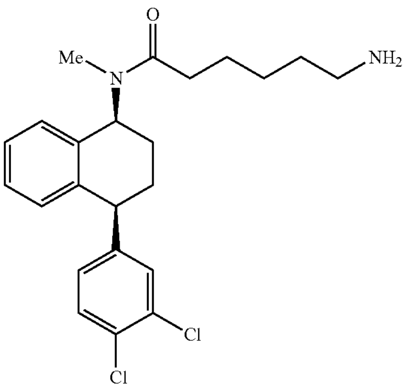

According to another aspect, the invention is directed to an intermediate of formula (X)

(X)

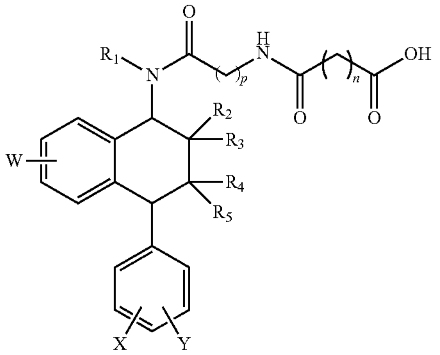

wherein $R^1$-$R^5$, X, Y, W, p and n are as defined above. In a preferred embodiment, $R^1$ is methyl, $R^2$-$R^5$ are hydrogen, X and Y are chloride, W is hydrogen, p is 5 and n is 2. More preferably, the compound of formula (VIII) is compound (4):

(4)

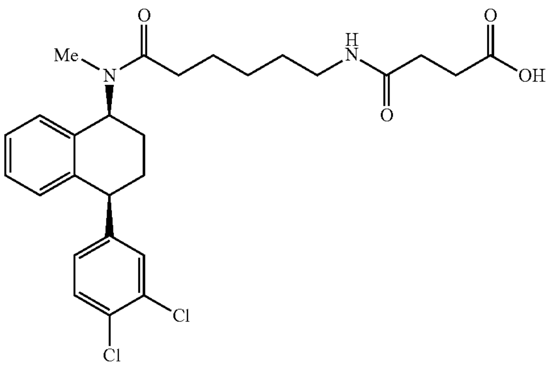

According to another aspect, the invention is directed to an intermediate of formula (II), (II)

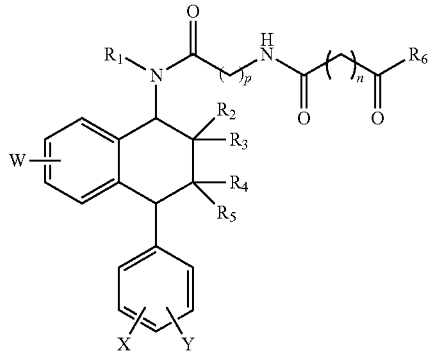

wherein $R^1$-$R^6$, X, Y, W, p and n are as defined above

According to another aspect, the invention is directed to an intermediate of formula (III)

(III)

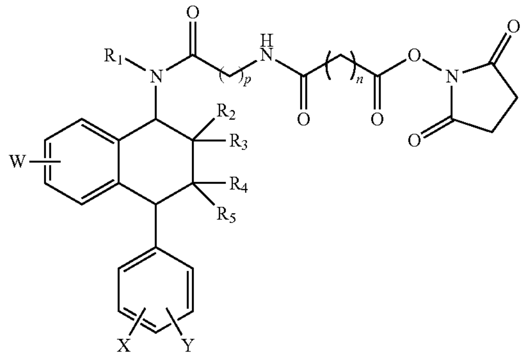

wherein $R^1$-$R^5$, X, Y, W, p and n are as defined above. In a preferred embodiment, $R^1$ is methyl, $R^2$-$R^5$ are hydrogen, X and Y are chloride, W is hydrogen, p is 5 and n is 2. More preferably, the compound of formula (II) is compound (1):

(1)

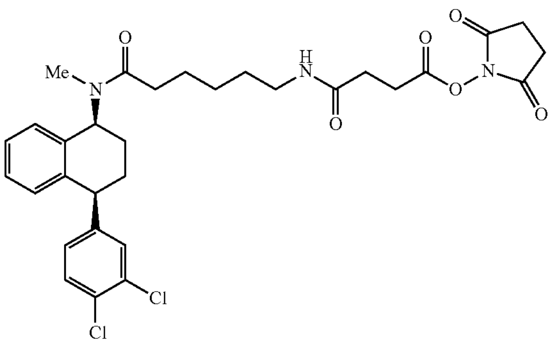

The siRNA strand which is going to be attached to the selectivity agent is formed by stepwise solid phase synthesis on a solid support following the method disclosed in "Oligonucleotide synthesis, a practical approach." edited by M. J. Gait. IRL Press-1985.

In order to conjugate the selectivity ligand, the oligonucleotide needs to be aminoderivatized. This can be done in the 5' or in the 3' end. In a preferred embodiment the selectivity ligand is attached to the 5' end.

According to one embodiment, the conjugates of formula (I) may be prepared by reacting a compound of formula (II) or (III) as described above and an amino-modified oligonucleotide of formula (XII):

(XII)

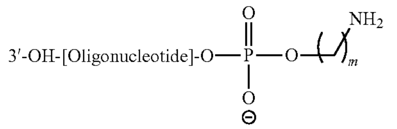

The general procedure for activating an oligonucleotide using an amino linker modifier will typically be according to the scheme below:

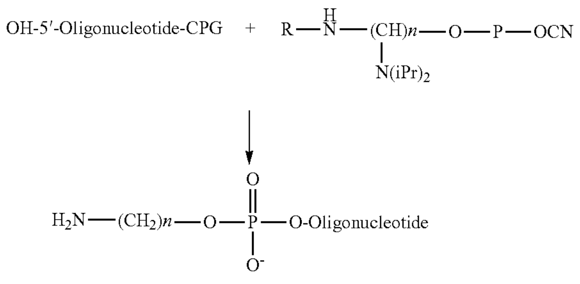

Compounds of formula (XII) may be prepared by reacting the 5'-OH group of an oligonucleotide with an aminomodifier of formula (XIII):

(XIII)

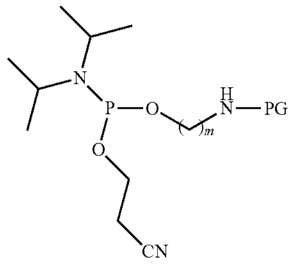

wherein m is as defined above and PG is an amine protecting group. Commonly used protecting groups for amines include carbamates, such as tert-butyl, benzyl, 2,2,2-trichloroethyl, 2-trimethylsilylethyl, 9H-fluorenylmethyl (Fmoc), allyl or nitrophenyl carbamates; amides, such as formamides, acetamides, trifluoroacetamides, sulfonamides, trifluoromethanesulfonyl amides or tert-butylsulfonyl amides; and aryl or arylakylamines, such as p-methoxyphenyl, benzyl, p-methoxybenzyl, 3,4-dimethoxybenzyl, dimethoxytrityl or monomethoxytrityl amines. In a particular embodiment, the amino linker of formula (XIII) is 6-(trifluoroacetylamino) hexyl-[(2-cyanoethyl)-(N,N-diisopropyl)]-phosphoramidite (5'-TFA-C6-aminomodifier-CEP) or 6-(4-Monomethoxytritylamino)hexyl-[(2-cyanoethyl)-(N,N-diisopropyl)]-phosphoramidite (5'-MMT-C6-aminomodifier-CEP).

After coupling the 5'-OH group of the oligonucleotide to the amino linker, the amine protecting group is removed under known conditions. For example, TFA-protected amino-derivatives may be deprotected by treatment with ammonia; whereas MMT-protected amino-derivatives may be deprotected by treatment with acetic acid, chloroacetic acid, dichloroacetic acid or trifluoroacetic acid.

General method of synthesis of the aminomodified oligonucleotide:

(i) prepare a solution of linker/modifier molecule (vacuum dried) in anhydrous acetonitrile (0.1M solution is used in most of the commercially available amidites) and place it into an extra reservoir in your synthesizer (Y)

(ii) at the start of the synthesis of the required oligonucleotide sequence, add the Y base at the 5' end. This will enable the linker/modifier molecule from Y reservoir to couple at the end of the oligonucleotide sequence.

(iii) start the synthesis using the appropriate coupling cycle. The same coupling cycle will be used to carry out the linker/modifier molecule coupling.

(iv) at the end of the oligonucleotide synthesis, wash the support and finally dry the support with gas (v) remove the solid support from the column and transfer it into a screw capped vial and complete the 2 step de-protection.

The aminomodified oligonucleotide should be deprotected for further conjugation with the selectivity agent. For this purpose all the remaining protecting groups in the oligonucleotide are removed as follows. 500 μl of a mixture containing 20% v/v of methylamine (aqueous solution 40% w/v) and 80% v/v of a saturated ammonia solution, (containing 30-32% w/v of $NH_3$) were added to an Eppendorf tube with the oligonucleotide (200 nmole scale). The tube was hermetically closed and heated for 45 minutes to a temperature of 65° C. This procedure eliminates the protecting groups in the phosphorous atom of the nucleotides (acetylation or benzoylation of the furanose and the 2-cyanoethylation of the phosphodiester linkages), and the protecting groups of the exocyclic amino groups (Bz, Ac, IBu). The mixture was then cooled and filtered and the supernatant was dried. The residual pellet was reacted with 1M triethylamine-HF for 3 hours at 65° C. to cleave the protecting groups at 2' of the nucleotides (2'-t-butyl dimethyl silyl—TBDMS). Finally, the resultant solution was desalted in a Sephadex column, leaving a aminomodified-5'-oligonucleotide.

In the case of incorporating the amino modifier linker in the 3'OH terminus; the corresponding polymer support (CPG balls) should be used and the synthesis scheme will correspond to the following diagram:

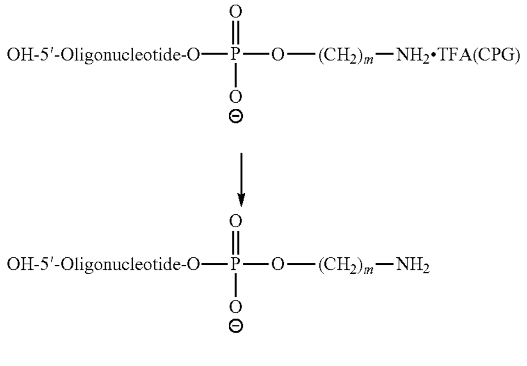

(the hydrolysis can be done by using ammonium hydroxide or Beckman reagent) (methyl amine:Ammonium hydroxide).

In both cases, the de-protection step will be identical and the conjugation approach in such event is also identical but with different degrees of efficiency. In most cases, better results are achieved with 5'-amino derivatization.

In a preferred embodiment, the oligonucleotide may comprise a sequence selected from the group of SEQ ID NO:5 to 12.

The amino activated oligonucleotide is then reacted with the activated derivative of a selectivity agent of formula (II) or (III) as defined above. A conjugate is obtained having the structure (XII)

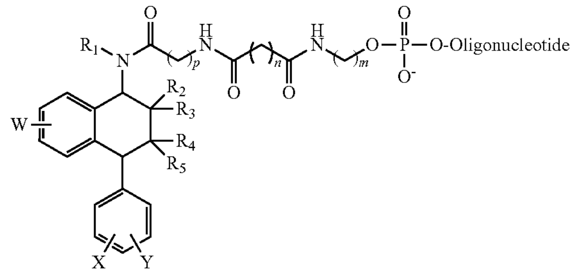

wherein $R^1$-$R^5$, X, Y, W, p and n are as defined above and m is 2 to 10.

In a preferred embodiment, the conjugate has the structure

-continued (XXI)

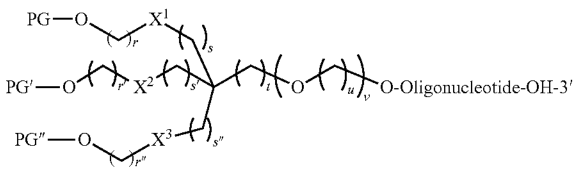

wherein

PG, PG" and PG"' are independently selected from H and a hydroxy protecting group;

r, r', r", s, s', s", t and u are independently selected from 0, 1, 2, 3, 4, 5, 6, 7, 8, 9, 10, 11, 12 and 13;

v is independently selected from 0 and 1; and $X^1$, $X^2$ and $X^3$ are independently selected from $CH_2$, O, S, NH, CO, C(O)O and C(O)NH.

Hydroxy protecting groups, as well as suitable protecting and deprotecting conditions, are known for the skilled person, for example in *Protecting Groups in Organic Synthesis*

(6)

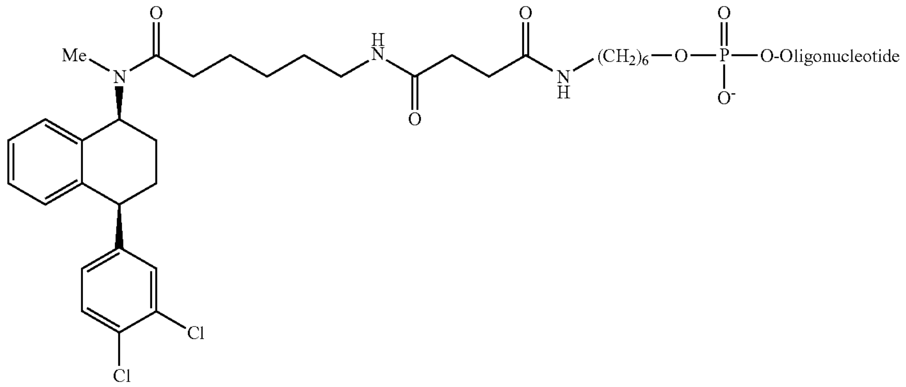

(Wuts, P. G. M. and Greene T. W., 4th Ed. Wiley-Interscience) and in *Protecting Groups* (Kocienski P. J., 3rd Ed. Georg Thieme Verlag).

In a particular embodiment, the oligonucleotide is previously reacted with a bivalent or trivalent phosphoramide. In this way a compound with two or three copupling positions can be obtained, so that two or three molecules of selectivity agent can be coupled to the oligonucleotide. Said two or three molecules of selectivity agent can be similar or different.

In a particular embodiment two or three molecules of the same selectivity agent are coupled to the oligonucleotide. In another embodiment, two or three different selectivity agents are coupled to the oligonucleotide.

In an embodiment, the oligonucleotide is reacted with a bivalent or trivalent phosphoramidite to yield a compound of formula (XX) or (XXI):

(XX)

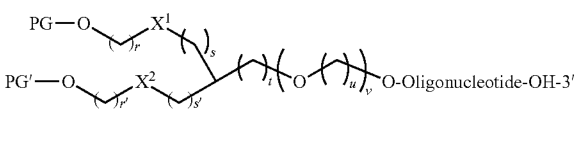

In a particular embodiment, the hydroxy protecting groups are selected from ethers, silyl ethers, esters, sulfonates, sulfenates, sulfenates, carbonates and carbamates. In a preferred embodiment, the hydroxyl protecting groups are selected from acetyl, benzoyl, benzyl, methoxyethoxymethyl ether (MEM), dimethoxytrityl (DMT), methoxymethyl ether (MOM), methoxytrityl (MMT), p-methoxybenzyl ether (PMB), methylthiomethyl ether, pivaloyl (Piv), tetrehydropyranyl (THP), Trityl (Tr), 9H-fluorenylmethyl (Fmoc), trimethyl silyl (TMS), tert-butyldimethylsilyl (TBDMS), tert-butyldimethylsilyloxymethyl (TOM), and triisopropylsilyl (TIPS) ether. Preferably, PG, PG' and PG" are independently selected from H, DMT and Fmoc.

In a particular embodiment, the hydroxyl protecting groups in the compound of formula (XX) or (XXI) are different, so that they can be selectively deprotected and coupled, if desired, with different molecules.

A particular embodiment is directed to a compound of formula (XX) wherein r and r' are 4, s and s' are 1, t and v are 0, $X^1$ and $X^2$ represent C(O)NH and $PG^1$ and $PG^2$ are independently selected from H, DMT and Fmoc. Another embodiment refers to a compound of formula (XX) wherein r is 2, r' is 0, s is 1, s' is 0, t and v are 0, $X^1$ and $X^2$ represent $CH_2$ and $PG^1$ and $PG^2$ are independently selected from H and DMT.

An embodiment is directed to a compound of formula (XXI) wherein r, r' and r'' are 3, s, s' and s'' are 1, t is 1, v is 0, X', $X^2$ and $X^3$ represent 0 and $PG^1$, $PG^2$ and $PG^3$ are independently selected from H and DMT. Another embodiment refers to a compound of formula (XXI) wherein r, r' and r'' are 3, s, s' and s'' are 1, t is 1, u is 3, v is 1, X', $X^2$ and $X^3$ represent 0 and $PG^1$, $PG^2$ and $PG^3$ are independently selected from H and DMT.

Compounds of formula (XX) and (XXI) are then deprotected, if needed, and reacted with an aminomodifier of formula (XIII):

(XIII)

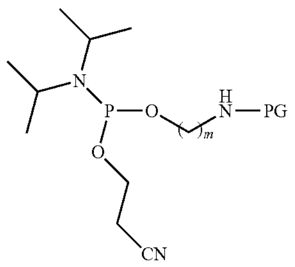

wherein m and PG are as defined above to give a compound of formula (XXII) or (XXIII), respectively:

(XXII)

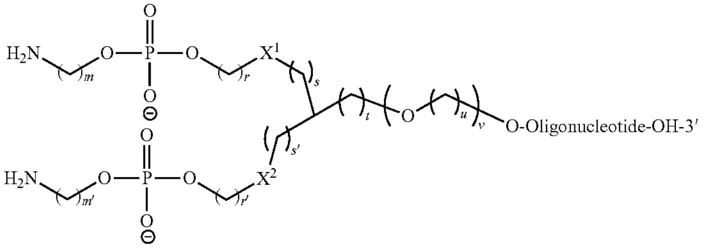

(XXIII)

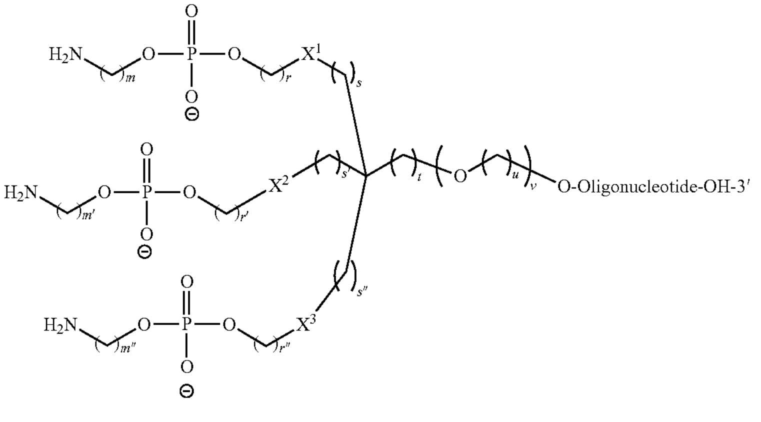

wherein m, m', m'', r, r', r'', s, s', s'', t, u, v, $X^1$, $X^2$ and $X^3$ are as defined previosly.

Compounds of formula (XXII) and (XXIII) can be further reacted with a compound of formula (II), preferable with a compound of formula (III), to yield conjugates (XXIV) and (XXV), respectively:

(XXIV)
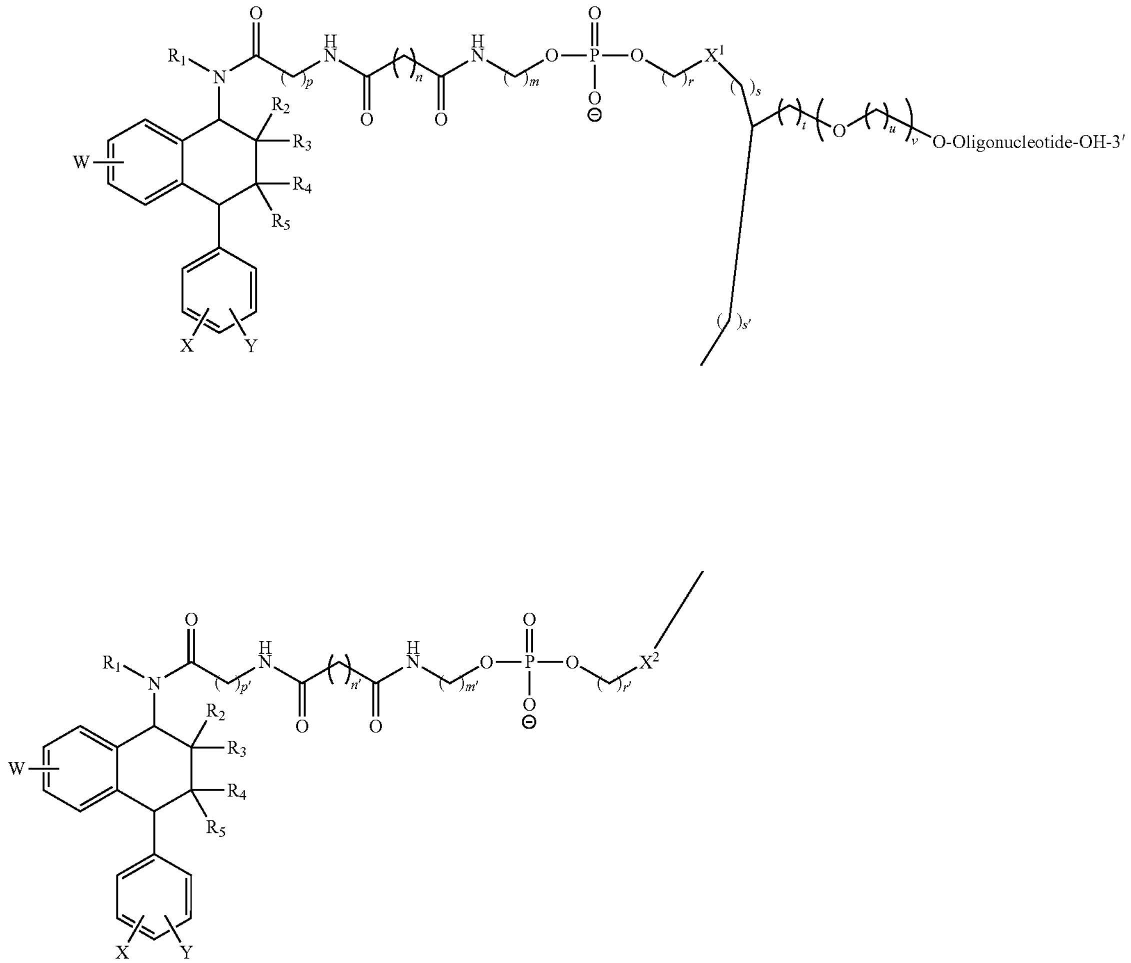
(XXV)
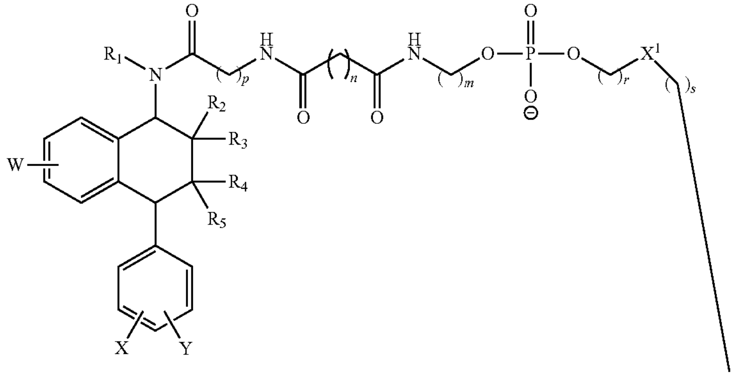

-continued

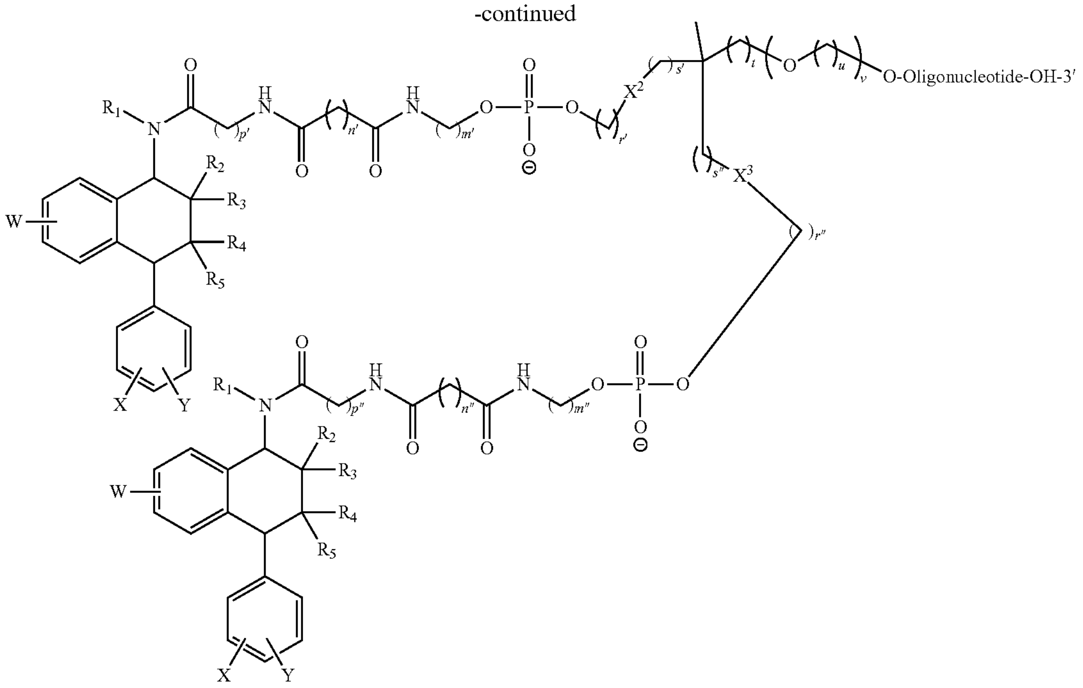

wherein m, m', m", n, n', n", p, p', p", r, r', r", s, s', s", t, u, v, $X^1$, $X^2$, $X^3$, $R^1$-$R^5$, W, X, Y and Z are as previously described.

A particular embodiment is directed to a compound of formula (XXIV) as defined above.

Another embodiment is directed to a compound of formula (XXIV) wherein the selectivity agent is Sertraline, p and p' are 5, n and n' are 2, m and m' are 6, r and r' are 4, s and s' are 1, t and v are 0 and X and X' represent C(O)NH. Another embodiment refers to a compound of formula (XXIV) wherein the selectivity agent is Sertraline, p and p' are 5, n and n' are 2, m and m' are 6, r is 2, r' is 0, s is 1, s' is 0, t and v are 0 and X and X' represent $CH_2$.

A particular embodiment is directed to a compound of formula (XXV) as defined above.

A particular embodiment is directed to a compound of formula (XXV) wherein the selectivity agent is Sertraline, p, p' and p" are 5, n, n' and n" are 2, m, m' and m" are 6, r, r' and r" are 3, s, s' and s" are 1, t is 1, v is 0 and X, X' and X" represent 0. Another embodiment refers to a compound of formula (XXV) wherein the selectivity agent is Sertraline, p, p' and p" are 5, n, n' and n" are 2, m, m' and m" are 6, r, r' and r" are 3, s, s' and s" are 1, t is 1, u is 3, v is 1 and X, X' and X" represent 0.

iI. Synthesis Using a Carboxyl-Derivatized Nucleic Acid and Amino-Derivatized Sertraline In another embodiment, the conjugate of the invention is obtained by the conjugation of a amino-derivatized selectivity agent and a carboxyl-derivatized oligonucleotide.

In a particular embodiment, the activated derivative of a selectivity agent is a compound of formula (VII):

(VII)

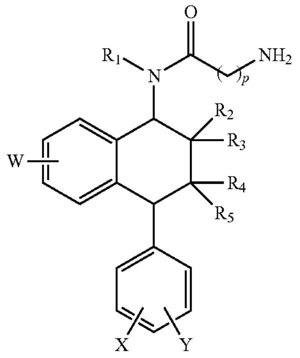

wherein $R_I$, $R_2$, $R_3$, $R_4$ and $R_5$ are independently selected from hydrogen and $C_1$-$C_6$ alkyl;

X and Y are independently selected from hydrogen, halogen, $C_1$-$C_3$ alkyl, $C_1$-$C_3$ haloalkyl, $OR^a$ and $SR^b$, wherein $R^a$ and $R^b$ are independently selected from $C_1$-$C_3$ alkyl and $C_6$-$C_{10}$ aryl;

W is selected from hydrogen, halogen, CN, $NO_2$, $C_1$-$C_3$ alkyl, $C_1$-$C_3$ haloalkyl, $NR^cR^d$, $SO_2NR^eR^f$, $NR^gSO_2R^h$, $CO_2R^i$, wherein $R^c$, $R^d$, $R^e$, $R^f$, $R^g$, $R^h$ and $R^i$ are independently selected from hydrogen and $C_1$-$C_3$ alkyl;

p is selected from 1, 2, 3, 4, 5, 6, 7, 8, 9, 10, 11, 12 and 13.

According to a particular embodiment, the activated compound of formula (II) is compound (3) as described above:

(3)

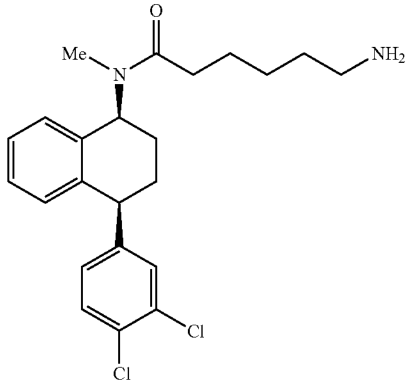

Compounds of formula (VII) may be prepared as described above by a sequence of steps comprising:

(i) reacting a compound of formula (IV)

(IV)

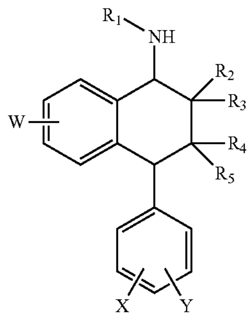

and an acylating agent of formula (V):

(V)

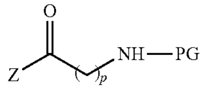

wherein p is as defined above, Z is halogen or OH and PG is an amine protecting group to yield a compound of formula (VI)

(VI)

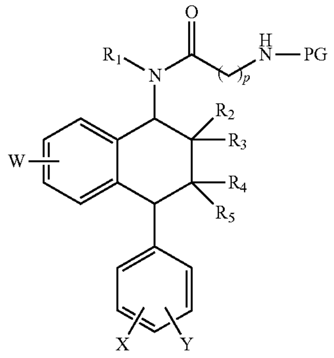

Commonly used protecting groups for amines include carbamates, such as tert-butyl, benzyl, 2,2,2-trichloroethyl, 2-trimethylsilylethyl, 9H-fluorenylmethyl (Fmoc), allyl or nitrophenyl carbamates; amides, such as formamides, acetamides, trifluoroacetamides, sulfonamides, trifluoromethanesulfonyl amides or tert-butylsulfonyl amides; and aryl or arylakylamines, such as p-methoxyphenyl, benzyl, p-methoxybenzyl, 3,4-dimethoxybenzyl, dimethoxytrityl or monomethoxytrityl amines. In a particular embodiment, the acylating agent of formula (VII) is 9H-fluorenylmethoxycarbonyl-6-aminohexanoic acid.

Compounds of formula (III) can in turn be prepared for example as described above.

(ii) deprotecting the amino protecting group in the compound of formula (VI) to yield a compound of formula (VII):

(VII)

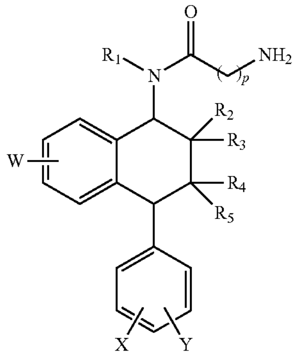

Suitable deprotecting conditions are known for the skilled person, for example in Protecting Groups in Organic Synthesis (Wuts, P. G. M. and Greene T. W., 4th Ed. Wiley-Interscience) and in Protecting Groups (Kocienski P. J., 3rd Ed. Georg Thieme Verlag). In a particular embodiment, the protecting group is removed in the presence of an amine, such as piperidine, morpholine, dicyclohexylamine, diisopropylethylamine or dimethylaminopyridine, preferably in the presence of piperidine.

In a preferred embodiment, the amino-modified selectivity agent corresponds to compound (3).

(3)

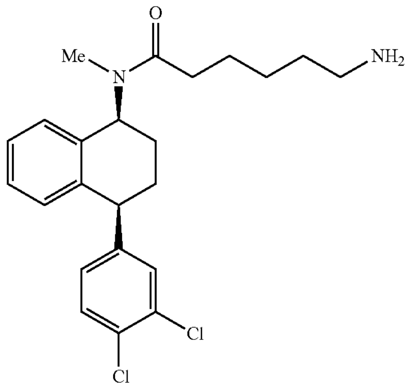

The siRNA strand which is going to be attached to the selectivity agent is formed by stepwise solidphase synthesis on a solid support following the method disclosed in "Oligonucleotide synthesis, a practical approach." edited by M. J. Gait. IRL Press-1985.

In order to conjugate the selectivity ligand, the oligonucleotide needs to be carboxyderivatized. This can be done in the 5' or in the 3' end. In a preferred embodiment the selectivity ligand is attached to the 5' end.

According to one embodiment, the conjugates of formula (XIV) may be prepared by reacting a compound of formula (VII) as described above and an carboxy-modified oligonucleotide of formula (XV):

(XV)

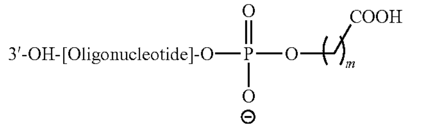

The general procedure for activating an oligonucleotide using a carboxyl linker a modifier will typically be according to the scheme below:

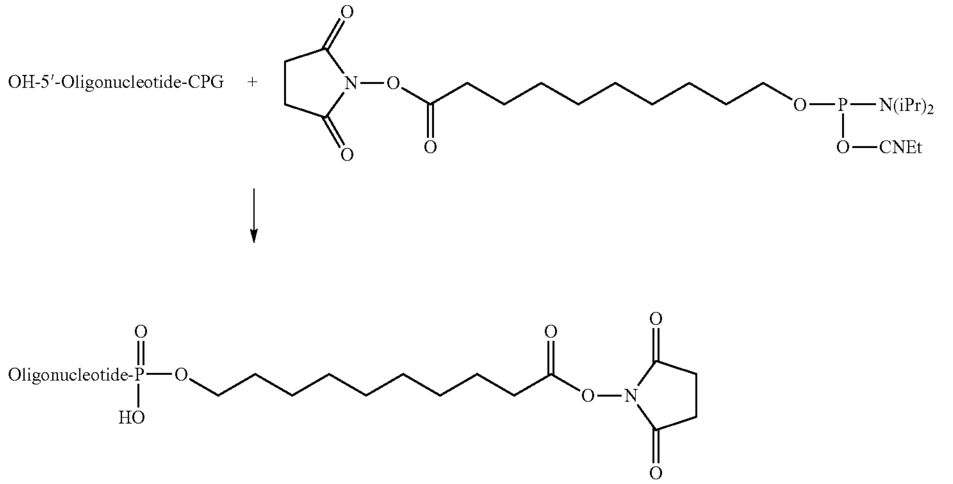

General method of synthesis of the carboxymodified oligonucleotide:

(i) prepare a solution of modifier molecule in anhydrous acetonitrile and place it into an extra reservoir in your synthesizer (Y)

(ii) at the start of the synthesis of the required oligonucleotide sequence, add the Y base at the 5' end. This will enable the linker/modifier molecule from Y reservoir to couple at the end of the oligonucleotide sequence.

(iii) start the synthesis using the appropriate coupling cycle. The same coupling cycle will be used to carry out the linker/modifier molecule coupling.

(iv) at the end of the oligonucleotide synthesis, wash the support and finally dry the support with gas (v) remove the solid support from the column and transfer it into a screw capped vial and complete the 2 step de-protection.

The carboxymodified oligonucleotide should be deprotected for further conjugation with the selectivity agent. For this purpose all the remaining protecting groups in the oligonucleotide are removed as follows. 500 μl of a mixture containing 20% v/v of methylamine (aqueous solution 40% w/v) and 80% v/v of a saturated ammonia solution, (containing 30-32% w/v of $NH_3$) were added to an Eppendorf tube with the oligonucleotide (200 nmole scale). The tube was hermetically closed and heated for 45 minutes to a temperature of 65° C. This procedure eliminates the protecting groups in the phosphorous atom of the nucleotides (acetylation or benzoylation of the furanose and the 2-cyanoethylation of the phosphodiester linkages), and the protecting groups of the exocyclic amino groups (Bz, Ac, IBu). The mixture was then cooled and filtered and the supernatant was dried. The residual pellet was reacted with 1M triethylamine-HF for 3 hours at 65° C. to cleave the protecting groups at 2' of the nucleotides (2'-t-butyl dimethyl silyl—TBDMS). Finally, the resultant solution was desalted in a Sephadex column, leaving a carboxymodified-5'-oligonucleotide.

In a preferred embodiment, the oligonucleotide may comprise a sequence selected from the group of SEQ ID NO:5 to 12.

The carboxyl-activaded oligonucleotide is then reacted with the activated derivative of a selectivity agent of formula (VII) as defined above. A compound is obtained having the general formula:

(XIV)

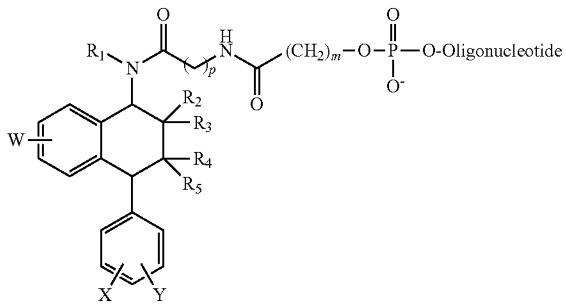

In a particular embodiment, the conjugate has the structure (7)

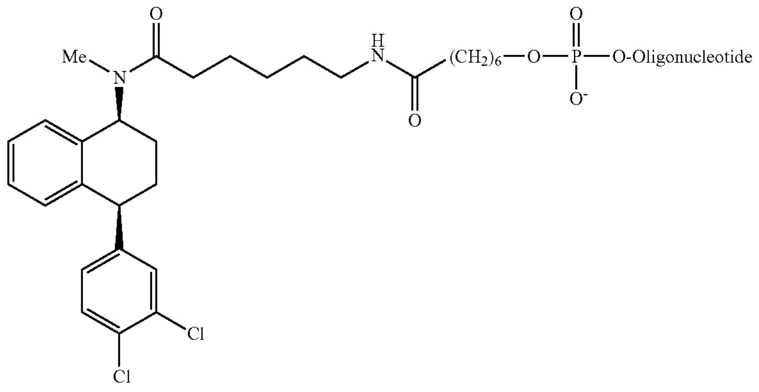

In another particular embodiment, the conjugate has the structure (10)

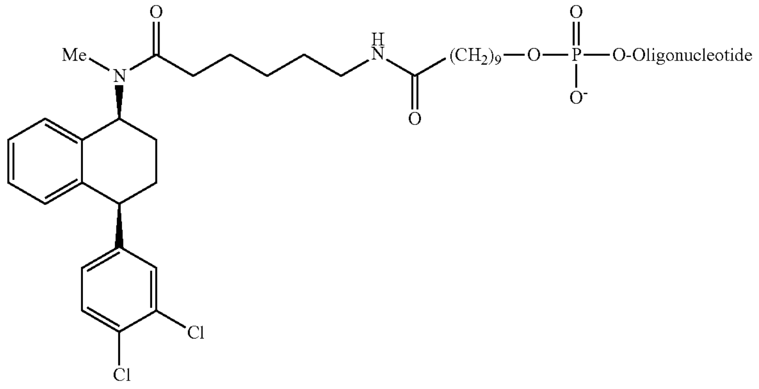

In an embodiment, the oligonucleotide is first reacted with a bivalent or trivalent phosphoramidite to yield a compound of formula (XX) or (XXI) as previously defined.

Compounds of formula (XX) and (XXI) are then deprotected, if needed, and reacted with a carboxy modifier to give a compound of formula (XXVI) or (XXVII), respectively:

(XXVI)

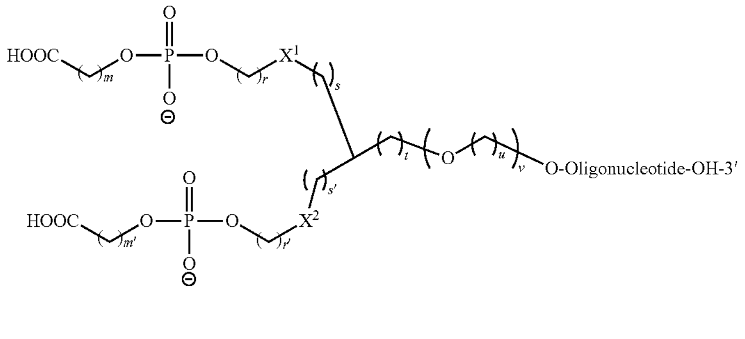

-continued
(XXVII)
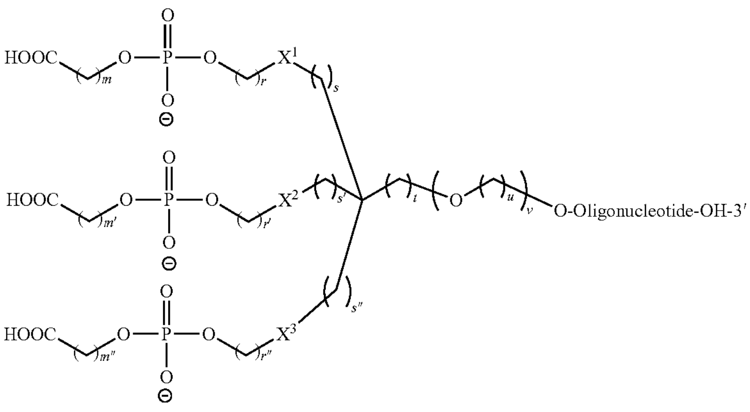
wherein
m, m', m", r, r', r", s, s', s", t, u, v, $X^1$, $X^2$ and $X^3$ areas defined previously.
Compounds of formula (XXVI) and (XXVII) can be further reacted with a compound of formula (VII), to yield conjugates (XXVIII) and (XXIX), respectively:
(XXVIII)
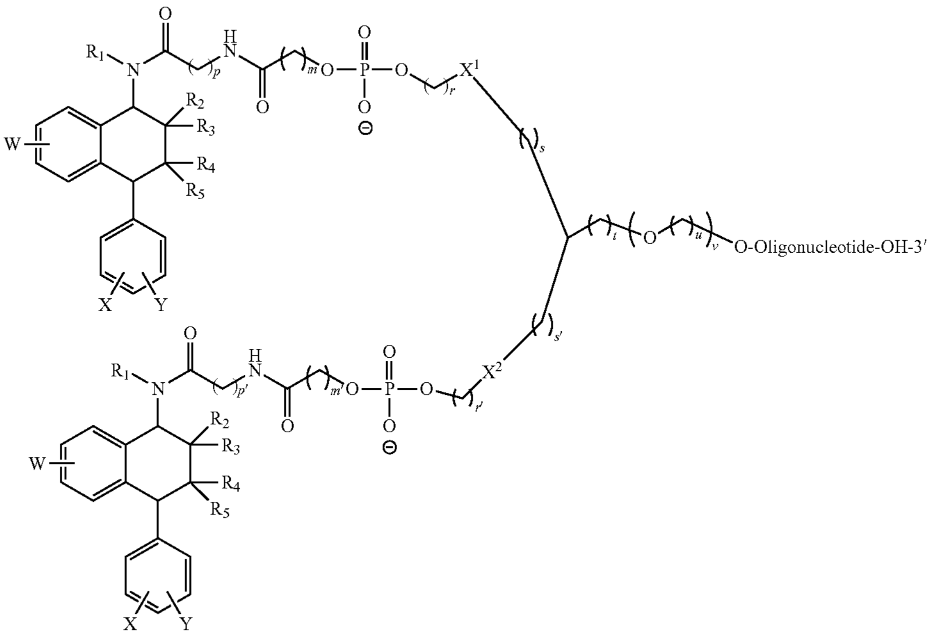
(XXIX)
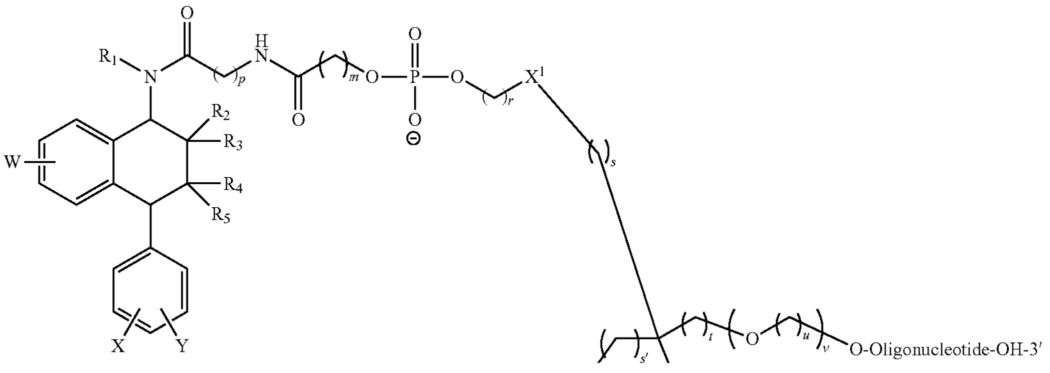

-continued

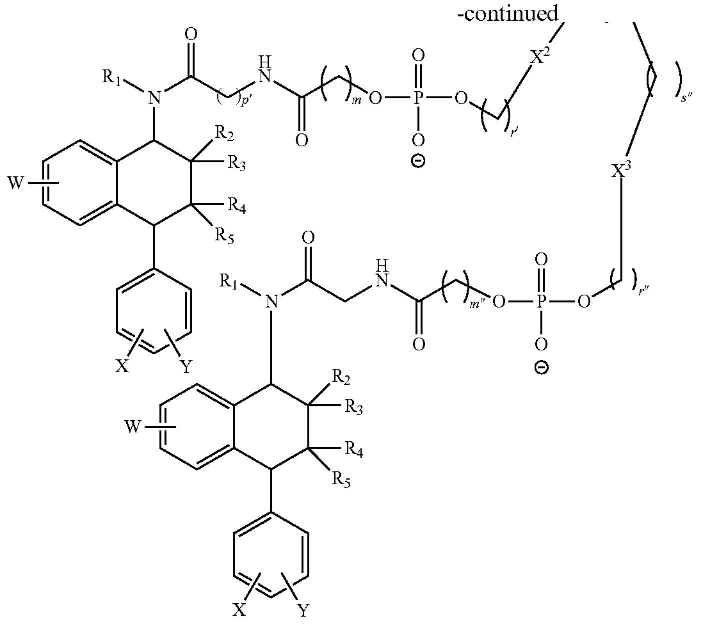

wherein m, m', m", p, p', p", r, r', r", s, s', s", t, u, v, $X^1$, $X^2$, $X^3$, $R^1$-$R^5$, W, X, Y and Z are as previously described.

A particular embodiment is directed to a compound of formula (XXVIII) as defined above.

A particular embodiment is directed to a compound of formula (XXVIII) wherein the selectivity agent is Sertraline, p and p' are 5, m and m' are 6, r and r' are 4, s and s' are 1, t and v are 0 and X and X' represent C(O)NH. Another embodiment refers to a compound of formula (XXVIII) wherein the selectivity agent is Sertraline, p and p' are 5, m and m' are 6, r is 2, r' is 0, s is 1, s' is 0, t and v are 0 and X and X' represent $CH_2$.

A particular embodiment is directed to a compound of formula (XXVIII) wherein the selectivity agent is Sertraline, p and p' are 5, m and m' are 9, r and r' are 4, s and s' are 1, t and v are 0 and X and X' represent C(O)NH. Another embodiment refers to a compound of formula (XXVIII) wherein the selectivity agent is Sertraline, p and p' are 5, m and m' are 9, r is 2, r' is 0, s is 1, s' is 0, t and v are 0 and X and X' represent $CH_2$.

A particular embodiment is directed to a compound of formula (XXIX) as defined above.

A particular embodiment is directed to a compound of formula (XXIX) wherein the selectivity agent is Sertraline, p, p' and p" are 5, m, m' and m" are 6, r, r' and r" are 3, s, s' and s" are 1, t is 1, v is 0 and X, X' and X" represent 0. Another embodiment refers to a compound of formula (XXIX) wherein the selectivity agent is Sertraline, p, p' and p" are 5, m, m' and m" are 6, r, r' and r" are 3, s, s' and s" are 1, t is 1, u is 3, v is 1 and X, X' and X" represent 0.

A particular embodiment is directed to a compound of formula (XXIX) wherein the selectivity agent is Sertraline, p, p' and p" are 5, m, m' and m" are 9, r, r' and r" are 3, s, s' and s" are 1, t is 1, v is 0 and X, X' and X" represent 0. Another embodiment refers to a compound of formula (XXIX) wherein the selectivity agent is Sertraline, p, p' and p" are 5, m, m' and m" are 9, r, r' and r" are 3, s, s' and s" are 1, t is I, u is 3, v is 1 and X, X' and X" represent 0.

iii. Synthesis Using a Carboxyl-Derivatized Nucleic Acid and Amino-Derivatized Nomifensine Nomifensine and analoges thereof contain an amino group which could be used in principle for coupling to a carboy-modified oilgionucleotide. However, the amino group is directly coupled to an aromatic ring, which results in a decreased reactivity and steric hindrance. Thus, an amino-modified nomifensine or variant thereof is prepared having the formula (XVI)

(XVI)

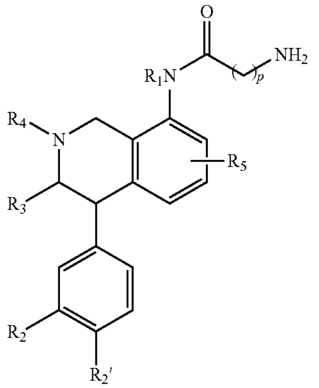

wherein $R_I$ denotes hydrogen, a alkyl $C_1$-$C_6$ group or a benzyl group $R_2$ denotes hydrogen, methyl, chlorine of fluorine groups $R_2$' denotes hydrogen, methyl, methoxy, hydroxyl or halogen atoms $R_3$ and $R_4$ denote hydrogen, a alkyl $C_1$-$C_6$ group $R_5$ denotes hydrogen, chlorine or methoxy group in the 5- or 6-position and p is 2-6

In a particular embodiment, the activated derivative of a selectivity agent is a compound (5) wherein $R_1$, $R_2$, $R_2$', $R_3$, and $R_5$ are H and $R_4$ is methyl.

(3)

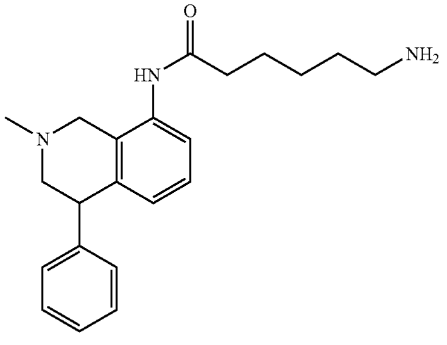

According to one embodiment, the compounds of formula (XVI) may be prepared by a sequence comprising:

a) reacting a compound of formula (XVII)

(XVII)

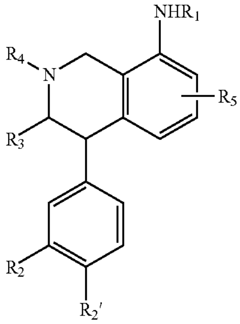

and an acylating agent of formula (V):

(V)

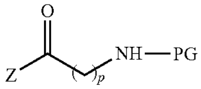

wherein p is as defined above, Z is halogen or OH and PG is an amine protecting group to yield a compound of formula (XVIII)

(XVIII)

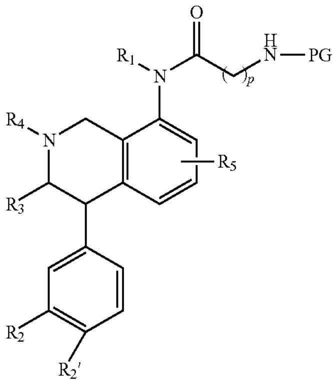

Commonly used protecting groups for amines include carbamates, such as tert-butyl, benzyl, 2,2,2-trichloroethyl, 2-trimethylsilylethyl, 9H-fluorenylmethyl (Fmoc), allyl or nitrophenyl carbamates; amides, such as formamides, acetamides, trifluoroacetamides, sulfonamides, trifluoromethanesulfonyl amides or tert-butylsulfonyl amides; and aryl or arylakylamines, such as p-methoxyphenyl, benzyl, p-methoxybenzyl, 3,4-dimethoxybenzyl, dimethoxytrityl or monomethoxytrityl amines. In a particular embodiment, the acylating agent of formula (V) is 9H-fluorenylmethoxycarbonyl-6-aminohexanoic acid.

Compounds of formula (XVII) can in turn be prepared for example as described in U.S. Pat. No. 4,185,105. In particular, when the compound of formula (III) is nomifensine, it can be obtained from the corresponding chlorohydrate (commercially available) by treatment with a suitable base, including organic or inorganic bases such a alkali or alkaline earth carbonates or hydroxides, ammonia or amines, such as trimethylamine, triethylamine, diisopropylethylamine, pyridine, piperidine, morpholine and the like.

b) deprotecting the amino protecting group in the compound of formula (XVIII) to yield a compound of formula (XIX):

(XVI)

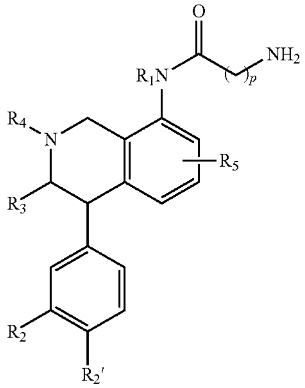

Suitable deprotecting conditions are known for the skilled person, for example in *Protecting Groups in Organic Synthesis* (Wuts, P. G. M. and Greene T. W., $4^{th}$ Ed. Wiley-Interscience) and in *Protecting Groups* (Kocienski P. J., $3^{rd}$ Ed. Georg Thieme Verlag). In a particular embodiment, the protecting group is removed in the presence of an amine, such as piperidine, morpholine, dicyclohexylamine, diisopropylethylamine or dimethylaminopyridine, preferably in the presence of piperidine.

According to another aspect, the invention is directed to an intermediate of formula (XVIII), (XVIII)

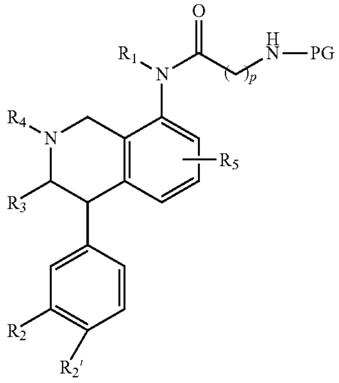

wherein $R^1$-$R^5$, X, Y, W, p and PG are as defined above. In a preferred embodiment, $R^1$ is methyl, $R^2$-$R^5$ are hydrogen, X and Y are chloride, W is hydrogen, p is 5 and PG is 9H-fluorenylmethoxycarbonyl. More preferably, the compound of formula (XVIII) is compound (8)

(8)

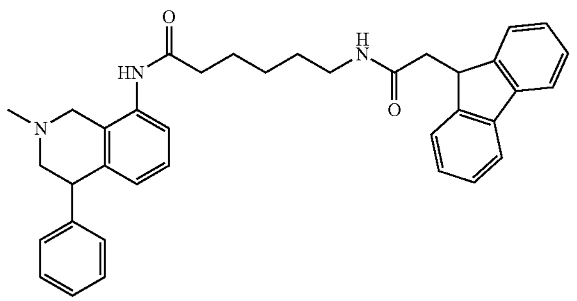

The nucleic which is going to be attached to the selectivity agent is formed by stepwise solidphase synthesis on a solid support following the method disclosed in "Oligonucleotide synthesis, a practical approach." edited by M. J. Gait. IRL Press-1985.

In order to conjugate the selectivity ligand, the oligonucleotide needs to be carboxyderivatized. This can be done in the 5' or in the 3' end. In a preferred embodiment the selectivity ligand is attached to the 5' end.

According to one embodiment, the conjugates of formula (XVI) may be prepared by reacting a compound of formula (XIX) as described above and an amino-modified oligonucleotide of formula (XV):

(XV)

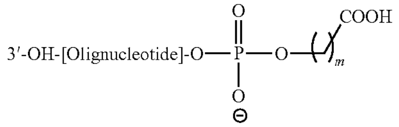

wherein m is 2 to 6

Activation of the oligonucleotide using a carboxy groupo is done as explained above.

In a preferred embodiment, the oligonucleotide which is coupled to the nomifensine or derivative thereof is selected from the group consisting of:

(i) a nucleic acid which is complementary to alpha-synuclein, preferably a nucleic acid comprising a sequence selected from any of SEQ ID NO:16-36.

(ii) a nucleic acid which is complementary to BAX, preferably a nucleic acid comprising a sequence of SEQ ID NO:38.

(iii) a nucleic acid which is complementary to Tau (iv) a nucleic acid which is complementary to NET and (v) a nucleic acid which is complementary to Huntingtin, preferably a nucleic acid comprising a sequence of selected from any of SEQ ID NO:39-55.

The carboxyl-activated oligonucleotide is then reacted with the activated derivative of a selectivity agent of formula (XVI) as defined above giving a compound of general structure:

(XIX)

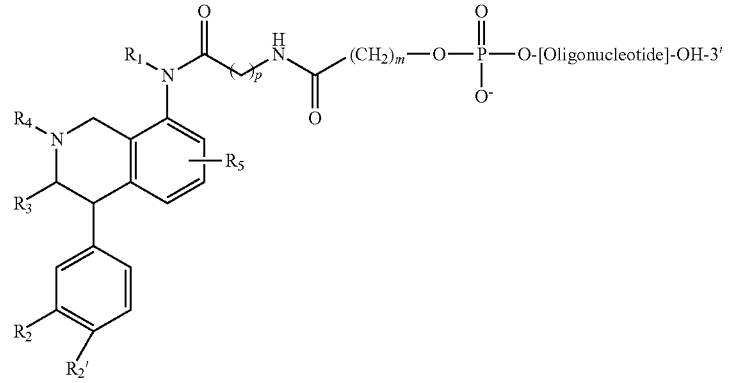

In a preferred embodiment, the conjugate has the structure (9)

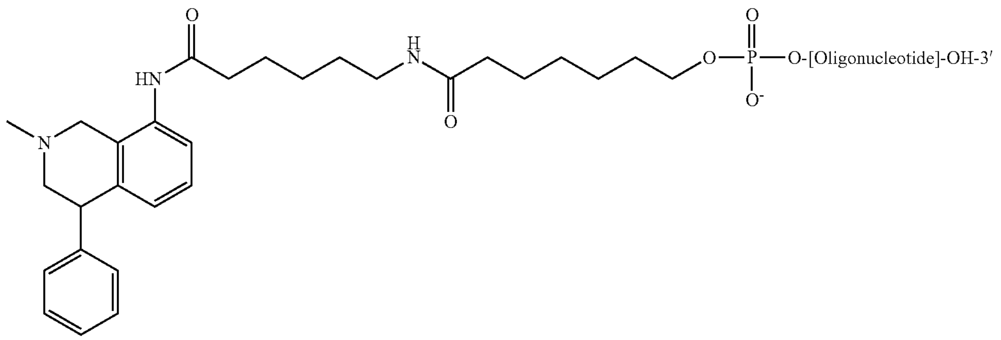

In another preferred embodiment, the conjugate has the structure
(11)
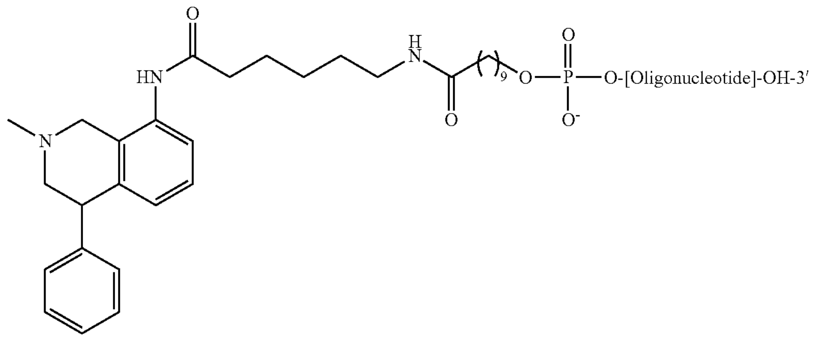
In a particular embodiment, the compound of formula (XVI) is reacted with a compound of formula (XXVI) or (XXVII), to yield conjugates (XXX) and (XXXI), respectively:
(XXX)
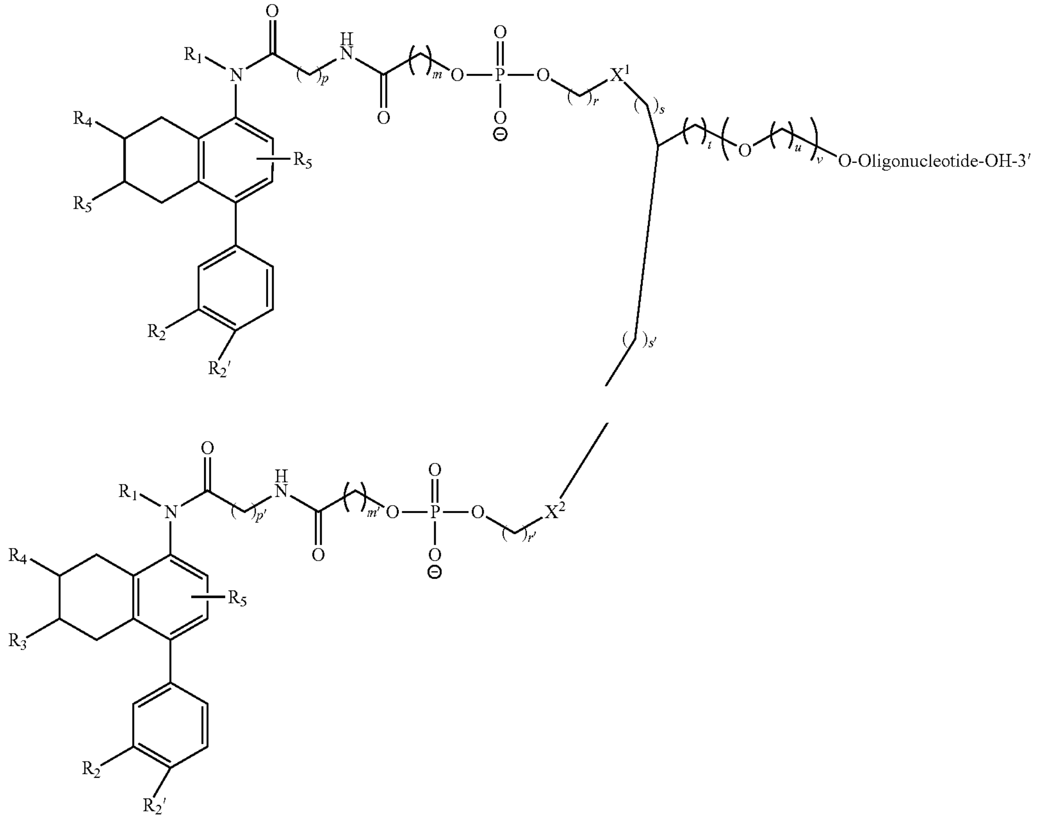

-continued (XXXI)

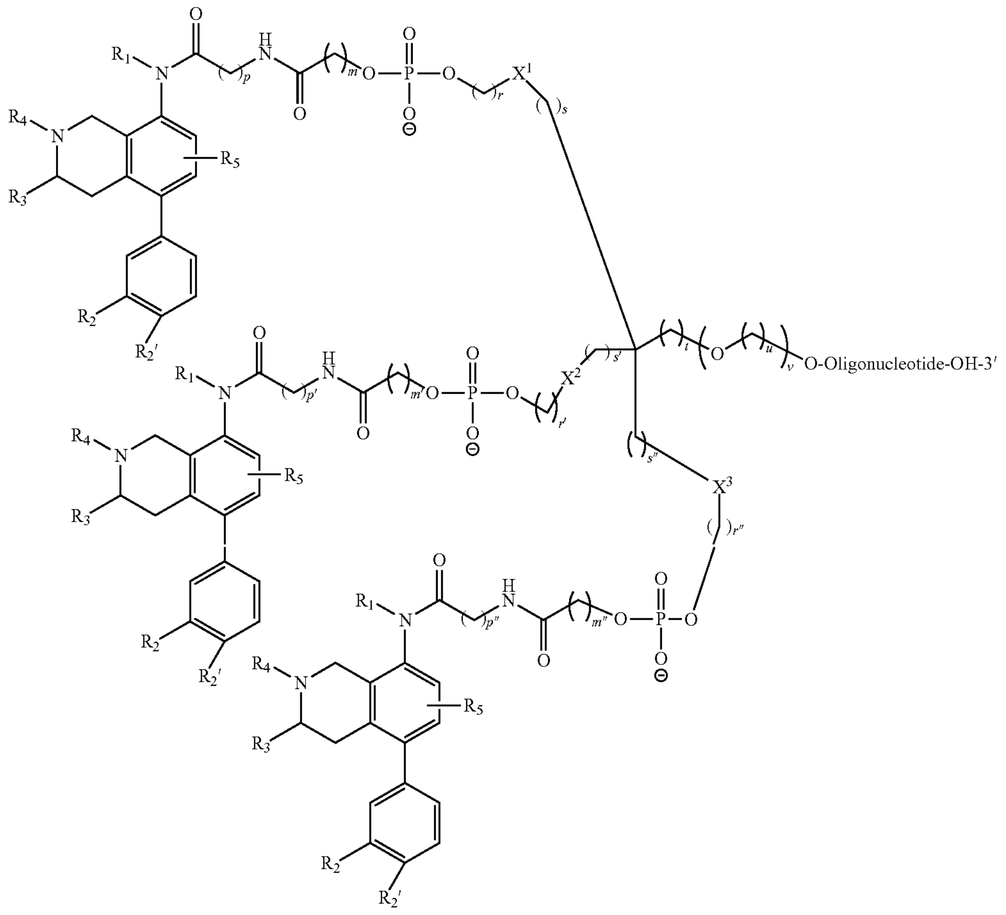

wherein m, m', m", p, p', p", r, r', r", s, s', s", t, u, v, $X^1$, $X^2$, $X^3$ and $R^1$-$R^5$ are as previously described.

A particular embodiment is directed to a compound of formula (XXX) as defined above.

A particular embodiment is directed to a compound of formula (XXX) wherein the selectivity agent is Nomifensine, p and p' are 5, m and m' are 6, r and r' are 4, s and s' are 1, t and v are 0 and X and X' represent C(O)NH. Another embodiment refers to a compound of formula (XXVIII) wherein the selectivity agent is Nomifensine, p and p' are 5, m and m' are 6, r is 2, r' is 0, s is 1, s' is 0, t and v are 0 and X and X' represent $CH_2$.

A particular embodiment is directed to a compound of formula (XXX) wherein the selectivity agent is Nomifensine, p and p' are 5, m and m' are 9, r and r' are 4, s and s' are 1, t and v are 0 and X and X' represent C(O)NH. Another embodiment refers to a compound of formula (XXVIII) wherein the selectivity agent is Nomifensine, p and p' are 5, m and m' are 9, r is 2, r' is 0, s is 1, s' is 0, t and v are 0 and X and X' represent $CH_2$.

A particular embodiment is directed to a compound of formula (XXXI) as defined above.

A particular embodiment is directed to a compound of formula (XXXI) wherein the selectivity agent is Nomifensine, p, p' and p" are 5, m, m' and m" are 6, r, r' and r" are 3, s, s' and s" are 1, t is 1, v is 0 and X, X' and X" represent 0. Another embodiment refers to a compound of formula (XXXI) wherein the selectivity agent is Nomifensine, p, p' and p" are 5, m, m' and m" are 6, r, r' and r" are 3, s, s' and s" are 1, t is 1, u is 3, v is 1 and X, X' and X" represent 0.A particular embodiment is directed to a compound of formula (XXXI) wherein the selectivity agent is Nomifensine, p, p' and p" are 5, m, m' and m" are 9, r, r' and r" are 3, s, s' and s" are 1, t is 1, v is 0 and X, X' and X" represent 0. Another embodiment refers to a compound of formula (XXXI) wherein the selectivity agent is Nomifensine, p, p' and p" are 5, m, m' and m" are 9, r, r' and r" are 3, s, s' and s" are 1, t is 1, u is 3, v is 1 and X, X' and X" represent 0.

iv. Synthesis of a Double Derivatized Oligonucleotide Using a Carboxyl-Derivatized Nucleic Acid, a Bifunctional Linker, Amino-Derivatized Nomifensine and Amino-Derivatized Sertraline Hydroxy protecting groups PG, PG' and PG" in the compounds of formula (XX) and (XXI) can be similar or different.

In a particular embodiment, PG and PG' in the compound of formula (XX) are different so that they can be independently deprotected and the compound of formula (XX) can be coupled if desired with two different activated selectivity agents.

In a particular embodiment, a compound of formula (XX) wherein PG and PG' are different, is sequentially reacted with a carboxy-modifier and then with a compound of formula (VII) whereas the other coupling position is reacted with a carboxy-modifier and then with a compound of formula (XVI), to yield a conjugate of formula (XXXII)

(XXXII)

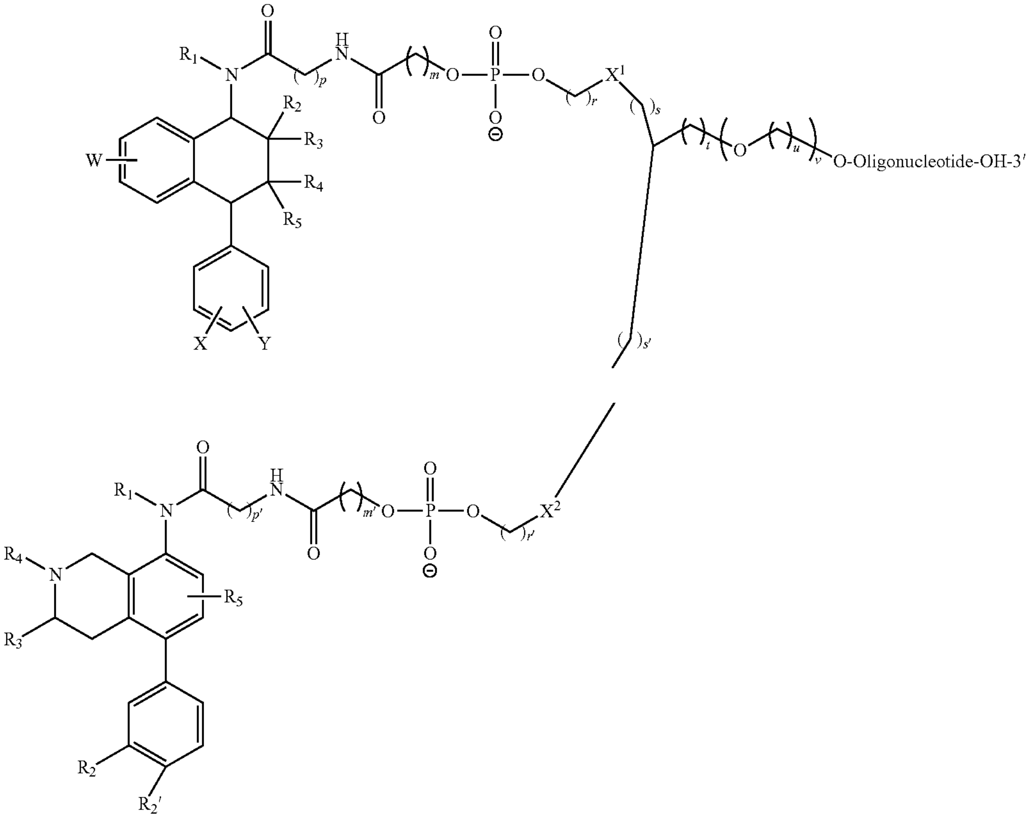

wherein m, m', p, p', r, r', s, s', t, u, v, $X^1$, $X^2$ and $R^1$-$R^5$, X, Y and Z are as previously described.

In a preferred embodiment, the compound of formula (XX) wherein PG and PG' are different, is sequentially reacted with a carboxy-modifier and then with a compound of formula (10) whereas the other coupling position is reacted with a carboxy-modifier and then with a compound of formula (II), to yield a conjugate of formula (XXXIIa)

(XXXIIa)

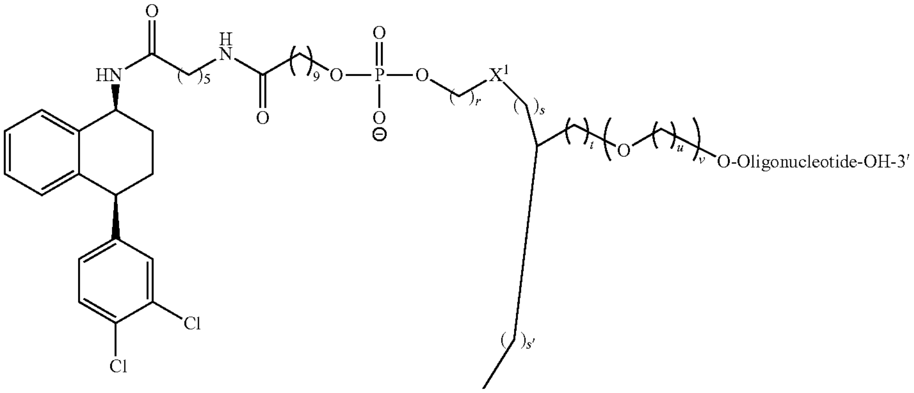

-continued

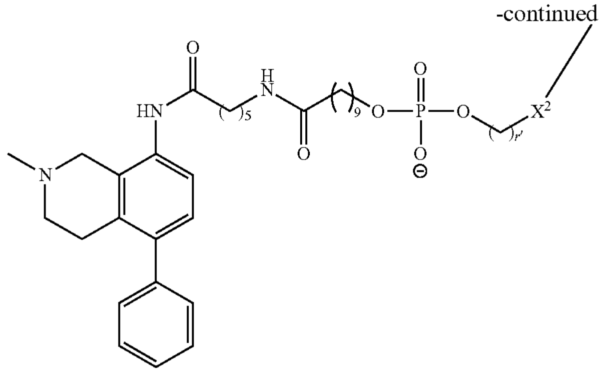

wherein r, r', s, s', t, u, v, $X^1$ and $X^2$ are as previously described.

In a particular embodiment, r and r' are 4, s and s' are 1, t and v are 0 and X and X' represent C(O)NH in the compounds of formula (XXXII) or (XXXIIa).

In a particular embodiment of the invention, the compound of formula (XX) wherein PG and PG' are different, is a compound of formula (XXa)

(XXa)

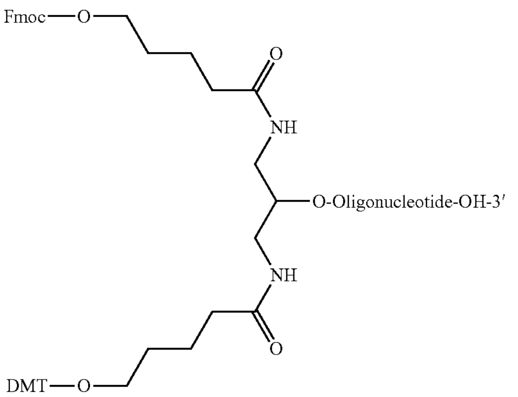

In a preferred embodiment, the compound of formula (XXXIIa) has the following formula (12)

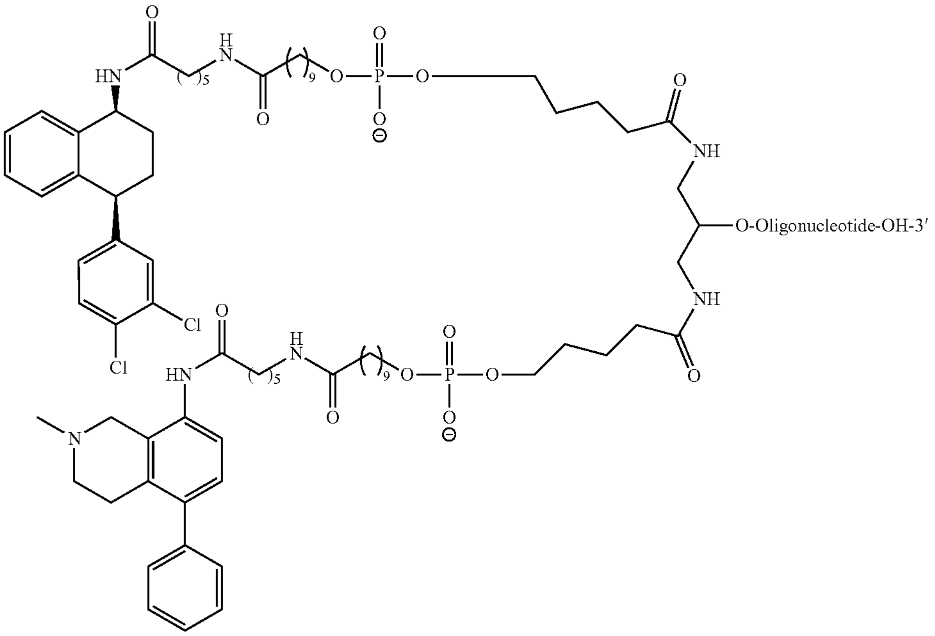

In a particular embodiment, the invention is directed to a compound of formula (XXXII) and (XXXIIa) wherein m, m', p, p', r, r', s, s', t, u, v, $X^1$, $X^2$ and $R^1$-$R^5$, X, Y and Z are as previously described.

In a preferred embodiment, the invention refers to compound (12) as defined above.

E.2. Synthesis of Conjugates Comprising a Nucleic Acid and a Protecting Group Attached to the 5' End The synthesis starts by adding the protecting group to the first strand. Wherein the protecting group is formed by a plurality of moieties, the different moieties which form part of the protecting groups are added to the nucleic acid using a similar approach as that used when adding nucleotides to a pre-existing nucleic acid. i.e. the groups to be added are first activated in order to increase the reactivity of free hydroxy groups. Suitable activating reagents include, without limitation, a phosphorothioate compound, a carbamate compound, a methyl-phosphonate compound, a guanidinium compound, a sulfamate compound, a sulfamide compound, a formacetal compound, a thioformacetal compound, a sulfone compound, a phosphoramidate compound. In a preferred embodiment, the groups of the protecting group are activated with a phosphoramidite compound and mixtures thereof.

Typical phosphoramidate suitable for activating free OH groups are, for instance, (2-cyanoethyl)N,N,N',N'-tetradiisopropylphosphorodiamidite of formula:

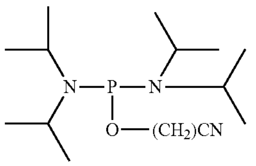

and (2-cyanoethyl)N-diisopropyl, N'-alkylaminephosphoramidite of formula:

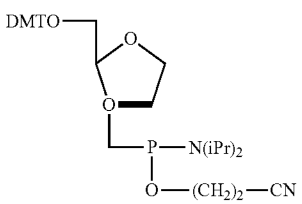

wherein n is 6 to 12

A typical reaction involves the following steps:

A) A furanose unit (the appropriate stoichiometry will be evident for one of ordinary skills in the art) is reacted with 4,4'-dimethoxytrityl chloride (DMTr-Cl) under conditions favoring reaction only at primary hydroxyl group positions. Then, the remaining hydroxyl groups are reacted with an acetylation or benzoylation protecting group. Typically, the activated furanose has the structure:

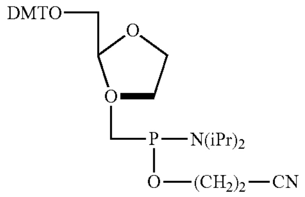

B) One strand of a siRNA (which can be the sense (s) strand or the anti-sense (a) strand) of interest is formed by stepwise solid-phase synthesis on a solid support, where the 5'-OH group of the terminal subunit in the growing strand, which is normally protected by diemethoxytrityl (DMT), is placed under acidic conditions to remove the 5'-OH DMT protecting group, while the purine and pyrimidine bases remain protected with (fluoren-9-yl)methoxycarbonyl (FMOC). Other suitable protecting groups are compounds having a 6-membered morpholine ring bound to a phosphoramidate compound, phosphorothioate compounds and O-methyl (oxomethyl) and O-ethyl (oxoethyl) groups.

C) The deprotected 5'-OH group of the siRNA strand is reacted with the reactive Furanose of step A); thus obtaining a primary-conjugated oligonucleotide. Finally, under acidic conditions the DMT protecting group of the primary hydroxyl of furanose is removed leaving a 5'-OH group.

D) A reactive C18 membered linker (hereinafter $C_{18}$) alkylene glycol monomer having 6 monomers of ethylene glycol (12 carbon atoms and 6 oxygen atoms) is formed by adding to a terminal OH group under phosphitylating conditions a phosphoramidite compound, such as the (2-cyanoethyl)N,N'-diisopropylphosphoramidite described above.

The phosphoramidite compounds are especially useful for the generation of phosphodiester links as those present in the polynucleotide or oligonucleotide backbone. Other suitable compounds to make reactive the polyethylene glycol are compounds having a 6-membered morpholine ring bound to a phosphoramidate compound, phosphorothioate compounds and O-methyl (oxomethyl) and O-ethyl (oxoethyl) groups.

Typically, the reactive ($C_{18}$) alkylene glycol monomer having 6 monomers of ethylene glycol has the structure

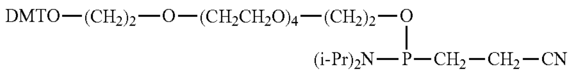

E) The deprotected 5'-OH group of the furanose-siRNA strand is reacted with the reactive ($C_{18}$) alkylene glycol monomer of step D), thus obtaining a secondary-conjugated oligonucleotide having the formula: DMT-($C_{18}$) alkylene glycol-phosphodiesther-furanose-phosphodiesther-RNA strand.

F) The DMT protecting group of the primary hydroxyl of ($C_{18}$) alkylene glycol is removed under acidic conditions leaving a 5'-OH group.

G) The deprotected 5'-OH group of the ($C_{18}$) alkylene glycol-phosphodiesther-furanose-phosphodiester-RNA strand is reacted with a second reactive ($C_{18}$) alkylene glycol monomer like that of step D), thus obtaining a third-conjugated oligonucleotide having the formula:

DMT-($C_{18}$) alkylene glycol-phosphodiesther-($C_{18}$) alkylene glycol-phosphodiesther-furanose-phosphodiesther-RNA strand.

H) The DMT protecting group of the primary hydroxyl of end ($C_{18}$) alkylene glycol is removed under acidic conditions leaving a 5'-OH group for further manipulations.

When the protecting group contains a lipid moiety, the method for obtaining the oligonucleotide construction according to the invention includes an additional step between steps H) and (I), wherein a lipid moiety, preferably in the form of an active ester, amine, thiol or acid of a fatty acid is bound to the terminal group (the furanose or the C18 alkylene glycol, as the case may be). A skilled person in the art can choose the appropriate conditions, reagents, etc to carry out said step, depending on the nature of the lipid and said group. Preferred conditions consists in fatty acid derivatization with phosphoramidite chemistry to create an activated molecule that can be condensed through a phosphodiester linkage to the oligonucleotide construction by the free terminal 5'-OH or 3'OH.

E.3. Synthesis of the siRNA by Annealing the Conjugate Comprising a First Nucleic Acid and a Protecting Group Attached to the 5' End and a Conjugate Comprising the Nucleic Acid Complementary Strand and a SSRI Attached to the 5'

The complementary strand of the siRNA conjugated to the SSRI obtained as described above in E.1. is annealed with the modified siRNA strand obtained as defined in E.2. For this purpose all the remaining protecting groups in the RNA strands are previously removed as follows. 500 μl of a mixture containing 20% v/v of methylamine (aqueous solution 40% w/v) and 80% v/v of a saturated ammonia solution, 30 (containing 30-32% v/v of $NH_3$) were added to an Eppendorf tube with the siRNA (200 nmole scale). The tube was hermetically closed and heated for 45 minutes to a temperature of 65° C. This procedure eliminates the protecting groups in the phosphorous atom of the nucleotides (acetylation or benzylation of the furanose and the 2-cyanoethylation of the phosphodiester linkages), and the protecting groups of the exocyclic amino groups (FMOC). The mixture was then cooled and filtered and the supernatant was dried. The residual pellet was reacted with 1 M triethylamine-HF for 3 hours at 65° c. to cleave the protecting groups at 2' of the nucleotides (2'-t-butyl dimethyl silyl—TBDMS). Finally, the resultant solution was desalted in a Sephadex column.

Conditions of nucleic acid annealing suitable for forming such double stranded structures are described by Joseph Sambrook, et al., (Molecular Cloning, A Laboratory Manual, Cold Spring Harbor Laboratory Press, Cold Spring Harbor, N.Y., 2001) and Haymes, B. D., et al. (Nucleic Acid Hybridization, A Practical Approach, IRL Press, Washington, D.C., 1985).

The effectiveness of the oligonucleotide constructions of the present invention is exemplified below. Example 2 demonstrates that siRNA oligonucleotide sequences of the invention, with a furanose and a two $C_{1-8}$ alkylene glycol linked to one strand of the siRNA, and a sertraline molecule linked to other strand trough a linker arm, blocked the expression of the target pre-synaptic 5-$HT_{1A}$ R to a greater extent than the corresponding siRNA in naked form.

F. Diagnostic Conjugates and Uses Thereof.

The possibility of specifically delivering a therapeutic compounds to a target-cell by using selectivity agents capable of binding with high affinity to neurotransmitter transporters can also be applied for the delivery of compounds that can be used for diagnostic purposes. Thus, in another embodiment, the invention provides a conjugate comprising a (i) at least one selectivity agent which binds specifically to one or more of a neurotransmitter transporter and (ii) an imaging agent.

The term "selectivity agent" and "neurotransmitter transporter" have been described in detail above and can be understood equally for the diagnostic conjugates of the invention.

The terms "imaging agent" and "constrast agent", are used herein interchangeably and refer to a biocompatible compound, the use of which facilitates the differentiation of different parts of the image, by increasing the "contrast" between those different regions of the image. The term "contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging). Suitable contrast agent include, without limitation, contrast agents for Radionuclide imaging, for computerized tomography, for Raman spectroscopy, for Magnetic resonance imaging (MRI) and for optical imaging.

Contrast agents for radionuclide imaging include radiopharmaceuticals are commonly labeled with positron-emitters such as $^{11}C$, $^{13}N$, $^{15}O$, $^{18}F$, $^{82}Rb$, $^{62}Cu$ and $^{68}Ga$. SPECT radiopharmaceuticals are commonly labeled with positron emitters such as $^{94}$ mTc, $^{201}TI$ and $^{67}Ga$. Radionuclide imaging modalities (positron emission tomography, (PET); single photon emission computed tomography (SPECT)) are diagnostic cross-sectional imaging techniques that map the location and concentration of radionuclide-labeled radiotracers. PET and SPECT can be used to localize and characterize a radionuclide by measuring metabolic activity. PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high. In certain embodiments of the invention, a cell is labeled ex vivo for PET or SPECT imaging in vivo. Closely related to PET is single-photon emission computed tomography, or SPECT. The major difference between the two is that instead of a positron-emitting substance, SPECT uses a radioactive tracer that emits low-energy photons.

Contrast agents for CT imaging include, for example, iodinated or brominated contrast media. Examples of these agents include iothalamate, iohexyl, diatrizoate, iopamidol, ethiodol and iopanoate. Gadolinium agents have also been reported to be of use as a CT contrast agent (see, e.g., Henson et al., 2004). For example, gadopentate agents has been used as a CT contrast agent (discussed in Strunk and Schild, 2004). Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth. In CT, intravenous injection of a radiopaque contrast agent such as those described herein can assist in the identification and delineation of soft tissue masses when initial CT scans are not diagnostic.

Contrast agents for optical imaging include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye and the various other fluorescent compounds disclosed herein.

In a preferred embodiment, the contrast agent is a compound that is able to be imaged by a magnetic resonance imaging apparatus. Contrast agents which can be imaged by a magnetic resonance imaging apparatus differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MM contrast agents include gadolinium chelates, manganese chelates, chromium chelates, and iron particles. In one particular embodiment, the MRI contrast agent is $^{19}F$. Both CT and MRI provide anatomical information that aid in distinguishing tissue boundaries. Compared to CT, the disadvantages of MRI include lower patient tolerance, contraindications in pacemakers and certain other implanted metallic devices, and artifacts related to multiple causes, not the least of which is motion. CT, on the other hand, is fast, well tolerated, and readily available but has lower contrast resolution than MRI and requires iodinated contrast and ionizing radiation. A disadvantage of both CT and MRI is that neither imaging modality provides functional information at the cellular level. For example, neither modality provides information regarding cellular viability. Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

MRI contrast agents include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). In a preferred embodiment, the compound that is able to be imaged by a magnetic resonance imaging apparatus is a gadolinium-based compound.

The term "gadolinium-based compound", as used herein, shall mean, where used with respect to imaging, any gadolinium-containing substance administrable to a subject which results in an intravascular enhancement. In another embodiment, the gadolinium-containing contrast agent is selected from the group consisting of gadolinium, gadolinium pentate, and gadodiamide.

The amount of the gadolinium-containing contrast agent to be administered varies in an amount of about 10 mg per kg body weight. In another embodiment, the second magnetic resonance image is acquired about 45 minutes after administering the gadolinium-containing contrast agent. This invention also provides the above-described method further comprising the step of intraperitoneally administering a saline solution (e.g. Ringer's solution) to the subject, which administering follows either step (c) or step (d).

The invention also provides the use of a conjugate as defined above as diagnostic agent and methods for the detection of cells expressing the neurotransmitter transporter on their surface.

Depending on the type of cell that has to be imaged, the conjugates will incorporate one or more of the selectivity agents. The following table describes the selectivity agents that can be used depending on the type of cell that has to be imaged

| Expressed neurotransmitter transporter | Selectivity agent |
|---|---|
| SERT | SSRI (sertraline) |
| SERT | SSRI (sertraline) |
| SERT | SSRI (sertraline) |
| SERT | SSRI (sertraline) |
| DAT, SERT or NET | SDNRI (TripleBlocker) or DNRI (Nomifensine) |
| DAT, SERT or NET | DAT, SERT or NET SDNRI (TripleBlocker) or DNRI (Nomifensine |
| DAT, SERT or NET | SDNRI (TripleBlocker) or DNRI (Nomifensine) |
| NET | NRI (Reboxetine) |
| NET | NRI (Reboxetine), SDNRI, DNRI |
| DAT, SERT or NET | SDNRI (TripleBlocker) or DNRI (Nomifensine) |
| DAT, SERT or NET | SDNRI (TripleBlocker) or DNRI (Nomifensine) |

The invention also provides multimodal imaging methods. Certain embodiments of the present invention pertain to methods of imaging a subject, or a site within a subject using multiple imaging modalities that involve measuring multiple signals. In certain embodiments, the multiple signals result from a single label on, or in a cell. As set forth above, any imaging modality known to those of ordinary skill in the art can be applied in these embodiments of the present imaging methods.

The imaging modalities are performed at any time during or after administration of the labeled composition, e.g., labeled cell. For example, the imaging studies may be performed during administration of the labeled cell of the present invention, i.e., to aid in guiding the delivery to a specific location, or at any time thereafter.

Additional imaging modalities may be performed concurrently with the first imaging modality, or at any time following the first imaging modality. For example, additional imaging modalities may be performed about 1 sec, about 1 hour, about 1 day, or any longer period of time following completion of the first imaging modality, or at any time in between any of these stated times. In certain embodiments of the present invention, multiple imaging modalities are performed concurrently such that they begin at the same time following administration of the labeled cell or agent. One of ordinary skill in the art would be familiar with performance of the various imaging modalities contemplated by the present invention.

In some embodiments of the present methods of imaging, the same imaging device is used to perform a first imaging modality and a second imaging modality. In other embodiments, different imaging devices are used to perform the different imaging modalities. One of ordinary skill in the art would be familiar with the imaging devices that are available for performance of the imaging modalities described herein.

The instant invention provides methods for imaging cells using one or more imaging modalities. In some embodiments the cells are labeled with multiple imaging agents, and in other aspects the cells are labeled with a single labeling agent. In certain embodiments, the single labeling agent is a multi-mode-detectable agent.

The following examples and drawings are provided by way of illustration, and are not intended to be limiting of the present invention.

EXAMPLES

Example 1

Synthesis of the Conjugate of the Invention Comprising Sertraline and an Oligonucleotide Synthesis of Activated Sertraline (4)

Activated sertraline was prepared as shown in the following scheme.

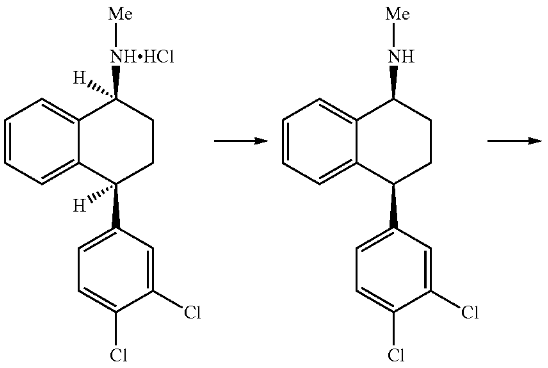

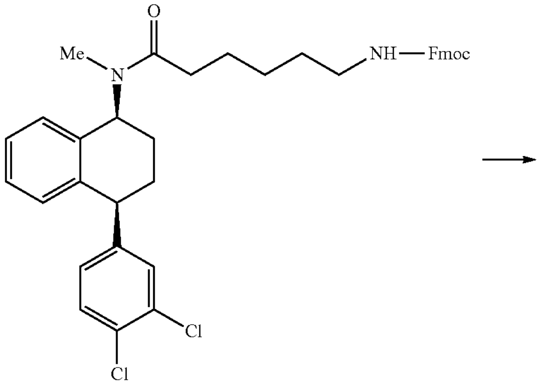

(1)

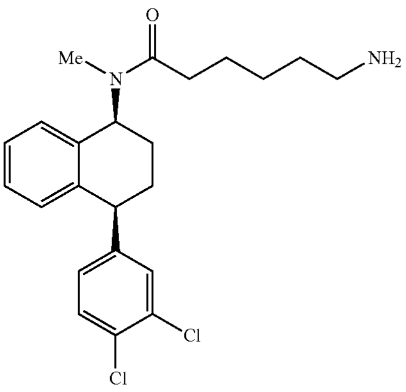

(2)

-continued

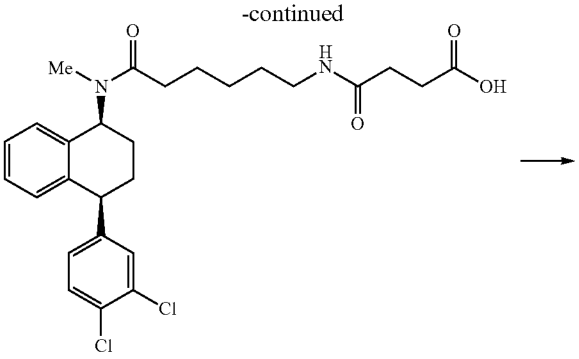

(3)

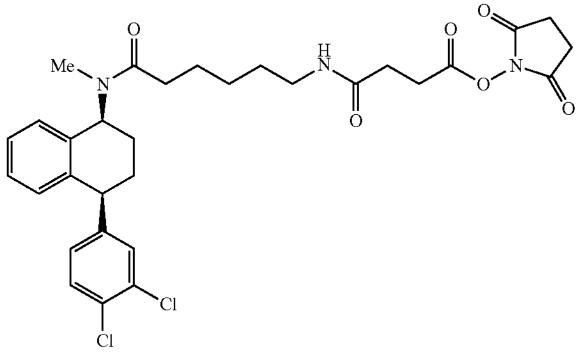

(4)

A.1. Synthesis of Compound (1)

A mixture of sertraline hydrochloride (commercially available, 34 mg), 9H-fluorenylmethoxycarbonyl-6-aminohexanoic acid (Fmoc-ACA, 49 mg), DMF (2 ml), N-methylmorpholine (22 μl) and O-(Benzotriazol-1-yl)-N,N,N',N'-tetramethyluronium tetrafluoroborate (TBTU, 68 mg) was stirred at room temperature overnight. The reaction was followed by TLC (10% $CH_3OH/CHCl_3$). The mixture was evaporated to yield a thick oil which was further washed with 3×5 ml of Pet-ether. 2 ml of water were added to the oily compound, the resulting precipitate was washed with 2×10 ml of water again. The precipitate was dissolved with 20 ml of methylene chloride (DCM) and worked up with 20 ml of NaCl solution, then dried over $Na_2SO_4$. The solution was evaporated to dryness and then dried in mechanical pump to afford a solid (129 mg crude product). The crude product was purified by silica gel column chromatography, eluting with 1% Methanol/DCM, 2%, then 5%. The fractions were combined and evaporated to dryness. The product was dried in vacuo for 6 hours to yield 90 mg of the pure compound (1).

A.2. Synthesis of Compound (2)

Compound (1) (90 mg) was dissolved in 3 ml of 20% Piperidine in DCM for 1 h. The reaction was followed by TLC (10% methanol/$CHCl_3$). The mixture was evaporated to afford an oil that was washed with 3×10 ml Pet-ether. The resulting crude compound (54 mg) was pure enough for next reaction without further purification.

A.3. Synthesis of Compound (3)

A mixture of compound (2) (54 mg), pyridine (3 ml), succinic anhydride (16 mg) and N,N-dimethylaminopyridine (DMAP, 18 mg) was stirred at room temperature overnight. The reaction was following by TLC (85:10:5=DCM: Methanol: Acetic acid). 10 ml of water were added to the reaction. The reaction mixture as concentrated to gum, then suspended in 10 ml of DCM. The organic phase was washed with 2×10 ml of 5% $NaHCO_3$ solution, 10 ml of 5% citric acid solution and 10 ml of Brine solution. The solution was dried over sodium sulfate and evaporated to yield compound (3) as a white foam (46 mg).

A.4. Synthesis of Compound (4)

A mixture of compound (3) (46 mg), hydroxysuccinimide (13 mg), N,N'-diisopropylcarbodiimide (DIC, 60 μl) and DCM (4 ml) was stirred at room temperature overnight and followed by TLC (10% methanol/$CHCl_3$). The solution was evaporated to dryness to give 150 mg of crude solid. The crude compound was purified by Preparative TLC (2 mm thickness, 20×20 cm), the TLC was developed by 7% Methanol/$CHCl_3$ containing 1% Acetic Acid. The proper band was cut out and placed in a filter funnel. After eluting with 15% Methanol/$CHCl_3$, the solution was evaporated to dryness to give 35 mg of compound (4) (HPLC 98% pure).

B. Synthesis of the Amino-Modified Oligonucleotides (5) and (6)

Synthesis was performed on an automated synthesizer, using commercially available amino linkers 6-(4-Monomethoxytritylamino)hexyl-[(2-cyanoethyl)-(N,N-diisopropyl)]-phosphoramidite (5'-MMT-C6-aminomodifier-CEP) and 6-(trifluoroacetylamino)hexyl-[(2-cyanoethyl)-(N,N-diisopropyl)]-phosphoram id ite (5'-TFA-C6-aminomodifier-CEP), respectively.

(5)

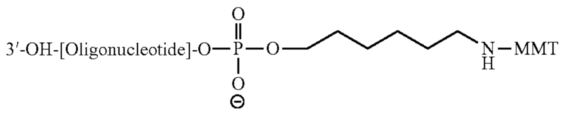

(6)

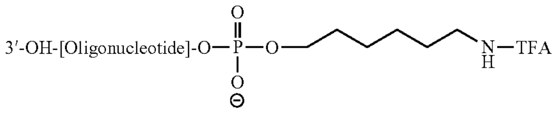

The next steps were followed:

1. —Amino-linkers-CEP were dissolved in anhydrous acetonitrile (100 μM in 1 mL) under inert atmosphere (Argon or Nitrogen). The solution was placed into a clean extra reservoir (position 5-9 in Expedite 8900 synthesizer or spare port on any other synthesizer). The line was primed manually for a few seconds or using the priming program so that the delivery tube was filled with this reagent.
2. —The desired sequence was written; the 5'-end having the spare base position (5-9), so that the modifying reagent was incorporated at the last step of synthesis by the instrument.
3. —The sequence was verified, having the DMT option for the synthesis program as the oligonucleotide need HPLC purification.
4. —The synthesis was started using an appropriate scale (0.2-1.0 μM) coupling program on the instrument.
5. —At the end of the synthesis, the column was detached from the instrument and the support washed with ethanol (3×1 mL) using a syringe to remove residual acid (from detritylation steps) and iodine (from oxidation steps).

C. Deprotection and Removal of Oligonucleotides from Supports

The following steps were performed:

1. —The dried support from the previous step was transferred into a screw-capped vial (1.5-2 mL).
2. —500 μL (0.2 μM scale) of concentrated $NH_4OH$ (30%) solution were added.
3. —The cap was tightly closed and the suspension incubated at 55° C. for at least 8 h to overnight (a longer time should was given for G-rich sequences).
4. —The supernatant was cooled to 0° C. and transferred into another microfuge tube.
5. —The support was rinsed with the same amount of d-water and this washing was added to the ammonia supernatant. The resulting ammonia solution contained full length oligonucleotide with either a free aminohexyl group at the 5'-end (in the case of the N-TFA-aminohexyl phosphoramidite incorporated) or protected aminohexyl linked oligonucleotide together with non nucleosidic material and short sequences. Purification of oligonucleotides with free aminohexyl linkers could be achieved by anion exchange HPLC, ethanol precipitation or polyacrylamide gel electrophoresis (PAGE).

D. Incorporation of the Activated Sertraline on to the Free Primary Amine.

Labeling of 5'-end amino linked oligonucleotides obtained in steps B and C with N-hydroxysuccinimide ester derivatives obtained in step A was carried out in solution phase in accordance with the following procedure:

A. —Marker Incorporation.

1. —Partially or fully purified amino linked oligonucleotide from previous step (20-25 ODU A260~700 μg) were dissolved in 250 μL of a mixture of 1.0M $NaHCO_3/Na_2CO_3$ (pH 9.0). pH of the resulting solution was checked to make sure it was basic.
2. —500 μl, of a solution of the activated derivative from stage A (5-6 mg) were added in a mixture of 1.0M, $NaHCO_3/Na_2CO_3$ buffer pH=9.0: DMF:Water (5:2:3 v/v).
3. —The mixture was vortexed and the Eppendorf tube wrapped with aluminum foil to prevent light exposure.
4. —After 20 h of incubation at room temperature, the mixture was quenched with a 1M TEAA solution.

B. —Removal of Excess Marker-Using a Shephadex G-25 Column.

1. —The activated derivative sample was applied onto the column.
2. —The column was eluted with water and 1.0 ml fractions were collected in Eppendorf tubes. The desired product started eluting after the void volume, with most of the desired product eluted in fractions 3-9.
3. —The fractions which contained most of the material were pooled and concentrated.
4. —Usually 12-15 ODU A260 (70%) is obtained, which is free from excess dye/marker molecule. If necessary, the product can be further purified by electrophoresis (20% PAGE) of RP HPLC.

Example 2

Sintesis of a siRNA Comprising a Sense Oligonucleotide Conjugated to Sertraline and an Antisense Oligonucleotide Comprising a Protecting Group of the Formula C18-L3-C18-L2-Furanose-L1[oligonucleotide]-3' Wherein L1, L2 and L3 are Phosphodiester Linkages The synthesis was carried out using the following steps:

(a) The RNA oligonucleotide is formed by stepwise solid-phase synthesis on a solid support, where the 5'-OH group of the terminal subunit in the growing strand, which is normally protected by diemethoxytrityl (DMT), is put under acidic conditions to remove the 5'-OH DMT protecting group, while the purine and pyrimidine bases remain protected with (fluoren-9-yl)methoxycarbonyl (FMOC).

(b) A furanose unit, such as a D-ribose or a D-(−)-fructofuranose is reacted with 4,4'-dimethoxytrityl chloride (DMTr-CI) under conditions favouring reaction only at primary hydroxyl group positions. Then, the remaining hydroxyl groups are reacted with an acetylation or benzylation protection group. Finally, under acidic conditions the DMT protecting group of the primary hydroxyl is removed. Said deprotected hydroxyl group of the furanose is reacted with the deprotected 5'-OH group of the siRNA strand obtained in step (a) thus obtaining a primary-conjugated oligonucleotide.

(c) A reactive polyethylene glycol having 6 monomers of Polyethylene glycol (PEG) giving a spacer of 18 covalent bond units (C18 spacer) was formed by adding to a terminal OH group under phosphitylating conditions a phosphoramidate compound, such as the (2-cyanoethyl) N,N'-diisopropylphosphoramidite of formula (II)

(II)

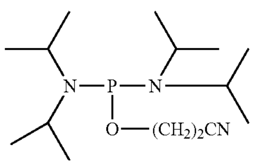

(d) The deprotected 5'-OH group of the furanose is reacted with the reactive polyethylene glycol of step (c), thus obtaining a siRNA strand having the structure: OH—C18-L2-Furanose-L1-[oligonucleotide]-3' wherein L1 and L2 are phosphodiester bonds.

(e) A second reactive polyethylene glycol having 6 monomers of Polyethylene glycol (PEG) giving a spacer of 18 covalent bond units (C18 spacer) was formed by adding to a terminal OH group under phosphitylating conditions a phosphoramidate compound, such as the (2-cyanoethyl)N,N'-diisopropylphosphoramidite of formula (II)

(II)

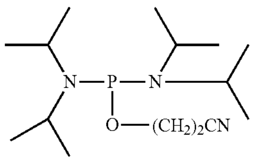

(f) The deprotected 5'-OH group of the C18 is reacted with the second reactive C18 polyethylene glycol from the step (e), thus obtaining a siRNA strand having the structure:

C18-L3-C18-L2-Furanose-L1-[oligonucleotide]-3' wherein L1, L2 and L3 are phosphodiester bonds.

(g) The complementary strand of the siRNA conjugated to sertraline as described in example 1 is annealed with the modified siRNA strand of step f). For this purpose all the remaining protecting groups in the RNA strands are previously removed as follows. 500 μl of a mixture containing 20% v/v of methylamine (aqueous solution 40% w/v) and 80% v/v of a saturated ammonia solution, (containing 30-32% v/v of NH3) were added to an Eppendorf tube with the siRNA (200 nmole scale). The tube was hermetically closed and heated for 45 minutes to a temperature of 65'C. This procedure eliminates the protecting groups in the phosphorous atom of the nucleotides (acetylation or benzylation of the furanose and the 2-cyanoethylation of the phosphodiester linkages), and the protecting groups of the exocyclic amino groups (FMOC). The mixture was then cooled and filtered and the supernatant was dried. The residual pellet was reacted with 1 M triethylamine-HF for 3 hours at 65° C. to cleave the protecting groups at 2 of the nucleotides (2'-t-butyl dimethyl silyl—TBDMS). Finally, the resultant solution was desalted in a Sephadex column.

Example 3

Efficacy Assay of an 5-HT$_{1A}$R-Targeting siRNA Conjugated to a Group of Formula (I) and One Targeting Agent (Hereinafter NLF-siRNA) and a Naked 5-HT$_{1A}$R-targeting siRNA (Hereinafter, Naked siRNA) by In Vivo Local Infusion into Dorsal Raphe Nucleous (DRN) of Mice This example shows that NLF-siRNA and a naked siRNA present a similar efficacy for knockdown the pre-synaptic 5-HT$_{1A}$R, as it was measured by its protein level decrease and its function, when is applied locally into dorsal raphe nucleae where the body of serotonergic neurons are located. This indicates that the group of formula (I) and the targeting agent used in the constructions of this invention do not interfere with the efficacy of the interference oligonucleotide.

A set of compounds having the structure of Examples 1 and 2 were synthesized as disclosed above and had the following structure.

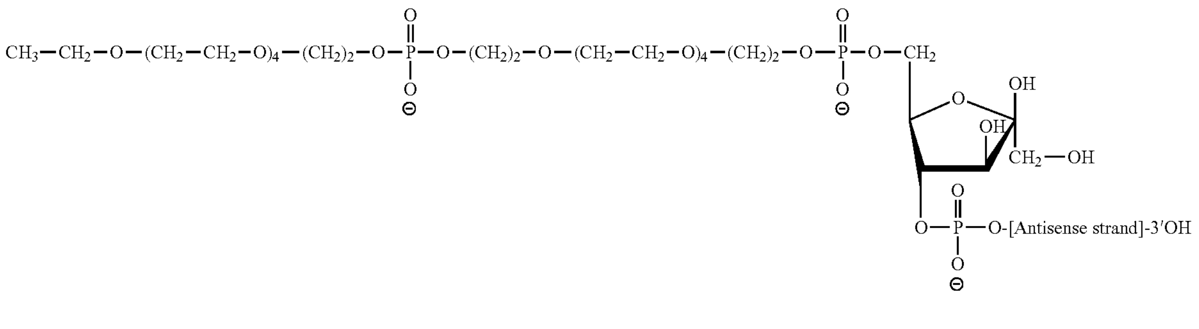

-continued

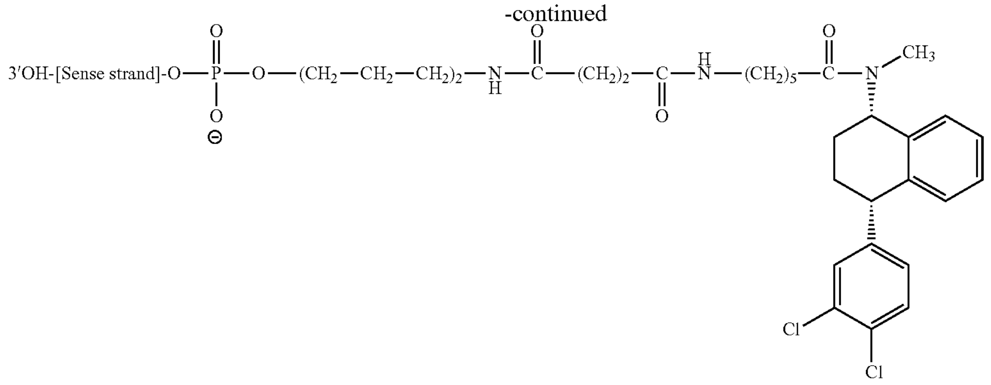

The siRNAs were designed to target the following regions of serotonin receptor 5-HT type 1A (5-$HT_{1A}$R) sequence from *Mus Musculus* (Mouse, GenBank Accession Number: NM_008308): 633-651, 852-870, 1889-1907 and 2167-2185. Antisense and sense strands of each siRNA were chemicaly synthesized (SEQ ID NO 5-10, Table 1) and were annealed in an isotonic RNA annealing buffer (100 mM potassium acetate, 30 mM HEPES-KOH pH: 7.4, 2 mM magnesium acetate), by combining a 50 μM solution of each strand. The solution is then incubated by 1 minute at 90° C., centrifugated by 15 seconds and then incubated by 1 hour at 37° C. The annealed solution is HPLC purified and selected fractions of siRNA are liophilizated. Stocks solutions of the siRNA were prepared by resuspending the liophilizated product in RNAse-free water and stored at −20° C. until use. Prior to usage, all siRNAs stock solutions were diluted to final concentration in aCSF (125 mM NaCl, 2.5 mM KCl, 1.26 mM $CaCl_2$, 1.18 mM $MgCl_2$ and 5% glucose), a appropriate vehicle for brain application (local and i.c.v. application).

TABLE 2

| RNA oligonucleotide identification (s:sense strand), (a:anti-sense strand), (si: small interfering) | Sequence (5'-3' direction) |
|---|---|
| siRNA-A-s (SEQ ID NO: 5) | GGAAGAGUGUAGGGCUUAC |
| siRNA-A-a (SEQ ID NO: 6) | GUAAGCCCUACACUCUUCC |
| siRNA-B-s (SEQ ID NO: 7) | CGAUACUGGCCUCUCCAAC |
| siRNA-B-a (SEQ ID NO: 8) | GUUGGAGAGGCCAGUAUCG |
| siRNA-C-s (SEQ ID NO: 9) | GGUGCUCAACAAGUGGACU |
| siRNA-C-a (SEQ ID NO: 10) | AGUCCACUUGUUGAGCACC |
| siRNA-D-s (SEQ ID NO: 11) | CGAUGGAAGUUUAAACCUC |
| siRNA-D-a (SEQ ID NO: 12) | GAGGUUUAAACUUCCAUCG |

All these siRNA sequences include the anti-sense sequences complementary to the mRNA of 5-$HT_{1A}$ receptor, thus being able to arrest said mRNA and to block its expression. An equimolar cocktail of these sequences was employed for all the experiments.

As control, a nonsense siRNA sequence (ns siRNA) was infused. This ns siRNA is not complementary to any mouse gene when compared in a Blast alignment algorithm to the full trasncriptome of mice. The ns siRNA had the following sequence:

SEQ ID NO: 56
ns siRNA-s AGUACUGCUUACGAUACGG

SEQ ID NO: 57
ns siRNA-a CCGUAUCGUAAGCAGUACU

All the sequences have terminal DNA dimers of nucleotides containing at least one timine (T), not shown, in order to avoid the interference with the proteins regulating mRNA of normal processes into the cell. This technique is well known by the skilled person in the art. With these terminal dimers the oligonucleotides have 21-23 base pairs, enabling an efficient RNAi mechanism.

The siRNA sequences of Table 1, conjugated to a group of formula (I) and one targeting agent as described above (NLF-siRNA), nonsense siRNA conjugated to a group of formula (I) and one targeting agent (ns NLF-siRNA) and naked oligonucleotides with no modifications (naked siRNA of Table 1 or ns naked siRNA) were used for the experiments.

For the infusion of siRNAs, a microcannula system was implanted using standard stereotaxic methods as previously described in the art. The inflow microcannula threaded through the 25 gauge tubing consisted of fused silica capillary tubing of 110 μm OD and 40 μm ID. The predetermined length of the microcannulae is decided based on the depth of the brain region to be targeted (i.e., 1 mm for dorsal raphe nuclei).

Male C57BL/6J mice (21-29 g, 9- to 12-week-old male) were implanted with one microcannula in the dorsal raphe nuclei (DRN). Stereotaxic coordinates (in mm) were AP: −4.5, L: −1.0, DV: −4.4, with a lateral angle of 20°, from bregma and top of the skull according to Franklin and Paxinos (1997). The microcannula was secured to the skull with dental cement and two 2-mm long, 0.95-mm diameter screws. Microinfusion experiments were conducted 20-24 h after surgery in awake mice. The injection microcannula was connected via polyethylene tubing to a syringe operated by a precision pump at a rate of 0.5 μL/min.

To test a functional measure of the pre-synaptic 5-$HT_{1A}$R activity, we evaluated the hypothermia response induced by (R)-(+)-8-hydroxy-2-(di-n-propylamino)tetralin hydrobromide (8-OH-DPAT, a selective 5-$HT_{1A}$R agonist) 24 hs after the infusion of a pool of naked siRNA or NLF-siRNA into dorsal raphe nucleus (DRN, 0.3 μg (0.02 nmoles)/1 μl/2 days). Control groups received the same amount of vehicle (aCSF: 125 mM NaCl, 2.5 mM KCl, 1.26 mM $CaCl_2$, 1.18 mM $MgCl_2$ and 5% glucose), ns naked siRNA and ns NLF-siRNA. Mice were kept in individual cages in experimental room at stable temperature of 22° C. 1 h before the experiment. All experiments were carried out between 10:00 a.m.

and 14:00 p.m. Body temperature was measured by inserting a lubricated probe into the rectum 5 min before the reading of the temperature while the mice was freely moving. The readings were obtained with a digital thermometer. A basal value was measured 5 min before and 15, 30, 60 and 120 min after 8-OH-DPAT administration. 8-OH-DPAT was dissolved in saline solution and injected intraperitoneally (i.p.) at 1 mg/kg in a volume of 5 ml/kg. The chosen dose of 8-OH-DPAT to induce hypothermia was based on previous works. Body temperature was assessed 24 hs after the last application of 5-$HT_{1A}$-targeting siRNAs into DRN in different groups of mice and in their respective controls. Additional experiments measuring body temperature rectally were performed in 5-$HT_{1A}$R KO mice (null 5-$HT_{1A}$R mice) to evaluate the absence of 8-OH-DPAT-induced hypothermia.

As can be seen in FIG. 1, the knockdown of 5-$HT_{1A}$R by local infusion of siRNAs shows a lack of hypothermia response induced by 8-OH-DPAT similar to 5-$HT_{1A}$R KO mice.

After this assay, mice were killed by decapitation and the brains rapidly removed, frozen on dry ice and stored at −20° C. Tissue sections, 14 μm thick, were cut using a microtome-cryostat, thaw-mounted onto APTS (3-aminopropyltriethoxysilane) coated slides and kept at −20° C. until use.

To assay the density of 5-$HT_{1A}$R protein we used [$^3$H]8-OH-DPAT for the autoradiographic visualization of 5-$HT_{1A}$ receptor sites. The experimental incubation conditions for [$^3$H]8-OH-DPAT have been previously described in the state of the art. Briefly, frozen tissue sections were thawed and dried, preincubated in 170 mM Tris-HCl pH 7.6, 4 mM $CaCl_2$ and 0.01% ascorbic acid for 30 minutes at room temperature, and then incubated in the same buffer, including 1 nM [$^3$H]-OH-DPAT (234.0 Ci/mmol) and $10^{-5}$ M pargyline for 60 minutes at room temperature. Non-specific binding was defined as that remaining in the presence of $10^{-5}$ M 5-HT. After incubation and washing, tissue sections were dipped in distilled ice-cold water and dried rapidly under a cold air stream. Tissues were exposed to tritium-sensitive film together with plastic $^3$H-standards for 60 days at 4° C.

The tissue DRN sections at 3 different antero-posterior (AP) coordinates in the mouse midbrain raphe nuclei (approximately AP −4.84, −4.60 and −4.24 mm) from bregma; Franklin and Paxinos, 1997) were used for quantification of receptor sites and they were processed simultaneously in the same experimental conditions. Quantitative analysis of the autoradiograms was done with $AIS^R$ computerized image analysis system.

Figure 2:
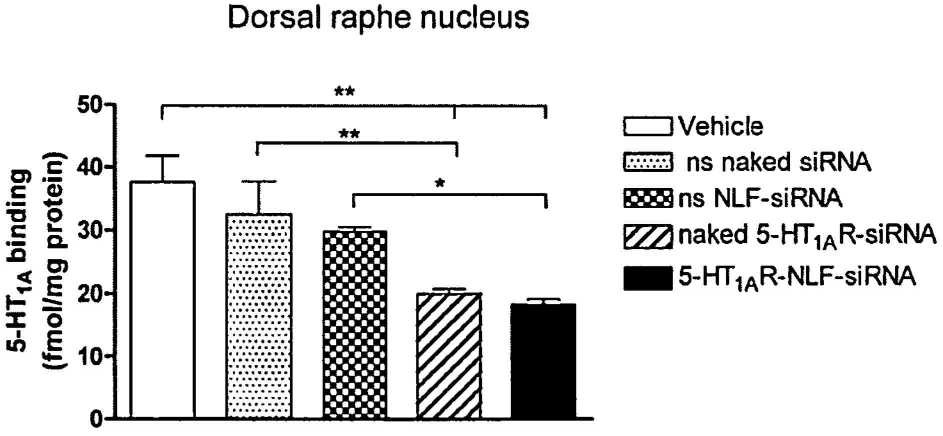
FIG. 2. Local infusion of 5-$HT_{1A}$R-targeting-siRNA (naked or conjugated) into dorsal raphe nucleus (DRN) induced specific knockdown of 5-$HT_{1A}$R protein levels. Mice received: i) vehicle, ii) nonsense naked siRNA (ns naked siRNA), iii) nonsense NLF-siRNA (ns NLF-siRNA), iv) naked 5-$HT_{1A}$R-siRNA or v) 5-$HT_{1A}$R-NLF-siRNA (0.3 μg/1 μl/2 days into DRN). Bars show densitometric quantification of [$^3$H]-8-OH-DPAT binding to 5-$HT_{1A}$R in DRN of mice expressed as mean 5-$HT_{1A}$R finoVmg tissue protein±SEM (two observations at 3 AP levels of dorsal raphe nucleus per animal and four to five animals per group). * $p<0.05$, ** $p<0.01$ significantly different from vehicle, ns naked siRNA and ns NLF-siRNA using one-way ANOVA followed by Newman-Keuls post hoc test.

As can be seen in FIG. 2, there is a decrease in 5-$HT_{1A}$R protein densities in naked siRNA and NLF-siRNA groups of approximately a 40-50% of control groups (vehicle, ns naked siRNA and ns NLF-siRNA). This change is paralleled with the suppression of the hypothermia response described in FIG. 1.

These experiments show that chemical modifications of NLF-siRNA in both strands does not reduce the ability of the siRNA to knock down the target gene when compared to the naked siRNA. Moreover, the local application of 5-$HT_{1A}$ receptor—specific siRNAs to the DRN by infusion results in the knockdown of the target mRNA, irrespective of whether the siRNA is naked or coupled to a targeting moiety. This can be explained since the administration method leads to the direct transfer of the siRNA to the neuronal body by means of the physical pressure exerted during the application and thus, no translocation across the neuronal membrane is required.

In the following examples, it will be shown that naked of 5-$HT_{1A}$ receptor—specific siRNAs are not capable of knocking down the target mRNA by either intracerebralventricular (i.c.v) or intranasal application and that the presence of a targeting molecule attached to the siRNA allows efficient knock down of the target mRNA.

Example 4

Differential Selectivity to Serotonergic Neurons in Midbrain Raphe Nuclei and Efficacy Assay of a NLF-siRNA Construction of this Invention Against Naked siRNA by In Vivo Intracerebro Ventricular (i.c.v.) Infusion into Dorsal 3$^{rd}$ Ventricle (D3V) of Mice This example shows that a NLF-siRNA construction and a naked siRNA show different selectivity for serotonergic neurons and efficacy for knocking-down the 5-$HT_{1A}$R when they are applied into dorsal 3$^{rd}$ ventricle (D3V) giving access to the whole brain trough the cerebro spinal fluid (CSF). This was evaluated by measurement of its mRNA expression level reduction, protein level decrease, functional changes and anti-depressant pharmacological potentiation.

A set of molecules (vehicle, ns naked siRNA, ns NLF-siRNA, naked siRNA and NLF-siRNA groups), as described in example 3, were infused at 30 μg/2.5 μl/1 day (2.3 nmoles) into dorsal 3$^{rd}$ ventricle (D3V) at the following stereotaxic coordinates (in mm: AP: −2.0, L: 0, DV: −2.1) using similar mice strain and infusion system of example 2. To determine the 5-$HT_{1A}$ R mRNA expression level we performed in situ hybridization assays using simultaneously four oligodeoxyribonucleotide probes for 5-$HT_{1A}$ R, complementary to bases 82-122, 123-171, 885-933 and 1341-1389. Each 5-$HT_{1A}$ receptor oligonucleotide was individually labeled (2 μmol) at its 3'-end with [$^{33}$P]-dATP (>2500 Ci/mmol) using terminal deoxynucleotidyltransferase, purified by centrifugation using QIAquick Nucleotide Removal Kit. The protocols for single label in situ hybridization were based on previously described procedures. Briefly, frozen tissue sections, as described in example 2, were first brought to room temperature, fixed for 20 min at 4° C. in 4% paraformaldehyde in phosphate buffered saline (1×PBS: 8 mM $Na_2HPO_4$, 1.4 mM $KH_2PO_4$, 136 mM NaCl, 2.6 mM KCl), washed for 5 min in 3×PBS at room temperature, twice for 5 min each in 1×PBS and incubated for 2 min at 21° C. in a solution of pre-digested pronase at a final concentration of 24 U/ml in 50 mM Tris-HCl pH 7.5, 5 mM EDTA. The enzymatic activity was stopped by immersion for 30 s in 2 mg/ml glycine in 1×PBS. Tissues were finally rinsed in 1×PBS and dehydrated through a graded series of ethanol. For hybridization, the radioactively labeled probes were diluted in a solution containing 50% formamide, 4×SSC (1×SSC: 150 mM NaCl, mM sodium citrate), 1×Denhardt's solution (0.02% Ficoll, 0.02% polyvinylpyrrolidone, 0.02% bovine serum albumin), 10% dextran sulfate, 1% sarkosyl, 20 mM phosphate buffer pH 7.0, 250 μg/ml yeast tRNA and 500 μg/ml salmon sperm DNA. The final concentrations of radioactive probes in the hybridization buffer were in the same range (1.5 nM). Tissue sections were covered with hybridization solution containing the labeled probes, overlaid with Nescofilm coverslips and incubated overnight at 42° C. in humid boxes. Sections were then washed four times (15 min each) in 1×SSC at 60° C. and once in 1×SSC at room temperature for 30 min, dehydrated and exposed to film for 3-4 weeks. Film optical densities were semiquantified with $AIS^R$ computerized image analysis system.

For the same group of mice used in in situ hybridization, we assayed the density of 5-$HT_{1A}$R protein using [$^3$H]8-OH- DPAT for the autoradiographic visualization of 5-$HT_{1A}$ receptor sites as was described in example 2.

The 5-$HT_{1A}$R proteins are heavily expressed presynaptically on serotonin neurons (midbrain raphe nuclei) and on neurons postsynaptically located to 5-HT nerve terminals, mainly in cortico-limbic areas. (ie. hippocampus).

As can be seen in FIGS. 3A and B, only NLF-siRNA molecules induced a specific knowdown of 5-$HT_{1A}$R mRNA level at three different anteroposterior coordinates in the mouse midbrain raphe nuclei, where the bodies of serotonergic neurons are located.

Figure 3:
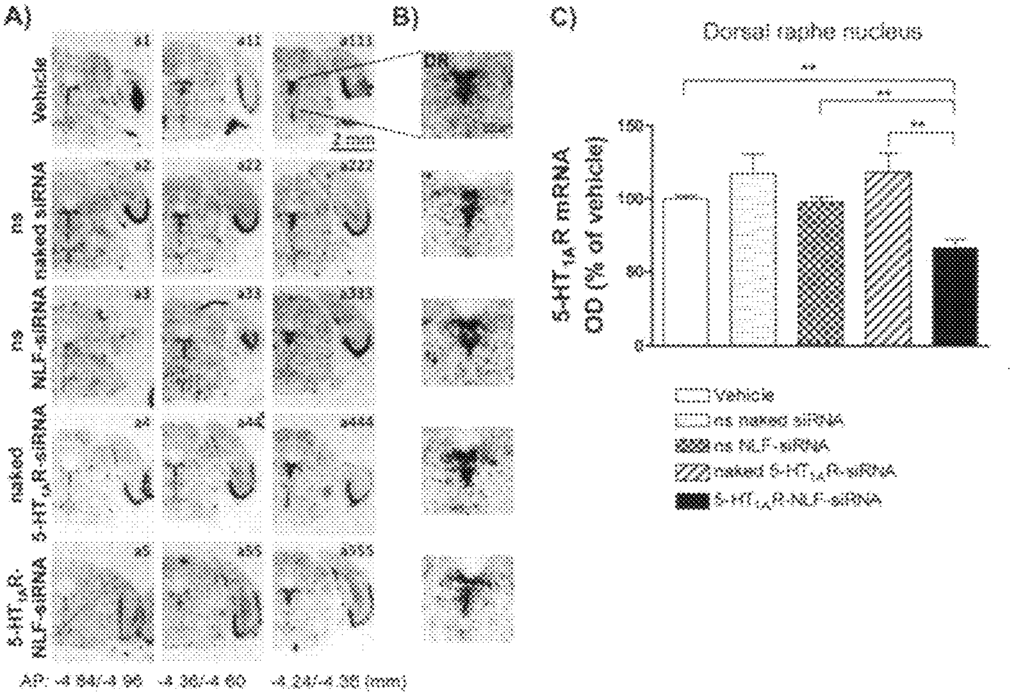
FIG. 3. Selective 5-$HT_{1A}$ autoreceptor silencing by intracerebroventricular (i.c.v) administration of conjugated 5-$HT_{1A}$R-NLF-siRNA. A) 5-$HT_{1A}$R expression in raphe nuclei was assessed by in situ hybridization. Mice received a single administration into dorsal 3 ventricle (D3V) of: i) vehicle, ii) nonsense naked siRNA (ns naked siRNA), iii) nonsense NLF-siRNA (ns NLF-siRNA), iv) naked 5-$HT_{1A}$R— siRNA or v) 5-$HT_{1A}$R-NLF-siRNA (30 μg/2.5 μl/1 day). a1-a555 show coronal sections of raphe nuclei of mice bound with $^{33}$P-labeled oligonucleotide at 3 different antero-posterior (AP) coordinates in mm: −4.84/−4.96, −4.36/−4.60 and −4.24/−4.36 from bregma (caudal-rostral from left to right). Scale bar, 2 mm. B) High magnification of section shown in a111-a555. Scale bar, 500 μm. C) Bar graphic showing 5-$HT_{1A}$R-NLF-siRNA induced a reduction of 5-$HT_{1A}$R mRNA level in dorsal raphe nucleus. Densitometric quantification of 5-$HT_{1A}$R mRNA positive grains measured in films is shown as mean optical densities (OD) percentage values±SEM (n=4-5 mice per group and two to four observations at 3 AP levels of dorsal raphe nucleus). ** $p<0.01$ significantly different from vehicle, ns NLF-siRNA and naked 5-$HT_{1A}$R-siRNA using one-way ANOVA followed by Newman-Keuls post hoc test.

As can be seen in FIG. 3. C, the densitometric quantification of 5-$HT_{1A}$R mRNA positive grains measures in films at Dorsal raphe nucleus showed a reduction of 50% on expression level in group of NLF-siRNA compared with the other assayed groups. Differences in 5-$HT_{1A}$R mRNA expression are mainly appreciated in the DRN area.

Figure 4:
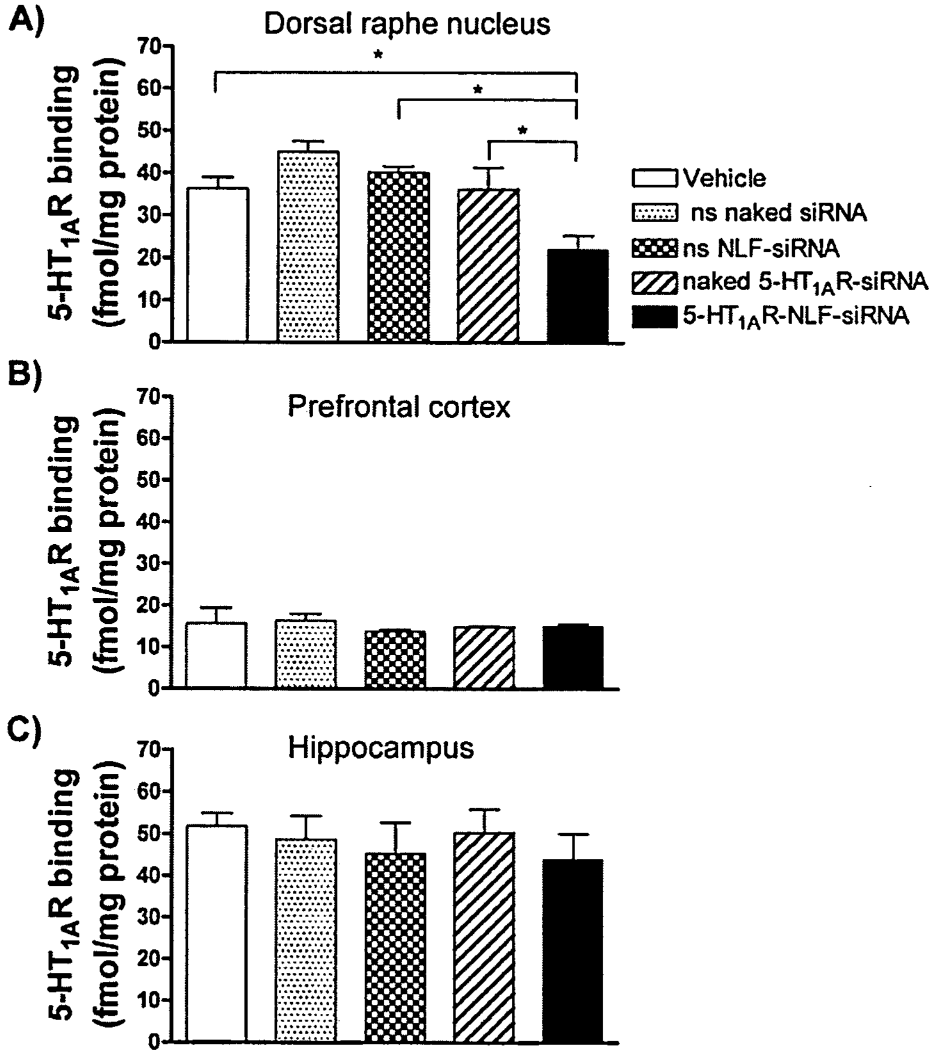
FIG. 4. 5-$HT_{1A}$R-NLF-siRNA induced specific knockdown of 5-$HT_{1A}$R at presynaptic, but not postsynaptic sites. 5-$HT_{1A}$R protein levels in dorsal raphe nucleus (A), prefrontal cortex (B) and hippocampus (C) were assessed by autoradiogaphic binding using $^{3}$[H]-8-OH-DPAT. Mice received a single administration into dorsal 3 ventricle (D3V) of i) vehicle, ii) nonsense naked siRNA (ns naked siRNA), iii) nonsense NLF-siRNA (ns NLF-siRNA), iv) naked 5-$HT_{1A}$R-siRNA or v) 5-$HT_{1A}$R-NLF-siRNA (30 μg/2.5 μl/1 day). Bars represent mean 5-$HT_{1A}$R fmol/mg tissue protein±SEM (n=4-5 mice per group and two observations at 3 AP levels of dorsal raphe nucleus and two observations at left and right sites of prefrontal cortex and hippocampus). * $p<0.05$ significantly different from all other treatments, using one-way ANOVA followed by Newman-Keuls post hoc test.

As can be seen in FIG. 4, only NLF-siRNA molecules induced a specific reduction of 5-$HT_{1A}$R protein level (about 50%) at presynaptic (Dorsal raphe nucleus), but not postsynaptic (hippocampus or Prefrontal cortex) brain areas. determined by binding assays on 5-$HT_{1A}$ receptor sites using [$^3$H] 8-OH-DPAT. Differences in 5-$HT_{1A}$R mRNA and protein expression are mainly appreciated in the DRN area.

These results indicated that the NLF-siRNA selectively direct the oligonucleotides that perform interference of the mRNA to specific serotonergic neurons localized in dorsal raphe nucleus thus enhancing the effectivity of said RNA interference with the expresion of the targeted neuronal receptors.

In order to check if the specific knockdown of 5-$HT_{1A}$ receptor could influence the expression of related 5-HT proteins like the serotonin transporter (5-HTT or SERT) or the 5-$HT_{1B}$ receptor, the density of the serotonin transporter protein and of the 5-HT1B receptor were determined in DRN.

To assay the density of serotonin transporter protein we used [$^3$H]citalopram for the autoradiographic visualization of 5-HTT sites. Briefly, frozen tissue sections were thawed and dried, preincubated in 50 mM Tris-HCl buffer (pH 7.4 at 25° C.) containing 120 mM NaCl and 5 mM KCl for 15 mm at room temperature. Then incubated in the same buffer containing 1.5 nM [$^3$H]citalopram (70.0 Ci/mmol) for 60 min at room time. Non-specific binding was defined as that remaining in the presence of 1 μM fluoxetine. After incubation and washing, tissue sections were dipped in distilled ice-cold water and dried rapidly under a cold air stream. Tissues were exposed to tritium-sensitive film together with plastic $^3$H-standards for 40 days at 4° C.

The tissue DRN sections at 3 different antero-posterior (AP) coordinates in the mouse midbrain raphe nuclei (approximately AP −4.84/−4.96, −4.60/−4.36 and −4.24 mm) from bregma; Franklin and Paxinos, 1997) were used for quantification of 5-HTT sites and they were processed simultaneously in the same experimental conditions. Quantitative analysis of the autoradiograms was done with AIS$^R$ computerized image analysis system. As can be seen in FIG. 5A., vehicle, naked siRNA and NLF-siRNA groups does not shown any reduction or change on 5-HTT (serotonin transporter, SERT) at protein level at Dorsal raphe nucleus.

Figure 5:
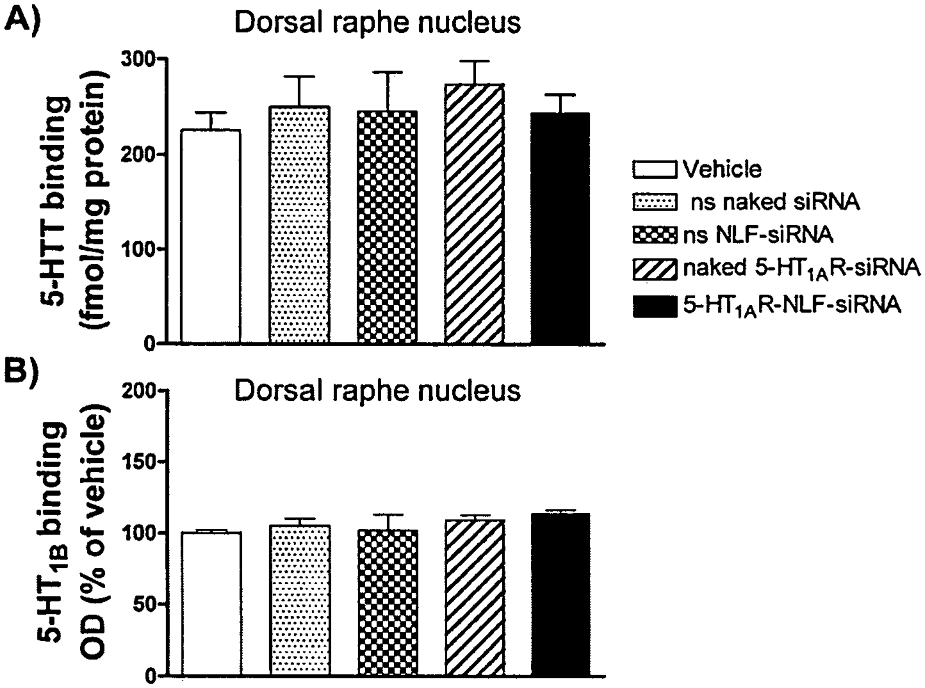
FIG. 5. Serotonin-5-HT transporter (5-HTT) and 5-$HT_{1B}$ receptor (5-$HT_{1B}$R) binding levels in dorsal raphe nucleus were unaltered by 5-$HT_{1A}$R-siRNA treatment. A) 5-HTT protein levels in dorsal raphe nucleus were assessed by autoradiogaphic binding using $^{3}$[H]-citalopram. B) 5-$HT_{1B}$R protein levels in dorsal raphe nucleus were evaluated by autoradiographic binding using $^{125}$[I]cyanopindolol in presence of isoprenaline to block β-adrenergic sites. Mice received a single administration into dorsal 3 ventricle (D3V) of: i) vehicle, ii) nonsense naked siRNA (ns naked siRNA), iii) nonsense NLF-siRNA (ns NLF-siRNA), iv) naked 5-$HT_{1A}$R— siRNA or v) 5-$HT_{1A}$R-NLF-siRNA (30 μg/2.5 μl/1 day). Bar graphics show: A) mean 5-HTT fmol/mg tissue protein±SEM and B) mean optical densities (OD) percentage values±SEM (n=4 mice per group and two observations at 3 AP levels of dorsal raphe nucleus).

To assay the density of 5-$HT_{1B}$ receptor (5-$HT_{1B}$R) protein we used [$^{125}$I]iodocyanopindolol for the autoradiographic visualization of 5-$HT_{1B}$R sites. Sections were preincubated for 10 min at room temperature in 170 mM Tris-HCl buffer (pH 7.4) containing 150 mM NaCl, and then incubated for 2 h in the same buffer supplemented with 100 μM [$^{125}$I]iodocyanopindolol ([$^{125}$I]CYP, 2000 Ci/mmol) and 100 nM 8-OH-DPAT to block 5-$HT_{1A}$R sites and 30 μM isoprenaline to block β-adrenergic sites. Non-specific binding was determined on adjacent sections incubated under the same conditions but in the presence of 10 μM 5-HT. Sections were rinsed twice in the same buffer, quickly dipped in distilled water at 4° C., dried under cold-air and exposed to a sensitive film (Hyperfilm-$^3$H) at 4° C. for one day. Film optical densities were semiquantified with AIS$^R$ computerized image analysis system. As can be seen in FIG. 5.B., vehicle, naked siRNA and NLF-siRNA groups does not shown any reduction or change on 5-$HT_{1B}$ receptor at protein level at Dorsal raphe nucleus.

Figure 6:
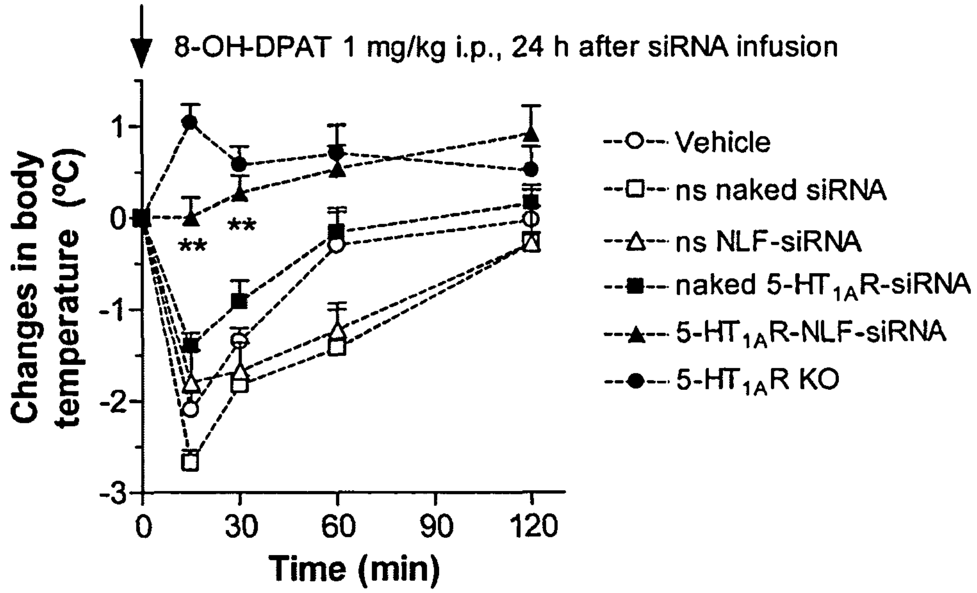
FIG. 6. Hypothermia response induced by (R)-(+)-8-hydroxy-2-(di-n-propylamino)tetralin hydrobromide (8-OH-DPAT, selective 5-$HT_{1A}$R agonist) as functional measure of presynaptic 5-$HT_{1A}$R activity. Mice received a single administration into dorsal 3 ventricle (D3V) of i) vehicle, ii) nonsense naked siRNA (ns naked siRNA), iii) nonsense NLF-siRNA (ns NLF-siRNA), iv) naked 5-$HT_{1A}$R-siRNA or v) 5-$HT_{1A}$R-NLF-siRNA (30 μg/2.5 μl/1 day). Additional group of 5-$HT_{1A}$R knockout (5-$HT_{1A}$R-KO) mice was also evaluated. Temperature body was assessed 5 min before and 15, 30, 60 and 120 min after 8-OH-DPAT administration (1 mg/kg i.p.). Note the absence of 8-OH-DPAT effect on body temperature in conjugated 5-$HT_{1A}$R-NLF-siRNA and 5-$HT_{1A}$R-KO mice. Values are shown as mean of changes in body temperature±SEM from 7-10 mice per group. ** $p<0.01$ significantly different from vehicle, ns naked siRNA, ns NLF-siRNA and naked 5-$HT_{1A}$R-siRNA, respectively using repeated-measure ANOVA with treatment as the between factor and time as within-subject variable followed by multiple comparison Newman-Keuls test.

To evaluate the NLF-siRNA effect on the functional features of 5-$HT_{1A}$R we assayed hypothermia response induced by 8-OH-DPAT and 5-HT release in the medial prefrontral cortex (mPFC). We evaluated the hypothermia response induced by 8-OH-DPAT 24 hs after the infusion of a pool of naked siRNAs or NLF-siRNA (as described in example 2) into dorsal 3$^{rd}$ ventricle (D3V, 30 μg/2.5 μl/1 day). As can be seen in FIG. 6, only the knockdown of 5-$HT_{1A}$R by infused NLF-siRNA showed a lack of hypothermia response induced by 8-OH-DPAT similar to 5-$HT_{1A}$R KO mice. Other naked siRNA and control (vehicle, ns naked siRNA and ns NLF-siRNA) groups did not show a knockdown effect on 5-$HT_{1A}$R (as was seen in FIGS. 4 and 5) and it was paralleled with a typical curve in the hypothermia response induced by 8-OH-DPAT.

As mentioned above, the activation of 5-$HT_{1A}$ R located in serotonergic neurons, by endogenous agonist 5-HT (neurotransmitter serotonin) or selective agonists (i.e. 8-OH-DPAT) suppresses cell firing and impulse-dependent 5-HT release in midbrain raphe nuclei and in terminal projections brain areas like medial prefrontal cortex, hippocampus, etc. resulting in lower 5-HT levels (8-OH-DPAT effect). To evaluate 5-HT release, an intracerebral microdyalisis procedure was used as has been described in the state of the art. In brief, the shaft of the probe was made up of 15-mm long, 25-gauge (501 μm OD, 300 μm ID) stainless-steel tubing. The inflow and outflow tubes threaded through the 25 gauge tubing consisted of fused silica capillary tubing of 110 μM OD and 40 μM ID. The upper exposed ends of silica tubing were inserted into 7-mm long, 27 gauge (410 μm OD, 220 μM ID) stainless-steel tubing. Mice were anesthetized with sodium pentobarbital (40 mg/kg, i.p.) and positioned in a stereotaxic frame. Each mouse was implanted with one dialysis probe equipped with a Cuprophan membrane (2-mm long; 5000 Da molecular weight cut-off) in the medial prefrontal cortex (mPFC) (in mm: AP +2.2, L −0.2, DV −3.4 from bregma, according to the atlas of Franklin and Paxinos, 1997).

Microdialysis experiments were conducted 48-72 h after surgery in freely moving mice by continuously perfusing probes with aCSF (125 mM NaCl, 2.5 mM KCl, 1.26 mM $CaCl_2$, 1.18 mM $MgCl_2$) at a rate of 2.0 μl/min with a WPI model sp220i syringe pump attached to an overhead liquid swivel. Dialysate samples of 60 μl were collected every 30 min in microcentrifuge vials.

Following an initial 60-min stabilization period, four baseline samples were collected before systemic 8-OH-DPAT administration (0.5 mg/kg i.p.) and then successive dialysate samples were collected. At the completion of dialysis experiments, mice were sacrificed and the brains were immediately removed and frozen at −70° C. Coronal sections (50 μm) of the brain were cut afterwards on a cryostat and stained with cresyl violet, according to standard procedures, for localization of the perfusion site. Only data obtained from animals with histologically correct probe placements were used for subsequent statistical analysis.

The concentration of 5-HT in dialysate samples was determined by HPLC using a 3-μm octadecylsilica (ODS) column (7.5 cm×0.46 cm) and detected amperometrically with a Hewlett-Packard 1049 detector set at an oxidation potential of 0.6 V. The mobile phase consisted of 0.15 M $NaH_2PO_4.H_2O$, 1.8 mM octyl sodium sulphate, 0.2 mM EDTA (pH 2.8 adjusted with phosphoric acid) and 30% methanol and was pumped at 0.7 ml/min. The retention time for 5-HT was 3.5-4 min and the detection limit was 2 fmol/sample.

Figure 7:
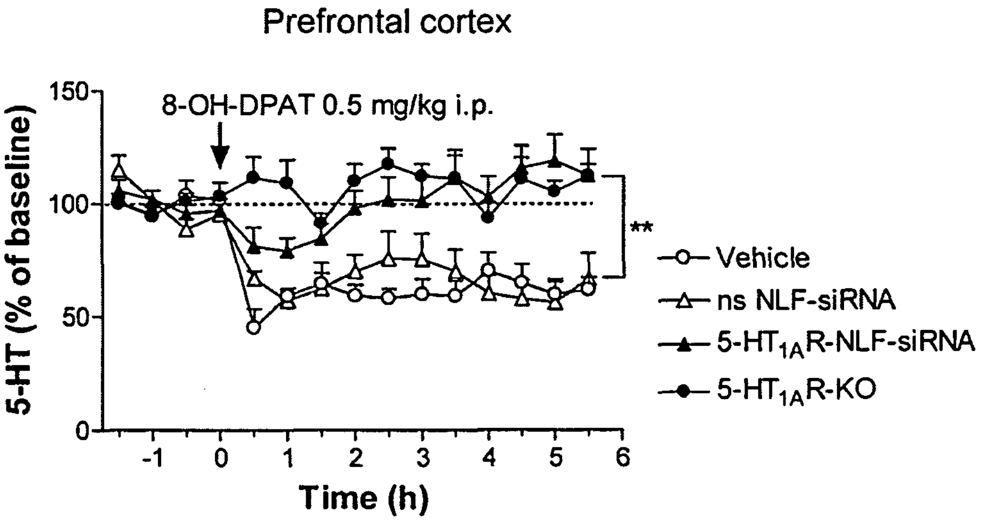
FIG. 7. Effect of systemic (R)-(+)-8-hydroxy-2-(di-n-propylamino)tetralin hydrobromide administration (8-OH-DPAT, 0.5 mg/kg i.p.) on dialysate 5-HT levels in medial prefrontal cortex (mPFC) of mice. The groups of mice were: i) vehicle, ii) nonsense NLF-siRNA (ns NLF-siRNA), iii) 5-$HT_{1A}$R-targeting NLF-siRNA (5-$HT_{1A}$R-NLF-siRNA) and iv) 5-$HT_{1A}$R knochout mice (5-$HT_{1A}$R-KO). Mice were infused with vehicle or siRNA at 30 μg/2.5 μl/1 day, i.c.v. and the microdialysis experiments were conducted 24-48 h after infusion. Note the absence of 8-OH-DPAT effect on reduced 5-HT levels in mPFC of 5-$HT_{1A}$ autoreceptor knockdown and 5-$HT_{1A}$R-KO mice. Data are expressed as percentage of baseline and are shown as mean±SEM (n=5-9 mice/group). ** $p<0.01$ significantly different from vehicle and ns NLF-siRNA groups, using repeated-measure ANOVA with treatment as the between factor and time as within-subject variable, followed by multiple comparison Newman-Keuls test.

As can be seen in FIG. 7 there was an absence of 8-OH-DPAT effect on prefrontal serotonin release in NLF-siRNA treated mice group mice compared with ns NLF-siRNA group mice. This evidences that a knockdown of the 5-$HT_{1A}$R in serotonergic neurons can be functionally evaluated by the reduction of agonist 8-OH-DPAT effects on 5-HT amount in terminal brain areas.

Example 5

Competitive Assays of Free Selectivity Ligand (Sertraline) and the NLF-siRNA Construction According to the Invention by Measuring Functional Parameters of the Serotonergic Neuron in Acutely Pretreated Mice with Ligand Followed by In Vivo Intracerebro Ventricular (i.c.v.) Infusion of the NLF-siRNA In order to determine if the selectivity ligand conjugated to the siRNA in NLF-siRNAs, is a key component of the delivery to dorsal raphe nucleus cells (mainly serotonergic neurons), some competitive assays were performed. Mice received an acute injection of the selective free ligand, the 5-HTT inhibitor sertraline (20 mg/kg i.p.) 3 h before siRNA infusion into D3V (30 μg/2.5 μl/1 day, i.c.v.). In addition, a group of mice received vehicle i.p. and vehicle into D3V.

The microdialysis experiments were conducted 24 h after i.c.v. vehicle or siRNA administrations. As can be seen in FIG. 8A, the acute sertraline injection (20 mg/kg i.p.) avoided the silencing of 5-$HT_{1A}$ autoreceptor by conjugated 5-$HT_{1A}$R-NLF-siRNA and the acute 8-OHDPAT administration (selective 5-$HT_{1A}$R agonist, 0.5 mg/kg i.p.) reduced the 5-HT levels in medial prefrontal cortex like control groups.

The effect of 8-OH-DPAT administration (1 mg/kg i.p.) on body temperature in NLF-siRNA mice previously treated with selective 5-HTT inhibitor, sertraline (20 mg/kg i.p.) was also evaluated in mice were similar to those used in FIG. 8A. FIG. 8B shows that sertraline efficiently competes with 5-$HT_{1A}$R-NLF-siRNAs thus resulting in an hypothermia response similar to control groups, indicating the ausence of transfection and knockdown of the 5-$HT_{1A}$R mRNA.

These results demonstrates that an acute administration of the free selectivity ligand (sertraline) blocks or compete with the sertraline conjugated siRNAs (NLF-siRNAs) by the same entry point to target neurons (i.e. 5-HTT, serotonin transporter). At first, sertraline has a high specificity and affinity (in the nanomolar range) by the 5-HT transporter, and by conjugating with siRNAs as in NLF-siRNAs, the new conjugate maintains the affinity by this 5-HT transporter. On the other hand, 5-HT transporter is only expressed in 5-HT neurons and this combination of high affinity by the transporter and cell-type specific expression determine the selectivity nature of the NLF-siRNAs that has a sertraline or SSRI ligand conjugated.

Example 6

Potentiation of the Increment on 5-HT Levels in Prefrontal Cortex after Acute Anti-Depressant Application (i.e. Fluoxetine) in In Vivo Intracerebro Ventricular (i.c.v.) Infusion of the NLF-siRNA into Dorsal 3rd Ventricle (D3V) Mice Compared to Control Groups In physiological conditions, SSRIs (i.e. fluoxetine) cause a marked enhancement of the extracellular concentration of serotonin in the midbrain raphe nuclei and forebrain. The increase of extracellular 5-HT produced by reuptake blockade of serotonin transporter (SERT) activates 5-$HT_{1A}$ autoreceptors in the midbrain raphe nuclei, suppressing cell firing and terminal release, an effect that attenuates the extracellular 5-HT increase produced by reuptake blockade. Consequently, the activation of postsynaptic serotonin receptors responsible for the therapeutic effect is lower than expected. It is known that the blockade of these negative feedback mechanisms with 5-$HT_{1A}$ receptor antagonists (i.e pindolol) potentiates the 5-HT increase produced by SSRIs and, therefore, might serve to accelerate the clinical effects of SSRIs.

Figure 9:
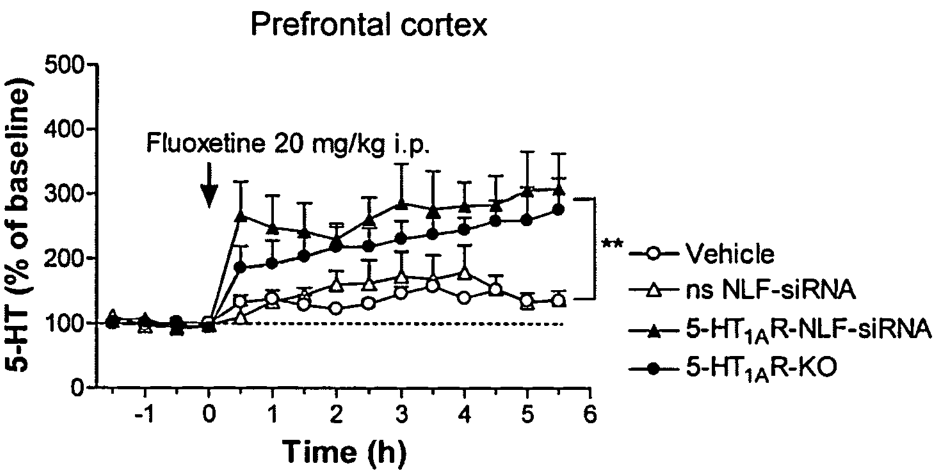
FIG. 9. Effect of acute fluoxetine (selective inhibitor of serotonin transporter-5-HTT, 20 mg/kg i.p.) administration on dialysate 5-HT levels in medial prefrontal cortex (mPFC) of mice. The groups of mice were: i) vehicle, ii) nonsense NLF-siRNA (ns NLF-siRNA), iii) 5-$HT_{1A}$R-targeting NLF-siRNA (5-$HT_{1A}$R-NLF-siRNA) and iv) 5-$HT_{1A}$R knockout (5-$HT_{1A}$R-KO). Mice were infused with vehicle or siRNA at 30 μg/2.5 μl/1 day, i.c.v. and the microdialysis experiments were conducted 24-48 h after infusion. Note the enhanced effect of fluoxetine on 5-HT levels in mPFC of 5-$HT_{1A}$ autoreceptor knockdown mice, similar those in 5-$HT_{1A}$R-KO mice. Data are expressed as percentage of baseline and are shown as mean±SEM (n=4-6 mice/group). ** $p<0.01$ significantly different from vehicle and ns NLF-siRNA groups, using repeated-measure ANOVA with treatment as the between factor and time as within-subject variable, followed by multiple comparison Newman-Keuls test.

As can be seen in FIG. 9, the dyalisate serotonin concentration in the medial prefrontal cortex was around a 50% higher than baseline after the systemic fluoxetine administration in nonsense NLF-siRNA (ns NLF-siRNA) mice group, where the 5-$HT_{1A}$ receptor was expected to be fully functional as showed before. In NLF-siRNA mice group, the knockdown of presynaptic 5-$HT_{1A}$ receptor potentiates the effect of systemic fluoxetine administration up to 150% of the baseline terminal 5-HT levels in medial prefrontal cortex.

These results clearly demonstrate that the oligonucleotide sequences of the invention (NLF-siRNA), coupled to a sertraline molecule, blocked the expression of the 5-$HT_{1A}$ receptor by knocking-down the corresponding mRNA transcript that was going to be translated. The oligonucleotide sequences of the invention (NLF-siRNA) knocked-down said expression in a major index than the corresponding siRNA in naked form (naked siRNA). Therefore, the oligonucleotides of the invention are more efficacious than equivalent amounts of the same sequences of siRNA, in which no modification is performed (naked siRNA).

These observations allow deducing that the group of formula (I) does not interfere in the knock-down of the expression of the receptor. Moreover, the presence of the additional conjugation molecule enhances the efficacy of the inhibition performed by the RNAi mechanism.

Example 7

Anti-Depressant and Anxiolitic Behavioural Study in Response to In Vivo Intracerebro Ventricular (i.c.v.) Infusion of NLF-siRNA and Comparison to 5-$HT_{1A}$R Knock-Out (KO) Mice To assay the potential anti-depressive effect of knocking down of presynaptic 5-$HT_{1A}$Receptor, behavioral analyses were performed in 9- to 12-week-old adult mice. They were conducted in the following order, with at least 1 day between tests: elevated plus maze and tail suspension test. The elevated plus maze was performed using a cross maze with 30 cm long and 5 cm wide-arms elevated 31 cm from the ground in a dimly lit room (50 lux). Animals were introduced to the middle portion of the maze facing an open arm and were allowed to explore freely for 5 min. Time spent and distance traveled in the open and closed arms were measured by a video-tracking system. The apparatus was wiped with 70% ethanol and allowed to dry between mice. All testing was performed between 11:00 AM and 4:00 PM. On test days, animals were transported to the dimly illuminated behavioral laboratory and were left undisturbed for at least 1 h before testing. In the tail suspension test mice were suspended by the tail and we use tape to secure them to a horizontal bar. The animlas were suspended for 6 min and the immobility during this period was assessed using an automated videotrack software package.

Figure 10:
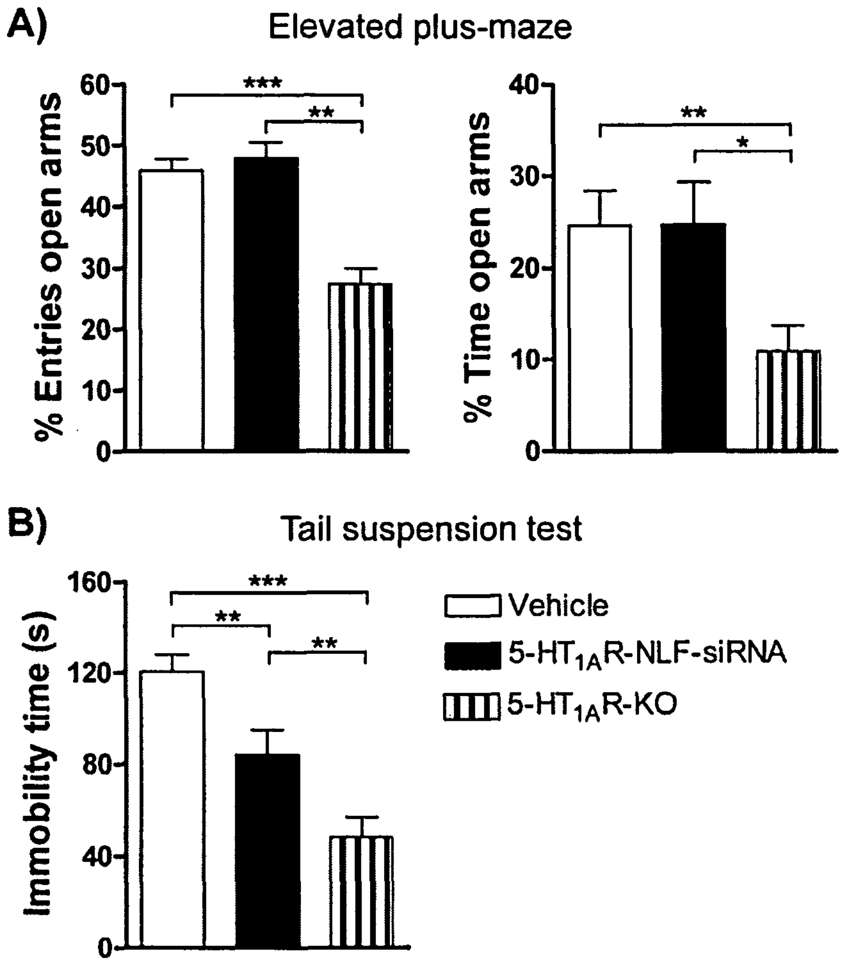
FIG. 10. No change in anxiety-like behavior, but altered response in stress/depression-related test in 5-$HT_{1A}$ autoreceptor knockdown mice. The groups of mice were: i) vehicle, ii) 5-$HT_{1A}$R-targeting NLF-siRNA (5-$HT_{1A}$R-NLF-siRNA) and iii) 5-$HT_{1A}$R knockout (5-$HT_{1A}$R-KO). Mice were infused into D3V with vehicle or siRNA at 30 μg/2.5 μl/1 day, i.c.v. A) The anxiety-like behavior was evaluated using the elevated plus-maze paradigm 24 h after vehicle or siRNA administrations. Unlike $5\text{-HT}_{1A}$R knockout mice ($5\text{-HT}_{1A}$R-KO), $5\text{-HT}_{1A}$ autoreceptor knockdown mice ($5\text{-HT}_{1A}$R-NLF-siRNA) displayed no difference in the number of entries and time spent in the open arms of elevated plus-maze. B) The tail suspension test was chosen paradigm to evaluate the response in an acute stress/depression situation. This test was assessed 48 h after vehicle or siRNA administrations. $5\text{-HT}_{1A}$ autoreceptor knockdown and $5\text{-HT}_{1A}$R-KO mice displayed increased mobility compared to vehicle group in a stressfull situation. Values are mean±SEM (n=12-18 mice/group). * p<0.05,  p<0.01, * p<0.001 significantly different from vehicle using one-way ANOVA followed by Newman-Keuls post hoc test.

As can be seen in FIG. 10, no changes were observed in anxiety-like behavior, but an altered response in stress/depression-related test in 5-$HT_{1A}$ autoreceptor knockdown mice. The potential anti-depressant capability of the NLF-siRNA is located between the KO mice and wild type control mice. It suggests that 5-$HT_{1A}$ receptor could become a new target for depression treatment. There are around a 40% of depressive patients that do not respond to conventional SSRI treatments and they could become the first candidates for a new therapeutic approach to the disease.

Example 8

Differential Efficacy of Knockdown by of 5-$HT_{1A}$R NLF-siRNA Vs. Nonsense NLF-siRNA in Functional Serotoninergic Measurements by In Vivo Intranasal (i.n) Application in Mice To validate the intranasal way of application as a potential therapeutic administration, vehicle and NLF-siRNAs were assayed to check hypothermia response, mRNA levels at Dorsal raphe nucleus and 5-HT dyalizate at Prefrontal cortex.

Mice were anesthetized with pentobarbital 40 mg/kg i.p and positioned on their backs. PBS or NLF-siRNA was slowly and gently dropped in alternating nostril with a micropipette tip in 5-ul aliquots.

Figure 11:
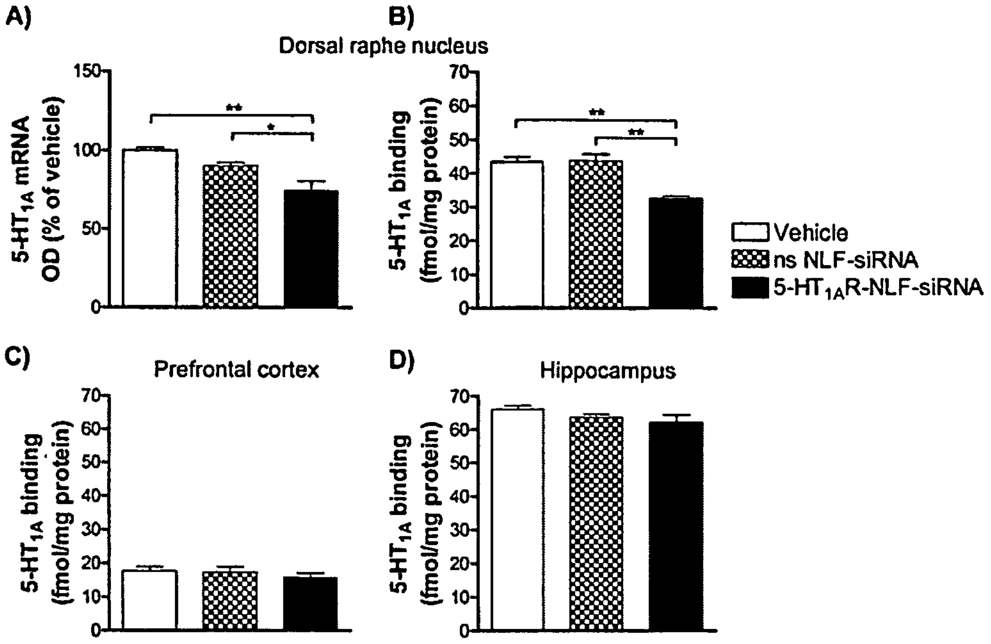
FIG. 11. Selective $5\text{-HT}_{1A}$ autoreceptor silencing by intranasal administration of conjugated $5\text{-HT}_{1A}$R-NLF-siRNA. Mice received a single intranasal administration of: i) vehicle, ii) nonsense NLF-siRNA (ns NLF-siRNA) and iii) $5\text{-HT}_{1A}$R-NLF-siRNA (15 μg/5 μl in each nostril). A) $5\text{-HT}_{1A}$R expression in dorsal raphe nucleus (DRN) was assessed by in situ hybridization. Bar graphic showing $5\text{-HT}_{1A}$R-NLF-siRNA induced a reduction of $5\text{-HT}_{1A}$R mRNA level in DRN. Densitometric quantification of $5\text{-HT}_{1A}$R mRNA positive grains measured in films is shown as mean optical densities (OD) percentage values±SEM (n=4 mice per group and two observations at 3 AP levels of DRN). B-D) $5\text{-HT}_{1A}$R-NLF-siRNA induced specific knockdown of $5\text{-HT}_{1A}$R at presynaptic, but not postsynaptic sites. $5\text{-HT}_{1A}$R protein levels in dorsal raphe nucleus (B), prefrontal cortex (C) and hippocampus (D) were assessed by autoradiogaphic binding using $^{3}$[H]-8-OH-DPAT. Bars represent mean $5\text{-HT}_{1A}$R fmol/mg tissue protein±SEM (n=4 mice per group and two observations at 3 AP levels of DRN and two observations at left and right sites of prefrontal cortex and hippocampus). * p<0.05, ** p<0.01 significantly different from vehicle and ns NLF-siRNA using one-way ANOVA followed by Newman-Keuls post hoc test.
Figure 12:
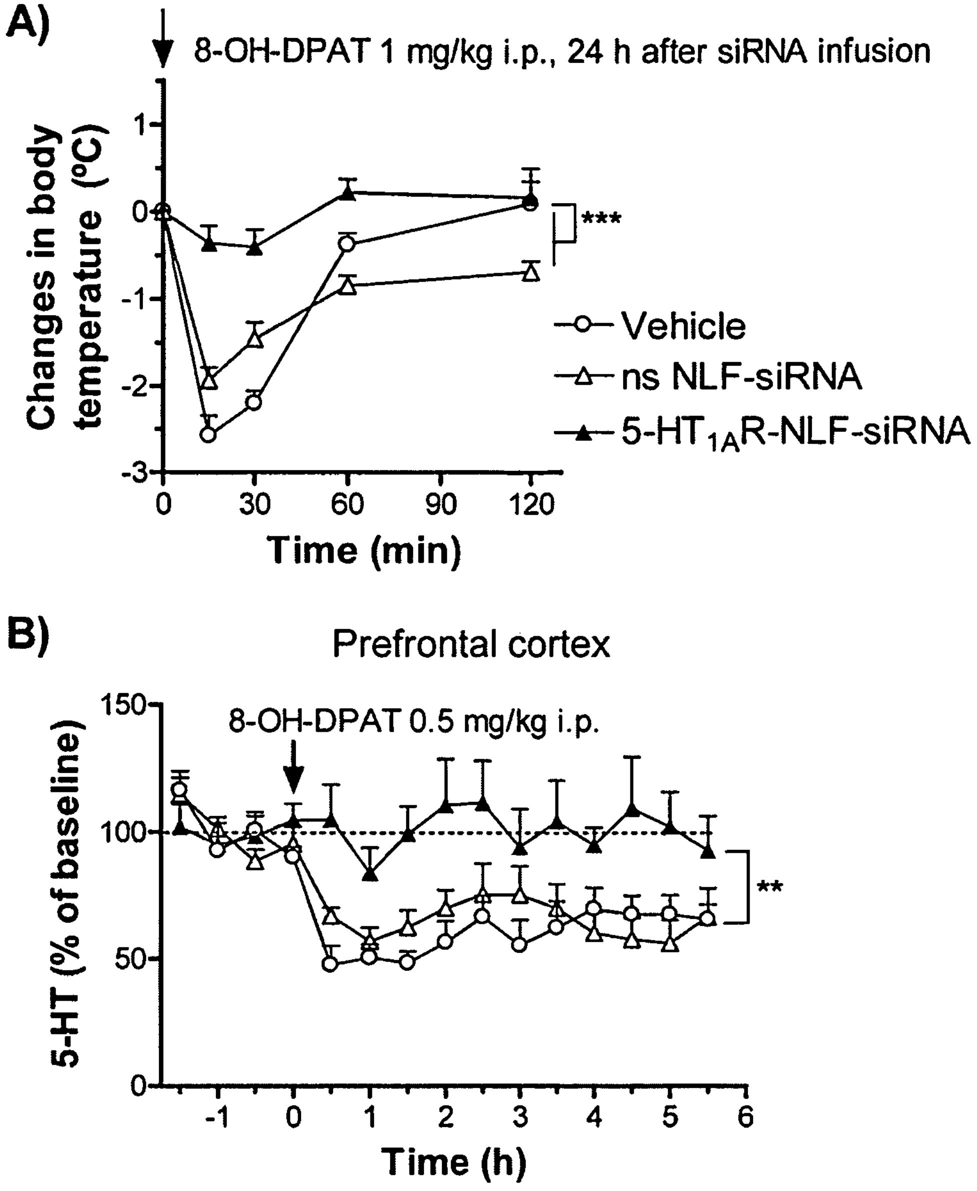
FIG. 12. Absence of 8-OH-DPAT effect (selective $5\text{-HT}_{1A}$R agonist) on physiological and neurochemical parameters in $5\text{-HT}_{1A}$ autoreceptor knockdown mice. The groups of mice received a single intranasal administration of i) vehicle, ii) nonsense NLF-siRNA (ns NLF-siRNA) and iii) $5\text{-HT}_{1A}$R-NLF-siRNA (15 μg/5 μl in each nostril). A) Unlike vehicle and ns NLF-siRNA treated-mice, 1 mg/kg i.p. dose of 8-OH-DPAT did not produce any change on body temperature in $5\text{-HT}_{1A}$R-NLF-siRNA mice. Values are shown as mean of changes in body temperature±SEM (n=4-7 mice per group). B) Extracellular 5-HT levels measured by in vivo microdialysis in mPFC of vehicle, ns NLF-siRNA and $5\text{-HT}_{1A}$R-NLF-siRNA mice, following systemic 8-OH-DPAT administration (0.5 mg/kg i.p.). 5-HT levels were reduced in mPFC of both vehicle and ns NLF-siRNA. However, $5\text{-HT}_{1A}$R-NLF-siRNA mice displayed an absence of 8-OH-DPAT effect on 5-HT levels in mPFC. Data are expressed as percentage of baseline and are shown as mean±SEM (n=4-9 mice/group).  p<0.01, * p<0.001 significantly different from vehicle and ns NLF-siRNA, respectively using one- or two-way ANOVA followed by multiple comparison Newman-Keuls test.

As can be seen in FIG. 11, the intranasal application of NLF-siRNAs or vehicle, resulted in a decrease in the mRNA 5-$HT_{1A}$ receptor as determined by in situ hibridization and a decrease in 5-$HT_{1A}$ receptor as determined by ligand binding assays which is similar to the results observed after the i.c.v application. In particular, the presynaptic knockdown was of 30% (when compared to 50% knock-down when the NLF-siRNA were applied intraventricularly) (see FIG. 11). Moreover, intranasal application of NLF-siRNAs resulted in a decrease in the hypothermia response after 8-OH-DPAT administration (see FIG. 12A) and a decrease in the reduction of 5-HT prefrontal cortex dyalizate level reduction after an acute application of 8-OH-DPAT (FIG. 12B).

Figure 13:
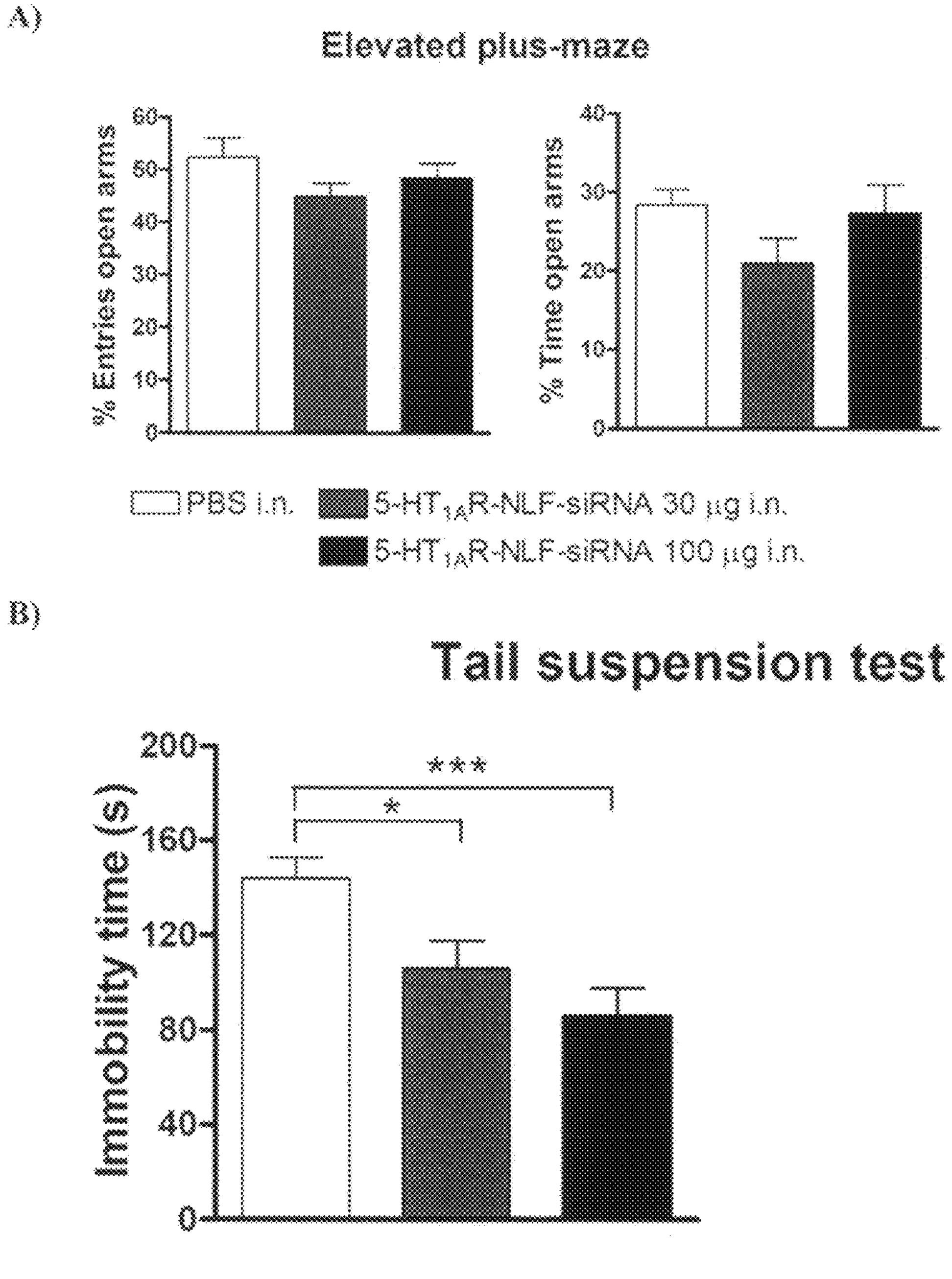
FIG. 13. Intranasal $5\text{-HT}_{1A}$R-NLF-siRNA silences $5\text{-HT}_{1A}$-autoreceptors and evokes antidepressant-like responses. Mice received a single intranasal administration of: i) vehicle, ii) $5\text{-HT}_{1A}$R-NLF-siRNA (15 μg/5 μl in each nostril) and iii) $5\text{-HT}_{1A}$R-NLF-siRNA (50 μg/5 μl in each nostril). A) Neither dose of $5\text{-HT}_{1A}$R-NLF-siRNA affected anxiety-like responses in the elevated plus-maze (n=6). Values are mean±SEM. B) Single intranasal $5\text{-HT}_{1A}$R-NLF-siRNA administration (30 or 100 μg) evoked a dose-dependent decreased immobility in the tail suspension test (n=10-15). Values are mean±SEM. One-way ANOVA showed a significant effect of group, $F_{2,34}=8.70$, p<0.001. p<0.05, *** p<0.001 versus vehicle C) Single intranasal $5\text{-HT}_{1A}$R-NLF-siRNA administration (100 μg) evoked a decreased immobility in the forced swim test (n=13-16). Values are mean±SEM. One-way ANOVA showed a significant effect of group, * p<0.05, ** p<0.01 versus vehicle.
Figure 13:
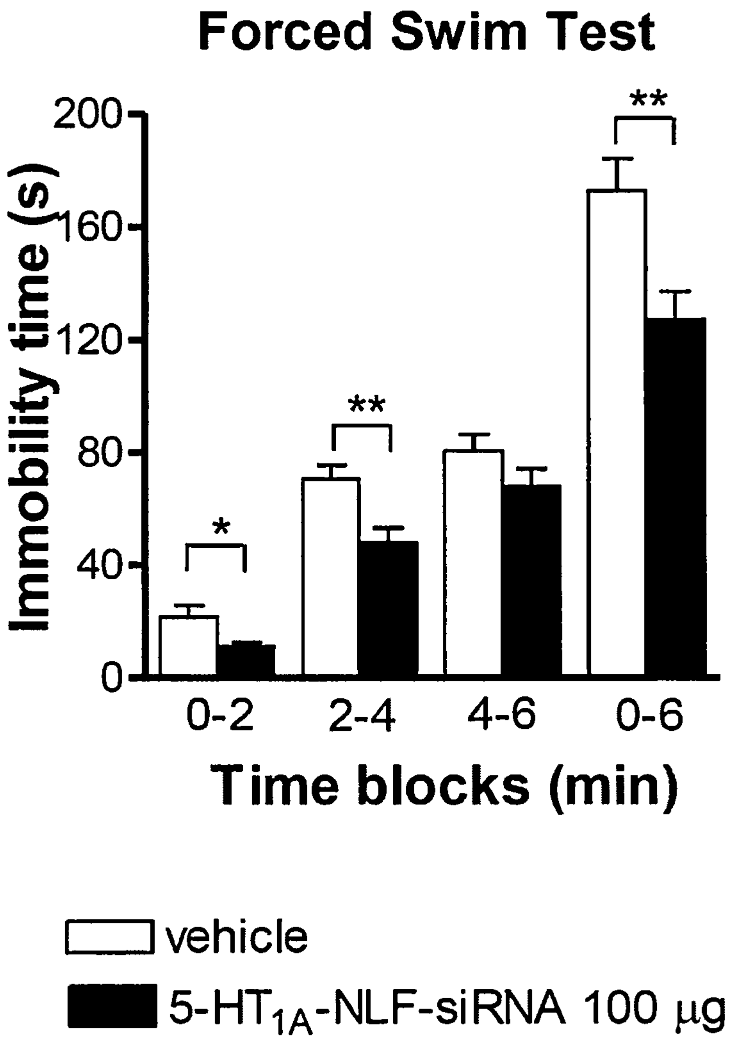

Moreover, the potential antidepressant effect of 5-$HT_{1A}$R-NLF-siRNA was evaluated using the tail suspension test as described in Example 7. Also, the anxiety-like behavior was evaluated by the elevated plus-maze. As can be seen in the FIG. 13, The experiments showed that no changes were observed in anxiety-like behaviour (FIG. 13A) but a decreased immobility time was elicited in stress/depression-related test in 5-$HT_{1A}$ autoreceptor knockdown mice (FIG. 13B) and a decreased immobility time in a forced swin test (FIG. 13C).

Example 9

Efficacy Assay of an 5-HTT-Targeted siRNA (Serotonin Transport siRNA) Conjugated to a Group of Formula (I) and One Targeting Agent (Hereinafter 5-HTT-NLF-siRNA) at 10 or 30 ug/Mice Dose and Vehicle as Control Group by In Vivo Intranasal Application in Mice A set of compounds having the structure of Examples 1 and 2 were synthesized as disclosed above. The siRNA was designed to target the following region of serotonin transporter (5-HTT) sequence from *Mus Musculus* (Mouse, GenBank Accession Number: NM_010484): 1230-1250. Antisense and sense strands of the siRNA were chemically synthesized (SEQ ID NO 1-2, Table 2) and were annealed in an isotonic RNA annealing buffer (100 mM potassium acetate, 30 mM HEPES-KOH pH: 7.4, 2 mM magnesium acetate), by combining a 50 μM solution of each strand. The solution is then incubated by 1 minute at 90° C., centrifugated by 15 seconds and then incubated by 1 hour at 37° C. The annealed solution is HPLC purified and selected fractions of siRNA are liophilizated. Stocks solutions of the siRNA were prepared by resuspending the liophilizated product in RNAse-free water and stored at −20° C. until use. Prior to usage, all siRNAs stock solutions were diluted to final concentration in PBS buffer a appropriate vehicle for intranasal application.

| RNA oligonucleotide identification | Sequence (5'-3' direction) | SEQ ID NO: |
|---|---|---|
| siRNA-A-s (sense) | GCUAGCUACAACAAGUUCATT | 14 |
| siRNA-A-a (antisense) | UGAACUUGUUGUAGCUAGCTT | 15 |

The siRNA sequence include the anti-sense sequences complementary to the mRNA of 5-HT transporter (5-HTT), thus being able to arrest said mRNA and to block its expression.

All the sequences have terminal DNA dimers of nucleotides containing at least one timine (T), not shown, in order to avoid the interference with the proteins regulating mRNA of normal processes into the cell. This technique is well known by the skilled person in the art. With these terminal dimmers the oligonucleotides have 21-23 base pairs, enabling an efficient RNAi mechanism.

The siRNA sequences of Table 2, conjugated to a group of formula (I) and one targeting agent as described above (5-HTT-NLF-siRNA) was used for the experiments.

Example 10

Differential Efficacy of Knockdown by Functional Measurements Assays of 5-HTT-NLF-siRNA at 2 Doses (10 and 30 μg/Mice) by In Vivo Intranasal (i.n) Application in Mice Male C57BL/6J mice (21-29 g, 9- to 12-week-old male) were anesthetised with pentobarbital 40 mg/kg i.p and positioned on their backs. PBS or 5-HTT-NLF-siRNA was slowly and gently dropped in alternating nostril with a micropipette tip in 5-ul aliquots. The assessed doses of 5-HTT-NLF-siRNA were: 5 μg/5 ul and 15 μg/5 ul in each nostril (total dose of NLF-siRNA: 10 and 30 μg/mice for one day).

Twenty-four h after treatment, mice were killed by decapitation and the brains rapidly removed, frozen on dry ice and stored at −20° C. Tissue sections, 14 μm thick, were cut using a microtome-cryostat, thaw-mounted onto APTS (3-aminopropyltriethoxysilane) coated slides and kept at −20° C. until use.

To determine 5-HTT mRNA expression level, in situ hybridization assays were performed using an oligodeoxyribonucleotide probe specific for 5-HTT, complementary to bases 820-863 (Mouse, GenBank Accession Number: NM_010484). The 5-HTT oligonucleotide was individually labeled (2 μmol) at its 3'-end with [$^{33}$P]-dATP (>2500 Ci/mmol) using terminal deoxynucleotidyltransferase, purified by centrifugation using QIAquick Nucleotide Removal Kit. The protocols for single label in situ hybridization were based on previously described procedures. Briefly, frozen tissue sections, as described in example 2, were first brought to room temperature, fixed for 20 min at 4° C. in 4% paraformaldehyde in phosphate buffered saline (1×PBS: 8 mM $Na_2HPO_4$, 1.4 mM $KH_2PO_4$, 136 mM NaCl, 2.6 mM KCl), washed for 5 min in 3×PBS at room temperature, twice for 5 min each in 1×PBS and incubated for 2 min at 21° C. in a solution of pre-digested pronase at a final concentration of 24 U/ml in 50 mM Tris-HCl pH 7.5, 5 mM EDTA. The enzymatic activity was stopped by immersion for 30 s in 2 mg/ml glycine in 1×PBS. Tissues were finally rinsed in 1×PBS and dehydrated through a graded series of ethanol. For hybridization, the radioactively labeled probe was diluted in a solution containing 50% formamide, 4×SSC (1×SSC: 150 mM NaCl, mM sodium citrate), 1×Denhardt's solution (0.02% Ficoll, 0.02% polyvinylpyrrolidone, 0.02% bovine serum albumin), 10% dextran sulfate, 1% sarkosyl, 20 mM phosphate buffer pH 7.0, 250 μg/ml yeast tRNA and 500 μg/ml salmon sperm DNA. The final concentration of radioactive probe in the hybridization buffer was in the same range (1.5 nM). Tissue sections were covered with hybridization solution containing the labeled probe, overlaid with Nescofilm coverslips and incubated overnight at 42° C. in humid boxes. Sections were then washed four times (15 min each) in 1×SSC at 60° C. and once in 1×SSC at room temperature for 30 min, dehydrated and exposed to film for 1-3 days. Film optical densities were semiquantified with $AIS^R$ computerized image analysis system As can be seen in FIG. 14A, both doses of 5-HTT-NLF-siRNA molecules induced a specific knowdown of 5-HTT mRNA in dorsal raphe nuclei at three different antero-posterior coordinates.

Figure 14:
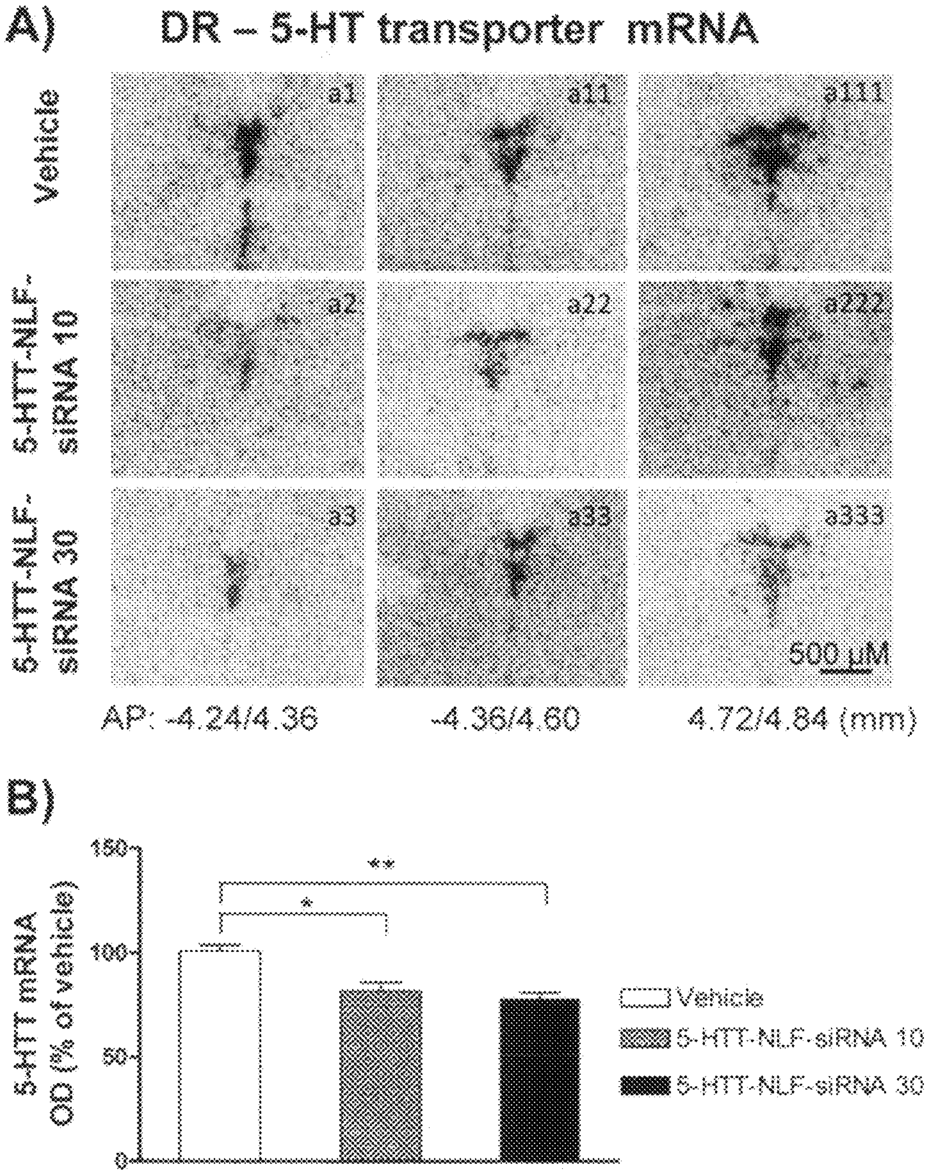
FIG. 14. Specific 5-HT transporter (5-HTT) silencing by intranasal administration of conjugated 5-HTT-NLF-siRNA. A) 5-HTT expression in dorsal raphe nucleus (DR) was assessed by in situ hybridization. Mice received a single administration of i) vehicle, ii) 5-HTT-NLF-siRNA 5 μg/5 μl in each nostril (5-HTT-NLF-siRNA 10) and, iii) 5-HTT-NLF-siRNA 15 μg/5 μl in each nostril (5-HTT-NLF-siRNA 30). a1-a333 show coronal sections of raphe nuclei of mice bound with $^{33}$P-labeled 5-HTT-specific oligonucleotide at 3 different antero-posterior (AP) coordinates in mm: −4.24/−4.36, −4.36/−4.60 and −4.72/−4.84 from bregma (rostral-caudal from left to right). Scale bar, 500 μm. B) Bar graphic showing 5-HTT-NLF-siRNA induced a reduction of 5-HTT mRNA level in dorsal raphe nucleus. Densitometric quantification of 5-HTT mRNA positive grains measured in films is shown as mean optical densities (OD) percentage values SEM (n=4 mice per group and two to four observations at 3 AP levels of dorsal raphe nucleus). * p<0.05, ** p<0.01 significantly different from vehicle using one-way ANOVA followed by Newman-Keuls post hoc test.

As can be seen in FIG. 14B, the densitometric quantification of 5-HTT mRNA positive grains measures in films at midbrain raphe nucleus showed a reduction of 30% on expression level in group of NLF-siRNA compared with vehicle group.

These results indicated that the NLF-siRNA selectively direct the oligonucleotides that perform interference of the mRNA to specific serotonergic neurons localized in midbrain raphe nuclei.

The density of serotonin transporter protein was assayed as described in Example 4 using [$^3$H]citalopram for the autoradiographic visualization of 5-HTT sites. 24-48. h after NLF-siRNA intranasal administration, mice were killed and their brains were removed and serial coronal sections of 14 μm thickness were obtained at the following AP coordinates, in mm, relative to bregma (Franklin and Paxinos, 1997): 2.2 (prefrontal cortex—PFC), 1.1 to 0.6 (caudate putamen—CPu, lateral and medial septal nucleus—Sep, ventral pallidum—VP), −1.5 to −1.8 (hippocampus—HPC, hypothalamus—Hip) and −4.24 to −4.96 (dorsal raphe nucleus—DR and median raphe nucleus—MnR). Briefly, frozen tissue sections were thawed and dried, preincubated in 50 mM Tris-HCl buffer (pH 7.4 at 25° C.) containing 120 mM NaCl and 5 mM KCl for 15 mm at room temperature. Then incubated in the same buffer containing 1.5 nM [$^3$H]citalopram (70.0 Ci/mmol) for 60 min at room time. Non-specific binding was defined as that remaining in the presence of 1 μM fluoxetine. After incubation and washing, tissue sections were dipped in distilled ice-cold water and dried rapidly under a cold air stream. Tissues were exposed to tritium-sensitive film together with plastic $^3$H-standards for 40 days at 4° C. Quantitative analysis of the autoradiograms was done with AIS computerized image analysis system. By using tissue-calibrated data from the co-exposed radioactive standards, OD values of autoradiograms were transformed to levels of radioactivity bound (nCi/mg tissue protein) to specific brain regions in tissue sections.

Figure 15:
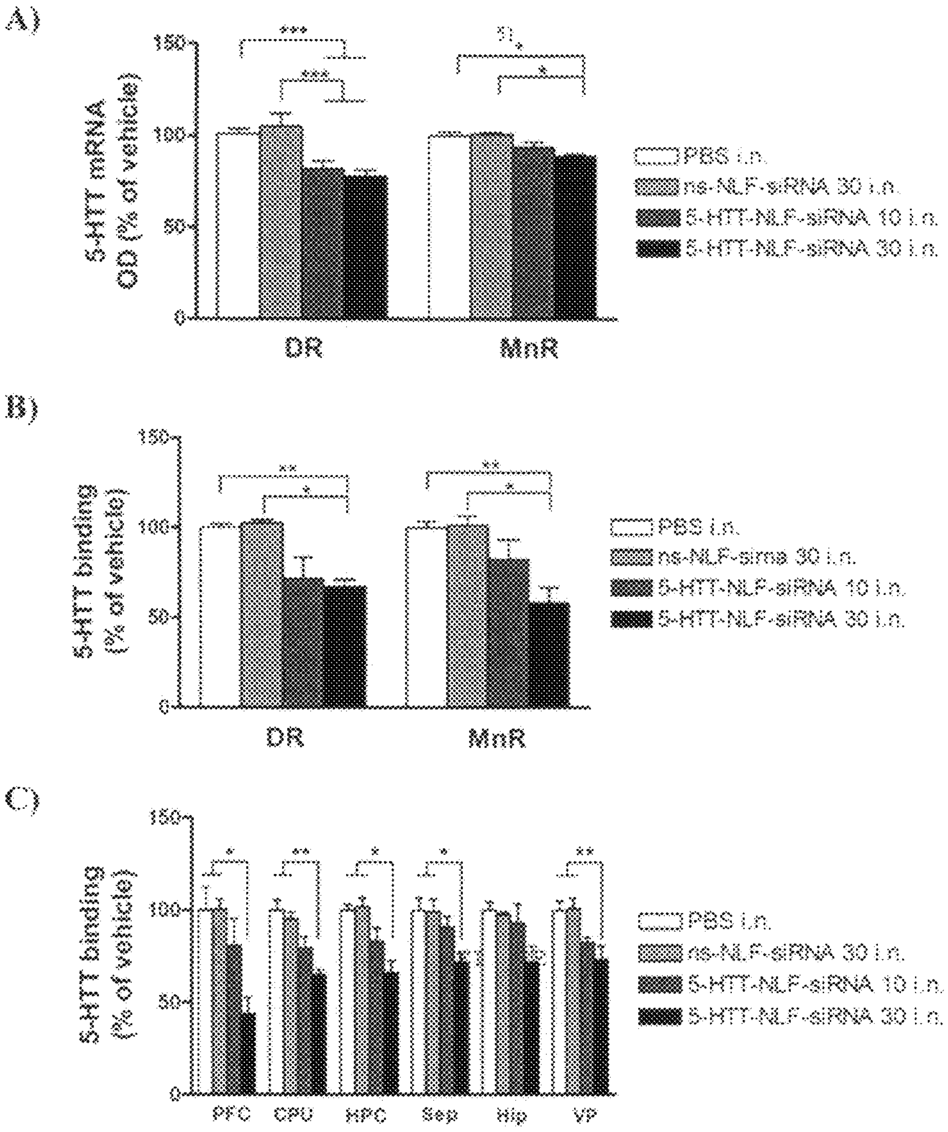
FIG. 15. 5-HTT-NLF-siRNA induced specific knockdown of serotonin transporter evaluated by in situ hibridization and autoradiographic binding. Mice received a single administration of: i) vehicle, ii) nonsense-NLF-siRNA 15 μg/5 μl in each nostril, iii) 5-HTT-NLF-siRNA 5 μg/5 μl in each nostril (5-HTT-NLF-siRNA 10) and, iv) 5-HTT-NLF-siRNA 15 μg/5 μl in each nostril (5-HTT-NLF-siRNA 30). A) Bar graphic showing 5-HTT-NLF-siRNA induced a reduction of 5-HTT mRNA level in dorsal (DR) and median (MnR) raphe nuclei. Densitometric quantification of 5-HTT mRNA positive grains measured in films is shown as mean optical densities (OD) percentage values±SEM (n=7-10 mice per group). * p<0.05, *** p<0.001 significantly different from vehicle and nonsense-NLF-siRNA in the same region using one-way ANOVA followed by Newman-Keuls post hoc test. B-C) Densitometric analysis of specific 5-HTT binding is presented as % binding in the corresponding region of vehicle-infused mice, in order to illustrate the extent of NLF-siRNA-induced 5-HTT downregulation in each region. Bars represent mean±SEM of 6-9 mice/group). * p<0.05, ** p<0.01 significantly different from vehicle and nonsense-NLF-siRNA in the same region using one-way ANOVA followed by Newman-Keuls post hoc test.

As can see in the FIG. 15, the intranasal application of 5-HTT-NLF-siRNA induced a reduction of the serotonin transporter levels in the different brain areas as compared with intranasal administration of vehicle or NLF-nonsense-siRNA determined by autoradiographic binding assays.

Example 11

Increment on 5-HT Levels in Prefrontal Cortex in Treated Mice by In Vivo Intranasal Application (i.n.) of 10 and 30 μg/Mice Dose of 5-HTT-NLF-siRNA Compared to Control Groups To evaluate the NLF-siRNA effects on the functional properties of 5-HTT, the neurochemical effects of selective 5-HT transporter inhibitors on 5-HT levels in the dorsal striatum in response to 5-HTT NLF-siRNA were assessed. For this purpose, male C57BL/6J mice (21-29 g, 9- to 12-week-old male) were anesthetised with pentobarbital 40 mg/kg i.p and positioned in a stereotaxic frame. Each mouse was implanted with one dialysis probe equipped with a Cuprophan membrane (1.5-mm long; 5000 Da molecular weight cut-off) in the dorsal striatum (mPFC) (in mm: AP +0.5, L −1.7, DV −4.5 from bregma, according to the atlas of Franklin and Paxinos, 1997).

Microdialysis experiments were conducted 24-72 h after surgery in freely moving mice by continuously perfusing probes with aCSF (125 mM NaCl, 2.5 mM KCl, 1.26 mM $CaCl_2$, 1.18 mM $MgCl_2$) at a rate of 2.0 μl/min with a WPI model sp220i syringe pump attached to an overhead liquid swivel. Dialysate samples of 60 μl were collected every 30 min in microcentrifuge vials.

Following an initial 60-min stabilization period, four-six baseline samples were collected before local citalopram (1-10-50 μM) or systemic fluoxetine (20 mg/kg i.p.) administration and then successive dialysate samples were collected. At the completion of dialysis experiments, mice were sacrificed and the brains were immediately removed and frozen at −70° C. Coronal sections (50 μm) of the brain were cut afterwards on a cryostat and stained with cresyl violet, according to standard procedures, for localization of the perfusion site. Only data obtained from animals with histological correct probe placements were used for subsequent statistical analysis.

The concentration of 5-HT in dialysate samples was determined by HPLC using a 3-μm octadecylsilica (ODS) column (7.5 cm×0.46 cm) and detected amperometrically with a Hewlett-Packard 1049 detector set at an oxidation potential of 0.6 V. The mobile phase consisted of 0.15 M $NaH_2PO_4.H_2O$, 1.8 mM octyl sodium sulphate, 0.2 mM EDTA (pH 2.8 adjusted with phosphoric acid) and 30% methanol and was pumped at 0.7 ml/min. The retention time for 5-HT was 3.5-4 min and the detection limit was 2 fmol/sample.

Figure 16:
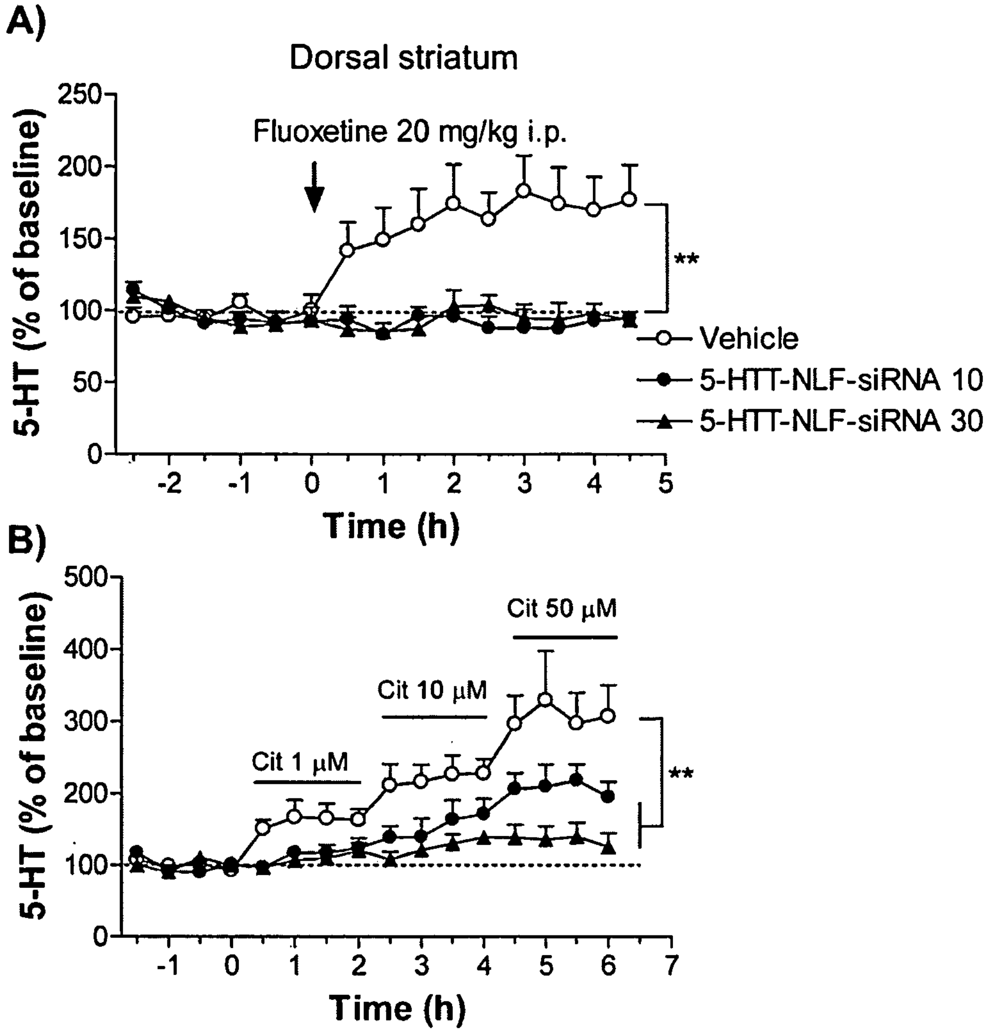
FIG. 16. A) Effect of acute fluoxetine (selective inhibitor of 5-HT transporter, 20 mg/kg i.p.) administration on dialysate 5-HT levels in dorsal striatum of mice. Mice received a single administration of: i) vehicle, ii) 5-HTT-NLF-siRNA 5 μg/5 μl in each nostril (5-HTT-NLF-siRNA 10) and, iii) 5-HTT-NLF-siRNA 15 μg/5 μl in each nostril (5-HTT-NLF-siRNA 30). Microdialysis experiments were conducted 24-48 h after application. Fluoxetine produced an increased 5-HT level in dorsal striatum of vehicle group, but not in 5-HTT-NLF-siRNA groups. B) Local effect of selective 5-HT transporter inhibitor, citalopram (Cit) on 5-HT levels in dorsal striatum of vehicle and 5-HTT-NLF-sirRNA mice. The local administration of citalopram increased 5-HT level in dorsal striatum of vehicle group in a concentration-depend manner. However, citalopram only at 50 μM produced a light increase of 5-HT levels in striatum of 5-HTT-NLF-siRNA groups. Data are expressed as percentage of baseline and are shown as mean±SEM (n=7-8 mice/group). ** $p<0.01$ significantly different from vehicle using repeated-measure ANOVA with treatment as the between factor and time as within-subject variable, followed by multiple comparison Newman-Keuls test.

As can be in FIG. 16, there was an absence or decreased 5-HTT response to selective 5-HTT inhibitors, including fluoxetine and citalopram on serotonin levels in dorsal striatum of 5-HTT-NLF-siRNA treated mice group compared with vehicle group. This evidences that a knockdown of the 5-HTT in serotonergic neurons can be functionally evaluated by the reduction of selective transporter inhibitor effects on 5-HT amount in terminal brain areas.

These results demonstrates that the administration of a sertraline conjugated siRNAs (NLF-siRNAs) target the serotonergic neurons by interacting selectively with the 5-HTT, besides the sequence of the nucleic acid component (siRNA).

Examples 3 to 8 shows that a NLF-siRNA directed against a 5-$HT_{1A}$R are capable of knocking down the target gene specifically in 5-HT neurons located in dorsal raphe nucleus. This effect is observed both after intrecerebro ventricular as well as after intranasal application.

Examples 10 and 11 show that NLF-siRNA specific against the 5-HTT are also capable of knocking down the target gene, in this case, the 5-HTT mRNA. The targeting capability of the NLF-siRNA construction of this invention has been observed both after intracerebro ventricular application in third ventricle (3DV) as well as by intranasal application in a dose of 0.3 to 1 mg/Kg (10 to 30 μg of siRNA molecule by mice). This is a common accepted therapeutic range for siRNA therapies and with potential upscale to human treatments. The non-invasive intranasal application also increases the feasibility of the NLF-siRNAs molecules to evolve as a therapeutic.

Example 12

Targeting Validation of a siRNA Conjugated to Nomifensin (NLF-NS-siRNA) by In Vivo Intracerebroventricular Infusion into the Right Lateral Ventricle This example shows that a NLF-NS-siRNA infused intracerebroventricularly is able to reach specific neurons in the brain located in the substancia nigra and locus ceruleus.

These cells are tyrosine hydroxylase positively stained, that is, they are dopaminergic or noradrenergic neurons.

The sequence used was a non-sense (ns) siRNA with no homology with any human, mouse or rat gene:

```
                                     SEQ ID NO: 69
NS siRNA-s        AGUACUGCUUACGAUACGG

                                     SEQ ID NO: 70
NS siRNA-a        CCGUAUCGUAAGCAGUACU
```

The sequence has terminal DNA dimers of nucleotides containing at least one timine (T), not shown, in order to avoid the interference with the proteins regulating mRNA of normal processes into the cell. This technique is well known by the skilled person in the art. With these terminal dimers the oligonucleotides have 21 base pairs, enabling an efficient RNAi mechanism. The antisense (a) sequence has also a Cy3 molecule to allow its viewing in confocal microscopy.

For the infusion of siRNAs, C57Bl/6Ncrl male mice were deeply anesthetized with isofluorane and placed in a mouse adaptor (Stoelting ref. 51625) attached to a stereotaxic frame with digital display readout (David Kopf Instruments, model 940). After performing a hole in the skull with a 21G×1.5 inch sterile needle, the injection syringe (10 p. 1 Hamilton) delivered 2 μl of the siRNA NLF-NS-siRNA-Cy3 solution in distilled water (100 μg total dose) or vehicle into the right lateral ventricle (from bregma AP +0.26; L −0.75 DV −2.5) by means of a syringe pump (KD Scientific, KDS 310) at a constant flow rate of 0.5 μl/min (n=2 for each time point). The needle was left in the place for 3 min to avoid upward flow of the siRNA solution.

The mice were perfused with 4% PFA at two different time points, 1 and 3 hours post-administration of the siRNA. Brains were dissected and post-fixed in a solution of 4% PFA for 24 h at 4° C. Then brains were placed in a 30% sucrose solution for 48 h at 4° C. Brains were frozen in 2-methylbutane at −30 to −40° C. and stored at −80° C. Brains were sectioned in a cryostat Leica CM3050 S (30 mm). Free-floating sections were washed and stored at 4° C. in 0.1 M PBS and 0.001% sodium azide.

Sections were washed in PBS, blocked with 2% goat serum and 0.1% Triton and incubated with anti-TH antibody (1:800 mouse) overnight at 4° C. After washing, sections were incubated with secondary antibody Alexa Fluor 647 anti-mouse (Invitrogen) for 1 h at room temperature. Finally sections were mounted with Dako Fluorescent Mounting Medium and analyzed using a confocal spectral microscope (FV1000 Olympus). Pictures were generated using FV10-ASW 1.7 Viewer.

Figure 17:
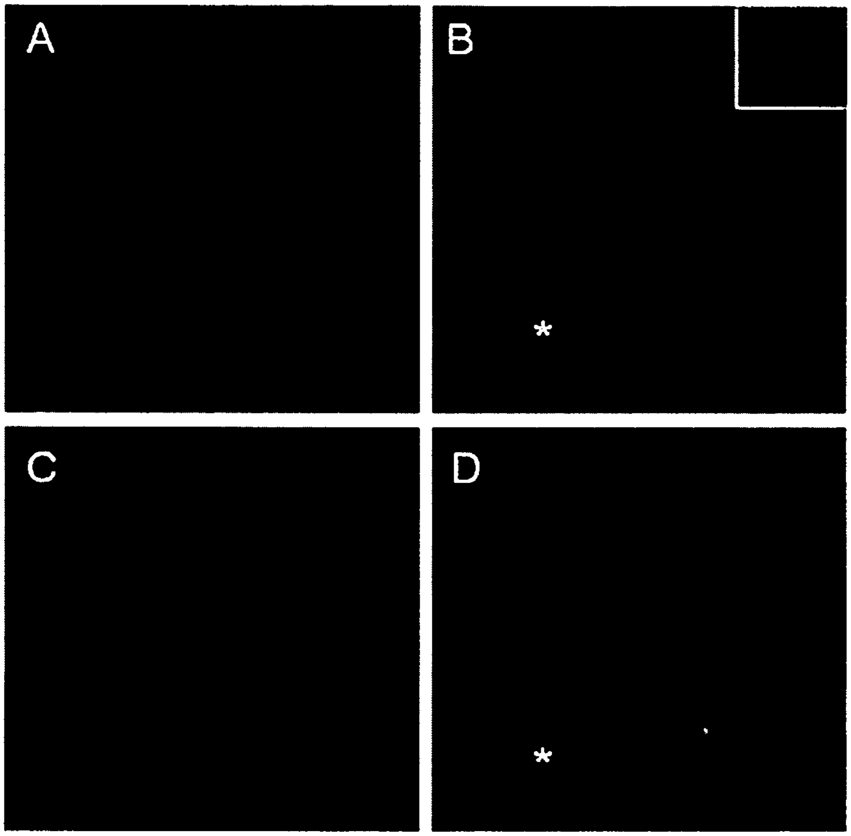
FIG. 17 Selective targeting of dopaminergic neurons of the substantia nigra pars compacta with NLF-NS-siRNA-$Cy_3$. A and C show the red labeling of NLF-NS-siRNA-Cy3 1 and 3 hours respectively after the ICV administration of the siRNA in the mouse ventral midbrain. B and D show the same labeling merged with tyrosine hydroxylase (TH) staining. After 1 hour of NLF-NS-siRNA-Cy3 ICV administration (A and B), red labeling (Cy3) can be detected within TH-positive nigral neurons (blue), but not in the gabaergic neurons of the substantia nigra reticulata (*). The red labeling follows a punctated pattern (inset). After 3 hours of the injection any red intracellular labeling can not be detected (C and D).
Figure 18:
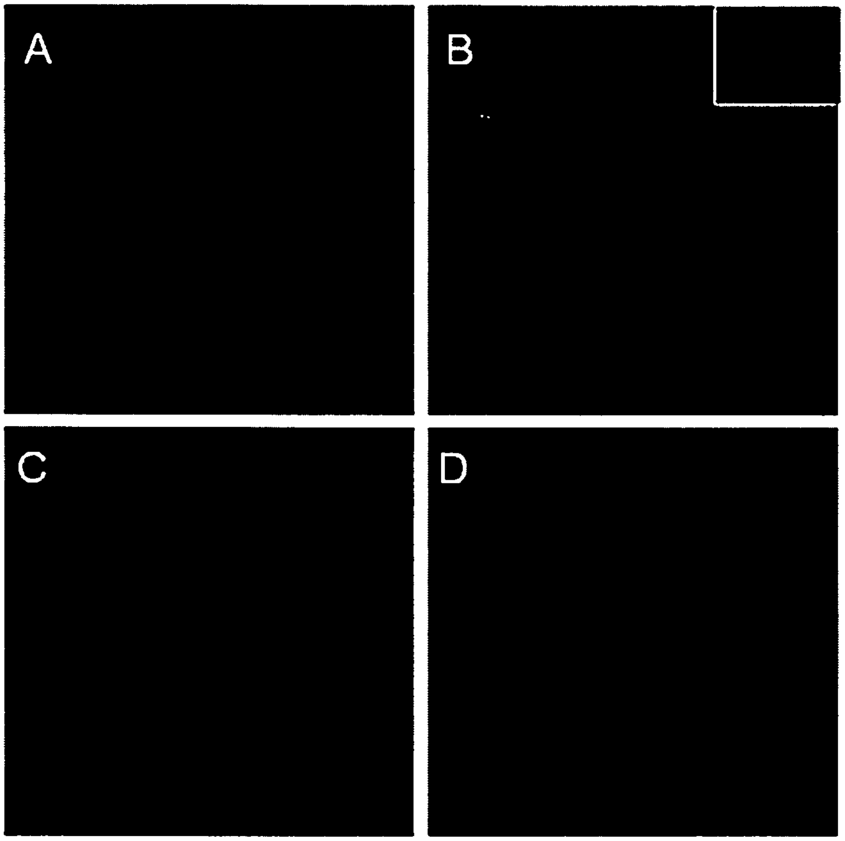
FIG. 18. Selective targeting of noradrenergic neurons of the locus coeruleus with NLF-NS-siRNA-Cy3. A and C show the red labeling of NLF-NS-siRNA-Cy3 1 and 3 hours respectively after the ICV administration of the siRNA. B and D shows the same labeling merged with tyrosine hydroxylase (TH) staining. After 1 hour of NLF-NS-siRNA-Cy3 ICV administration (A and B), red labeling (Cy3) can be detected mainly within TH-positive noradrenergic neurons (blue). The red labeling follows a punctated pattern (inset). After 3 hours of the injection any red intracellular labeling can not be detected (C and D).

As can be seen in FIGS. 17 and 18, after 1 h of icy infusion, some TH positive cells in the substantia nigra pars compacta and locus coeruleus were also positive for Cy3. Not all the TH positive cells were positive for Cy3, but a great percentage of them had Cy3 fluorescence inside indicating that the NLF-NS-siRNA-Cy3 molecule was incorporated into some TH-positive neurons.

Example 13

Figure 19:
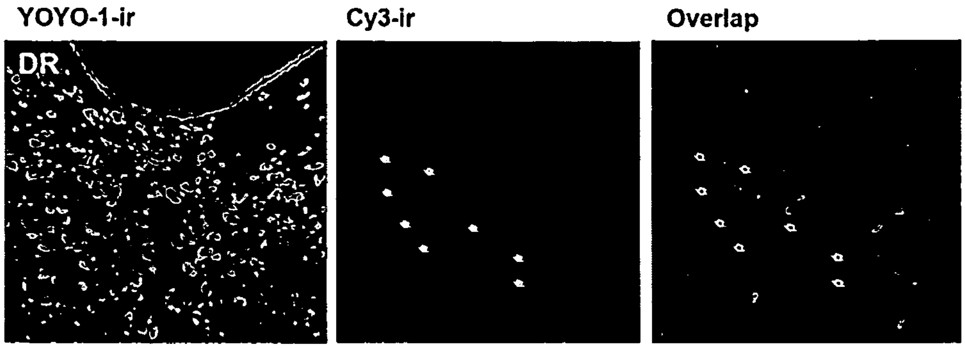
FIG. 19. Selective accumulation of sertraline-conjugated 2-O'-methyl (TOM)-modified nonsense oligonucleotide (C-ns-TOM) in raphe serotonin neurons. Mice received a single intracerebronventricular infusion of Cy3-labeled C-ns-TOM (30 μg) into dorsal third ventricle and were killed 24 h post-infusion (n=2 mice). Laser confocal images of YOYO1-immunoreactive cell nuclei (green) showing the immunolocalized Cy3-labeled C-ns-TOM (red). Scale bar is 40 μm.

Targeting Validation of a Cy3-Labeled Nonsense 2-O'-Methyl-Modified Gapmer Conjugated to Sertraline to Serotoninergic Neurons by Intraventricular Administration A conjugate was synthesized comprising a gapmer comprising RNA wings of 3 nucleotides each containing 2-O'-methyl and a 10 nucleotides long nonsense gap region with a nonspecific (nonsense) sequence. The gapmer is conjugated to sertraline via its 5' end and to Cy3 via its 3' end. Mice received a single intracerebronventricular infusion (30 μg) of Cy3 the conjugate into dorsal third ventricle and were killed 24 h post-infusion (n=2 mice). Localization of the Cy3 labelled was then determined by laser confocal microscopy. The experiment shows (FIG. 19) that the gapmer is specifically localized to serotoninergic neurons.

The invention claimed is:

1. A conjugate comprising at least one selectivity agent which binds specifically to at least one neurotransmitter transporter and is covalently coupled to at least one nucleic acid which is capable of specifically binding to a mRNA encoding a polypeptide which is expressed in the same cell as the neurotransmitter transporter or to said polypeptide itself, and wherein the covalent coupling is either direct or via a linker, and wherein the selectivity agent is selected from the group consisting of a dopamine reuptake inhibitor (DRI), a selective serotonin reuptake inhibitor (SSRI), a noradrenaline reuptake inhibitor (NRI), a norepinephrine-dopamine reuptake inhibitor (NDRI), and a serotonin-norepinephrine-dopamine reuptake inhibitor (SNDRI).

2. A conjugate according to 1 wherein the nucleic acid which is capable of specifically binding to a mRNA is selected from the group consisting of: a double stranded RNA interference oligonucleotide, a siRNA, a shRNA, a microRNa, an antisense oligonucleotide, a gapmer, a Peptide Nucleic Acid (PNA), a Locked Nucleic acid (LNA), an Intercalating Nucleic Acid (INA), a Hexitol Nucleic Acid (HNA), a ribozyme, a RNA enzyme, a catalytic RNA, a Morpholino, and an aptamer.

3. A conjugate according to claim 1, wherein the binding of the nucleic acid to the mRNA results in an inhibition of the activity of the mRNA.

4. A conjugate according to claim 1, wherein the selectivity agent is conjugated to the 5' end of the nucleic acid.

5. A conjugate according to claim 1, wherein the selectivity agent and the nucleic acid are connected by a linking group.

6. A conjugate according to claim 5, wherein the at least one nucleic acid comprises a first nucleic acid and a second nucleic acid molecule, and wherein the second nucleic acid molecule is complementary to the first nucleic acid molecule.

7. A conjugate according to claim 2, wherein the nucleic acid is siRNA.

8. A conjugate according to claim 6, further comprising a protecting group which is attached to the 5' end of the second nucleic acid molecule.

9. A conjugate according to claim 8, wherein the protecting group attached to the 5' end of the second nucleic acid molecule has the structure $$M\text{-}L1_d\text{-}[(A\text{-}L2)a\text{-}(B\text{-}L3)b]c$$

wherein:

M is H or a lipid moiety

A and B represent monomer units independently selected from the group consisting of a monosaccharide and a ($C_2$-$C_{20}$) alkylene glycol;

a and b are integers ranging from 0 to 50;

c is an integer ranging from 0 and 30;

L1, L2 and L3 are linking compounds independently selected from the group consisting of phosphodiester, phosphorothioate, carbamate, methylphosphonate, guanidinium, sulfamate, sulfamide, formacetal, thioformacetal, sulfone, amide and mixtures thereof;

d is 0 or 1.

10. A conjugate according to claim 9, wherein the monosaccharide is selected from the group consisting of furanose, fructose, glucose, galactose, mannose, a modified monosaccharide, sialic acid, and eritrose.

11. A conjugate according to claim 9, wherein the ($C_2$-$C_{20}$) alkylene glycol is selected from the group consisting of ethylene glycol, propylene glycol, and mixtures thereof.

12. A conjugate according to claim 11, wherein M is H, A is a furanose; B is a $C_{18}$ ethylene glycol; a, b and c are 1, d is 0; and L2 and L3 are phosphodiester bonds.

13. A conjugate according to 1 wherein the at least one selectivity agent is selected from the group consisting of: a selective serotonin reuptake inhibitor (SSRI), a noradrenaline reuptake inhibitor (NRI), a dopamine reuptake inhibitor (DRI), and a Norepinephrine-Dopamine Reuptake Inhibitor (NDRI).

14. A conjugate according to claim 13, wherein the selectivity agent is a selective serotonin reuptake inhibitor (SSRI).

15. A conjugate according to claim 14, wherein the selective serotonin reuptake inhibitor (SSRI) is selected from the group consisting of: sertraline, a sertraline structural analog, fluoxetine, fluvoxamine, paroxetine, indapline, zimelidine, citalopram, dapoxetine, escitalopram, and mixtures thereof, and the sequence of the nucleic acid molecule is complementary to the mRNA.

16. A conjugate according to 1 wherein the nucleic acid is capable of specifically binding to a mRNA encoding a polypeptide selected from the group consisting of: the serotonin receptor type 1A (5-HT1A) polypeptide, the serotonin transporter (5-HHT transporter or SERT) polypeptide, the serotonin receptor type 1B (5-HT1B) polypeptide, the TREK-1 potassium channel polypeptide, the Gir-K potassium channel polypeptide, the alpha-synuclein polypeptide, polypeptide, the dopamine beta hydroxylase polypeptide, the Norepinephrine transporter (NET) polypeptide, the Tau polypeptide, and the Huntingtin polypeptide.

17. The conjugate according to claim 16 wherein the nucleic acid is capable of specifically binding to the mRNA encoding the serotonin receptor type 1A (5-HT1A) and comprises a sequence selected from the group consisting of SEQ ID NO: 1, SEQ ID NO: 2, SEQ ID NO: 3 and SEQ ID NO: 4.

18. A conjugate according to claim 1 wherein the selectivity agent is selected from the group consisting of: a dopamine reuptake inhibitor (DRI), a Norepinephrine-Dopamine Reuptake Inhibitor (NDRI) and a serotonin-Norepinephrine—Dopamine Reuptake Inhibitor (SNDRI), and the nucleic acid binds to the mRNA encoding alpha-synuclein or to alpha-synuclein.

19. A conjugate according to claim 1, wherein the selectivity agent is a Norepinephrine Reuptake Inhibitor (NRI) and wherein the nucleic acid binds dopamine-β-hydroxylase or the mRNA encoding dopamine-β-hydroxylase.

20. A conjugate according to claim 1, wherein the selectivity agent is selected from the group consisting of: a dopamine reuptake inhibitor (DRI), a Norepinephrine-Dopamine Reuptake Inhibitor (NDRI) and a serotonin-Norepinephrine-Dopamine Reuptake Inhibitor (SNDRI), and the nucleic acid binds or the mRNA encoding BAX.

21. A conjugate according to claim 1, wherein the selectivity agent is selected from the group consisting of a dopamine reuptake inhibitor (DRI), a Norepinephrine-Dopamine Reuptake Inhibitor (NDRI) and a serotonin-Norepinephrine-Dopamine Reuptake Inhibitor (SNDRI) and the nucleic acid binds to the mRNA encoding Tau.

22. A conjugate according to claim 1 wherein the selectivity agent is selected from the group consisting of: a dopamine reuptake inhibitor (DRI), a Norepinephrine-Dopamine Reuptake Inhibitor (NDRI) and a serotonin-Norepinephrine-Dopamine Reuptake Inhibitor (SNDRI) and the nucleic acid binds to Huntingtin or the mRNA encoding Huntingtin.

23. A conjugate according to claim 1 having the structure

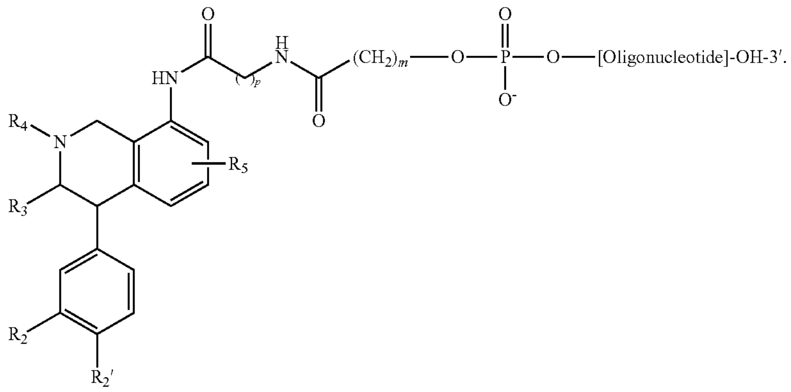

24. A conjugate according to claim 1 having the structure

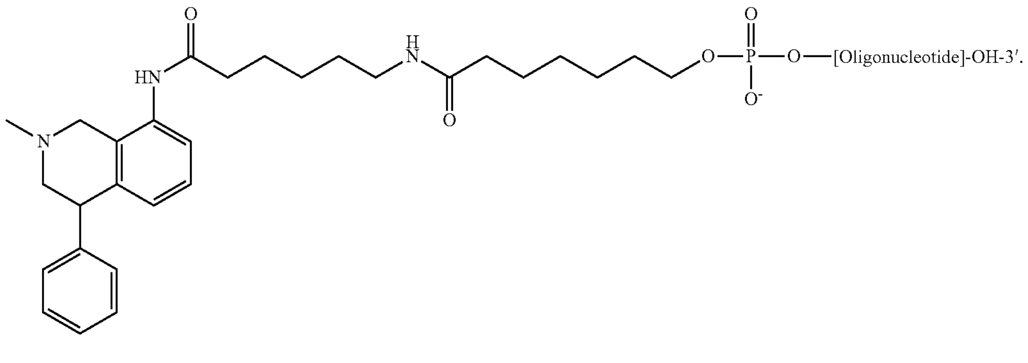

25. A pharmaceutical composition suitable for therapeutic administration comprising a conjugate according to claim 1.

26. A method of treating or preventing a brain pathology comprising administering to a subject in need thereof a conjugate according to claim 1 in an amount sufficient to treat or prevent a brain pathology.

27. A method according to claim 26, wherein said brain pathology is a depression-related disorder, the selectivity agent is a selective serotonin reuptake inhibitor (SSRI); and wherein the nucleic acid specifically binds to the mRNA encoding the serotonin receptor type 1A ($5\text{-}HT_{1A}$) or the mRNA encoding the serotonin transporter 1A.

28. A method according to claim 27, wherein the depression-related disorder is selected from the group consisting of: major depression, obsessive-compulsive disorder (OCD), pervasive developmental disorder (PDD), post-traumatic stress disorder (PTSD), anxiety disorder, bipolar disorder, eating disorder, and chronic pain.

29. A method according to claim 26, wherein said brain pathology is a disease associated with the deposit of Lewy bodies, the selectivity agent is selected from the group consisting of a dopamine reuptake inhibitor (DRI) and a Norepinephrine-Dopamine Reuptake Inhibitor (NDRI), and wherein the nucleic acid specifically binds to mRNA encoding alpha-synuclein.

30. A method according to claim 29, wherein the disease associated with the deposit of Lewy bodies is selected from the group consisting of Parkinson's disease, dementia with Lewy bodies, and multiple system atrophy.

31. A method according to claim 26, wherein said brain pathology is a disease associated with a dopamine deficit in noradrenergic projections, the selectivity agent is a Norepinephrine Reuptake Inhibitor (NRI) and the nucleic acid specifically binds to the mRNA encoding dopamine-β-hydrolase.

32. A method according to claim 26, wherein said brain pathology is a disease associated with a dopamine deficit in noradrenergic projections, the selectivity agent is a Norepinephrine Reuptake Inhibitor (NRI), and the nucleic acid specifically binds to the mRNA encoding the norepinephrine transporter (NET).

33. A method according to claim 32, wherein the disease associated with a dopamine deficit in noradrenergic projections is a memory or cognitive process associated with dementia, depression and neurodegenerative diseases.

34. A method according to claim 26, wherein the brain pathology is a disease associated with neuronal apoptosis and cell death, the selectivity agent is selected from the group consisting of a dopamine reuptake inhibitor (DRI), a Norepinephrine-Dopamine Reuptake Inhibitor (NDRI) and a serotonin-Norepinephrine-Dopamine Reuptake Inhibitor (SNDRI), and wherein the nucleic acid specifically binds BAX or the mRNA encoding BAX.

35. A method according to claim 34, wherein the disease associated with neuronal apoptosis and cell death is selected from the group consisting of: Alzheimer's disease, Parkinson's disease, Huntingtin's disease, stroke/trauma, and multiple and amyotrophic lateral sclerosis.

36. A method according to claim 26, wherein said brain pathology is a tau associated disease, the selectivity agent is selected from the group consisting of: a dopamine reuptake inhibitor (DRI), a Norepinephrine-Dopamine Reuptake Inhibitor (NDRI) and a serotonin-Norepinephrine—Dopamine Reuptake Inhibitor (SNDRI), and wherein the nucleic acid specifically binds to Tau or the mRNA encoding Tau.

37. A method according to claim 36, wherein the tau-associated disease is a disease associated with abnormalities in Tau or a tauopathy.

38. A method according to claim 37, wherein the Tau associated disease is selected from the group consisting of: frontotemporal dementia, including the subtype of frontotemporal dementia and Parkinsonism linked to chromosome 17 (FTDP-17), progressive supranuclear palsy, corticobasal degeneration, Pick's disease, agyrophilic grain disease, as well as Parkinson's disease, Down syndrome, post-encephalic Parkinsonism, myotonic dystrophy, Niemann-Pick C disease, dementia Blint disease, prion diseases, amyotrophic lateral sclerosis, Parkinsonism-dementia complex of Guam, multiple sclerosis, glaucoma, diabetic retinopathy, and traumatic brain injury; as well as Huntington's disease, Lewy body dementia, Charcot-Marie-Tooth disease, hereditary spastic paraplegia, and multiple system atrophy.

39. A method according to claim 26, wherein said brain pathology is Huntington disease, the selectivity agent is selected from the group consisting of: dopamine reuptake inhibitor (DRI), Norepinephrine-Dopamine Reuptake Inhibitor (NDRI) and serotonin-Norepinephrine-Dopamine Reuptake Inhibitor (SNDRI), and wherein the nucleic acid specifically binds the mRNA encoding Huntington.

40. A method according to claim 26, wherein said conjugate is administered intraventricularly or intranasally.

41. A method according to claim 26, wherein said brain pathology is a depression-related disorder, a disease associated with impairments in neurotransmitter vesicle function and the deposition of Lewy bodies, a disease associated with neuronal apoptosis and cell death (i.e. Parkinson and Alzheimer), a disease associated with dopamine deficit in noradrenergic projections like memory and cognitive process associated with dementia, depression and neurodegenerative diseases, a disease associated with dopamine deficit in noradrenergic projections like memory and cognitive process associated with dementia, depression and neurodegenerative diseases, a disease associated with neurodegeneration by mutations in tau protein like Alzheimer, a neurodegenerative disease produced by the accumulation of a altered (intra-gene duplication) expression of Huntingtin, a disease associated dopamine deficit in noradrenergic projections like memory and cognitive process associated with dementia, depression and neurodegenerative diseases.

42. A conjugate according to claim 1, wherein the covalent coupling is by a bivalent or trivalent linker.

43. A conjugate according to claim 1, wherein the selectivity agent is selected from the group consisting of: a selective serotonin reuptake inhibitor (SSRI), wherein the nucleic acid specifically binds to a target molecule selected from the group consisting of: an mRNA encoding the serotonin receptor type 1A ($5\text{-}HT_{1A}$), an mRNA encoding the serotonin transporter, and an mRNA encoding for TREK-1 polypeptide, and wherein the inhibitor and the nucleic acid are covalently coupled either directly or via a linker.

* * * * *